United States Patent
Dousson et al.

(10) Patent No.: US 10,030,044 B2
(45) Date of Patent: Jul. 24, 2018

(54) NUCLEOTIDES FOR THE TREATMENT OF LIVER CANCER

(71) Applicant: IDENIX PHARMACEUTICALS LLC, Cambridge, MA (US)

(72) Inventors: Cyril B. Dousson, Canet (FR); David Dukhan, Saint Gely du Fesc (FR); Christophe Claude Parsy, Jacou (FR)

(73) Assignee: IDENIX PHARMACEUTICALS LLC, Cambridge, MA (US)

(*) Notice: Subject to any disclaimer, the term of this patent is extended or adjusted under 35 U.S.C. 154(b) by 0 days.

(21) Appl. No.: 15/039,176

(22) PCT Filed: Nov. 25, 2014

(86) PCT No.: PCT/US2014/067485
§ 371 (c)(1),
(2) Date: May 25, 2016

(87) PCT Pub. No.: WO2015/081133
PCT Pub. Date: Jun. 4, 2015

(65) Prior Publication Data
US 2017/0029456 A1   Feb. 2, 2017

Related U.S. Application Data

(60) Provisional application No. 61/909,941, filed on Nov. 27, 2013.

(51) Int. Cl.
| | | |
|---|---|---|
| A01N 43/04 | (2006.01) | |
| A61K 31/70 | (2006.01) | |
| C07H 19/207 | (2006.01) | |
| A61K 31/7076 | (2006.01) | |
| C07H 19/16 | (2006.01) | |
| C07H 19/06 | (2006.01) | |
| C07H 19/10 | (2006.01) | |
| C07H 19/20 | (2006.01) | |
| A61K 31/7072 | (2006.01) | |
| A61K 31/708 | (2006.01) | |
| A61K 31/7068 | (2006.01) | |
| A61K 31/706 | (2006.01) | |
| A61K 31/7052 | (2006.01) | |
| A61K 31/7064 | (2006.01) | |

(52) U.S. Cl.
CPC ....... *C07H 19/207* (2013.01); *A61K 31/7076* (2013.01); *C07H 19/06* (2013.01); *C07H 19/10* (2013.01); *C07H 19/16* (2013.01); *C07H 19/20* (2013.01); *A61K 31/706* (2013.01); *A61K 31/708* (2013.01); *A61K 31/7052* (2013.01); *A61K 31/7064* (2013.01); *A61K 31/7068* (2013.01); *A61K 31/7072* (2013.01)

(58) Field of Classification Search
None
See application file for complete search history.

(56) References Cited

U.S. PATENT DOCUMENTS

| | | | |
|---|---|---|---|
| 2004/0077588 A1 | 4/2004 | Shepard et al. | |
| 2010/0227834 A1 | 9/2010 | Fahrig et al. | |
| 2012/0070411 A1 | 3/2012 | Beigelman et al. | |
| 2012/0142627 A1* | 6/2012 | Schinazi | A61K 31/675 514/50 |
| 2016/0031927 A1 | 2/2016 | Ivachtchenko | |

FOREIGN PATENT DOCUMENTS

| | | |
|---|---|---|
| CN | 104119385 A | 10/2014 |
| WO | 2005012327 A2 | 1/2005 |
| WO | 2006100439 A1 | 9/2006 |
| WO | 2009052050 A1 | 4/2009 |
| WO | 2012040127 A1 | 3/2012 |
| WO | 2012088155 A1 | 6/2012 |

(Continued)

OTHER PUBLICATIONS

Liang et al. Bioorganic & Medicinal Chemistry (2006), vol. 14, pp. 2178-2189.*
Bondada et al. ACS Med. Chem. Lett. (2013), vol. 4, pp. 747-751.*
Derudas, M et al., Evaluation of novel phosphoramidate ProTides of the 2'-fluoro derivatives of a potent anti-varicella zoster virus bicyclic nucleoside analogue, aNTIVIRAL Chemistry & Chemotherapy, 2010, pp. 15-31, 21.
Gudmundsson, KS et al., Phosphoramidate Protides of 2',3'-Dideoxy-3'-fluoroadenosine and related Nucleosides with Potent Activity Against HIV and HBV, Nucleosides, Nucleotides & Nucleic Acids, 2003, pp. 1953-1961, 22 (10).
McGuigan, C et al., Anti-cancer ProTides: tuning the activity of BVDU phosphoramidates related to thymectacin, Bioorganic & Medicinal Chemistry, 2005, pp. 3219-3227, 13 (9).

(Continued)

*Primary Examiner* — Patrick T Lewis
(74) *Attorney, Agent, or Firm* — Keith D. MacMillan; Catherine D. Fitch

(57) ABSTRACT

Provided herein are compounds, compositions and methods for the treatment of liver cancer such as hepatocellular carcinoma, cholangiocarcinoma, or biliary tract cancer. In certain embodiments, compounds and compositions of nucleoside derivatives are disclosed, which can be administered either alone or in combination with other anti-cancer agents. In certain embodiments, the compounds are nucleoside analogs of Formula I: (I); or a pharmaceutically acceptable salt thereof, wherein Base, $Z^1$, $Z^2$, $Z^3$, $Z^4$, V, W, X, Ar, $R^1$ and $R^2$ are as described herein.

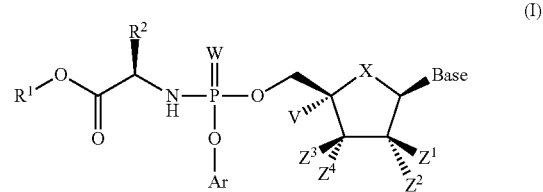

(I)

46 Claims, No Drawings

(56) References Cited

FOREIGN PATENT DOCUMENTS

| WO | 2014076490 A1 | 5/2014 |
|----|---------------|--------|
| WO | 2014148949 A1 | 9/2014 |
| WO | 2015034420 A1 | 3/2015 |
| WO | 2015056213 A1 | 4/2015 |
| WO | 2015134334 A1 | 9/2015 |

OTHER PUBLICATIONS

Quintiliani, M et al., Design, Synthesis and Biological Evaluation of 2'-deoxy-2'-2'-difluoro-5-halouridine phosphoramidate ProTides, Bioorganic & Medicinal Chemistry, 2011, pp. 4338-4345, 19.

Slusarczyl, M.; et al., Application of ProTide Technology to Gemcitabine: A Successful Approach to Overcome the Key Cancer Resistance Mechanisms Leads to a New Agent (NUC-1031) in Clinical Development, Journal of Medicinal Chemistry, 2014, pp. 1531-1542, 57.

\* cited by examiner

NUCLEOTIDES FOR THE TREATMENT OF LIVER CANCER

PRIOR RELATED APPLICATION

This application claims the benefit of, and priority to, U.S. Provisional Patent Application No. 61/909,941 entitled "Nucleotides for the Treatment of Liver Cancer" filed 27 Nov. 2013, which is hereby incorporated, in its entirety, by reference.

FIELD

Provided herein are compounds, methods and pharmaceutical compositions for use in treatment of liver cancers in subjects in need thereof. In certain embodiments, nucleoside and nucleotide compounds and prodrugs are provided which can display remarkable efficacy and bioavailability for the treatment of, for example, liver cancers in a human. Liver cancers which can be treated include primary and secondary liver cancers. In particular embodiments, the liver cancer is hepatocellular carcinoma, cholangiocarcinoma, or biliary tract cancer. In particular embodiments, the liver cancer is a metastasis in the liver originated from other cancers (such as colon cancer, pancreatic cancer, etc.).

BACKGROUND

Primary liver cancer is one of the most common forms of cancer in the world. Hepatocellular carcinoma, also known as malignant hepatoma, is the most common form of primary liver cancer, and develops within the hepatocyte. Hepatocellular carcinoma occurs mostly in men and patients that suffer from cirrhosis. It has been the third leading cause of cancer deaths worldwide (Block T M et al., 2003, *Oncogene* 22:5093-5107). Many patients with hepatocellular carcinoma remain asymptomatic until the disease is in its advanced stages, resulting in ineffective treatment and poor prognosis; the majority of unresectable hepatocellular carcinoma patients die within one year.

Treatment options for hepatocellular carcinoma have been limited, especially in the case of advanced or recurrent hepatocellular carcinoma. Surgery and radiation therapy are options for early stage liver cancer, but not very effective for advanced or recurrent hepatocellular carcinoma. Systematic chemotherapies have not been particularly effective, and there are a very limited number of drugs available for use. The recently approved kinase inhibitor sorafenib has been shown to be effective in treating hepatocellular carcinoma. However, it can slow or stop advanced liver cancer from progressing for only a few months longer than without treatment.

New therapies for the treatment or prevention of liver cancer such as hepatocellular carcinoma are needed.

SUMMARY

Provided herein are compounds useful, for example, for the treatment of liver cancer. The compounds are nucleoside and nucleotide analogs linked to a 5'-D-amino acid phosphoramidate group. In certain embodiments the nucleoside and nucleotide analogs linked to a 5'-D-amino acid phosphoramidate group can display remarkable efficacy or bioavailability, or both, for the treatment of, for example, liver cancer in a human. Liver cancers which can be treated include primary and secondary liver cancers. In particular embodiments, the liver cancer is hepatocellular carcinoma, cholangiocarcinoma, or biliary tract cancer. In particular embodiments, the liver cancer is a metastasis in the liver originated from other cancers (such as colon cancer, pancreatic cancer, etc.).

In certain embodiments, the compounds provided herein are useful in the prevention and treatment of liver cancer such as hepatocellular carcinoma, cholangiocarcinoma, or biliary tract cancer. These compounds or formulations can also be used prophylactically to prevent or retard the progression of clinical illness in individuals who have symptoms of liver cancer such as hepatocellular carcinoma, cholangiocarcinoma, or biliary tract cancer.

A method for the treatment of a liver cancer such as hepatocellular carcinoma, cholangiocarcinoma, or biliary tract cancer, or metastasis in the liver originated from other cancers (such as colon cancer, pancreatic cancer, etc.), in a subject, such a human, is also provided that includes administering an effective amount of a compound provided herein, administered either alone or in combination or alternation with another anti-cancer agent, optionally in a pharmaceutically acceptable carrier.

In certain embodiments, provided herein are compounds according to Formula I:

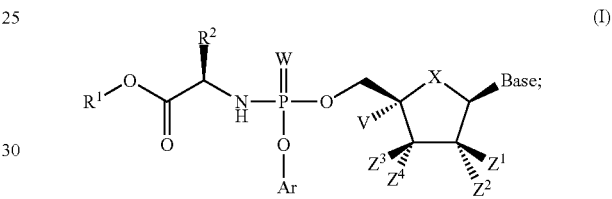

or a pharmaceutically acceptable salt, solvate, stereoisomeric form, tautomeric form or polymorphic form thereof, wherein:

Base is a nucleobase;
X is O or S;
W is O or S;
Ar is aryl or heteroaryl;
$R^1$ is hydrogen, alkyl, arylalkyl, or heteroarylalkyl;
$R^2$ is alkyl, arylalkyl, heterocycloalkyl, carboxylalkyl, heteroarylalkyl, aminoalkyl, hydroxylalkyl, aminoiminoaminoalkyl, aminocarbonylalkyl, sulfanylalkyl, carbamoylalkyl, alkylsulfanylalkyl, or hydroxylarylalkyl;
$Z^1$ is hydrogen, hydroxyl, halogen, or cyano;
$Z^2$ is hydrogen, hydroxyl, or halogen;
$Z^3$ is hydrogen;
$Z^4$ is hydroxyl, halogen, amino, or alkynyl;
V is hydrogen, halogen, or amino;
subject to the proviso that when, in Formula I: $Z^1$ is hydrogen, then: either V is halogen; or $Z^4$ is halogen, amino, or alkynyl; or Base is a nucleobase other than adenine, guanine, cytosine, thymine, or uracil.

In certain embodiments, provided herein are compounds according to Formula VI:

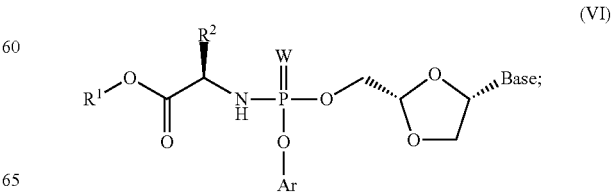

or a pharmaceutically acceptable salt, solvate, stereoisomeric form, tautomeric form or polymorphic form thereof, wherein:

Base is a nucleobase;

W is O or S;

Ar is aryl or heteroaryl;

$R^1$ is hydrogen, alkyl, arylalkyl, or heteroarylalkyl; and $R^2$ is alkyl, arylalkyl, heterocycloalkyl, carboxylalkyl, heteroarylalkyl, aminoalkyl, hydroxylalkyl, aminoiminoaminoalkyl, aminocarbonylalkyl, sulfanylalkyl, carbamoylalkyl, alkylsulfanylalkyl, or hydroxylarylalkyl.

In one aspect, the compounds provided herein are provided or administered in combination with a second therapeutic agent, such as one useful for the treatment or prevention of cancer. Exemplary second therapeutic agents are provided in detail elsewhere herein.

In another aspect, provided herein are pharmaceutical compositions, single unit dosage forms, and kits suitable for use in treating or preventing disorders such as liver cancer which comprise a therapeutically or prophylactically effective amount of a compound provided herein, e.g., of Formulas I-XVIII and 1-477c, and a therapeutically or prophylactically effective amount of a second therapeutic agent such as one useful for the treatment or prevention of liver cancer.

In certain embodiments, a method of treatment of a liver disorder is provided comprising administering to an individual in need thereof a treatment effective amount of a 5'-D-amino acid phosphoramidate compound described herein.

Liver cancers which can be treated include primary and secondary liver cancers. In particular embodiments, the liver cancer is hepatocellular carcinoma, cholangiocarcinoma, or biliary tract cancer.

DESCRIPTION OF EXEMPLARY EMBODIMENTS

Provided herein are compounds, compositions, and methods useful for treating liver disorders, such as liver cancer, in a subject. Further provided are dosage forms useful for such methods.

Definitions

When referring to the compounds provided herein, the following terms have the following meanings unless indicated otherwise. Unless defined otherwise, all technical and scientific terms used herein have the same meaning as is commonly understood by one of ordinary skill in the art. In the event that there is a plurality of definitions for a term herein, those in this section prevail unless stated otherwise.

The term "alkyl," as used herein, unless otherwise specified, refers to a saturated straight or branched hydrocarbon. In certain embodiments, the alkyl group is a primary, secondary, or tertiary hydrocarbon. In certain embodiments, the alkyl group includes one to ten carbon atoms, i.e., $C_1$ to $C_{10}$ alkyl. In certain embodiments, the alkyl group is methyl, $CF_3$, $CCl_3$, $CFCl_2$, $CF_2Cl$, ethyl, $CH_2CF_3$, $CF_2CF_3$, propyl, isopropyl, butyl, isobutyl, secbutyl, t-butyl, pentyl, isopentyl, neopentyl, hexyl, isohexyl, 3-methylpentyl, 2,2-dimethylbutyl, or 2,3-dimethylbutyl. The term includes both substituted and unsubstituted alkyl groups, including halogenated alkyl groups. In certain embodiments, the alkyl group is a fluorinated alkyl group. Non-limiting examples of moieties with which the alkyl group can be substituted include halogen (fluoro, chloro, bromo or iodo), oxo, epoxy, hydroxyl, carbonyl, cycloalkyl, aralkyl, sulfanyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., Protective Groups in Organic Synthesis, John Wiley and Sons, Second Edition, 1991, hereby incorporated by reference. In certain embodiments, alkyl is $C_1$ to $C_{10}$ unsubstituted alkyl. In certain embodiments, alkyl is $C_1$ to $C_{10}$ alkyl substituted with fluoro, chloro, bromo, iodo, oxo, epoxy, hydroxyl, carbonyl, sulfanyl, $-NH_2$, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate.

The term "lower alkyl," as used herein, and unless otherwise specified, refers to a saturated straight or branched hydrocarbon having one to six carbon atoms, i.e., $C_1$ to $C_6$ alkyl. In certain embodiments, the lower alkyl group is a primary, secondary, or tertiary hydrocarbon. The term includes both substituted and unsubstituted moieties.

The term "upper alkyl," as used herein, and unless otherwise specified, refers to a saturated straight or branched hydrocarbon having seven to thirty carbon atoms, i.e., $C_7$ to $C_{30}$ alkyl. In certain embodiments, the upper alkyl group is a primary, secondary, or tertiary hydrocarbon. The term includes both substituted and unsubstituted moieties.

The term "cycloalkyl," as used herein, unless otherwise specified, refers to a saturated cyclic hydrocarbon. In certain embodiments, the cycloalkyl group may be a saturated, and/or bridged, and/or non-bridged, and/or a fused bicyclic group. In certain embodiments, the cycloalkyl group includes three to ten carbon atoms, i.e., $C_3$ to $C_{10}$ cycloalkyl. In some embodiments, the cycloalkyl has from 3 to 15 ($C_{3-15}$), from 3 to 10 ($C_{3-10}$), or from 3 to 7 ($C_{3-7}$) carbon atoms. In certain embodiments, the cycloalkyl group is cyclopropyl, cyclobutyl, cyclopentyl, cyclohexyl, cyclohexylmethyl, cycloheptyl, bicyclo[2.1.1]hexyl, bicyclo[2.2.1] heptyl, decalinyl or adamantyl. The term includes both substituted and unsubstituted cycloalkyl groups, including halogenated cycloalkyl groups. In certain embodiments, the cycloalkyl group is a fluorinated cycloalkyl group. Non-limiting examples of moieties with which the cycloalkyl group can be substituted include halogen (fluoro, chloro, bromo or iodo), oxo, epoxy, hydroxyl, carbonyl, sulfanyl, amino, alkylamino, arylamino, alkoxy, aryloxy, nitro, cyano, sulfonic acid, sulfate, phosphonic acid, phosphate, or phosphonate, either unprotected, or protected as necessary. In certain embodiments, cycloalkyl is $C_3$-$C_{15}$ unsubstituted cycloalkyl or $C_3$-$C_{15}$ cycloalkyl substituted with fluoro, chloro, bromo, iodo, oxo, epoxy, hydroxyl, carbonyl, sulfanyl, $-NH_2$, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate.

"Alkylene" refers to divalent saturated aliphatic hydrocarbon groups, including those having from one to eleven carbon atoms which can be straight-chained or branched. In certain embodiments, the alkylene group contains 1 to 10 carbon atoms. The term includes both substituted and unsubstituted moieties. This term is exemplified by groups such as methylene ($-CH_2-$), ethylene ($-CH_2CH_2-$), the propylene isomers (e.g., $-CH_2CH_2CH_2-$ and $-CH(CH_3)CH_2-$) and the like. The term includes halogenated alkylene groups. In certain embodiments, the alkylene group is a fluorinated alkylene group. Non-limiting examples of moieties with which the alkylene group can be substituted include halogen (fluoro, chloro, bromo or iodo), oxo, epoxy, hydroxyl, carbonyl, sulfanyl, amino, alkylamino, alkylaryl, arylamino, alkoxy, aryloxy, nitro, cyano, sulfonic acid, sulfate, phosphonic acid, phosphate, and phosphonate, either unprotected, or protected as necessary. In certain embodiments, alkylene is $C_1$ to $C_{10}$ unsubstituted alkylene. In certain embodiments, alkylene is $C_1$ to $C_{10}$ alkylene substituted with fluoro, chloro, bromo, iodo, oxo, epoxy, hydroxyl, carbonyl, sulfanyl, $NH_2$, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate.

"Alkenyl" refers to monovalent olefinically unsaturated hydrocarbon groups, in certain embodiments, having up to about 11 carbon atoms, including from 2 to 8 carbon atoms, or from 2 to 6 carbon atoms, which can be straight-chained or branched and having at least 1, including from 1 to 2, site of olefinic unsaturation. The term includes both substituted and unsubstituted moieties. Exemplary alkenyl groups include ethenyl (i.e., vinyl, or —CH=$CH_2$), n-propenyl (—$CH_2$CH=$CH_2$), isopropenyl (—C($CH_3$)=$CH_2$), and the like. The term includes halogenated alkenyl groups. In certain embodiments, the alkenyl group is a fluorinated alkenyl group. Non-limiting examples of moieties with which the alkenyl group can be substituted include halogen (fluoro, chloro, bromo or iodo), oxo, epoxy, hydroxyl, carbonyl, sulfanyl, amino, alkylamino, arylamino, alkoxy, aryloxy, nitro, cyano, sulfonic acid, sulfate, phosphonic acid, phosphate, or phosphonate, either unprotected, or protected as necessary. In certain embodiments, alkenyl is $C_2$-$C_{11}$ unsubstituted alkenyl. In certain embodiments, alkenyl is a $C_2$-$C_{11}$ straight-chained or branched olefinically unsaturated hydrocarbon having at least one site of olefinic unsaturation substituted with fluoro, chloro, bromo, iodo, oxo, epoxy, hydroxyl, carbonyl, sulfanyl, —$NH_2$, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate.

The term "cycloalkenyl," as used herein, unless otherwise specified, refers to an unsaturated cyclic hydrocarbon. In certain embodiments, cycloalkenyl refers to mono- or multicyclic ring systems that include at least one double bond. In certain embodiments, the cycloalkenyl group may be a bridged, non-bridged, and/or a fused bicyclic group. In certain embodiments, the cycloalkyl group includes at least three carbon atoms, including three to ten carbon atoms, i.e., $C_3$ to $C_{10}$ cycloalkyl. In some embodiments, the cycloalkenyl has from 3 to 10 ($C_{3-10}$), or from 4 to 7 ($C_{4-7}$) carbon atoms. The term includes both substituted and unsubstituted cycloalkenyl groups, including halogenated cycloalkenyl groups. In certain embodiments, the cycloalkenyl group is a fluorinated cycloalkenyl group. Non-limiting examples of moieties with which the cycloalkenyl group can be substituted include halogen (fluoro, chloro, bromo or iodo), oxo, epoxy, hydroxyl, carbonyl, sulfanyl, amino, alkylamino, arylamino, alkoxy, aryloxy, nitro, cyano, sulfonic acid, sulfate, phosphonic acid, phosphate, or phosphonate, either unprotected, or protected as necessary.

"Alkenylene" refers to divalent olefinically unsaturated hydrocarbon groups, in certain embodiments, having up to about 11 carbon atoms or from 2 to 6 carbon atoms which can be straight-chained or branched and having at least 1 or from 1 to 2 sites of olefinic unsaturation. This term is exemplified by groups such as ethenylene (—CH=CH—), the propenylene isomers (e.g., —CH=$CHCH_2$— and —C($CH_3$)=CH— and —CH=C($CH_3$)—) and the like. The term includes both substituted and unsubstituted alkenylene groups, including halogenated alkenylene groups. In certain embodiments, the alkenylene group is a fluorinated alkenylene group. Non-limiting examples of moieties with which the alkenylene group can be substituted include halogen (fluoro, chloro, bromo or iodo), oxo, epoxy, hydroxyl, carbonyl, sulfanyl, amino, alkylamino, arylamino, alkoxy, aryloxy, nitro, cyano, sulfonic acid, sulfate, phosphonic acid, phosphate, or phosphonate, either unprotected, or protected as necessary.

"Alkynyl" refers to acetylenically unsaturated hydrocarbon groups, in certain embodiments, having up to about 11 carbon atoms or from 2 to 6 carbon atoms which can be straight-chained or branched and having at least 1 or from 1 to 2 sites of alkynyl unsaturation. Non-limiting examples of alkynyl groups include acetylenic, ethynyl (—C≡CH), propargyl (—$CH_2$C≡CH), and the like. The term includes both substituted and unsubstituted alkynyl groups, including halogenated alkynyl groups. In certain embodiments, the alkynyl group is a fluorinated alkynyl group. Non-limiting examples of moieties with which the alkynyl group can be substituted include halogen (fluoro, chloro, bromo or iodo), oxo, epoxy, hydroxyl, carbonyl, sulfanyl, amino, alkylamino, arylamino, alkoxy, aryloxy, nitro, cyano, sulfonic acid, sulfate, phosphonic acid, phosphate, or phosphonate, either unprotected, or protected as necessary. In certain embodiments, alkynyl is $C_2$-$C_{11}$ unsubstituted alkynyl. In certain embodiments, alkynyl is a $C_2$-$C_{11}$ straight-chained or branched olefinically unsaturated hydrocarbon having at least one site of olefinic unsaturation substituted with fluoro, chloro, bromo, iodo, oxo, epoxy, hydroxyl, carbonyl, sulfanyl, —$NH_2$, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate.

The term "aryl," as used herein, and unless otherwise specified, refers to a substituent derived from an aromatic ring. In an embodiment, an aryl group is a $C_6$-$C_{12}$ aryl group. In an embodiment, an aryl group is phenyl, biphenyl or naphthyl. The term includes both substituted and unsubstituted moieties. An aryl group can be substituted with any described moiety, including, but not limited to, one or more moieties selected from the group halogen (fluoro, chloro, bromo or iodo), alkyl, haloalkyl, hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991. In certain embodiments, aryl is $C_6$-$C_{12}$ unsubstituted aryl. In certain embodiments, aryl is $C_6$-$C_{12}$ aryl substituted with one or more fluoro, chloro, bromo, iodo, methyl, $CF_3$, $CCl_3$, $CFCl_2$, $CF_2Cl$, ethyl, $CH_2CF_3$, $CF_2CF_3$, propyl, isopropyl, butyl, isobutyl, secbutyl, t-butyl, pentyl, isopentyl, neopentyl, hexyl, isohexyl, 3-methylpentyl, 2,2-dimethylbutyl, 2,3-dimethylbutyl, hydroxyl, —$NH_2$, —NH—($C_1$ to $C_{10}$ unsubstituted alkyl), —NH—($C_1$ to $C_{10}$ substituted alkyl), —NH-aryl, —NH—($C_3$-$C_{15}$ cycloalkyl), methoxy, ethoxy, n-propoxy, isopropoxy, n-butoxy, tert-butoxy, sec-butoxy, n-pentoxy, n-hexoxy, 1,2-dimethylbutoxy, oxo, epoxy, hydroxyl, nitro, cyano, sulfonic acid, sulfate, phosphonic acid, phosphate, or phosphonate.

"Alkoxy" and "alkoxyl" refer to the group —OR' where R' is alkyl or cycloalkyl as defined herein. In certain embodiments, the alkoxyl or alkoxy group is —OR', wherein R' is alkyl or cycloalkyl, and wherein alkyl is $C_1$ to $C_{10}$ alkyl, and cycloalkyl is $C_3$ to $C_{15}$ cycloalkyl. Alkoxy and alkoxyl groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Alkylcarbonyloxy" refers to a radical —O—C(O)-alkyl, wherein alkyl is as defined herein.

"Alkoxylcarbonyl" refers to a radical —C(O)-alkoxyl where alkoxyl is as defined herein.

"Alkoxylalkylcarbonyl" refers to a radical —C(O)-alkyl-alkoxyl where alkoxyl and alkyl are as defined herein.

"Alkoxylcarbonylalkyl" refers to a radical -alkyl-C(O)-alkoxyl where alkoxyl and alkyl are as defined herein.

"Alkoxylcarbonylamino" refers to a radical -amino-C(O)-alkoxyl where alkoxyl and amino are as defined herein.

As used herein, "alkylcarbonylthioalkyl" refers to a radical alkyl-S—C(O)-alkyl, where alkyl is as defined herein.

As used herein, "(alkoxylcarbonyl)(alkoxylcarbonylamino)alkyl" refers to an alkyl radical substituted with both an alkoxylcarbonyl and an alkoxylcarbonylamino group, where "alkoxylcarbonyl" and "alkoxylcarbonylamino" are as described herein. In an embodiment, the term refers to a radical of formula

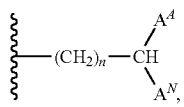

wherein n is an integer selected over the range of 1-10, $A^A$ is —C(O)—O—$R^{100}$, $A^N$ is —NH—C(O)—O—$R^{101}$, and each of $R^{100}$ and $R^{101}$ is independently lower alkyl. In an embodiment, each of $R^{100}$ and $R^{101}$ is independently $C_1$-$C_5$ alkyl.

"Amino" refers to the group —$NR^{1'}R^{2'}$ or —$NR^{1'}$—, wherein $R^{1'}$ and $R^{2'}$ are independently hydrogen, alkyl, alkenyl, alkynyl, cycloalkyl, heterocyclic, aryl, or heteroaryl, each of which is as defined herein.

The term "alkylamino" or "arylamino" refers to an amino group that has one or two alkyl or aryl substituents, respectively. In certain embodiments, the alkyl substituent is an upper alkyl. In certain embodiments, the alkyl substituent is a lower alkyl. In another embodiment, the alkyl, upper alkyl, or lower alkyl is unsubstituted.

"Oxo" refers to the group =O.

"Epoxy" refers to an oxygen atom bonded to two carbon atoms, where the two carbon atoms are also bonded to each other.

"Amino alcohol" refers to the radical —NHLOH, wherein L is alkylene.

"Carboxyl" or "carboxy" refers to the radical —C(O)OH.

"Halogen" or "halo" refers to chloro, bromo, fluoro, or iodo.

"Monoalkylamino" refers to the group —NR'-alkyl, wherein R' is selected from hydrogen, alkyl, and cycloalkyl.

"Thioalkoxyl" refers to the group —SR' where R' is alkyl or cycloalkyl.

The term "heterocyclo" or "heterocyclic" refers to a monovalent monocyclic non-aromatic ring system and/or multicyclic ring system that contains at least one non-aromatic ring, wherein one or more of the non-aromatic ring atoms are heteroatoms independently selected from O, S, or N; and the remaining ring atoms are carbon atoms. In certain embodiments, the heterocyclo or heterocyclic group has from 3 to 20, from 3 to 15, from 3 to 10, from 3 to 8, from 4 to 7, or from 5 to 6 ring atoms. Heterocyclo groups are bonded to the rest of the molecule through the non-aromatic ring. In certain embodiments, the heterocyclo is a monocyclic, bicyclic, tricyclic, or tetracyclic ring system, which may include a fused or bridged ring system, and in which the nitrogen or sulfur atoms may be optionally oxidized, the nitrogen atoms may be optionally quaternized, and some rings may be partially or fully saturated, or aromatic. The heterocyclo may be attached to the main structure at any heteroatom or carbon atom which results in the creation of a stable compound. Examples of such heterocyclic radicals include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, β-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, heterocyclic may also be optionally substituted as described herein. Non-limiting examples of moieties with which the heterocyclic group can be substituted include halogen (fluoro, chloro, bromo or iodo), oxo, epoxy, hydroxyl, carbonyl, alkoxycarbonyl, alkoxycarbonylalkyl, sulfanyl, amino, alkylamino, arylamino, alkoxy, aryloxy, nitro, cyano, sulfonic acid, sulfate, phosphonic acid, phosphate, or phosphonate, either unprotected, or protected as necessary.

The term "heteroaryl" refers to a monovalent monocyclic aromatic group and/or multicyclic aromatic group that contain at least one aromatic ring, wherein at least one aromatic ring contains one or more heteroatoms independently selected from O, S and N in the ring. Heteroaryl groups are bonded to the rest of the molecule through the aromatic ring. Each ring of a heteroaryl group can contain one or two O atoms, one or two S atoms, and/or one to four N atoms, provided that the total number of heteroatoms in each ring is four or less and each ring contains at least one carbon atom. In certain embodiments, the heteroaryl has from 5 to 20, from 5 to 15, or from 5 to 10 ring atoms. Examples of monocyclic heteroaryl groups include, but are not limited to, furanyl, imidazolyl, isothiazolyl, isoxazolyl, oxadiazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl and xanthenyl. In certain embodiments, heteroaryl may also be optionally substituted as described herein.

The term "alkylaryl" refers to an aryl group with an alkyl substituent, wherein aryl and alkyl are as defined herein. The term "aralkyl" or "arylalkyl" refers to an alkyl group with an aryl substituent, wherein aryl and alkyl are as defined herein.

The term "alkylheterocyclo" refers to a heterocyclo group with an alkyl substituent. The term "heterocycloalkyl" refers to an alkyl group with a heterocyclo substituent.

The term "alkylheteroaryl" refers to a heteroaryl group with an alkyl substituent. The term "heteroarylalkyl" refers to an alkyl group with a heteroaryl substituent.

As used herein, the term "hydantoinyl" refers to the group

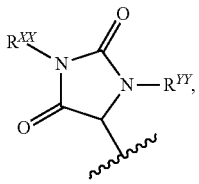

where $R^{XX}$ and $R^{YY}$ are each independently hydrogen or lower alkyl.

As used herein, the term "hydantoinylalkyl" refers to the group -alkyl-hydantoinyl, where alkyl and hydantoinyl are as described herein.

The term "protecting group" as used herein and unless otherwise defined refers to a group that is added to an oxygen, nitrogen or phosphorus atom to prevent its further reaction or for other purposes. A wide variety of oxygen and nitrogen protecting groups are known to those skilled in the art of organic synthesis.

"Pharmaceutically acceptable salt" refers to any salt of a compound provided herein which retains its biological properties and which is not toxic or otherwise undesirable for pharmaceutical use. Such salts may be derived from a variety of organic and inorganic counter-ions well known in the art. Such salts include, but are not limited to: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids; or (2) base addition salts formed when an acidic proton present in the parent compound either (a) is replaced by a metal ion, e.g., an alkali metal ion, an alkaline earth ion or an aluminum ion, or alkali metal or alkaline earth metal hydroxides, such as sodium, potassium, calcium, magnesium, aluminum, lithium, zinc, and barium hydroxide, ammonia or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like.

Pharmaceutically acceptable salts further include, by way of example only and without limitation, sodium, potassium, calcium, magnesium, ammonium, tetraalkylammonium and the like, and when the compound contains a basic functionality, salts of non-toxic organic or inorganic acids, such as hydrohalides, e.g. hydrochloride and hydrobromide, sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate, fumarate, tartarate, citrate, benzoate, 3-(4-hydroxybenzoyl)benzoate, picrate, cinnamate, mandelate, phthalate, laurate, methanesulfonate (mesylate), ethanesulfonate, 1,2-ethane-disulfonate, 2-hydroxyethanesulfonate, benzenesulfonate (besylate), 4-chlorobenzenesulfonate, 2-naphthalenesulfonate, 4-toluenesulfonate, camphorate, camphorsulfonate, 4-methylbicyclo[2.2.2]-oct-2-ene-1-carboxylate, glucoheptonate, 3-phenylpropionate, trimethylacetate, tert-butylacetate, lauryl sulfate, gluconate, benzoate, glutamate, hydroxynaphthoate, salicylate, stearate, cyclohexylsulfamate, quinate, muconate and the like.

As used herein, the term "nucleobase" refers to the base portion of a nucleoside or nucleotide. In certain embodiments, a nucleobase is a purine or pyrimidine base, as defined herein. In certain embodiments, nucleobase includes 2-chloro-adenine, 5-fluoro-uracil, 5-aza-cytosine, 6-thioguanine, 6-ethylthio-guanine, and imidazo(4,5-d)(1,3)diazepin-8-ol.

The term "purine" or "pyrimidine" base refers to, but is not limited to, adenine, $N^6$-alkylpurines, $N^6$-acylpurines (wherein acyl is C(O)(alkyl, aryl, alkylaryl, or arylalkyl), $N^6$-benzylpurine, $N^6$-halopurine, $N^6$-vinylpurine, $N^6$-acetylenic purine, $N^6$-acyl purine, $N^6$-hydroxyalkyl purine, $N^6$-alkylaminopurine, $N^6$-thioalkyl purine, $N^2$-alkylpurines, $N^2$-alkyl-6-thiopurines, thymine, cytosine, 5-fluorocytosine, 5-methylcytosine, 6-azapyrimidine, including 6-azacytosine, 2- and/or 4-mercaptopyrmidine, uracil, 5-halouracil, including 5-fluorouracil, $C^5$-alkylpyrimidines, $C^5$-benzylpyrimidines, $C^5$-halopyrimidines, $C^5$-vinylpyrimidine, $C^5$-acetylenic pyrimidine, $C^5$-acyl pyrimidine, $C^5$-hydroxyalkyl purine, $C^5$-amidopyrimidine, $C^5$-cyanopyrimidine, $C^5$-iodopyrimidine, $C^6$-iodo-pyrimidine, $C^5$—Br-vinyl pyrimidine, $C^6$—Br-vinyl pyrimidine, $C^5$-nitropyrimidine, $C^5$-amino-pyrimidine, $N^2$-alkylpurines, $N^2$-alkyl-6-thiopurines, 5-azacytidine, 5-azauracil, triazolopyridine, imidazolopyridine, pyrrolopyrimidine, and pyrazolopyrimidine. Purine bases include, but are not limited to, guanine, adenine, hypoxanthine, 7-deazaguanine, 7-deazaadenine, 2,6-diaminopurine, and 6-chloropurine. Functional oxygen and nitrogen groups on the base can be protected as necessary or desired. Suitable protecting groups are well known to those skilled in the art, and include trimethylsilyl, dimethylhexylsilyl, t-butyldimethylsilyl, and t-butyldiphenylsilyl, trityl, alkyl groups, and acyl groups such as acetyl and propionyl, methanesulfonyl, and p-toluenesulfonyl.

The term "acyl" or "O-linked ester" refers to a group of the formula C(O)R', wherein R' is alkyl or cycloalkyl (including lower alkyl), carboxylate residue of amino acid, aryl including phenyl, alkaryl, arylalkyl including benzyl, alkoxyalkyl including methoxymethyl, aryloxyalkyl such as phenoxymethyl; or substituted alkyl (including lower alkyl), aryl including phenyl optionally substituted with chloro, bromo, fluoro, iodo, $C_1$ to $C_4$ alkyl or $C_1$ to $C_4$ alkoxy, sulfonate esters such as alkyl or arylalkyl sulphonyl including methanesulfonyl, the mono, di or triphosphate ester, trityl or monomethoxy-trityl, substituted benzyl, alkaryl, arylalkyl including benzyl, alkoxyalkyl including methoxymethyl, aryloxyalkyl such as phenoxymethyl. Aryl groups in the esters optimally comprise a phenyl group. In particular, acyl groups include acetyl, trifluoroacetyl, methylacetyl, cyclopropylacetyl, propionyl, butyryl, hexanoyl, heptanoyl, octanoyl, neo-heptanoyl, phenylacetyl, 2-acetoxy-2-phenylacetyl, diphenylacetyl, α-methoxy-α-trifluoromethyl-phenylacetyl, bromoacetyl, 2-nitro-benzeneacetyl, 4-chloro-benzeneacetyl, 2-chloro-2,2-diphenylacetyl, 2-chloro-2-phenylacetyl, trimethylacetyl, chlorodifluoroacetyl, perfluoroacetyl, fluoroacetyl, bromodifluoroacetyl, methoxyacetyl, 2-thiopheneacetyl, chlorosulfonylacetyl, 3-methoxyphenylacetyl, phenoxyacetyl, tert-butylacetyl, trichloroacetyl, monochloro-acetyl, dichloroacetyl, 7H-dodecafluoro-heptanoyl, perfluoro-heptanoyl, 7H-dodeca-fluoroheptanoyl, 7-chlorododecafluoro-heptanoyl, 7-chloro-dodecafluoro-heptanoyl, 7H-dodecafluoro-heptanoyl, 7H-dodeca-fluoroheptanoyl, nona-fluoro-3,6-dioxa-heptanoyl, nonafluoro-3,6-dioxaheptanoyl, perfluoroheptanoyl, methoxybenzoyl, methyl 3-amino-5-phenylthiophene-2-carboxyl, 3,6-dichloro-2-methoxy-benzoyl, 4-(1,1,2,2-tetrafluoro-ethoxy)-benzoyl, 2-bromo-propionyl, omega-aminocapryl, decanoyl, n-pentadecanoyl, stearyl, 3-cyclopentyl-propionyl, 1-benzene-carboxyl, O-acetylmandelyl, pivaloyl acetyl, 1-adamantane-carboxyl, cyclohexane-carboxyl, 2,6-pyridinedicarboxyl, cyclopropane-carboxyl, cyclobutane-carboxyl, perfluorocyclohexyl carboxyl, 4-methylbenzoyl, chloromethyl isoxazolyl carbonyl, perfluorocyclohexyl carboxyl, crotonyl, 1-methyl-1H-indazole-3-carbonyl, 2-propenyl, isovaleryl, 1-pyrrolidinecarbonyl, 4-phenylbenzoyl.

The term "amino acid" refers to naturally occurring and synthetic α, β, γ, or δ amino acids, and includes but is not limited to, amino acids found in proteins, i.e. glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. In certain embodiments, the amino acid is in the L-configuration. In certain embodiments, the amino acid is in the D-configuration. In certain embodiments, the amino acid is provided as a substituent of a compound described herein, wherein the amino acid is a residue selected from alanyl, valinyl, leucinyl, isoleuccinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleuccinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl, or β-histidinyl.

The term "amino acid derivative" refers to a group derivable from a naturally or non-naturally occurring amino acid, as described and exemplified herein. Amino acid derivatives are apparent to those of skill in the art and include, but are not limited to, ester, amino alcohol, amino aldehyde, amino lactone, and N-methyl derivatives of naturally and non-naturally occurring amino acids. In an embodiment, an amino acid derivative is provided as a substituent of a compound described herein, wherein the substituent is —NR$^X$-G(S$_C$)—C(O)-Q$^1$, wherein Q$^1$ is —SR$^Y$, —NR$^Y$R$^Y$, or alkoxyl, R$^Y$ is hydrogen or alkyl, S$_C$ is a side chain of a naturally occurring or non-naturally occurring amino acid, G is C$_1$-C$_2$ alkylene, and R$^X$ is hydrogen or R$^X$ and S$_C$, together with the atoms to which they are attached, combine to form a five-membered heterocyclic ring. In an embodiment, an amino acid derivative is provided as a substituent of a compound described herein, wherein the substituent is —O—C(O)-G(S$_C$)—NH-Q$^2$, wherein Q$^2$ is hydrogen or alkoxyl, S$_C$ is a side chain of a naturally occurring or non-naturally occurring amino acid and G is C$_1$-C$_2$ alkylene. In certain embodiments, Q$^2$ and S$_C$, together with the atoms to which they are attached, combine to form a five-membered heterocyclic ring. In certain embodiments, G is C$_1$ alkylene and S$_C$ is hydrogen, alkyl, arylalkyl, heterocycloalkyl, carboxylalkyl, heteroarylalkyl, aminoalkyl, hydroxylalkyl, aminoiminoaminoalkyl, aminocarbonylalkyl, sulfanylalkyl, carbamoylalkyl, alkylsulfanylalkyl, or hydroxylarylalkyl. In an embodiment, an amino acid derivative is provided as a substituent of a compound described herein, wherein the amino acid derivative is in the D-configuration. In an embodiment, an amino acid derivative is provided as a substituent of a compound described herein, wherein the amino acid derivative is in the L-configuration.

As used herein, the term "aminoalkyl" refers to an alkyl group with an amino substituent, where alkyl and amino are as described herein.

As used herein, the terms "hydroxylalkyl" and "hydroxyalkyl" refer to an alkyl group with a hydroxyl substituent, where alkyl is as described herein.

As used herein, the term "carboxylalkyl" refers to the group -alkyl-C(O)OH, where alkyl is as described herein.

As used herein, the term "aminoiminoaminoalkyl" refers to the group -alkyl-amino-C(NH)-amino, where alkyl and amino are as described herein.

As used herein, the term "aminocarbonylalkyl" refers to the group -alkyl-C(O)-amino, where alkyl and amino are as described herein.

As used herein, the term "sulfanylalkyl" refers to the group -alkyl-SH, where alkyl is as described herein.

As used herein, the term "carbamoylalkyl" refers to the group -alkyl-C(O)-amino, where alkyl and amino are as described herein.

As used herein, the term "alkylsulfanylalkyl" refers to the group -alkyl-S-alkyl, where alkyl is as described herein.

As used herein, the term "hydroxylarylalkyl" refers to the group -alkyl-aryl-OH, where alkyl and aryl are as described herein.

Unless expressly stated to the contrary, substitution by a named substituent is permitted on any atom in a chain or ring provided such substitution is chemically allowed and results in a stable compound. A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject).

To the extent substituents and substituent patterns provide for the existence of tautomers (e.g., keto-enol tautomers) in the compounds described herein, all tautomeric forms of these compounds, whether present individually or in mixtures, are within the scope of the present disclosure. Compounds of the present disclosure having a hydroxy substituent on a carbon atom of a heteroaromatic ring are understood to include compounds in which only the hydroxy is present, compounds in which only the tautomeric keto form (i.e., an oxo substituent) is present, and compounds in which the keto and enol forms are both present.

As used herein when referring to a substituent on a sugar ring of a nucleoside, the term "alpha" refers to a substituent on the same side of the plane of the sugar ring as the 5' carbon and the term "beta" refers to a substituent on the opposite side of the plane of the sugar ring from the 5' carbon. As shown below, substituent "A" is in the "alpha" position, and substituent "B" is in the "beta" position with respect to the 5' carbon:

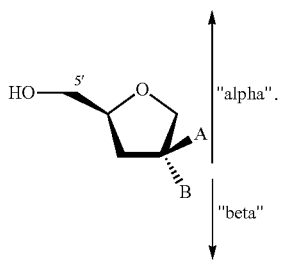

The term "substantially free of" or "substantially in the absence of," when used in connection with an article (including, but not limited to, a compound, a salt thereof, a solvate thereof, a solid form thereof, and the like), refers to the article that includes at least 85% or 90% by weight, in certain embodiments, 95%, 98%, 99%, or 100% by weight, of the designated article. For example, the term "substantially free of" or "substantially in the absence of" with respect to a nucleoside composition can refer to a nucleoside composition that includes at least 85% or 90% by weight, in certain embodiments, 95%, 98%, 99%, or 100% by weight, of the designated stereoisomer of that nucleoside. In certain embodiments, in the methods and compounds provided herein, the compounds are substantially free of undesignated stereoisomers or other compounds. For another example, the term "substantially free of" or "substantially in the absence of" with respect to a solid form can refer to a solid form that includes at least 85% or 90% by weight, in certain embodiments, 95%, 98%, 99%, or 100% by weight, of the designated solid form. In certain embodiments, in the methods and compounds provided herein, the solid form is substantially free of other solid forms.

Similarly, the term "isolated" with respect to a nucleoside composition refers to a nucleoside composition that includes at least 85%, 90%, 95%, 98%, or 99% to 100% by weight, of the nucleoside, the remainder comprising other chemical species or stereoisomers. Similarly, the term "isolated" with respect to a solid form of a compound refers to a solid that includes at least 85%, 90%, 95%, 98%, or 99% to 100% by weight, of such solid form of the compound, the remainder comprising other solid forms of the compound, other compounds, solvents, and/or other impurities.

"Solvate" refers to a compound provided herein or a salt thereof, that further includes a stoichiometric or non-stoichiometric amount of solvent bound by non-covalent intermolecular forces. Where the solvent is water, the solvate is a hydrate.

"Isotopic composition" refers to the amount of each isotope present for a given atom, and "natural isotopic composition" refers to the naturally occurring isotopic composition or abundance for a given atom. Atoms containing their natural isotopic composition may also be referred to herein as "non-enriched" atoms. Unless otherwise designated, the atoms of the compounds recited herein are meant to represent any stable isotope of that atom. For example, unless otherwise stated, when a position is designated specifically as "H" or "hydrogen," the position is understood to have hydrogen at its natural isotopic composition.

"Isotopic enrichment" refers to the percentage of incorporation of an amount of a specific isotope at a given atom in a molecule in the place of that atom's natural isotopic abundance. For example, deuterium enrichment of 1% at a given position means that 1% of the molecules in a given sample contain deuterium at the specified position. Because the naturally occurring distribution of deuterium is about 0.0156%, deuterium enrichment at any position in a compound synthesized using non-enriched starting materials is about 0.0156%. The isotopic enrichment of the compounds provided herein can be determined using conventional analytical methods known to one of ordinary skill in the art, including mass spectrometry and nuclear magnetic resonance spectroscopy.

"Isotopically enriched" refers to an atom having an isotopic composition other than the natural isotopic composition of that atom. "Isotopically enriched" may also refer to a compound containing at least one atom having an isotopic composition other than the natural isotopic composition of that atom.

As used herein, "alkyl," "cycloalkyl," "alkenyl," "cycloalkenyl," "alkynyl," "aryl," "alkoxy," "alkoxycarbonyl," "alkoxycarbonylalkyl," "amino," "carboxyl," "alkylamino," "arylamino," "thioalkyoxy," "heterocyclo," "heteroaryl," "alkylheterocyclo," "alkylheteroaryl," "acyl," "aralkyl," "alkaryl," "purine," "pyrimidine," "carboxyl" and "amino acid" groups optionally comprise deuterium at one or more positions where hydrogen atoms are present, and wherein the deuterium composition of the atom or atoms is other than the natural isotopic composition.

Also as used herein, "alkyl," "cycloalkyl," "alkenyl," "cycloalkenyl," "alkynyl," "aryl," "alkoxy," "alkoxycarbonyl," "alkoxycarbonylalkyl," "carboxyl," "alkylamino," "arylamino," "thioalkyoxy," "heterocyclo," "heteroaryl," "alkylheterocyclo," "alkylheteroaryl," "acyl," "aralkyl," "alkaryl," "purine," "pyrimidine," "carboxyl" and "amino acid" groups optionally comprise carbon-13 at an amount other than the natural isotopic composition.

As used herein, $EC_{50}$ refers to a dosage, concentration or amount of a particular test compound that elicits a dose-dependent response at 50% of maximal expression of a particular response that is induced, provoked or potentiated by the particular test compound.

As used herein, the $IC_{50}$ refers to an amount, concentration or dosage of a particular test compound that achieves a 50% inhibition of a maximal response in an assay that measures such response.

The term "host," as used herein, refers to any unicellular or multicellular organism in which the virus can replicate, including cell lines and animals, and in certain embodiments, a human. Alternatively, the host can be carrying a part of the Flaviviridae viral genome, whose replication or function can be altered by the compounds of the present invention. The term host specifically includes infected cells, cells transfected with all or part of the Flaviviridae genome and animals, in particular, primates (including chimpanzees) and humans. In most animal applications of the present invention, the host is a human patient. Veterinary applications, in certain indications, however, are clearly anticipated by the present invention (such as chimpanzees).

As used herein, the terms "subject" and "patient" are used interchangeably herein. The terms "subject" and "subjects" refer to an animal, such as a mammal including a non-primate (e.g., a cow, pig, horse, cat, dog, rat, and mouse) and a primate (e.g., a monkey such as a cynomolgous monkey, a chimpanzee and a human), and for example, a human. In certain embodiments, the subject is refractory or non-responsive to current treatments for hepatitis C infection. In another embodiment, the subject is a farm animal (e.g., a horse, a cow, a pig, etc.) or a pet (e.g., a dog or a cat). In certain embodiments, the subject is a human.

As used herein, the terms "therapeutic agent" and "therapeutic agents" refer to any agent(s) which can be used in the treatment or prevention of a disorder or one or more symptoms thereof. In certain embodiments, the term "therapeutic agent" includes a compound provided herein. In certain embodiments, a therapeutic agent is an agent which is known to be useful for, or has been or is currently being used for the treatment or prevention of a disorder or one or more symptoms thereof.

"Therapeutically effective amount" refers to an amount of a compound or composition that, when administered to a subject for treating a disease, is sufficient to effect such treatment for the disease. A "therapeutically effective amount" can vary depending on, inter alia, the compound, the disease and its severity, and the age, weight, etc., of the subject to be treated.

"Treating" or "treatment" of any disease or disorder refers, in certain embodiments, to ameliorating a disease or disorder that exists in a subject. In another embodiment, "treating" or "treatment" includes ameliorating at least one physical parameter, which may be indiscernible by the subject. In yet another embodiment, "treating" or "treatment" includes modulating the disease or disorder, either physically (e.g., stabilization of a discernible symptom) or physiologically (e.g., stabilization of a physical parameter) or both. In yet another embodiment, "treating" or "treatment" includes delaying the onset of the disease or disorder.

As used herein, the terms "prophylactic agent" and "prophylactic agents" as used refer to any agent(s) which can be used in the prevention of a disorder or one or more symptoms thereof. In certain embodiments, the term "prophylactic agent" includes a compound provided herein. In certain other embodiments, the term "prophylactic agent" does not refer a compound provided herein. For example, a prophylactic agent is an agent which is known to be useful for, or has been or is currently being used to prevent or impede the onset, development, progression and/or severity of a disorder.

As used herein, the phrase "prophylactically effective amount" refers to the amount of a therapy (e.g., prophylactic agent) which is sufficient to result in the prevention or reduction of the development, recurrence or onset of one or more symptoms associated with a disorder, or to enhance or improve the prophylactic effect(s) of another therapy (e.g., another prophylactic agent).

Compounds

Provided herein are nucleoside compounds useful for the treatment of liver cancers such as hepatocellular carcinoma, cholangiocarcinoma, or biliary tract cancer. The nucleoside compounds can be formed as described herein and used for the treatment of liver cancers such as hepatocellular carcinoma, cholangiocarcinoma, or biliary tract cancer.

The compounds described herein may optionally be used in the form of a pharmaceutically acceptable salt. It is understood that references to compounds or pharmaceutically salts thereof would include compounds in present form as well as in different forms, such as polymorphs and solvates (including hydrates), as applicable.

In certain embodiments, provided herein are compounds according to any of Formulas I, Ia or Ib:

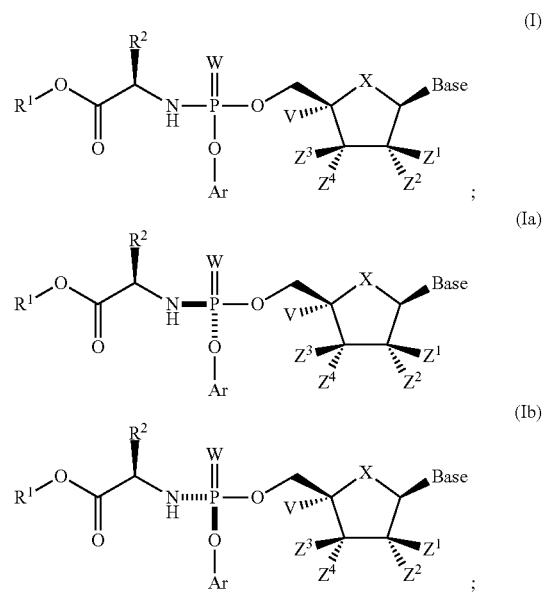

or a pharmaceutically acceptable salt, solvate, stereoisomeric form, tautomeric form, or polymorphic form thereof, wherein:

Base is a nucleobase;
X is O or S;
W is O or S;
Ar is aryl or heteroaryl;
$R^1$ is hydrogen, alkyl, arylalkyl, or heteroarylalkyl;
$R^2$ is alkyl, arylalkyl, heterocycloalkyl, carboxyalkyl, heteroarylalkyl, aminoalkyl, hydroxylalkyl, aminoiminoaminoalkyl, aminocarbonylalkyl, sulfanylalkyl, carbamoylalkyl, alkylsulfanylalkyl, or hydroxylarylalkyl;
$Z^1$ is hydrogen, hydroxyl, halogen, or cyano;
$Z^2$ is hydrogen, hydroxyl, or halogen;
$Z^3$ is hydrogen;
$Z^4$ is hydroxyl, halogen, amino, or alkynyl;
V is hydrogen, halogen, or amino;
subject to the proviso that when: $Z^1$ is hydrogen, then: V is halogen; or $Z^4$ is halogen, amino or alkynyl; or Base is a nucleobase other than adenine, guanine, cytosine, thymine or uracil.

Formula I includes a chiral amino acid residue linked to a 5'-phosphoramidate group. Those of skill in the art will recognize that the amino acid residue has R stereochemistry at the carbon bonded to $R^2$; i.e., that it is a D-amino acid residue. In certain embodiments, $R^2$ is the side chain of an amino acid. The side chain can be the side chain of any amino acids known to those of skill. In certain embodiments, the side chain is the side chain of histidine, alanine, isoleucine, arginine, leucine, asparagine, lysine, aspartic acid, methionine, cysteine, phenylalanine, glutamic acid, threonine, glutamine, tryptophan, valine, ornithine, selenocysteine, serine or tyrosine. In particular embodiments, the side chain is the side chain of alanine.

The compounds provided herein are based, at least in part, on the discovery that D-amino acid phosphoramidate prodrugs can provide superior human pharmacokinetics including superior accumulation of active nucleoside and nucleotide analogs in target cells, such as liver cells. In certain embodiments, the compounds provided herein are D-amino acid, $R_P$ phosphoramidate compounds. In certain embodiments, the compounds provided herein are D-amino acid, $S_P$ phosphoramidate compounds. Any compound provided herein is preferably in the form of a composition that is substantially free of other stereoisomers of the compound, as described herein.

In Formula I, Ar is aryl or heteroaryl. Useful aryl groups include phenyl and napthyl. Useful heteroaryl groups are described above. These groups can be substituted or unsubstituted. In certain embodiments, they are unsubstituted. In certain embodiments, they are substituted. Useful substituents are described in in the definition of aryl herein. Exemplary substituents include $-NO_2$, $-F$, $-OMe$, $-NH_2$, $-NMe_2$, -Me, $-CF_3$, $-Cl$, $-OH$, $-CN$, and $-OCF_3$.

In Formula I, $R^1$ is hydrogen, alkyl, arylalkyl or heteroarylalkyl. The alkyl groups can be substituted or unsubstituted. In certain embodiments, the alkyl groups are unsubstituted. In certain embodiments, the alkyl groups are substituted. Useful substituents are described in the definition of alkyl above. The aryl and heteroaryl groups can be substituted or unsubstituted. In certain embodiments, they are unsubstituted. In certain embodiments, they are substituted. Useful substituents are described in in the definition of aryl herein. Exemplary substituents include $-NO_2$, $-F$, $-OMe$, $-NH_2$, $-NMe_2$, -Me, $-CF_3$, $-Cl$, $-OH$, $-CN$, and $-OCF_3$.

In an embodiment, provided herein is a compound according to according to any of Formulas I, Ia or Ib, or a pharmaceutically acceptable salt, solvate, tautomeric form, or polymorphic form thereof, wherein:

Base is

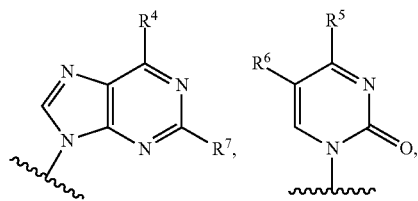

or a tautomeric form thereof;

Ar is aryl or heteroaryl;

$R^1$ is hydrogen, $C_1$ to $C_{10}$ unsubstituted alkyl, $C_1$ to $C_{10}$ substituted alkyl, $-(C_1$ to $C_{10}$ unsubstituted alkyl)-aryl, $-(C_1$ to $C_{10}$ substituted alkyl)-aryl, $-(C_1$ to $C_{10}$ unsubstituted alkyl)-heteroaryl, or $-(C_1$ to $C_{10}$ substituted alkyl)-heteroaryl;

$R^2$ is $C_1$ to $C_{10}$ unsubstituted alkyl, $C_1$ to $C_{10}$ substituted alkyl, $-(C_1$ to $C_{10}$ unsubstituted alkyl)-aryl, $-(C_1$ to $C_{10}$ substituted alkyl)-aryl, $-(C_1$ to $C_{10}$ unsubstituted alkyl)-heterocyclo, $-(C_1$ to $C_{10}$ substituted alkyl)-heterocyclo, $-(C_1$ to $C_{10}$ unsubstituted alkyl)-C(O)OH, $-(C_1$ to $C_{10}$ substituted alkyl)-C(O)OH, $-(C_1$ to $C_{10}$ unsubstituted alkyl)-heteroaryl, $-(C_1$ to $C_{10}$ substituted alkyl)-heteroaryl, $-(C_1$ to $C_{10}$ unsubstituted alkyl)-$NR^{1'}R^{2'}$, $-(C_1$ to $C_{10}$ substituted alkyl)-$NR^{1'}R^{2'}$, $-(C_1$ to $C_{10}$ unsubstituted alkyl)-OH, $-(C_1$ to $C_{10}$ substituted alkyl)-OH, $-(C_1$ to $C_{10}$ unsubstituted alkyl)-$NR^{1'}$—C(NH)—$NR^{1'}R^{2'}$, $-(C_1$ to $C_{10}$ substituted alkyl)-$NR^{1'}$—C(NH)—$NR^{1'}R^2$, $-(C_1$ to $C_{10}$ unsubstituted alkyl)-C(O)—$NR^{1'}R^{2'}$, $-(C_1$ to $C_{10}$ substituted alkyl)-C(O)—$NR^{1'}R^{2'}$, $-(C_1$ to $C_{10}$ unsubstituted alkyl)-SH, $-(C_1$ to $C_{10}$ substituted alkyl)-SH, $-(C_1$ to $C_{10}$ unsubstituted alkyl)-C(O)—$NR^{1'}R^{2'}$, $-(C_1$ to $C_{10}$ substituted alkyl)-C(O)—$NR^{1'}R^{2'}$, $-(C_1$ to $C_{10}$ unsubstituted alkyl)-S—$(C_1$ to $C_{10}$ unsubstituted alkyl), $-(C_1$ to $C_{10}$ unsubstituted alkyl)-S—$(C_1$ to $C_{10}$ substituted alkyl), $-(C_1$ to $C_{10}$ substituted alkyl)-S—$(C_1$ to $C_{10}$ unsubstituted alkyl), $-(C_1$ to $C_{10}$ substituted alkyl)-S—$(C_1$ to $C_{10}$ substituted alkyl), $-(C_1$ to $C_{10}$ unsubstituted alkyl)-aryl-OH, or $-(C_1$ to $C_{10}$ substituted alkyl)-aryl-OH;

$Z^1$ is hydrogen, hydroxyl, chloro, bromo, fluoro, iodo, or cyano;

$Z^2$ is hydrogen, hydroxyl, chloro, bromo, fluoro, or iodo;

$Z^3$ is hydrogen;

$Z^4$ is hydroxyl, chloro, bromo, fluoro, iodo, $-NR^{1'}R^{2'}$, $C_2$-$C_{11}$ unsubstituted alkynyl, or $C_2$-$C_{11}$ substituted alkynyl;

V is hydrogen, chloro, bromo, fluoro, iodo, or $-NR^{1'}R^{2'}$;

$R^4$ is hydrogen, hydroxyl, $-OR'$, chloro, bromo, fluoro, iodo, sulfanyl, $-NR^{1'}R^{2'}$, $-(C_1$ to $C_{10}$ unsubstituted alkyl)-$NR^{1'}R^{2'}$, or $-(C_1$ to $C_{10}$ substituted alkyl)-$NR^{1'}R^{2'}$;

$R^5$ is hydrogen, hydroxyl, $-NR^{1'}R^{2'}$, azido, or $-OR'$;

$R^6$ is hydrogen, chloro, bromo, fluoro, iodo, $C_1$ to $C_{10}$ unsubstituted alkyl, or $C_1$ to $C_{10}$ substituted alkyl;

$R^7$ is hydrogen, hydroxyl, chloro, bromo, fluoro, iodo, or $-NR^{1'}R^{2'}$;

$R^{1'}$ and $R^{2'}$ at each occurrence are independently hydrogen, $C_1$ to $C_{10}$ unsubstituted alkyl, $C_1$ to $C_{10}$ substituted alkyl, $C_2$-$C_{11}$ unsubstituted alkenyl, $C_2$-$C_{11}$ substituted alkenyl, $C_2$-$C_{11}$ unsubstituted alkynyl, $C_2$-$C_{11}$ substituted alkynyl, cycloalkyl, heterocyclo, aryl, or heteroaryl;

$R'$ at each occurrence is independently $C_1$ to $C_{10}$ unsubstituted alkyl, $C_1$ to $C_{10}$ substituted alkyl, or cycloalkyl;

aryl at each occurrence is independently $C_6$-$C_{12}$ unsubstituted aryl; or $C_6$-$C_{12}$ aryl substituted with one or more fluoro, chloro, bromo, iodo, methyl, $CF_3$, $CCl_3$, $CFCl_2$, $CF_2Cl$, ethyl, $CH_2CF_3$, $CF_2CF_3$, propyl, isopropyl, butyl, isobutyl, secbutyl, t-butyl, pentyl, isopentyl, neopentyl, hexyl, isohexyl, 3-methylpentyl, 2,2-dimethylbutyl, 2,3-dimethylbutyl, hydroxyl, $-NH_2$, $-NH-(C_1$ to $C_{10}$ unsubstituted alkyl), $-NH-(C_1$ to $C_{10}$ substituted alkyl), $-NH$-aryl, $-NH-(C_3$-$C_{15}$ cycloalkyl), methoxy, ethoxy, n-propoxy, isopropoxy, n-butoxy, tert-butoxy, sec-butoxy, n-pentoxy, n-hexoxy, 1,2-dimethylbutoxy, oxo, epoxy, hydroxyl, nitro, cyano, sulfonic acid, sulfate, phosphonic acid, phosphate, or phosphonate;

cycloalkyl at each occurrence is independently $C_3$-$C_{15}$ unsubstituted cycloalkyl or $C_3$-$C_{15}$ cycloalkyl substituted with fluoro, chloro, bromo, iodo, oxo, epoxy, hydroxyl, carbonyl, sulfanyl, $-NH_2$, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate;

heterocyclo at each occurrence is independently a monovalent monocyclic or multicyclic non-aromatic that contains at least one non-aromatic ring containing one or more heteroatoms independently selected from O, S, and N in the ring, wherein heterocyclo is bonded through the non-aromatic ring, and wherein heterocyclo has from three to twenty ring atoms;

heteroaryl at each occurrence is independently a monovalent monocyclic or multicyclic aromatic that contains at least one aromatic ring containing one or more heteroatoms independently selected from O, S, and N in the ring, wherein heteroaryl is bonded through the aromatic ring, wherein the total number of heteroatoms in each ring is four or less and each ring contains at least one carbon atom, and wherein heteroaryl has from five to twenty ring atoms;

substituted alkenyl at each occurrence is independently a straight-chained or branched olefinically unsaturated hydrocarbon having at least one site of olefinic unsaturation substituted with fluoro, chloro, bromo, iodo, oxo, epoxy, hydroxyl, carbonyl, sulfanyl, —NH$_2$, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate;

substituted alkynyl at each occurrence is independently a straight-chained or branched acetylenically unsaturated hydrocarbon having at least one site of alkynyl unsaturation substituted with fluoro, chloro, bromo, iodo, oxo, epoxy, hydroxyl, carbonyl, sulfanyl, —NH$_2$, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate;

substituted alkyl at each occurrence is independently alkyl substituted with fluoro, chloro, bromo, iodo, oxo, epoxy, hydroxyl, carbonyl, sulfanyl, —NH$_2$, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate; and subject to the proviso that when, in Formula I: $Z^1$ is hydrogen, then: either V is chloro, bromo, fluoro, iodo; or $Z^4$ is chloro, bromo, fluoro, iodo, —NR$^{1'}$R$^{2'}$, C$_2$-C$_{11}$ unsubstituted alkynyl, or C$_2$-C$_{11}$ substituted alkynyl; or Base is a nucleobase other than adenine, guanine, cytosine, thymine, or uracil.

In certain embodiments, provided herein are compounds according to any of Formulae II-IIb:

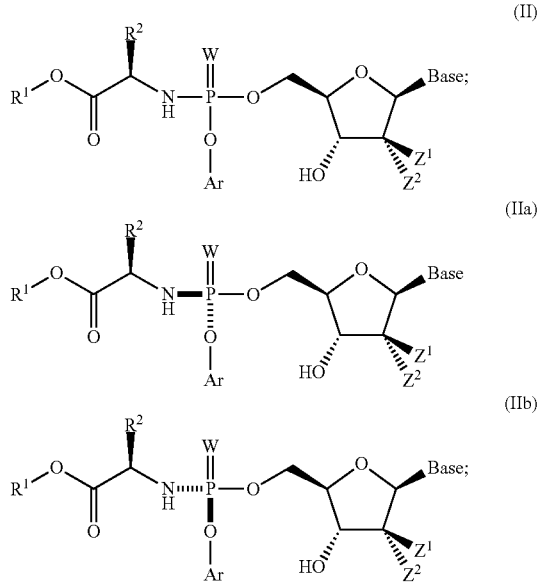

or a pharmaceutically acceptable salt, solvate, stereoisomeric form, tautomeric form or polymorphic form thereof, wherein: $Z^1$ is hydrogen, hydroxyl, halogen, or cyano; Base, $Z^2$, W, Ar, $R^1$ and $R^2$ are as described in the context of Formula I, Ia or Ib. In certain embodiments, $Z^1$ is hydroxyl. In certain embodiments, $Z^1$ is fluoro. In certain embodiments, $Z^1$ is chloro. In certain embodiments, $Z^1$ is hydroxyl and $Z^2$ is hydrogen or fluoro. In certain embodiments, $Z^1$ is fluoro and $Z^2$ is hydrogen, fluoro, chloro or hydroxyl. In certain embodiments, $Z^1$ is chloro and $Z^2$ is hydrogen, chloro or fluoro. In certain embodiments, $Z^1$ is cyano and $Z^2$ is hydrogen.

In certain embodiments, provided herein are compounds according to any of Formulae II-IIb, or a pharmaceutically acceptable salt, solvate, tautomeric form, or polymorphic form thereof, wherein:

Base is

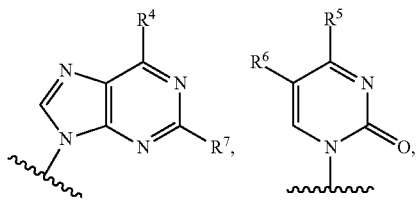

or a tautomeric form thereof;

W is O or S;

Ar is aryl or heteroaryl;

$R^1$ is hydrogen, C$_1$ to C$_{10}$ unsubstituted alkyl, C$_1$ to C$_{10}$ substituted alkyl, —(C$_1$ to C$_{10}$ unsubstituted alkyl)-aryl, —(C$_1$ to C$_{10}$ substituted alkyl)-aryl, —(C$_1$ to C$_{10}$ unsubstituted alkyl)-heteroaryl, or —(C$_1$ to C$_{10}$ substituted alkyl)-heteroaryl;

$R^2$ is C$_1$ to C$_{10}$ unsubstituted alkyl, C$_1$ to C$_{10}$ substituted alkyl, —(C$_1$ to C$_{10}$ unsubstituted alkyl)-aryl, —(C$_1$ to C$_{10}$ substituted alkyl)-aryl, —(C$_1$ to C$_{10}$ unsubstituted alkyl)-heterocyclo, —(C$_1$ to C$_{10}$ substituted alkyl)-heterocyclo, —(C$_1$ to C$_{10}$ unsubstituted alkyl)-C(O)OH, —(C$_1$ to C$_{10}$ substituted alkyl)-C(O)OH, —(C$_1$ to C$_{10}$ unsubstituted alkyl)-heteroaryl, —(C$_1$ to C$_{10}$ substituted alkyl)-heteroaryl, —(C$_1$ to C$_{10}$ unsubstituted alkyl)-NR$^{1'}$R$^{2'}$, —(C$_1$ to C$_{10}$ substituted alkyl)-NR$^{1'}$R$^{2'}$, —(C$_1$ to C$_{10}$ unsubstituted alkyl)-OH, —(C$_1$ to C$_{10}$ substituted alkyl)-OH, —(C$_1$ to C$_{10}$ unsubstituted alkyl)-NR$^{1'}$—C(NH)—NR$^{1'}$R$^{2'}$, —(C$_1$ to C$_{10}$ substituted alkyl)-NR$^{1'}$—C(NH)—NR$^{1'}$R$^{2'}$, —(C$_1$ to C$_{10}$ unsubstituted alkyl)-C(O)—NR$^{1'}$R$^{2'}$, —(C$_1$ to C$_{10}$ substituted alkyl)-C(O)—NR$^{1'}$R$^{2'}$, —(C$_1$ to C$_{10}$ unsubstituted alkyl)-SH, —(C$_1$ to C$_{10}$ substituted alkyl)-SH, —(C$_1$ to C$_{10}$ unsubstituted alkyl)-C(O)—NR$^{1'}$R$^{2'}$, —(C$_1$ to C$_{10}$ substituted alkyl)-C(O)—NR$^{1'}$R$^{2'}$, —(C$_1$ to C$_{10}$ unsubstituted alkyl)-S—(C$_1$ to C$_{10}$ unsubstituted alkyl), —(C$_1$ to C$_{10}$ unsubstituted alkyl)-S—(C$_1$ to C$_{10}$ substituted alkyl), —(C$_1$ to C$_{10}$ substituted alkyl)-S—(C$_1$ to C$_{10}$ unsubstituted alkyl), —(C$_1$ to C$_{10}$ substituted alkyl)-S—(C$_1$ to C$_{10}$ substituted alkyl), —(C$_1$ to C$_{10}$ unsubstituted alkyl)-aryl-OH, or —(C$_1$ to C$_{10}$ substituted alkyl)-aryl-OH;

$Z^1$ is hydrogen, hydroxyl, chloro, bromo, fluoro, iodo, or cyano;

$Z^2$ is hydrogen, hydroxyl, chloro, bromo, fluoro, or iodo;

$R^4$ is hydrogen, hydroxyl, —OR', chloro, bromo, fluoro, iodo, sulfanyl, —NR$^{1'}$R$^{2'}$, —(C$_1$ to C$_{10}$ unsubstituted alkyl)-NR$^{1'}$R$^{2'}$, or —(C$_1$ to C$_{10}$ substituted alkyl)-NR$^{1'}$R$^{2'}$;

$R^5$ is hydrogen, hydroxyl, —NR$^{1'}$R$^{2'}$, azido, or —OR';

$R^6$ is hydrogen, chloro, bromo, fluoro, iodo, C$_1$ to C$_{10}$ unsubstituted alkyl, or C$_1$ to C$_{10}$ substituted alkyl;

$R^7$ is hydrogen, hydroxyl, chloro, bromo, fluoro, iodo, or —NR$^{1'}$R$^{2'}$;

$R^{1'}$ and $R^{2'}$ at each occurrence are independently hydrogen, C$_1$ to C$_{10}$ unsubstituted alkyl, C$_1$ to C$_{10}$ substituted alkyl, C$_2$-C$_{11}$ unsubstituted alkenyl, C$_2$-C$_{11}$ substituted alkenyl, C$_2$-C$_{11}$ unsubstituted alkynyl, C$_2$-C$_{11}$ substituted alkynyl, cycloalkyl, heterocyclo, aryl, or heteroaryl;

R' at each occurrence is independently $C_1$ to $C_{10}$ unsubstituted alkyl, $C_1$ to $C_{10}$ substituted alkyl, or cycloalkyl;

aryl at each occurrence is independently $C_6$-$C_{12}$ unsubstituted aryl; or $C_6$-$C_{12}$ aryl substituted with one or more fluoro, chloro, bromo, iodo, methyl, $CF_3$, $CCl_3$, $CFCl_2$, $CF_2Cl$, ethyl, $CH_2CF_3$, $CF_2CF_3$, propyl, isopropyl, butyl, isobutyl, secbutyl, t-butyl, pentyl, isopentyl, neopentyl, hexyl, isohexyl, 3-methylpentyl, 2,2-dimethylbutyl, 2,3-dimethylbutyl, hydroxyl, —$NH_2$, —NH—($C_1$ to $C_{10}$ unsubstituted alkyl), —NH—($C_1$ to $C_{10}$ substituted alkyl), —NH-aryl, —NH—($C_3$-$C_{15}$ cycloalkyl), methoxy, ethoxy, n-propoxy, isopropoxy, n-butoxy, tert-butoxy, sec-butoxy, n-pentoxy, n-hexoxy, 1,2-dimethylbutoxy, oxo, epoxy, hydroxyl, nitro, cyano, sulfonic acid, sulfate, phosphonic acid, phosphate, or phosphonate;

cycloalkyl at each occurrence is independently $C_3$-$C_{15}$ unsubstituted cycloalkyl or $C_3$-$C_{15}$ cycloalkyl substituted with fluoro, chloro, bromo, iodo, oxo, epoxy, hydroxyl, carbonyl, sulfanyl, —$NH_2$, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate;

heterocyclo at each occurrence is independently a monovalent monocyclic or multicyclic non-aromatic that contains at least one non-aromatic ring containing one or more heteroatoms independently selected from O, S, and N in the ring, wherein heterocyclo is bonded through the non-aromatic ring, and wherein heterocyclo has from three to twenty ring atoms;

heteroaryl at each occurrence is independently a monovalent monocyclic or multicyclic aromatic that contains at least one aromatic ring containing one or more heteroatoms independently selected from O, S, and N in the ring, wherein heteroaryl is bonded through the aromatic ring, wherein the total number of heteroatoms in each ring is four or less and each ring contains at least one carbon atom, and wherein heteroaryl has from five to twenty ring atoms;

substituted alkenyl at each occurrence is independently a straight-chained or branched olefinically unsaturated hydrocarbon having at least one site of olefinic unsaturation substituted with fluoro, chloro, bromo, iodo, oxo, epoxy, hydroxyl, carbonyl, sulfanyl, —$NH_2$, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate;

substituted alkynyl at each occurrence is independently a straight-chained or branched acetylenically unsaturated hydrocarbon having at least one site of alkynyl unsaturation substituted with fluoro, chloro, bromo, iodo, oxo, epoxy, hydroxyl, carbonyl, sulfanyl, —$NH_2$, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate;

substituted alkyl at each occurrence is independently alkyl substituted with fluoro, chloro, bromo, iodo, oxo, epoxy, hydroxyl, carbonyl, sulfanyl, —$NH_2$, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate; and subject to the proviso that when, in Formula II: $Z^1$ is hydrogen, then: either $Z^4$ is chloro, bromo, fluoro, iodo, —$NR^1R^{2'}$, $C_2$-$C_{11}$ unsubstituted alkynyl, or $C_2$-$C_{11}$ substituted alkynyl; or Base is a nucleobase other than adenine, guanine, cytosine, thymine, or uracil.

In certain embodiments, provided herein are compounds according to any of Formulae III-IIIb:

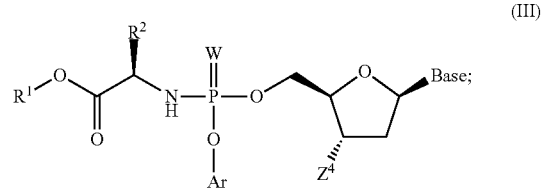

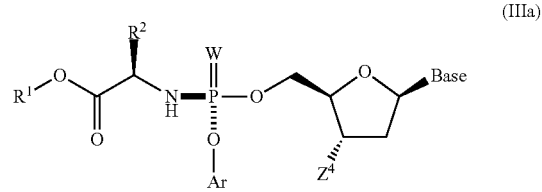

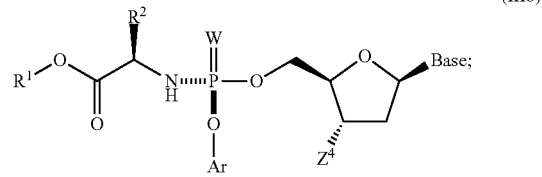

or a pharmaceutically acceptable salt, solvate, stereoisomeric form, tautomeric form or polymorphic form thereof, wherein: $Z^4$ is fluoro, amino, or alkynyl; and Base, W, Ar, $R^1$ and $R^2$ are as described in the context of Formula I, Ia or Ib. In certain embodiments, $Z^4$ is fluoro. In certain embodiments, $Z^4$ is —$NH_2$. In certain embodiments, $Z^4$ is —C≡CH.

In certain embodiments, provided herein are compounds according to any of Formulae III-IIIb, or a pharmaceutically acceptable salt, solvate, tautomeric form, or polymorphic form thereof, wherein:

Base is

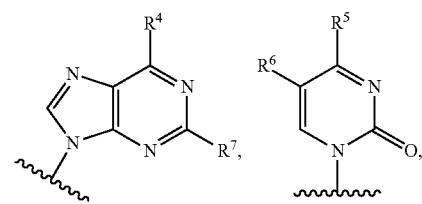

or a tautomeric form thereof;

W is O or S;

Ar is aryl or heteroaryl;

$R^1$ is hydrogen, $C_1$ to $C_{10}$ unsubstituted alkyl, $C_1$ to $C_{10}$ substituted alkyl, —($C_1$ to $C_{10}$ unsubstituted alkyl)-aryl, —($C_1$ to $C_{10}$ substituted alkyl)-aryl, —($C_1$ to $C_{10}$ unsubstituted alkyl)-heteroaryl, or —($C_1$ to $C_{10}$ substituted alkyl)-heteroaryl;

$R^2$ is $C_1$ to $C_{10}$ unsubstituted alkyl, $C_1$ to $C_{10}$ substituted alkyl, —($C_1$ to $C_{10}$ unsubstituted alkyl)-aryl, —($C_1$ to $C_{10}$ substituted alkyl)-aryl, —($C_1$ to $C_{10}$ unsubstituted alkyl)-heterocyclo, —($C_1$ to $C_{10}$ substituted alkyl)-heterocyclo, —($C_1$ to $C_{10}$ unsubstituted alkyl)-C(O)OH, —($C_1$ to $C_{10}$ substituted alkyl)-C(O)OH, —($C_1$ to $C_{10}$ unsubstituted alkyl)-heteroaryl, —($C_1$ to $C_{10}$ substituted alkyl)-heteroaryl, —($C_1$ to $C_{10}$ unsubstituted alkyl)-$NR^1R^{2'}$, —($C_1$ to $C_{10}$ substituted alkyl)-$NR^1R^{2'}$, —($C_1$ to $C_{10}$ unsubstituted alkyl)-OH, —($C_1$ to $C_{10}$ substituted alkyl)-OH, —($C_1$ to $C_{10}$ unsubstituted alkyl)-$NR^{1'}$—C(NH)—$NR^{1'}R^{2'}$, —($C_1$ to $C_{10}$ substituted alkyl)-$NR^{1'}$—C(NH)—$NR^{1'}R^{2'}$, —($C_1$ to $C_{10}$ unsubstituted alkyl)-C(O)—$NR^{1'}R^{2'}$, —($C_1$ to $C_{10}$ substituted alkyl)-C(O)—$NR^{1'}R^{2'}$, —($C_1$ to $C_{10}$ unsubstituted alkyl)-SH, —($C_1$ to $C_{10}$ substituted alkyl)-SH, —($C_1$ to $C_{10}$ unsubstituted alkyl)-C(O)—$NR^{1'}R^{2'}$, —($C_1$ to $C_{10}$ substituted alkyl)-C(O)—$NR^{1'}R^{2'}$, —($C_1$ to $C_{10}$ unsubstituted alkyl)-S—($C_1$ to $C_{10}$ unsubstituted alkyl), —($C_1$ to $C_{10}$ unsubstituted alkyl)-S—($C_1$ to $C_{10}$ substituted alkyl), —($C_1$ to $C_{10}$ substituted alkyl)-S—($C_1$ to $C_{10}$ unsubstituted alkyl), —($C_1$ to $C_{10}$ substituted alkyl)-S—($C_1$ to $C_{10}$ substituted alkyl), —($C_1$ to $C_{10}$ unsubstituted alkyl)-aryl-OH, or —($C_1$ to $C_{10}$ substituted alkyl)-aryl-OH;

$Z^4$ is fluoro, —$NR^{1'}R^{2'}$, $C_2$-$C_{11}$ unsubstituted alkynyl, or $C_2$-$C_{11}$ substituted alkynyl;

$R^4$ is hydrogen, hydroxyl, —OR', chloro, bromo, fluoro, iodo, sulfanyl, —$NR^{1'}R^{2'}$, —($C_1$ to $C_{10}$ unsubstituted alkyl)-$NR^{1'}R^{2'}$, or —($C_1$ to $C_{10}$ substituted alkyl)-$NR^{1'}R^{2'}$;

$R^5$ is hydrogen, hydroxyl, —$NR^{1'}R^{2'}$, azido, or —OR';

$R^6$ is hydrogen, chloro, bromo, fluoro, iodo, $C_1$ to $C_{10}$ unsubstituted alkyl, or $C_1$ to $C_{10}$ substituted alkyl;

$R^7$ is hydrogen, hydroxyl, chloro, bromo, fluoro, iodo, or —$NR^{1'}R^{2'}$;

$R^{1'}$ and $R^{2'}$ at each occurrence are independently hydrogen, $C_1$ to $C_{10}$ unsubstituted alkyl, $C_1$ to $C_{10}$ substituted alkyl, $C_2$-$C_{11}$ unsubstituted alkenyl, $C_2$-$C_{11}$ substituted alkenyl, $C_2$-$C_{11}$ unsubstituted alkynyl, $C_2$-$C_{11}$ substituted alkynyl, cycloalkyl, heterocyclo, aryl, or heteroaryl;

R' at each occurrence is independently $C_1$ to $C_{10}$ unsubstituted alkyl, $C_1$ to $C_{10}$ substituted alkyl, or cycloalkyl;

aryl at each occurrence is independently $C_6$-$C_{12}$ unsubstituted aryl; or $C_6$-$C_{12}$ aryl substituted with one or more fluoro, chloro, bromo, iodo, methyl, $CF_3$, $CCl_3$, $CFCl_2$, $CF_2Cl$, ethyl, $CH_2CF_3$, $CF_2CF_3$, propyl, isopropyl, butyl, isobutyl, secbutyl, t-butyl, pentyl, isopentyl, neopentyl, hexyl, isohexyl, 3-methylpentyl, 2,2-dimethylbutyl, 2,3-dimethylbutyl, hydroxyl, —$NH_2$, —NH—($C_1$ to $C_{10}$ unsubstituted alkyl), —NH—($C_1$ to $C_{10}$ substituted alkyl), —NH-aryl, —NH—($C_3$-$C_{15}$ cycloalkyl), methoxy, ethoxy, n-propoxy, isopropoxy, n-butoxy, tert-butoxy, sec-butoxy, n-pentoxy, n-hexoxy, 1,2-dimethylbutoxy, oxo, epoxy, hydroxyl, nitro, cyano, sulfonic acid, sulfate, phosphonic acid, phosphate, or phosphonate;

cycloalkyl at each occurrence is independently $C_3$-$C_{15}$ unsubstituted cycloalkyl or $C_3$-$C_{15}$ cycloalkyl substituted with fluoro, chloro, bromo, iodo, oxo, epoxy, hydroxyl, carbonyl, sulfanyl, —$NH_2$, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate;

heterocyclo at each occurrence is independently a monovalent monocyclic or multicyclic non-aromatic that contains at least one non-aromatic ring containing one or more heteroatoms independently selected from O, S, and N in the ring, wherein heterocyclo is bonded through the non-aromatic ring, and wherein heterocyclo has from three to twenty ring atoms;

heteroaryl at each occurrence is independently a monovalent monocyclic or multicyclic aromatic that contains at least one aromatic ring containing one or more heteroatoms independently selected from O, S, and N in the ring, wherein heteroaryl is bonded through the aromatic ring, wherein the total number of heteroatoms in each ring is four or less and each ring contains at least one carbon atom, and wherein heteroaryl has from five to twenty ring atoms;

substituted alkenyl at each occurrence is independently a straight-chained or branched olefinically unsaturated hydrocarbon having at least one site of olefinic unsaturation substituted with fluoro, chloro, bromo, iodo, oxo, epoxy, hydroxyl, carbonyl, sulfanyl, —$NH_2$, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate;

substituted alkynyl at each occurrence is independently a straight-chained or branched acetylenically unsaturated hydrocarbon having at least one site of alkynyl unsaturation substituted with fluoro, chloro, bromo, iodo, oxo, epoxy, hydroxyl, carbonyl, sulfanyl, —$NH_2$, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate;

substituted alkyl at each occurrence is independently alkyl substituted with fluoro, chloro, bromo, iodo, oxo, epoxy, hydroxyl, carbonyl, sulfanyl, —$NH_2$, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate; and subject to the proviso that Base is a nucleobase other than adenine, guanine, cytosine, thymine, or uracil.

In certain embodiments, provided herein are compounds according to any of Formulae IV-IVb:

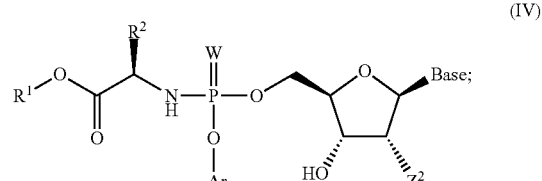

(IV)

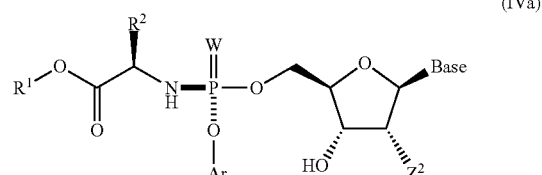

(IVa)

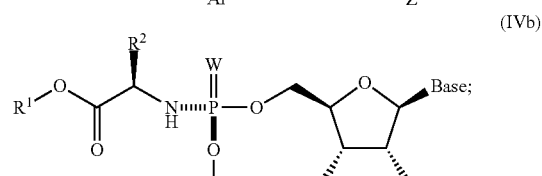

(IVb)

or a pharmaceutically acceptable salt, solvate, stereoisomeric form, tautomeric form or polymorphic form thereof, wherein: $Z^2$ is hydrogen or hydroxyl; Base is other than adenine, guanosine, cytosine, thymine or uracil; and W, Ar, $R^1$ and $R^2$ are as described in the context of Formula I, Ia or Ib. In certain embodiments, Base is selected from the group consisting of 2-chloro-adenine, 5-fluoro-uracil, 5-aza-cytosine, 6-thio-guanine, S-ethyl-6-thio-guanine, and imidazo(4,5-d)(1,3)diazepin-8-ol. In certain embodiments, $Z^2$ is hydrogen; and Base is selected from the group consisting of 2-chloro-adenine, 5-fluoro-uracil, 5-aza-cytosine, and imidazo(4,5-d)(1,3)diazepin-8-ol. In certain embodiments, $Z^2$ is hydroxyl and Base 6-thio-guanine or S-ethyl-6-thio-guanine.

In certain embodiments, provided herein are compounds according to any of Formulae IV-IVb, or a pharmaceutically acceptable salt, solvate, tautomeric form, or polymorphic form thereof, wherein:

Base is

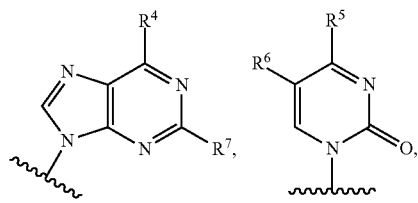

or a tautomeric form thereof, wherein Base is other than adenine, guanosine, cytosine, thymine, or uracil;

$Z^2$ is hydrogen or hydroxyl;

W is O or S;

Ar is aryl or heteroaryl;

$R^1$ is hydrogen, $C_1$ to $C_{10}$ unsubstituted alkyl, $C_1$ to $C_{10}$ substituted alkyl, —($C_1$ to $C_{10}$ unsubstituted alkyl)-aryl, —($C_1$ to $C_{10}$ substituted alkyl)-aryl, —($C_1$ to $C_{10}$ unsubstituted alkyl)-heteroaryl, or —($C_1$ to $C_{10}$ substituted alkyl)-heteroaryl;

$R^2$ is $C_1$ to $C_{10}$ unsubstituted alkyl, $C_1$ to $C_{10}$ substituted alkyl, —($C_1$ to $C_{10}$ unsubstituted alkyl)-aryl, —($C_1$ to $C_{10}$ substituted alkyl)-aryl, —($C_1$ to $C_{10}$ unsubstituted alkyl)-heterocyclo, —($C_1$ to $C_{10}$ substituted alkyl)-heterocyclo, —($C_1$ to $C_{10}$ unsubstituted alkyl)-C(O)OH, —($C_1$ to $C_{10}$ substituted alkyl)-C(O)OH, —($C_1$ to $C_{10}$ unsubstituted alkyl)-heteroaryl, —($C_1$ to $C_{10}$ substituted alkyl)-heteroaryl, —($C_1$ to $C_{10}$ unsubstituted alkyl)-$NR^{1'}R^{2'}$, —($C_1$ to $C_{10}$ substituted alkyl)-$NR^{1'}R^{2'}$, —($C_1$ to $C_{10}$ unsubstituted alkyl)-OH, —($C_1$ to $C_{10}$ substituted alkyl)-OH, —($C_1$ to $C_{10}$ unsubstituted alkyl)-$NR^{1'}$—C(NH)—$NR^{1'}R^{2'}$, —($C_1$ to $C_{10}$ substituted alkyl)-$NR^{1'}$—C(NH)—$NR^{1'}R^{2'}$, —($C_1$ to $C_{10}$ unsubstituted alkyl)-C(O)—$NR^{1'}R^{2'}$, —($C_1$ to $C_{10}$ substituted alkyl)-C(O)—$NR^{1'}R^{2'}$, —($C_1$ to $C_{10}$ unsubstituted alkyl)-SH, —($C_1$ to $C_{10}$ substituted alkyl)-SH, —($C_1$ to $C_{10}$ unsubstituted alkyl)-C(O)—$NR^{1'}R^{2'}$, —($C_1$ to $C_{10}$ substituted alkyl)-C(O)—$NR^{1'}R^{2'}$, —($C_1$ to $C_{10}$ unsubstituted alkyl)-S—($C_1$ to $C_{10}$ unsubstituted alkyl), —($C_1$ to $C_{10}$ unsubstituted alkyl)-S—($C_1$ to $C_{10}$ substituted alkyl), —($C_1$ to $C_{10}$ substituted alkyl)-S—($C_1$ to $C_{10}$ unsubstituted alkyl), —($C_1$ to $C_{10}$ substituted alkyl)-S—($C_1$ to $C_{10}$ substituted alkyl), —($C_1$ to $C_{10}$ unsubstituted alkyl)-aryl-OH, or —($C_1$ to $C_{10}$ substituted alkyl)-aryl-OH;

$R^4$ is hydrogen, hydroxyl, —OR', chloro, bromo, fluoro, iodo, sulfanyl, —$NR^{1'}R^{2'}$, —($C_1$ to $C_{10}$ unsubstituted alkyl)-$NR^{1'}R^{2'}$, or —($C_1$ to $C_{10}$ substituted alkyl)-$NR^{1'}R^{2'}$;

$R^5$ is hydrogen, hydroxyl, —$NR^{1'}R^{2'}$, azido, or —OR';

$R^6$ is hydrogen, chloro, bromo, fluoro, iodo, $C_1$ to $C_{10}$ unsubstituted alkyl, or $C_1$ to $C_{10}$ substituted alkyl;

$R^7$ is hydrogen, hydroxyl, chloro, bromo, fluoro, iodo, or —$NR^{1'}R^{2'}$;

$R^{1'}$ and $R^{2'}$ at each occurrence are independently hydrogen, $C_1$ to $C_{10}$ unsubstituted alkyl, $C_1$ to $C_{10}$ substituted alkyl, $C_2$-$C_{11}$ unsubstituted alkenyl, $C_2$-$C_{11}$ substituted alkenyl, $C_2$-$C_{11}$ unsubstituted alkynyl, $C_2$-$C_{11}$ substituted alkynyl, cycloalkyl, heterocyclo, aryl, or heteroaryl;

R' at each occurrence is independently $C_1$ to $C_{10}$ unsubstituted alkyl, $C_1$ to $C_{10}$ substituted alkyl, or cycloalkyl;

aryl at each occurrence is independently $C_6$-$C_{12}$ unsubstituted aryl; or $C_6$-$C_{12}$ aryl substituted with one or more fluoro, chloro, bromo, iodo, methyl, $CF_3$, $CCl_3$, $CFCl_2$, $CF_2Cl$, ethyl, $CH_2CF_3$, $CF_2CF_3$, propyl, isopropyl, butyl, isobutyl, secbutyl, t-butyl, pentyl, isopentyl, neopentyl, hexyl, isohexyl, 3-methylpentyl, 2,2-dimethylbutyl, 2,3-dimethylbutyl, hydroxyl, —$NH_2$, —NH—($C_1$ to $C_{10}$ unsubstituted alkyl), —NH—($C_1$ to $C_{10}$ substituted alkyl), —NH-aryl, —NH—($C_3$-$C_{15}$ cycloalkyl), methoxy, ethoxy, n-propoxy, isopropoxy, n-butoxy, tert-butoxy, sec-butoxy, n-pentoxy, n-hexoxy, 1,2-dimethylbutoxy, oxo, epoxy, hydroxyl, nitro, cyano, sulfonic acid, sulfate, phosphonic acid, phosphate, or phosphonate;

cycloalkyl at each occurrence is independently $C_3$-$C_{15}$ unsubstituted cycloalkyl or $C_3$-$C_{15}$ cycloalkyl substituted with fluoro, chloro, bromo, iodo, oxo, epoxy, hydroxyl, carbonyl, sulfanyl, —$NH_2$, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate;

heterocyclo at each occurrence is independently a monovalent monocyclic or multicyclic non-aromatic that contains at least one non-aromatic ring containing one or more heteroatoms independently selected from O, S, and N in the ring, wherein heterocyclo is bonded through the non-aromatic ring, and wherein heterocyclo has from three to twenty ring atoms;

heteroaryl at each occurrence is independently a monovalent monocyclic or multicyclic aromatic that contains at least one aromatic ring containing one or more heteroatoms independently selected from O, S, and N in the ring, wherein heteroaryl is bonded through the aromatic ring, wherein the total number of heteroatoms in each ring is four or less and each ring contains at least one carbon atom, and wherein heteroaryl has from five to twenty ring atoms;

substituted alkenyl at each occurrence is independently a straight-chained or branched olefinically unsaturated hydrocarbon having at least one site of olefinic unsaturation substituted with fluoro, chloro, bromo, iodo, oxo, epoxy, hydroxyl, carbonyl, sulfanyl, —$NH_2$, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate;

substituted alkynyl at each occurrence is independently a straight-chained or branched acetylenically unsaturated hydrocarbon having at least one site of alkynyl unsaturation substituted with fluoro, chloro, bromo, iodo, oxo, epoxy, hydroxyl, carbonyl, sulfanyl, —$NH_2$, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate; and substituted alkyl at each occurrence is independently alkyl substituted with fluoro, chloro, bromo, iodo, oxo, epoxy, hydroxyl, carbonyl, sulfanyl, —$NH_2$, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate.

In certain embodiments, provided herein are compounds according to any of Formulae V-Vb:

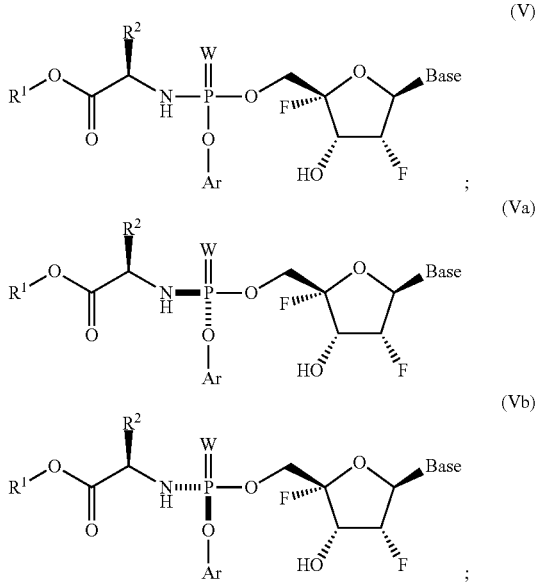

or a pharmaceutically acceptable salt, solvate, stereoisomeric form, tautomeric form or polymorphic form thereof, wherein: Base, W, Ar, $R^1$ and $R^2$ are as described in the context of Formula I, Ia or Ib. In particular embodiments, Base is cytosine.

In certain embodiments, provided herein are compounds according to any of Formulae V-Vb, or a pharmaceutically acceptable salt, solvate, tautomeric form, or polymorphic form thereof, wherein:

Base is

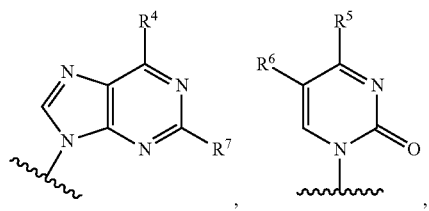

or a tautomeric form thereof;

Ar is aryl or heteroaryl;

$R^1$ is hydrogen, $C_1$ to $C_{10}$ unsubstituted alkyl, $C_1$ to $C_{10}$ substituted alkyl, —($C_1$ to $C_{10}$ unsubstituted alkyl)-aryl, —($C_1$ to $C_{10}$ substituted alkyl)-aryl, —($C_1$ to $C_{10}$ unsubstituted alkyl)-heteroaryl, or —($C_1$ to $C_{10}$ substituted alkyl)-heteroaryl;

$R^2$ is $C_1$ to $C_{10}$ unsubstituted alkyl, $C_1$ to $C_{10}$ substituted alkyl, —($C_1$ to $C_{10}$ unsubstituted alkyl)-aryl, —($C_1$ to $C_{10}$ substituted alkyl)-aryl, —($C_1$ to $C_{10}$ unsubstituted alkyl)-heterocyclo, —($C_1$ to $C_{10}$ substituted alkyl)-heterocyclo, —($C_1$ to $C_{10}$ unsubstituted alkyl)-C(O)OH, —($C_1$ to $C_{10}$ substituted alkyl)-C(O)OH, —($C_1$ to $C_{10}$ unsubstituted alkyl)-heteroaryl, —($C_1$ to $C_{10}$ substituted alkyl)-heteroaryl, —($C_1$ to $C_{10}$ unsubstituted alkyl)-$NR^{1'}R^{2'}$, —($C_1$ to $C_{10}$ substituted alkyl)-$NR^{1'}R^{2'}$, —($C_1$ to $C_{10}$ unsubstituted alkyl)-OH, —($C_1$ to $C_{10}$ substituted alkyl)-OH, —($C_1$ to $C_{10}$ unsubstituted alkyl)-$NR^{1'}$—C(NH)—$NR^{1'}R^2$, —($C_1$ to $C_{10}$ substituted alkyl)-$NR^{1'}$—C(NH)—$NR^{1'}R^2$, —($C_1$ to $C_{10}$ unsubstituted alkyl)-C(O)—$NR^{1'}R^{2'}$, —($C_1$ to $C_{10}$ substituted alkyl)-C(O)—$NR^{1'}R^{2'}$, —($C_1$ to $C_{10}$ unsubstituted alkyl)-SH, —($C_1$ to $C_{10}$ substituted alkyl)-SH, —($C_1$ to $C_{10}$ unsubstituted alkyl)-C(O)—$NR^{1'}R^{2'}$, —($C_1$ to $C_{10}$ substituted alkyl)-C(O)—$NR^{1'}R^{2'}$, —($C_1$ to $C_{10}$ unsubstituted alkyl)-S—($C_1$ to $C_{10}$ unsubstituted alkyl), —($C_1$ to $C_{10}$ unsubstituted alkyl)-S—($C_1$ to $C_{10}$ substituted alkyl), —($C_1$ to $C_{10}$ substituted alkyl)-S—($C_1$ to $C_{10}$ unsubstituted alkyl), —($C_1$ to $C_{10}$ substituted alkyl)-S—($C_1$ to $C_{10}$ substituted alkyl), —($C_1$ to $C_{10}$ unsubstituted alkyl)-aryl-OH, or —($C_1$ to $C_{10}$ substituted alkyl)-aryl-OH;

$R^4$ is hydrogen, hydroxyl, —OR', chloro, bromo, fluoro, iodo, sulfanyl, —$NR^{1'}R^{2'}$, —($C_1$ to $C_{10}$ unsubstituted alkyl)-$NR^{1'}R^{2'}$, or —($C_1$ to $C_{10}$ substituted alkyl)-$NR^{1'}R^{2'}$;

$R^5$ is hydrogen, hydroxyl, —$NR^{1'}R^{2'}$, azido, or —OR';

$R^6$ is hydrogen, chloro, bromo, fluoro, iodo, $C_1$ to $C_{10}$ unsubstituted alkyl, or $C_1$ to $C_{10}$ substituted alkyl;

$R^7$ is hydrogen, hydroxyl, chloro, bromo, fluoro, iodo, or —$NR^{1'}R^{2'}$;

$R^{1'}$ and $R^{2'}$ at each occurrence are independently hydrogen, $C_1$ to $C_{10}$ unsubstituted alkyl, $C_1$ to $C_{10}$ substituted alkyl, $C_2$-$C_{11}$ unsubstituted alkenyl, $C_2$-$C_{11}$ substituted alkenyl, $C_2$-$C_{11}$ unsubstituted alkynyl, $C_2$-$C_{11}$ substituted alkynyl, cycloalkyl, heterocyclo, aryl, or heteroaryl;

R' at each occurrence is independently $C_1$ to $C_{10}$ unsubstituted alkyl, $C_1$ to $C_{10}$ substituted alkyl, or cycloalkyl;

aryl at each occurrence is independently $C_6$-$C_{12}$ unsubstituted aryl; or $C_6$-$C_{12}$ aryl substituted with one or more fluoro, chloro, bromo, iodo, methyl, $CF_3$, $CCl_3$, $CFCl_2$, $CF_2Cl$, ethyl, $CH_2CF_3$, $CF_2CF_3$, propyl, isopropyl, butyl, isobutyl, secbutyl, t-butyl, pentyl, isopentyl, neopentyl, hexyl, isohexyl, 3-methylpentyl, 2,2-dimethylbutyl, 2,3-dimethylbutyl, hydroxyl, —$NH_2$, —NH—($C_1$ to $C_{10}$ unsubstituted alkyl), —NH—($C_1$ to $C_{10}$ substituted alkyl), —NH-aryl, —NH—($C_3$-$C_{15}$ cycloalkyl), methoxy, ethoxy, n-propoxy, isopropoxy, n-butoxy, tert-butoxy, sec-butoxy, n-pentoxy, n-hexoxy, 1,2-dimethylbutoxy, oxo, epoxy, hydroxyl, nitro, cyano, sulfonic acid, sulfate, phosphonic acid, phosphate, or phosphonate;

cycloalkyl at each occurrence is independently $C_3$-$C_{15}$ unsubstituted cycloalkyl or $C_3$-$C_{15}$ cycloalkyl substituted with fluoro, chloro, bromo, iodo, oxo, epoxy, hydroxyl, carbonyl, sulfanyl, —$NH_2$, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate;

heterocyclo at each occurrence is independently a monovalent monocyclic or multicyclic non-aromatic that contains at least one non-aromatic ring containing one or more heteroatoms independently selected from O, S, and N in the ring, wherein heterocyclo is bonded through the non-aromatic ring, and wherein heterocyclo has from three to twenty ring atoms;

heteroaryl at each occurrence is independently a monovalent monocyclic or multicyclic aromatic that contains at least one aromatic ring containing one or more heteroatoms independently selected from O, S, and N in the ring, wherein heteroaryl is bonded through the aromatic ring, wherein the total number of heteroatoms in each ring is four or less and each ring contains at least one carbon atom, and wherein heteroaryl has from five to twenty ring atoms;

substituted alkenyl at each occurrence is independently a straight-chained or branched olefinically unsaturated hydrocarbon having at least one site of olefinic unsaturation substituted with fluoro, chloro, bromo, iodo, oxo, epoxy, hydroxyl, carbonyl, sulfanyl, —$NH_2$, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate;

substituted alkynyl at each occurrence is independently a straight-chained or branched acetylenically unsaturated hydrocarbon having at least one site of alkynyl unsaturation substituted with fluoro, chloro, bromo, iodo, oxo, epoxy, hydroxyl, carbonyl, sulfanyl, —NH$_2$, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate; and substituted alkyl at each occurrence is independently alkyl substituted with fluoro, chloro, bromo, iodo, oxo, epoxy, hydroxyl, carbonyl, sulfanyl, —NH$_2$, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate.

In certain embodiments, provided herein are compounds according to any of Formulae VI-VIb:

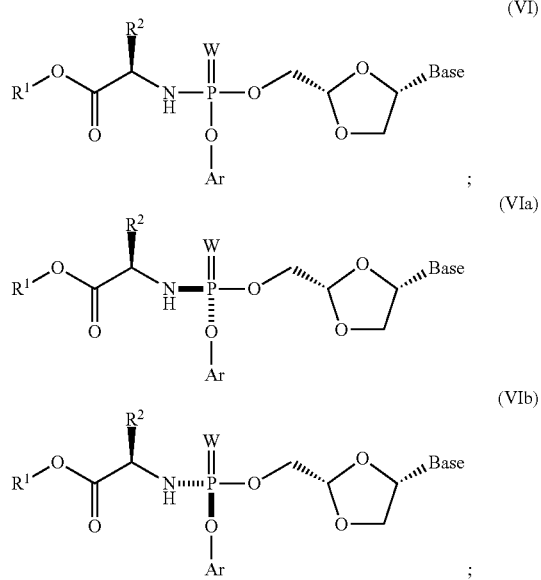

or a pharmaceutically acceptable salt, solvate, stereoisomeric form, tautomeric form or polymorphic form thereof, wherein: W is O or S; Ar is aryl or heteroaryl; and Base, $R^1$ and $R^2$ are as described in the context of Formula I, Ia or Ib. In certain embodiments, Base is cytosine.

In certain embodiments, provided herein are compounds according to any of Formulae VI-VIb, or a pharmaceutically acceptable salt, solvate, tautomeric form, or polymorphic form thereof, wherein:
Base is cytosine;
W is O or S;
Ar is aryl or heteroaryl;
$R^1$ is hydrogen, $C_1$ to $C_{10}$ unsubstituted alkyl, $C_1$ to $C_{10}$ substituted alkyl, —($C_1$ to $C_{10}$ unsubstituted alkyl)-aryl, —($C_1$ to $C_{10}$ substituted alkyl)-aryl, —($C_1$ to $C_{10}$ unsubstituted alkyl)-heteroaryl, or —($C_1$ to $C_{10}$ substituted alkyl)-heteroaryl;

$R^2$ is $C_1$ to $C_{10}$ unsubstituted alkyl, $C_1$ to $C_{10}$ substituted alkyl, —($C_1$ to $C_{10}$ unsubstituted alkyl)-aryl, —($C_1$ to $C_{10}$ substituted alkyl)-aryl, —($C_1$ to $C_{10}$ unsubstituted alkyl)-heterocyclo, —($C_1$ to $C_{10}$ substituted alkyl)-heterocyclo, —($C_1$ to $C_{10}$ unsubstituted alkyl)-C(O)OH, —($C_1$ to $C_{10}$ substituted alkyl)-C(O)OH, —($C_1$ to $C_{10}$ unsubstituted alkyl)-heteroaryl, —($C_1$ to $C_{10}$ substituted alkyl)-heteroaryl, —($C_1$ to $C_{10}$ unsubstituted alkyl)-NR$^{1'}$R$^{2'}$, —($C_1$ to $C_{10}$ substituted alkyl)-NR$^{1'}$R$^{2'}$, —($C_1$ to $C_{10}$ unsubstituted alkyl)-OH, —($C_1$ to $C_{10}$ substituted alkyl)-OH, —($C_1$ to $C_{10}$ unsubstituted alkyl)-NR$^{1'}$—C(NH)—NR$^{1'}$R$^{2'}$, —($C_1$ to $C_{10}$ substituted alkyl)-NR$^{1'}$—C(NH)—NR$^{1'}$R$^2$, —($C_1$ to $C_{10}$ unsubstituted alkyl)-C(O)—NR$^{1'}$R$^{2'}$, —($C_1$ to $C_{10}$ substituted alkyl)-C(O)—NR$^{1'}$R$^{2'}$, —($C_1$ to $C_{10}$ unsubstituted alkyl)-SH, —($C_1$ to $C_{10}$ substituted alkyl)-SH, —($C_1$ to $C_{10}$ unsubstituted alkyl)-C(O)—NR$^{1'}$R$^{2'}$, —($C_1$ to $C_{10}$ substituted alkyl)-C(O)—NR$^{1'}$R$^{2'}$, —($C_1$ to $C_{10}$ unsubstituted alkyl)-S—($C_1$ to $C_{10}$ unsubstituted alkyl), —($C_1$ to $C_{10}$ unsubstituted alkyl)-S—($C_1$ to $C_{10}$ substituted alkyl), —($C_1$ to $C_{10}$ substituted alkyl)-S—($C_1$ to $C_{10}$ unsubstituted alkyl), —($C_1$ to $C_{10}$ substituted alkyl)-S—($C_1$ to $C_{10}$ substituted alkyl), —($C_1$ to $C_{10}$ unsubstituted alkyl)-aryl-OH, or —($C_1$ to $C_{10}$ substituted alkyl)-aryl-OH;

$R^{1'}$ and $R^{2'}$ at each occurrence are independently hydrogen, $C_1$ to $C_{10}$ unsubstituted alkyl, $C_1$ to $C_{10}$ substituted alkyl, $C_2$-$C_{11}$ unsubstituted alkenyl, $C_2$-$C_{11}$ substituted alkenyl, $C_2$-$C_{11}$ unsubstituted alkynyl, $C_2$-$C_{11}$ substituted alkynyl, cycloalkyl, heterocyclo, aryl, or heteroaryl;

aryl at each occurrence is independently $C_6$-$C_{12}$ unsubstituted aryl; or $C_6$-$C_{12}$ aryl substituted with one or more fluoro, chloro, bromo, iodo, methyl, CF$_3$, CCl$_3$, CFCl$_2$, CF$_2$Cl, ethyl, CH$_2$CF$_3$, CF$_2$CF$_3$, propyl, isopropyl, butyl, isobutyl, secbutyl, t-butyl, pentyl, isopentyl, neopentyl, hexyl, isohexyl, 3-methylpentyl, 2,2-dimethylbutyl, 2,3-dimethylbutyl, hydroxyl, —NH$_2$, —NH—($C_1$ to $C_{10}$ unsubstituted alkyl), —NH—($C_1$ to $C_{10}$ substituted alkyl), —NH-aryl, —NH—($C_3$-$C_{15}$ cycloalkyl), methoxy, ethoxy, n-propoxy, isopropoxy, n-butoxy, tert-butoxy, sec-butoxy, n-pentoxy, n-hexoxy, 1,2-dimethylbutoxy, oxo, epoxy, hydroxyl, nitro, cyano, sulfonic acid, sulfate, phosphonic acid, phosphate, or phosphonate;

cycloalkyl at each occurrence is independently $C_3$-$C_{15}$ unsubstituted cycloalkyl or $C_3$-$C_{15}$ cycloalkyl substituted with fluoro, chloro, bromo, iodo, oxo, epoxy, hydroxyl, carbonyl, sulfanyl, —NH$_2$, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate;

heterocyclo at each occurrence is independently a monovalent monocyclic or multicyclic non-aromatic that contains at least one non-aromatic ring containing one or more heteroatoms independently selected from O, S, and N in the ring, wherein heterocyclo is bonded through the non-aromatic ring, and wherein heterocyclo has from three to twenty ring atoms;

heteroaryl at each occurrence is independently a monovalent monocyclic or multicyclic aromatic that contains at least one aromatic ring containing one or more heteroatoms independently selected from O, S, and N in the ring, wherein heteroaryl is bonded through the aromatic ring, wherein the total number of heteroatoms in each ring is four or less and each ring contains at least one carbon atom, and wherein heteroaryl has from five to twenty ring atoms;

substituted alkenyl at each occurrence is independently a straight-chained or branched olefinically unsaturated hydrocarbon having at least one site of olefinic unsaturation substituted with fluoro, chloro, bromo, iodo, oxo, epoxy, hydroxyl, carbonyl, sulfanyl, —NH$_2$, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate;

substituted alkynyl at each occurrence is independently a straight-chained or branched acetylenically unsaturated hydrocarbon having at least one site of alkynyl unsaturation substituted with fluoro, chloro, bromo, iodo, oxo, epoxy, hydroxyl, carbonyl, sulfanyl, —NH$_2$, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate; and substituted alkyl at each occurrence is independently alkyl substituted with fluoro, chloro, bromo, iodo, oxo, epoxy, hydroxyl, carbonyl, sulfanyl, —NH$_2$, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate.

In certain embodiments, provided herein are compounds according to any of Formulae VII-X:

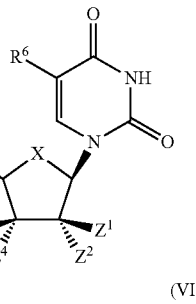

(VII)

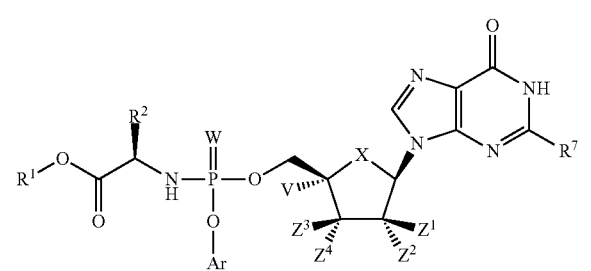

(VIII)

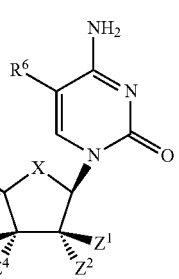

(IX)

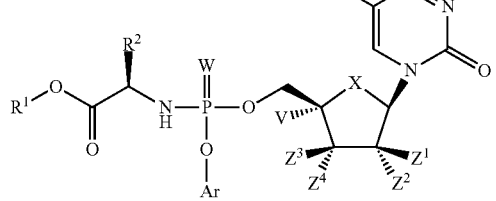

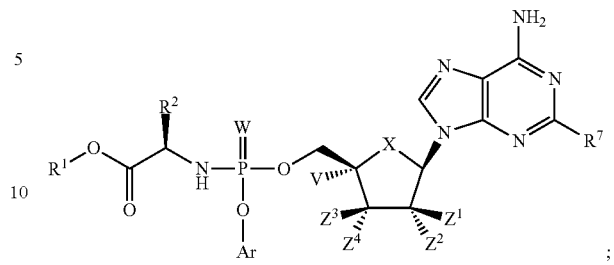

(X)

or a pharmaceutically acceptable salt, solvate, stereoisomeric form, tautomeric form or polymorphic form thereof, wherein: $Z^1$, $Z^2$, $Z^3$, $Z^4$, W, V, X, Ar, $R^1$ and $R^2$ are as described in the context of Formula I; $R^6$ is hydrogen, alkyl or halogen; and $R^7$ is hydrogen, halogen, hydroxyl or amino.

In certain embodiments, provided herein are compounds according to any of Formulae VII-X, or a pharmaceutically acceptable salt, solvate, tautomeric form, or polymorphic form thereof, wherein:

Ar is aryl or heteroaryl;

$R^1$ is hydrogen, $C_1$ to $C_{10}$ unsubstituted alkyl, $C_1$ to $C_{10}$ substituted alkyl, —($C_1$ to $C_{10}$ unsubstituted alkyl)-aryl, —($C_1$ to $C_{10}$ substituted alkyl)-aryl, —($C_1$ to $C_{10}$ unsubstituted alkyl)-heteroaryl, or —($C_1$ to $C_{10}$ substituted alkyl)-heteroaryl;

$R^2$ is $C_1$ to $C_{10}$ unsubstituted alkyl, $C_1$ to $C_{10}$ substituted alkyl, —($C_1$ to $C_{10}$ unsubstituted alkyl)-aryl, —($C_1$ to $C_{10}$ substituted alkyl)-aryl, —($C_1$ to $C_{10}$ unsubstituted alkyl)-heterocyclo, —($C_1$ to $C_{10}$ substituted alkyl)-heterocyclo, —($C_1$ to $C_{10}$ unsubstituted alkyl)-C(O)OH, —($C_1$ to $C_{10}$ substituted alkyl)-C(O)OH, —($C_1$ to $C_{10}$ unsubstituted alkyl)-heteroaryl, —($C_1$ to $C_{10}$ substituted alkyl)-heteroaryl, —($C_1$ to $C_{10}$ unsubstituted alkyl)-NR$^{1'}$R$^{2'}$, —($C_1$ to $C_{10}$ substituted alkyl)-NR$^{1'}$R$^{2'}$, —($C_1$ to $C_{10}$ unsubstituted alkyl)-OH, —($C_1$ to $C_{10}$ substituted alkyl)-OH, —($C_1$ to $C_{10}$ unsubstituted alkyl)-NR$^{1'}$—C(NH)—NR$^{1'}$R$^{2'}$, —($C_1$ to $C_{10}$ substituted alkyl)-NR$^{1'}$—C(NH)—NR$^{1'}$R$^2$, —($C_1$ to $C_{10}$ unsubstituted alkyl)-C(O)—NR$^{1'}$R$^{2'}$, —($C_1$ to $C_{10}$ substituted alkyl)-C(O)—NR$^{1'}$R$^{2'}$, —($C_1$ to $C_{10}$ unsubstituted alkyl)-SH, —($C_1$ to $C_{10}$ substituted alkyl)-SH, —($C_1$ to $C_{10}$ unsubstituted alkyl)-C(O)—NR$^{1'}$R$^{2'}$, —($C_1$ to $C_{10}$ substituted alkyl)-C(O)—NR$^{1'}$R$^{2'}$, —($C_1$ to $C_{10}$ unsubstituted alkyl)-S—($C_1$ to $C_{10}$ unsubstituted alkyl), —($C_1$ to $C_{10}$ unsubstituted alkyl)-S—($C_1$ to $C_{10}$ substituted alkyl), —($C_1$ to $C_{10}$ substituted alkyl)-S—($C_1$ to $C_{10}$ unsubstituted alkyl), —($C_1$ to $C_{10}$ substituted alkyl)-S—($C_1$ to $C_{10}$ substituted alkyl), —($C_1$ to $C_{10}$ unsubstituted alkyl)-aryl-OH, or —($C_1$ to $C_{10}$ substituted alkyl)-aryl-OH;

$Z^1$ is hydrogen, hydroxyl, chloro, bromo, fluoro, iodo, or cyano;

$Z^2$ is hydrogen, hydroxyl, chloro, bromo, fluoro, or iodo;

$Z^3$ is hydrogen;

$Z^4$ is hydroxyl, chloro, bromo, fluoro, iodo, —NR$^{1'}$R$^{2'}$, $C_2$-$C_{11}$ unsubstituted alkynyl, or $C_2$-$C_{11}$ substituted alkynyl;

V is hydrogen, chloro, bromo, fluoro, iodo, or —NR$^{1'}$R$^{2'}$;

$R^6$ is hydrogen, chloro, bromo, fluoro, iodo, $C_1$ to $C_{10}$ unsubstituted alkyl, or $C_1$ to $C_{10}$ substituted alkyl;

$R^7$ is hydrogen, hydroxyl, chloro, bromo, fluoro, iodo, or —NR$^{1'}$R$^{2'}$;

R$^{1'}$ and R$^{2'}$ at each occurrence are independently hydrogen, $C_1$ to $C_{10}$ unsubstituted alkyl, $C_1$ to $C_{10}$ substituted alkyl, $C_2$-$C_{11}$ unsubstituted alkenyl, $C_2$-$C_{11}$ substituted alkenyl, $C_2$-$C_{11}$ unsubstituted alkynyl, $C_2$-$C_{11}$ substituted alkynyl, cycloalkyl, heterocyclo, aryl, or heteroaryl;

R' at each occurrence is independently $C_1$ to $C_{10}$ unsubstituted alkyl, $C_1$ to $C_{10}$ substituted alkyl, or cycloalkyl;

aryl at each occurrence is independently $C_6$-$C_{12}$ unsubstituted aryl; or $C_6$-$C_{12}$ aryl substituted with one or more fluoro, chloro, bromo, iodo, methyl, $CF_3$, $CCl_3$, $CFCl_2$, $CF_2Cl$, ethyl, $CH_2CF_3$, $CF_2CF_3$, propyl, isopropyl, butyl, isobutyl, secbutyl, t-butyl, pentyl, isopentyl, neopentyl, hexyl, isohexyl, 3-methylpentyl, 2,2-dimethylbutyl, 2,3-dimethylbutyl, hydroxyl, —$NH_2$, —NH—($C_1$ to $C_{10}$ unsubstituted alkyl), —NH—($C_1$ to $C_{10}$ substituted alkyl), —NH-aryl, —NH—($C_3$-$C_{15}$ cycloalkyl), methoxy, ethoxy, n-propoxy, isopropoxy, n-butoxy, tert-butoxy, sec-butoxy, n-pentoxy, n-hexoxy, 1,2-dimethylbutoxy, oxo, epoxy, hydroxyl, nitro, cyano, sulfonic acid, sulfate, phosphonic acid, phosphate, or phosphonate;

cycloalkyl at each occurrence is independently $C_3$-$C_{15}$ unsubstituted cycloalkyl or $C_3$-$C_{15}$ cycloalkyl substituted with fluoro, chloro, bromo, iodo, oxo, epoxy, hydroxyl, carbonyl, sulfanyl, —$NH_2$, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate;

heterocyclo at each occurrence is independently a monovalent monocyclic or multicyclic non-aromatic that contains at least one non-aromatic ring containing one or more heteroatoms independently selected from O, S, and N in the ring, wherein heterocyclo is bonded through the non-aromatic ring, and wherein heterocyclo has from three to twenty ring atoms;

heteroaryl at each occurrence is independently a monovalent monocyclic or multicyclic aromatic that contains at least one aromatic ring containing one or more heteroatoms independently selected from O, S, and N in the ring, wherein heteroaryl is bonded through the aromatic ring, wherein the total number of heteroatoms in each ring is four or less and each ring contains at least one carbon atom, and wherein heteroaryl has from five to twenty ring atoms;

substituted alkenyl at each occurrence is independently a straight-chained or branched olefinically unsaturated hydrocarbon having at least one site of olefinic unsaturation substituted with fluoro, chloro, bromo, iodo, oxo, epoxy, hydroxyl, carbonyl, sulfanyl, —$NH_2$, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate;

substituted alkynyl at each occurrence is independently a straight-chained or branched acetylenically unsaturated hydrocarbon having at least one site of alkynyl unsaturation substituted with fluoro, chloro, bromo, iodo, oxo, epoxy, hydroxyl, carbonyl, sulfanyl, —$NH_2$, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate;

substituted alkyl at each occurrence is independently alkyl substituted with fluoro, chloro, bromo, iodo, oxo, epoxy, hydroxyl, carbonyl, sulfanyl, —$NH_2$, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate; and subject to the proviso that when, in Formula VII-X: $Z^1$ is hydrogen, then: either V is chloro, bromo, fluoro, iodo; or $Z^4$ is chloro, bromo, fluoro, iodo, —$NR^{1'}R^{2'}$, $C_2$-$C_{11}$ unsubstituted alkynyl, or $C_2$-$C_{11}$ substituted alkynyl; or Base is a nucleobase other than adenine, guanine, cytosine, thymine, or uracil.

In certain embodiments, provided herein are compounds according to any of Formulae XI-XVIII:

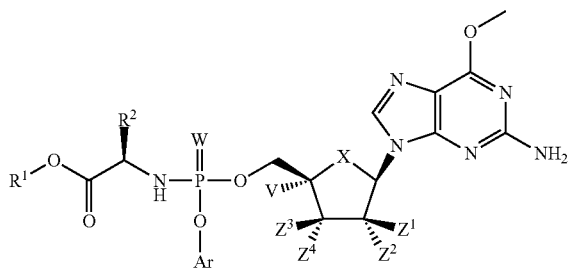

(XI)

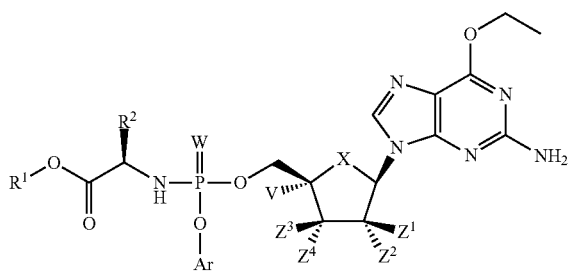

(XII)

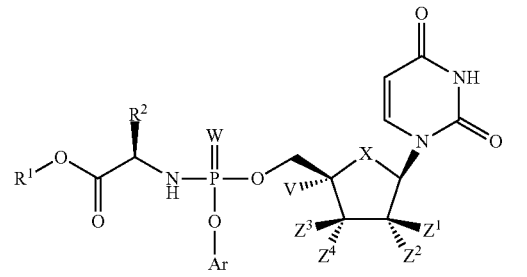

(XIII)

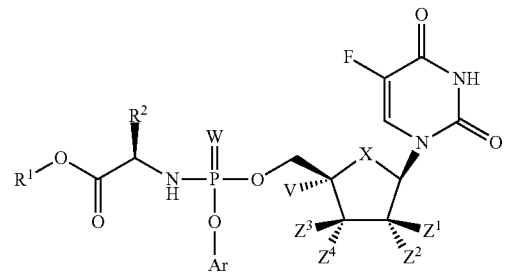

(XIV)

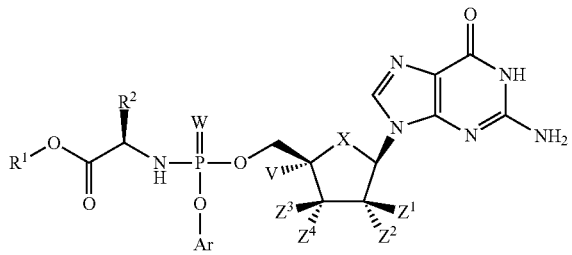

(XV)

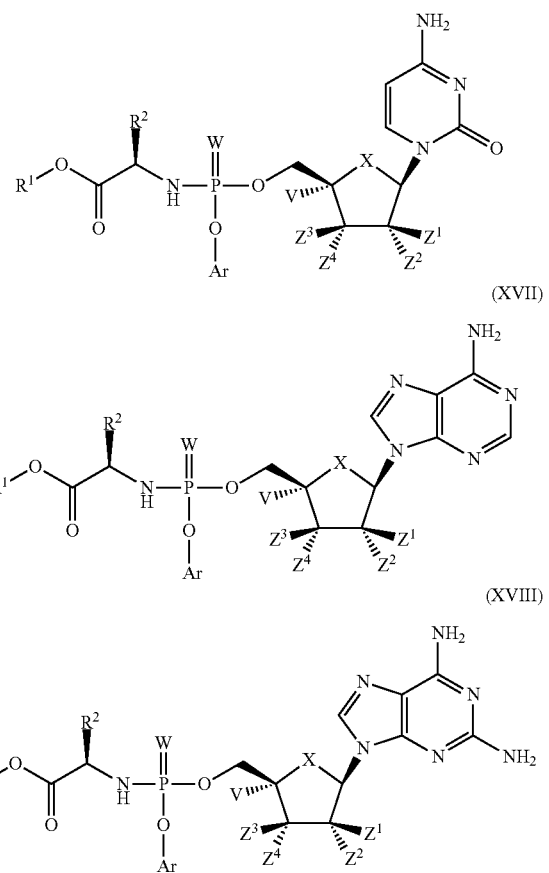

or a pharmaceutically acceptable salt, solvate, stereoisomeric form, tautomeric form or polymorphic form thereof, wherein $Z^1$, $Z^2$, $Z^3$, $Z^4$, W, V, X, Ar, $R^1$ and $R^2$ are as described in the context of Formula I.

In certain embodiments, provided herein are compounds according to any of Formulae XI-XVIII, or a pharmaceutically acceptable salt, solvate, tautomeric form, or polymorphic form thereof, wherein:

Ar is aryl or heteroaryl;

$R^1$ is hydrogen, $C_1$ to $C_{10}$ unsubstituted alkyl, $C_1$ to $C_{10}$ substituted alkyl, —($C_1$ to $C_{10}$ unsubstituted alkyl)-aryl, —($C_1$ to $C_{10}$ substituted alkyl)-aryl, —($C_1$ to $C_{10}$ unsubstituted alkyl)-heteroaryl, or —($C_1$ to $C_{10}$ substituted alkyl)-heteroaryl;

$R^2$ is $C_1$ to $C_{10}$ unsubstituted alkyl, $C_1$ to $C_{10}$ substituted alkyl, —($C_1$ to $C_{10}$ unsubstituted alkyl)-aryl, —($C_1$ to $C_{10}$ substituted alkyl)-aryl, —($C_1$ to $C_{10}$ unsubstituted alkyl)-heterocyclo, —($C_1$ to $C_{10}$ substituted alkyl)-heterocyclo, —($C_1$ to $C_{10}$ unsubstituted alkyl)-C(O)OH, —($C_1$ to $C_{10}$ substituted alkyl)-C(O)OH, —($C_1$ to $C_{10}$ unsubstituted alkyl)-heteroaryl, —($C_1$ to $C_{10}$ substituted alkyl)-heteroaryl, —($C_1$ to $C_{10}$ unsubstituted alkyl)-$NR^{1'}R^{2'}$, —($C_1$ to $C_{10}$ substituted alkyl)-$NR^{1'}R^{2'}$, —($C_1$ to $C_{10}$ unsubstituted alkyl)-OH, —($C_1$ to $C_{10}$ substituted alkyl)-OH, —($C_1$ to $C_{10}$ unsubstituted alkyl)-$NR^{1'}$—C(NH)—$NR^{1'}R^{2'}$, —($C_1$ to $C_{10}$ substituted alkyl)-$NR^{1'}$—C(NH)—$NR^{1'}R^{2'}$, —($C_1$ to $C_{10}$ unsubstituted alkyl)-C(O)—$NR^{1'}R^{2'}$, —($C_1$ to $C_{10}$ substituted alkyl)-C(O)—$NR^{1'}R^{2'}$, —($C_1$ to $C_{10}$ unsubstituted alkyl)-SH, —($C_1$ to $C_{10}$ substituted alkyl)-SH, —($C_1$ to $C_{10}$ unsubstituted alkyl)-C(O)—$NR^{1'}R^{2'}$, —($C_1$ to $C_{10}$ substituted alkyl)-C(O)—$NR^{1'}R^{2'}$, —($C_1$ to $C_{10}$ unsubstituted alkyl)-S—($C_1$ to $C_{10}$ unsubstituted alkyl), —($C_1$ to $C_{10}$ unsubstituted alkyl)-S—($C_1$ to $C_{10}$ substituted alkyl), —($C_1$ to $C_{10}$ substituted alkyl)-S—($C_1$ to $C_{10}$ unsubstituted alkyl), —($C_1$ to $C_{10}$ substituted alkyl)-S—($C_1$ to $C_{10}$ substituted alkyl), —($C_1$ to $C_{10}$ unsubstituted alkyl)-aryl-OH, or —($C_1$ to $C_{10}$ substituted alkyl)-aryl-OH;

$Z^1$ is hydrogen, hydroxyl, chloro, bromo, fluoro, iodo, or cyano;

$Z^2$ is hydrogen, hydroxyl, chloro, bromo, fluoro, or iodo;

$Z^3$ is hydrogen;

$Z^4$ is hydroxyl, chloro, bromo, fluoro, iodo, —$NR^{1'}R^{2'}$, $C_2$-$C_{11}$ unsubstituted alkynyl, or $C_2$-$C_{11}$ substituted alkynyl;

V is hydrogen, chloro, bromo, fluoro, iodo, or —$NR^{1'}R^{2'}$;

$R^{1'}$ and $R^{2'}$ at each occurrence are independently hydrogen, $C_1$ to $C_{10}$ unsubstituted alkyl, $C_1$ to $C_{10}$ substituted alkyl, $C_2$-$C_{11}$ unsubstituted alkenyl, $C_2$-$C_{11}$ substituted alkenyl, $C_2$-$C_{11}$ unsubstituted alkynyl, $C_2$-$C_{11}$ substituted alkynyl, cycloalkyl, heterocyclo, aryl, or heteroaryl;

R' at each occurrence is independently $C_1$ to $C_{10}$ unsubstituted alkyl, $C_1$ to $C_{10}$ substituted alkyl, or cycloalkyl;

aryl at each occurrence is independently $C_6$-$C_{12}$ unsubstituted aryl; or $C_6$-$C_{12}$ aryl substituted with one or more fluoro, chloro, bromo, iodo, methyl, $CF_3$, $CCl_3$, $CFCl_2$, $CF_2Cl$, ethyl, $CH_2CF_3$, $CF_2CF_3$, propyl, isopropyl, butyl, isobutyl, secbutyl, t-butyl, pentyl, isopentyl, neopentyl, hexyl, isohexyl, 3-methylpentyl, 2,2-dimethylbutyl, 2,3-dimethylbutyl, hydroxyl, —$NH_2$, —NH—($C_1$ to $C_{10}$ unsubstituted alkyl), —NH—($C_1$ to $C_{10}$ substituted alkyl), —NH-aryl, —NH—($C_3$-$C_{15}$ cycloalkyl), methoxy, ethoxy, n-propoxy, isopropoxy, n-butoxy, tert-butoxy, sec-butoxy, n-pentoxy, n-hexoxy, 1,2-dimethylbutoxy, oxo, epoxy, hydroxyl, nitro, cyano, sulfonic acid, sulfate, phosphonic acid, phosphate, or phosphonate;

cycloalkyl at each occurrence is independently $C_3$-$C_{15}$ unsubstituted cycloalkyl or $C_3$-$C_{15}$ cycloalkyl substituted with fluoro, chloro, bromo, iodo, oxo, epoxy, hydroxyl, carbonyl, sulfanyl, —$NH_2$, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate;

heterocyclo at each occurrence is independently a monovalent monocyclic or multicyclic non-aromatic that contains at least one non-aromatic ring containing one or more heteroatoms independently selected from O, S, and N in the ring, wherein heterocyclo is bonded through the non-aromatic ring, and wherein heterocyclo has from three to twenty ring atoms;

heteroaryl at each occurrence is independently a monovalent monocyclic or multicyclic aromatic that contains at least one aromatic ring containing one or more heteroatoms independently selected from O, S, and N in the ring, wherein heteroaryl is bonded through the aromatic ring, wherein the total number of heteroatoms in each ring is four or less and each ring contains at least one carbon atom, and wherein heteroaryl has from five to twenty ring atoms;

substituted alkenyl at each occurrence is independently a straight-chained or branched olefinically unsaturated hydrocarbon having at least one site of olefinic unsaturation substituted with fluoro, chloro, bromo, iodo, oxo, epoxy, hydroxyl, carbonyl, sulfanyl, —$NH_2$, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate;

substituted alkynyl at each occurrence is independently a straight-chained or branched acetylenically unsaturated hydrocarbon having at least one site of alkynyl unsaturation substituted with fluoro, chloro, bromo, iodo, oxo, epoxy, hydroxyl, carbonyl, sulfanyl, —$NH_2$, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate;

substituted alkyl at each occurrence is independently alkyl substituted with fluoro, chloro, bromo, iodo, oxo, epoxy, hydroxyl, carbonyl, sulfanyl, —$NH_2$, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate; and subject to the proviso that when, in Formula XI-XVIII: $Z^1$ is hydrogen, then: either V is chloro, bromo, fluoro, iodo; or $Z^4$ is chloro, bromo, fluoro, iodo, —$NR^{1'}R^{2'}$, $C_2$-$C_{11}$ unsubstituted alkynyl, or $C_2$-$C_{11}$ substituted alkynyl; or Base is a nucleobase other than adenine, guanine, cytosine, thymine, or uracil.

In certain embodiments according to any of formulas I-XVIII, $Z^1$ —OH; $Z^2$ is —H; $Z^3$ is —H; $Z^4$ is —OH; and V is —H. In certain embodiments according to any of formulas I-XVIII, $Z^1$ is —OH; $Z^2$ is —H; $Z^3$ is —H; $Z^4$ is —OH; V is —H; and $R^2$ is a side chain of an amino acid. In certain embodiments according to any of formulas I-XVIII, $Z^1$ is —OH; $Z^2$ is —H; $Z^3$ is —H; $Z^4$ is —OH; V is —H; and $R^2$ is methyl. In certain embodiments according to any of formulas I-XVIII, $Z^1$ is —OH; $Z^2$ is —H; $Z^3$ is —H; $Z^4$ is —OH; V is —H; $R^2$ is methyl; and Ar is phenyl. In certain embodiments according to any of formulas I-XVIII, $Z^1$ is —OH; $Z^2$ is —H; $Z^3$ is —H; $Z^4$ is —OH; V is —H; $R^2$ is methyl; Ar is phenyl; and W is O. In certain embodiments according to any of formulas I-XVIII, $Z^1$ is —OH; $Z^2$ is —H; $Z^3$ is —H; $Z^4$ is —OH; V is —H; $R^2$ is methyl; Ar is phenyl; and W is S. In certain embodiments according to any of formulas I-XVIII, $Z^1$ is —OH; $Z^2$ is —H; $Z^3$ is —H; $Z^4$ is —OH; V is H; $R^2$ is methyl; Ar is phenyl; W is S; and $R^1$ is isopropyl. In certain embodiments according to any of formulas I-XVIII, $Z^1$ is —OH; $Z^2$ is —H; $Z^3$ is —H; $Z^4$ is —OH; V is —H; $R^2$ is methyl; Ar is phenyl; W is O; and $R^2$ is isopropyl.

In certain embodiments according to any of formulas I-XVIII, $Z^1$ is —OH; $Z^2$ is —F; $Z^3$ is —H; $Z^4$ is —OH; and V is —H. In certain embodiments according to any of formulas I-XVIII, $Z^1$ is —OH; $Z^2$ is —F; $Z^3$ is —H; $Z^4$ is —OH; V is —H; and $R^2$ is a side chain of an amino acid. In certain embodiments according to any of formulas I-XVIII, $Z^1$ is —OH; $Z^2$ is —F; $Z^3$ is —H; $Z^4$ is —OH; V is —H; and $R^2$ is methyl. In certain embodiments according to any of formulas I-XVIII, $Z^1$ is —OH; $Z^2$ is —F; $Z^3$ is —H; $Z^4$ is —OH; V is —H; $R^2$ is methyl; and Ar is phenyl. In certain embodiments according to any of formulas I-XVIII, $Z^1$ is —OH; $Z^2$ is —F; $Z^3$ is —H; $Z^4$ is —OH; V is —H; $R^2$ is methyl; Ar is phenyl; and W is O. In certain embodiments according to any of formulas I-XVIII, $Z^1$ is —OH; $Z^2$ is —F; $Z^3$ is —H; $Z^4$ is —OH; V is —H; $R^2$ is methyl; Ar is phenyl; and W is S. In certain embodiments according to any of formulas I-XVIII, $Z^1$ is —OH; $Z^2$ is —F; $Z^3$ is —H; $Z^4$ is —OH; V is —H; $R^2$ is methyl; Ar is phenyl; W is S; and $R^1$ is isopropyl. In certain embodiments according to any of formulas I-XVIII, $Z^1$ is —OH; $Z^2$ is —F; $Z^3$ is —H; $Z^4$ is —OH; V is —H; $R^2$ is methyl; Ar is phenyl; W is O; and $R^2$ is isopropyl.

In certain embodiments according to any of formulas I-XVIII, $Z^1$ is —F; $Z^2$ is —OH; $Z^3$ is —H; $Z^4$ is —H; and V is —H. In certain embodiments according to any of formulas I-XVIII, $Z^1$ is —F; $Z^2$ is —OH; $Z^3$ is —H; $Z^4$ is —H; V is —H; and $R^2$ is a side chain of an amino acid. In certain embodiments according to any of formulas I-XVIII, $Z^1$ is —F; $Z^2$ is —OH; $Z^3$ is —H; $Z^4$ is —H; V is —H; and $R^2$ is methyl. In certain embodiments according to any of formulas I-XVIII, $Z^1$ is —F; $Z^2$ is —OH; $Z^3$ is —H; $Z^4$ is —H; V is —H; $R^2$ is methyl; and Ar is phenyl. In certain embodiments according to any of formulas I-XVIII, $Z^1$ is —F; $Z^2$ is —OH; $Z^3$ is —H; $Z^4$ is —H; V is —H; $R^2$ is methyl; Ar is phenyl; and W is O. In certain embodiments according to any of formulas I-XVIII, $Z^1$ is —F; $Z^2$ is —OH; $Z^3$ is —H; $Z^4$ is —H; V is —H; $R^2$ is methyl; Ar is phenyl; and W is S. In certain embodiments according to any of formulas I-XVIII, $Z^1$ is —F; $Z^2$ is —OH; $Z^3$ is —H; $Z^4$ is —H; V is —H; $R^2$ is methyl; Ar is phenyl; W is S; and $R^1$ is isopropyl. In certain embodiments according to any of formulas I-XVIII, $Z^1$ is —F; $Z^2$ is —OH; $Z^3$ is —H; $Z^4$ is —H; V is —H; $R^2$ is methyl; Ar is phenyl; W is O; and $R^2$ is isopropyl.

In certain embodiments according to any of formulas I-XVIII, $Z^1$ is —F; $Z^2$ is —F; $Z^3$ is —H; $Z^4$ is —OH; and V is —H. In certain embodiments according to any of formulas I-XVIII, $Z^1$ is —F; $Z^2$ is —F; $Z^3$ is —H; $Z^4$ is —OH; V is —H; and $R^2$ is a side chain of an amino acid. In certain embodiments according to any of formulas I-XVIII, $Z^1$ is —F; $Z^2$ is —F; $Z^3$ is —H; $Z^4$ is —OH; V is —H; and $R^2$ is methyl. In certain embodiments according to any of formulas I-XVIII, $Z^1$ is —F; $Z^2$ is —F; $Z^3$ is —H; $Z^4$ is —OH; V is —H; $R^2$ is methyl; and Ar is phenyl. In certain embodiments according to any of formulas I-XVIII, $Z^1$ is —F; $Z^2$ is —F; $Z^3$ is —H; $Z^4$ is —OH; V is —H; $R^2$ is methyl; Ar is phenyl; and W is O. In certain embodiments according to any of formulas I-XVIII $Z^1$ is —F; $Z^2$ is —F; $Z^3$ is —H; $Z^4$ is —OH; V is —H; $R^2$ is methyl; Ar is phenyl; and W is S. In certain embodiments according to any of formulas I-XVIII, $Z^1$ is —F; $Z^2$ is —F; $Z^3$ is —H; $Z^4$ is —OH; V is —H; $R^2$ is methyl; Ar is phenyl; W is S; and $R^1$ is isopropyl. In certain embodiments according to any of formulas I-XVIII, $Z^1$ is —F; $Z^2$ is —F; $Z^3$ is —H; $Z^4$ is —OH; V is —H; $R^2$ is methyl; Ar is phenyl; W is O; and $R^2$ is isopropyl.

In certain embodiments according to any of formulas I-XVIII, $Z^1$ is —F; $Z^2$ is —H; $Z^3$ is —H; $Z^4$ is —OH; and V is —H. In certain embodiments according to any of formulas I-XVIII, $Z^1$ is —F; $Z^2$ is —H; $Z^3$ is —H; $Z^4$ is —OH; V is —H; and $R^2$ is a side chain of an amino acid. In certain embodiments according to any of formulas I-XVIII, $Z^1$ is —F; $Z^2$ is —H; $Z^3$ is —H; $Z^4$ is —OH; V is —H; and $R^2$ is methyl. In certain embodiments according to any of formulas I-XVIII, $Z^1$ is —F; $Z^2$ is —H; $Z^3$ is —H; $Z^4$ is —OH; V is —H; $R^2$ is methyl; and Ar is phenyl. In certain embodiments according to any of formulas I-XVIII, $Z^1$ is —F; $Z^2$ is —H; $Z^3$ is —H; $Z^4$ is —OH; V is —H; $R^2$ is methyl; Ar is phenyl; and W is O. In certain embodiments according to any of formulas I-XVIII, $Z^1$ is —F; $Z^2$ is —H; $Z^3$ is —H; $Z^4$ is —OH; V is —H; $R^2$ is methyl; Ar is phenyl; and W is S. In certain embodiments according to any of formulas I-XVIII, $Z^1$ is —F; $Z^2$ is —H; $Z^3$ is —H; $Z^4$ is —OH; V is —H; $R^2$ is methyl; Ar is phenyl; W is S; and $R^1$ is isopropyl. In certain embodiments according to any of formulas I-XVIII, $Z^1$ is —F; $Z^2$ is —H; $Z^3$ is —H; $Z^4$ is —OH; V is —H; $R^2$ is methyl; Ar is phenyl; W is O; and $R^2$ is isopropyl.

In certain embodiments according to any of formulas I-XVIII, wherein $Z^1$ is —F; $Z^2$ is —Cl; $Z^3$ is —H; $Z^4$ is —OH; and V is —H. In certain embodiments according to any of formulas I-XVIII, $Z^1$ is —F; $Z^2$ is —Cl; $Z^3$ is —H; $Z^4$ is —OH; V is —H; and $R^2$ is a side chain of an amino acid. In certain embodiments according to any of formulas I-XVIII, $Z^1$ is —F; $Z^2$ is —Cl; $Z^3$ is —H; $Z^4$ is —OH; V is —H; and $R^2$ is methyl. In certain embodiments according to any of formulas I-XVIII, $Z^1$ is —F; $Z^2$ is —Cl; $Z^3$ is —H; $Z^4$ is —OH; V is —H; $R^2$ is methyl; and Ar is phenyl. In certain embodiments according to any of formulas I-XVIII, $Z^1$ is —F; $Z^2$ is —Cl; $Z^3$ is —H; $Z^4$ is —OH; V is —H; $R^2$ is methyl; Ar is phenyl; and W is O. In certain embodiments according to any of formulas I-XVIII, $Z^1$ is —F; $Z^2$ is —Cl; $Z^3$ is —H; $Z^4$ is —OH; V is —H; $R^2$ is methyl; Ar is phenyl; and W is S. In certain embodiments according to any of formulas I-XVIII, $Z^1$ is —F; $Z^2$ is —Cl; $Z^3$ is —H; $Z^4$ is —OH; V is —H; $R^2$ is methyl; Ar is phenyl; W is S; and $R^1$ is isopropyl. In certain embodiments according to any of formulas I-XVIII, $Z^1$ is —F; $Z^2$ is —Cl; $Z^3$ is —H; $Z^4$ is —OH; V is —H; $R^2$ is methyl; Ar is phenyl; W is O; and $R^2$ is isopropyl.

In certain embodiments according to any of formulas I-XVIII, wherein $Z^1$ is —Cl; $Z^2$ is —Cl; $Z^3$ is —H; $Z^4$ is —OH; and V is —H. In certain embodiments according to any of formulas I-XVIII, $Z^1$ is —Cl; $Z^2$ is —Cl; $Z^3$ is —H; $Z^4$ is —OH; V is —H; and $R^2$ is a side chain of an amino acid. In certain embodiments according to any of formulas I-XVIII, $Z^1$ is —Cl; $Z^2$ is —Cl; $Z^3$ is —H; $Z^4$ is —OH; V is —H; and $R^2$ is methyl. In certain embodiments according to any of formulas I-XVIII, $Z^1$ is —Cl; $Z^2$ is —Cl; $Z^3$ is —H; $Z^4$ is —OH; V is —H; $R^2$ is methyl; and Ar is phenyl. In certain embodiments according to any of formulas I-XVIII, $Z^1$ is —Cl; $Z^2$ is —Cl; $Z^3$ is —H; $Z^4$ is —OH; V is —H; $R^2$ is methyl; Ar is phenyl; and W is O. In certain embodiments according to any of formulas I-XVIII, $Z^1$ is —Cl; $Z^2$ is —Cl; $Z^3$ is —H; $Z^4$ is —OH; V is —H; $R^2$ is methyl; Ar is phenyl; and W is S. In certain embodiments according to any of formulas I-XVIII, $Z^1$ is —Cl; $Z^2$ is —Cl; $Z^3$ is —H; $Z^4$ is —OH; V is —H; $R^2$ is methyl; Ar is phenyl; W is S; and $R^1$ is isopropyl. In certain embodiments according to any of formulas I-XVIII, $Z^1$ is —Cl; $Z^2$ is —Cl; $Z^3$ is —H; $Z^4$ is —OH; V is —H; $R^2$ is methyl; Ar is phenyl; W is O; and $R^2$ is isopropyl.

In certain embodiments according to any of formulas I-XVIII, wherein $Z^1$ is —Cl; $Z^2$ is —H; $Z^3$ is —H; $Z^4$ is —OH; and V is —H. In certain embodiments according to any of formulas I-XVIII, $Z^1$ is —Cl; $Z^2$ is —H; $Z^3$ is —H; $Z^4$ is —OH; V is —H; and $R^2$ is a side chain of an amino acid. In certain embodiments according to any of formulas I-XVIII, $Z^1$ is —Cl; $Z^2$ is —H; $Z^3$ is —H; $Z^4$ is —OH; V is —H; and $R^2$ is methyl. In certain embodiments according to any of formulas I-XVIII, $Z^1$ is —Cl; $Z^2$ is —H; $Z^3$ is —H; $Z^4$ is —OH; V is —H; $R^2$ is methyl; and Ar is phenyl. In certain embodiments according to any of formulas I-XVIII, $Z^1$ is —Cl; $Z^2$ is —H; $Z^3$ is —H; $Z^4$ is —OH; V is —H; $R^2$ is methyl; Ar is phenyl; and W is O. In certain embodiments according to any of formulas I-XVIII, $Z^1$ is —Cl; $Z^2$ is —H; $Z^3$ is —H; $Z^4$ is —OH; V is —H; $R^2$ is methyl; Ar is phenyl; and W is S. In certain embodiments according to any of formulas I-XVIII, $Z^1$ is —Cl; $Z^2$ is —H; $Z^3$ is —H; $Z^4$ is —OH; V is —H; $R^2$ is methyl; Ar is phenyl; W is S; and $R^1$ is isopropyl. In certain embodiments according to any of formulas I-XVIII, $Z^1$ is —Cl; $Z^2$ is —H; $Z^3$ is —H; $Z^4$ is —OH; V is —H; $R^2$ is methyl; Ar is phenyl; W is O; and $R^2$ is isopropyl.

In certain embodiments according to any of formulas I-XVIII, wherein $Z^1$ is —Cl; $Z^2$ is —F; $Z^3$ is —H; $Z^4$ is —OH; and V is —H. In certain embodiments according to any of formulas I-XVIII, $Z^1$ is —Cl; $Z^2$ is —F; $Z^3$ is —H; $Z^4$ is —OH; V is —H; and $R^2$ is a side chain of an amino acid. In certain embodiments according to any of formulas I-XVIII, $Z^1$ is —Cl; $Z^2$ is —F; $Z^3$ is —H; $Z^4$ is —OH; V is —H; and $R^2$ is methyl. In certain embodiments according to any of formulas I-XVIII, $Z^1$ is —Cl; $Z^2$ is —F; $Z^3$ is —H; $Z^4$ is —OH; V is —H; $R^2$ is methyl; and Ar is phenyl. In certain embodiments according to any of formulas I-XVIII, $Z^1$ is —Cl; $Z^2$ is —F; $Z^3$ is —H; $Z^4$ is —OH; V is —H; $R^2$ is methyl; Ar is phenyl; and W is O. In certain embodiments according to any of formulas I-XVIII, $Z^1$ is —Cl; $Z^2$ is —F; $Z^3$ is —H; $Z^4$ is —OH; V is —H; $R^2$ is methyl; Ar is phenyl; and W is S. In certain embodiments according to any of formulas I-XVIII, $Z^1$ is —Cl; $Z^2$ is —F; $Z^3$ is —H; $Z^4$ is —OH; V is —H; $R^2$ is methyl; Ar is phenyl; W is S; and $R^1$ is isopropyl. In certain embodiments according to any of formulas I-XVIII, $Z^1$ is —Cl; $Z^2$ is —F; $Z^3$ is —H; $Z^4$ is —OH; V is —H; $R^2$ is methyl; Ar is phenyl; W is O; and $R^2$ is isopropyl.

In certain embodiments according to any of formulas I-XVIII, wherein $Z^1$ is —F; $Z^2$ is —F; $Z^3$ is —H; $Z^4$ is —OH; and V is —H. In certain embodiments according to any of formulas I-XVIII, $Z^1$ is —F; $Z^2$ is —F; $Z^3$ is —H; $Z^4$ is —OH; V is —H; and $R^2$ is a side chain of an amino acid. In certain embodiments according to any of formulas I-XVIII, $Z^1$ is —F; $Z^2$ is —F; $Z^3$ is —H; $Z^4$ is —OH; V is —H; and $R^2$ is methyl. In certain embodiments according to any of formulas I-XVIII, $Z^1$ is —F; $Z^2$ is —F; $Z^3$ is —H; $Z^4$ is —OH; V is —H; $R^2$ is methyl; and Ar is phenyl. In certain embodiments according to any of formulas I-XVIII, $Z^1$ is —F; $Z^2$ is —F; $Z^3$ is —H; $Z^4$ is —OH; V is —H; $R^2$ is methyl; Ar is phenyl; and W is O. In certain embodiments according to any of formulas I-XVIII, $Z^1$ is —F; $Z^2$ is —F; $Z^3$ is —H; $Z^4$ is —OH; V is —H; $R^2$ is methyl; Ar is phenyl; and W is S. In certain embodiments according to any of formulas I-XVIII, $Z^1$ is —F; $Z^2$ is —F; $Z^3$ is —H; $Z^4$ is —OH; V is —H; $R^2$ is methyl; Ar is phenyl; W is S; and $R^1$ is isopropyl. In certain embodiments according to any of formulas I-XVIII, $Z^1$ is —F; $Z^2$ is —F; $Z^3$ is —H; $Z^4$ is —OH; V is —H; $R^2$ is methyl; Ar is phenyl; W is O; and $R^2$ is isopropyl.

In certain embodiments according to any of formulas I-XVIII, wherein $Z^1$ is —CN; $Z^2$ is —H; $Z^3$ is —H; $Z^4$ is —OH; and V is —H. In certain embodiments according to any of formulas I-XVIII, $Z^1$ is —CN; $Z^2$ is —H; $Z^3$ is —H; $Z^4$ is —OH; V is —H; and $R^2$ is a side chain of an amino acid. In certain embodiments according to any of formulas I-XVIII, $Z^1$ is —CN; $Z^2$ is —H; $Z^3$ is —H; $Z^4$ is —OH; V is —H; and $R^2$ is methyl. In certain embodiments according to any of formulas I-XVIII, $Z^1$ is —CN; $Z^2$ is —H; $Z^3$ is —H; $Z^4$ is —OH; V is —H; $R^2$ is methyl; and Ar is phenyl. In certain embodiments according to any of formulas I-XVIII, $Z^1$ is —CN; $Z^2$ is —H; $Z^3$ is —H; $Z^4$ is —OH; V is —H; $R^2$ is methyl; Ar is phenyl; and W is O. In certain embodiments according to any of formulas I-XVIII, $Z^1$ is —CN; $Z^2$ is —H; $Z^3$ is —H; $Z^4$ is —OH; V is —H; $R^2$ is methyl; Ar is phenyl; and W is S. In certain embodiments according to any of formulas I-XVIII, $Z^1$ is —CN; $Z^2$ is —H; $Z^3$ is —H; $Z^4$ is —OH; V is —H; $R^2$ is methyl; Ar is phenyl; W is S; and $R^1$ is isopropyl. In certain embodiments according to any of formulas I-XVIII, $Z^1$ is —CN; $Z^2$ is —H; $Z^3$ is —H; $Z^4$ is —OH; V is —H; $R^2$ is methyl; Ar is phenyl; W is O; and $R^2$ is isopropyl.

In certain embodiments according to any of formulas I-XVIII, wherein $Z^1$ is —H; $Z^2$ is —H; $Z^3$ is —H; $Z^4$ is —C≡CH; and V is —H. In certain embodiments according to any of formulas I-XVIII, $Z^1$ is —H; $Z^2$ is —H; $Z^3$ is —H; $Z^4$ is —C≡CH; V is —H; and $R^2$ is a side chain of an amino acid. In certain embodiments according to any of formulas I-XVIII, $Z^1$ is —H; $Z^2$ is —H; $Z^3$ is —H; $Z^4$ is —C≡CH; and V is —H; and $R^2$ is methyl. In certain embodiments according to any of formulas I-XVIII $Z^1$ is —H; $Z^2$ is —H; $Z^3$ is —H; $Z^4$ is —C≡CH; and V is —H; $R^2$ is methyl; and Ar is phenyl. In certain embodiments according to any of formulas I-XVIII, $Z^1$ is —H; $Z^2$ is —H; $Z^3$ is —H; $Z^4$ is —C≡CH; and V is —H; $R^2$ is methyl; Ar is phenyl; and W is O. In certain embodiments according to any of formulas I-XVIII, $Z^1$ is —H; $Z^2$ is —H; $Z^3$ is —H; $Z^4$ is —C≡CH; and V is —H; $R^2$ is methyl; Ar is phenyl; and W is S. In certain embodiments according to any of formulas I-XVIII, $Z^1$ is —H; $Z^2$ is —H; $Z^3$ is —H; $Z^4$ is —C≡CH; and V is —H $R^2$ is methyl; Ar is phenyl; W is S; and $R^1$ is isopropyl. In certain embodiments according to any of formulas I-XVIII $Z^1$ is —H; $Z^2$ is —H; $Z^3$ is —H; $Z^4$ is —C≡CH; and V is —H; $R^2$ is methyl; Ar is phenyl; W is O; and $R^2$ is isopropyl.

In certain embodiments according to any of formulas I-XVIII, wherein $Z^1$ is —H; $Z^2$ is —H; $Z^3$ is —H; $Z^4$ is —F; and V is —H. In certain embodiments according to any of formulas I-XVIII, $Z^1$ is —H; $Z^2$ is —H; $Z^3$ is —H; $Z^4$ is —F; V is —H; and $R^2$ is a side chain of an amino acid. In certain embodiments according to any of formulas I-XVIII, $Z^1$ is —H; $Z^2$ is —H; $Z^3$ is —H; $Z^4$ is —F; and V is —H; and $R^2$ is methyl. In certain embodiments according to any of formulas I-XVIII $Z^1$ is —H; $Z^2$ is —H; $Z^3$ is —H; $Z^4$ is —F; and V is —H; $R^2$ is methyl; and Ar is phenyl. In certain embodiments according to any of formulas I-XVIII, $Z^1$ is —H; $Z^2$ is —H; $Z^3$ is —H; $Z^4$ is —F; and V is —H; $R^2$ is methyl; Ar is phenyl; and W is O. In certain embodiments according to any of formulas I-XVIII, $Z^1$ is —H; $Z^2$ is —H; $Z^3$ is —H; $Z^4$ is —F; and V is —H; $R^2$ is methyl; Ar is phenyl; and W is S. In certain embodiments according to any of formulas I-XVIII, $Z^1$ is —H; $Z^2$ is —H; $Z^3$ is —H; $Z^4$ is —F; and V is —H $R^2$ is methyl; Ar is phenyl; W is S; and $R^1$ is isopropyl. In certain embodiments according to any of formulas I-XVIII $Z^1$ is —H; $Z^2$ is —H; $Z^3$ is —H; $Z^4$ is —F; and V is —H; $R^2$ is methyl; Ar is phenyl; W is O; and $R^2$ is isopropyl.

In certain embodiments according to any of formulas I-XVIII, wherein $Z^1$ is —H; $Z^2$ is —H; $Z^3$ is —H; $Z^4$ is —NH$_2$; and V is —H. In certain embodiments according to any of formulas I-XVIII, $Z^1$ is —H; $Z^2$ is —H; $Z^3$ is —H; $Z^4$ is —NH$_2$; V is —H; and $R^2$ is a side chain of an amino acid. In certain embodiments according to any of formulas I-XVIII, $Z^1$ is —H; $Z^2$ is —H; $Z^3$ is —H; $Z^4$ is —NH$_2$; and V is —H; and $R^2$ is methyl. In certain embodiments according to any of formulas I-XVIII, $Z^1$ is —H; $Z^2$ is —H; $Z^3$ is —H; $Z^4$ is —NH$_2$; and V is —H; $R^2$ is methyl; and Ar is phenyl. In certain embodiments according to any of formulas I-XVIII, $Z^1$ is —H; $Z^2$ is —H; $Z^3$ is —H; $Z^4$ is —NH$_2$; and V is —H; $R^2$ is methyl; Ar is phenyl; and W is O. In certain embodiments according to any of formulas I-XVIII, $Z^1$ is —H; $Z^2$ is —H; $Z^3$ is —H; $Z^4$ is —NH$_2$; and V is —H; $R^2$ is methyl; Ar is phenyl; and W is S. In certain embodiments according to any of formulas I-XVIII, $Z^1$ is —H; $Z^2$ is —H; $Z^3$ is —H; $Z^4$ is —NH$_2$; and V is —H $R^2$ is methyl; Ar is phenyl; W is S; and $R^1$ is isopropyl. In certain embodiments according to any of formulas I-XVIII, $Z^1$ is —H; $Z^2$ is —H; $Z^3$ is —H; $Z^4$ is —NH$_2$; and V is —H; $R^2$ is methyl; Ar is phenyl; W is O; and $R^2$ is isopropyl.

In certain embodiments according to any of formulas I-XVIII, wherein $Z^1$ is —H; $Z^2$ is —F; $Z^3$ is —H; $Z^4$ is —OH; and V is —F. In certain embodiments according to any of formulas I-XVIII, $Z^1$ is —H; $Z^2$ is —F; $Z^3$ is —H; $Z^4$ is —OH; V is —F; and $R^2$ is a side chain of an amino acid. In certain embodiments according to any of formulas I-XVIII, $Z^1$ is —H; $Z^2$ is —F; $Z^3$ is —H; $Z^4$ is —OH; V is —F; and $R^2$ is methyl. In certain embodiments according to any of formulas I-XVIII, $Z^1$ is —H; $Z^2$ is —F; $Z^3$ is —H; $Z^4$ is —OH; V is —F; $R^2$ is methyl; and Ar is phenyl. In certain embodiments according to any of formulas I-XVIII, $Z^1$ is —H; $Z^2$ is —F; $Z^3$ is —H; $Z^4$ is —OH; V is —F; $R^2$ is methyl; Ar is phenyl; and W is O. In certain embodiments according to any of formulas I-XVIII, $Z^1$ is —H; $Z^2$ is —F; $Z^3$ is —H; $Z^4$ is —OH; V is —F; $R^2$ is methyl; Ar is phenyl; and W is S. In certain embodiments according to any of formulas I-XVIII, $Z^1$ is —H; $Z^2$ is —F; $Z^3$ is —H; $Z^4$ is —OH; V is —F; $R^2$ is methyl; Ar is phenyl; W is S; and $R^1$ is isopropyl. In certain embodiments according to any of formulas I-XVIII, $Z^1$ is —H; $Z^2$ is —F; $Z^3$ is —H; $Z^4$ is —OH; V is —F; $R^2$ is methyl; Ar is phenyl; W is O; and $R^2$ is isopropyl.

In certain embodiments according to any of formulas I-XVIII, wherein $Z^1$ is —CN; $Z^2$ is —H; $Z^3$ is —H; $Z^4$ is —OH; and V is —H. In certain embodiments according to any of formulas I-XVIII, $Z^1$ is —CN; $Z^2$ is —H; $Z^3$ is —H; $Z^4$ is —OH; V is —H; and $R^2$ is a side chain of an amino acid. In certain embodiments according to any of formulas I-XVIII, $Z^1$ is —CN; $Z^2$ is —H; $Z^3$ is —H; $Z^4$ is —OH; V is —H; and $R^2$ is methyl. In certain embodiments according to any of formulas I-XVIII, $Z^1$ is —CN; $Z^2$ is —H; $Z^3$ is —H; $Z^4$ is —OH; V is —H; $R^2$ is methyl; and Ar is phenyl. In certain embodiments according to any of formulas I-XVIII, $Z^1$ is —CN; $Z^2$ is —H; $Z^3$ is —H; $Z^4$ is —OH; V is —H; $R^2$ is methyl; Ar is phenyl; and W is O. In certain embodiments according to any of formulas I-XVIII, $Z^1$ is —CN; $Z^2$ is —H; $Z^3$ is —H; $Z^4$ is —OH; V is —H; $R^2$ is methyl; Ar is phenyl; and W is S. In certain embodiments according to any of formulas I-XVIII, $Z^1$ is —CN; $Z^2$ is —H; $Z^3$ is —H; $Z^4$ is —OH; V is —H; $R^2$ is methyl; Ar is phenyl; W is S; and $R^1$ is isopropyl. In certain embodiments according to any of formulas I-XVIII, $Z^1$ is —CN; $Z^2$ is —H; $Z^3$ is —H; $Z^4$ is —OH; V is —H; $R^2$ is methyl; Ar is phenyl; W is O; and $R^2$ is isopropyl.

In certain embodiments according to any of formulas I-XVIII, wherein $Z^1$ is —CN; $Z^2$ is —H; $Z^3$ is —H; $Z^4$ is —OH; and V is —NH$_2$. In certain embodiments according to any of formulas I-XVIII, $Z^1$ is —CN; $Z^2$ is —H; $Z^3$ is —H; $Z^4$ is —OH; V is —NH$_2$; and $R^2$ is a side chain of an amino acid. In certain embodiments according to any of formulas I-XVIII, $Z^1$ is —CN; $Z^2$ is —H; $Z^3$ is —H; $Z^4$ is —OH; V is —NH$_2$; and $R^2$ is methyl. In certain embodiments according to any of formulas I-XVIII, $Z^1$ is —CN; $Z^2$ is —H; $Z^3$ is —H; $Z^4$ is —OH; V is —NH$_2$; $R^2$ is methyl; and Ar is phenyl. In certain embodiments according to any of formulas I-XVIII, $Z^1$ is —CN; $Z^2$ is —H; $Z^3$ is —H; $Z^4$ is —OH; V is —NH$_2$; $R^2$ is methyl; Ar is phenyl; and W is O. In certain embodiments according to any of formulas I-XVIII, $Z^1$ is —CN; $Z^2$ is —H; $Z^3$ is —H; $Z^4$ is —OH; V is —NH$_2$; R$^2$ is methyl; Ar is phenyl; and W is S. In certain embodiments according to any of formulas I-XVIII, Z$^1$ is —CN; Z$^2$ is —H; Z$^3$ is —H; Z$^4$ is —OH; V is —NH$_2$; R$^2$ is methyl; Ar is phenyl; W is S; and R$^1$ is isopropyl. In certain embodiments according to any of formulas I-XVIII, Z$^1$ is —CN; Z$^2$ is —H; Z$^3$ is —H; Z$^4$ is —OH; V is —NH$_2$; R$^2$ is methyl; Ar is phenyl; W is O; and R$^1$ is isopropyl.

In certain embodiments according to any of formulas I-XVIII, R$^2$ is a side chain of an amino acid. In certain embodiments according to any of formulas I-XVIII, R$^2$ is methyl. In certain embodiments according to any of formulas I-XVIII, R$^2$ is methyl; and Ar is phenyl. In certain embodiments according to any of formulas I-XVIII, R$^2$ is methyl; Ar is phenyl; and W is O. In certain embodiments according to any of formulas I-XVIII, R$^2$ is methyl; Ar is phenyl; and W is S. In certain embodiments according to any of formulas I-XVIII, R$^2$ is methyl; Ar is phenyl; W is S; and R$^1$ is isopropyl. In certain embodiments according to any of formulas I-XVIII, R$^2$ is methyl; Ar is phenyl; W is O; and R$^1$ is isopropyl.

In certain embodiments, provided herein are compounds according to any of the above embodiments, wherein:

Base is

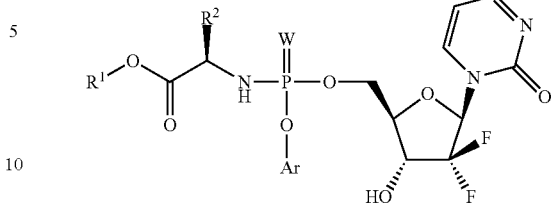

or a tautomeric form thereof;

R$^4$ is hydrogen, hydroxyl, alkoxyl, halogen, sulfanyl, amino, or aminoalkyl;

R$^5$ is hydrogen, hydroxyl, amino, azido, or alkoxyl;

R$^6$ is hydrogen, halogen, or alkyl; and

R$^7$ is hydrogen, halogen, hydroxyl, or amino.

In certain embodiments, provided herein are compounds according to any of the following formulae:

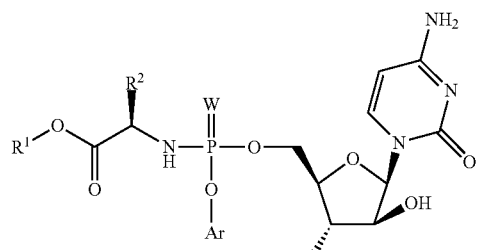

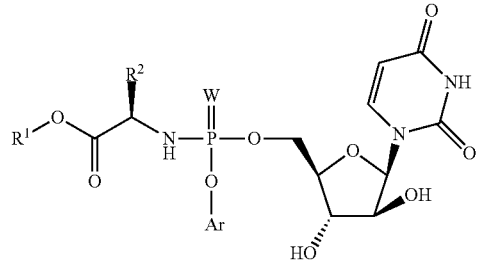

-continued

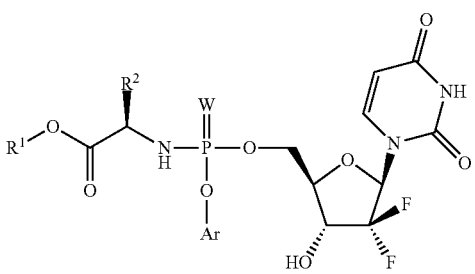

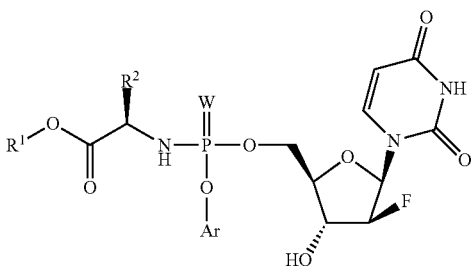

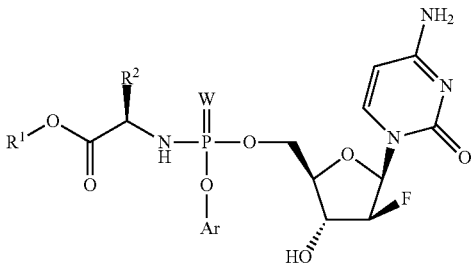

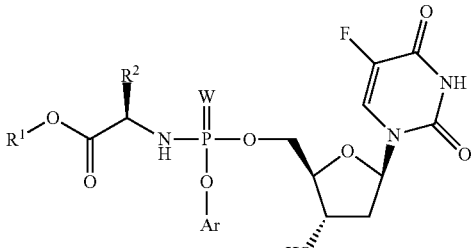

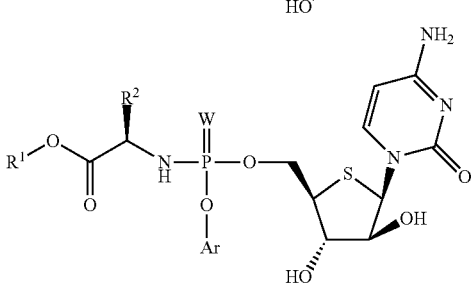

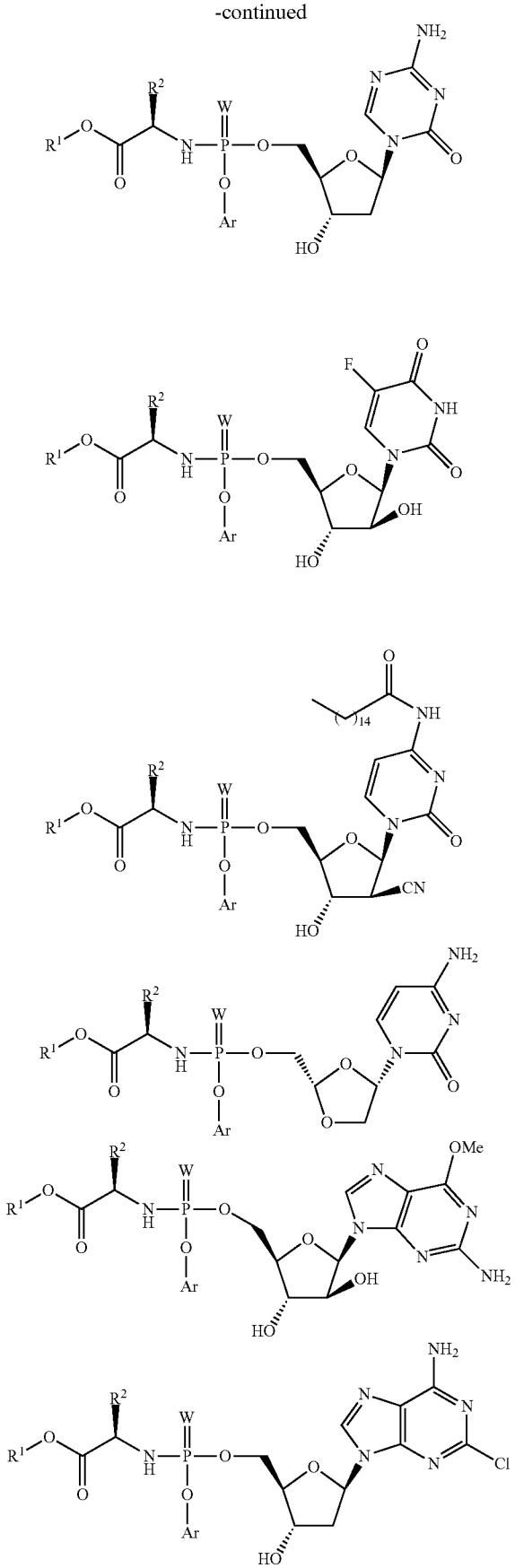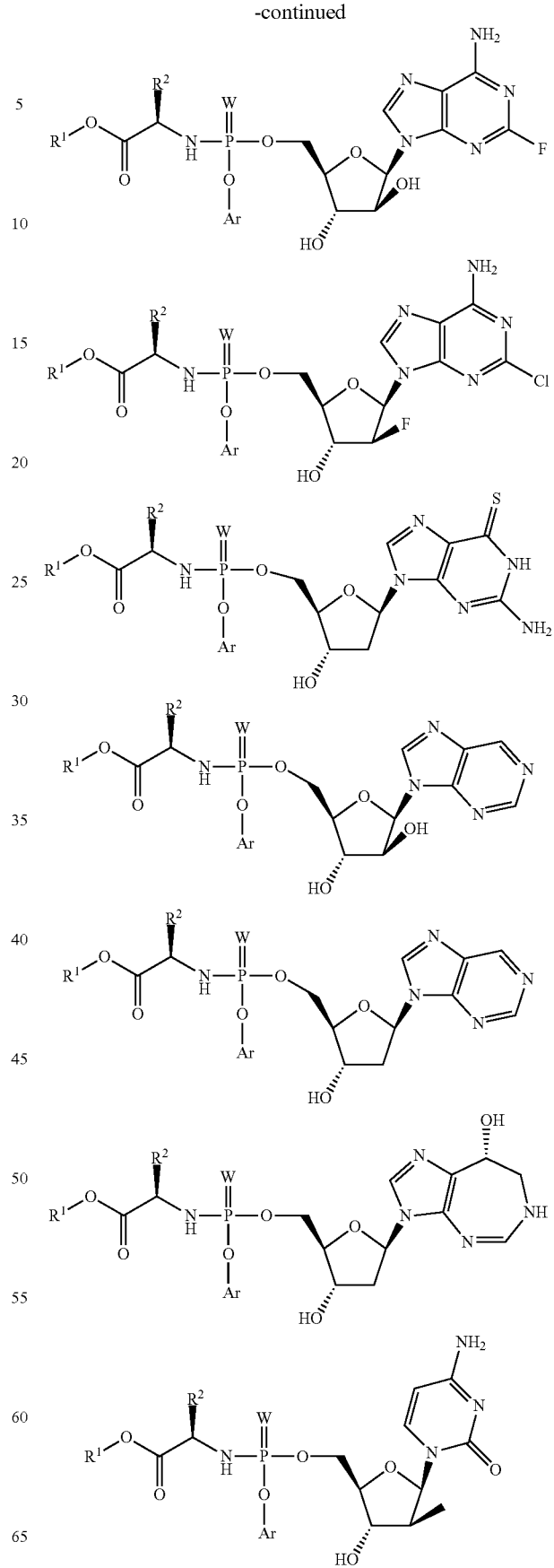

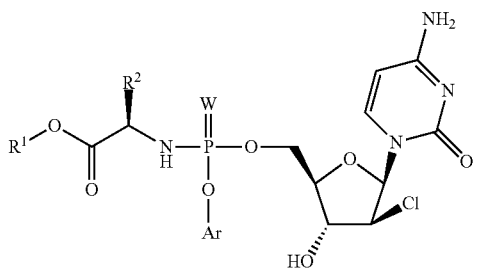
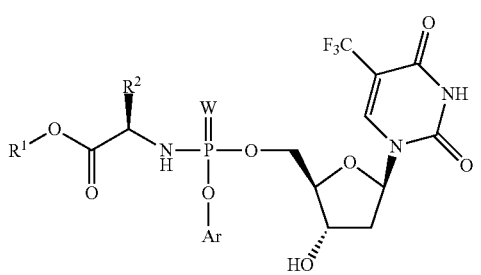
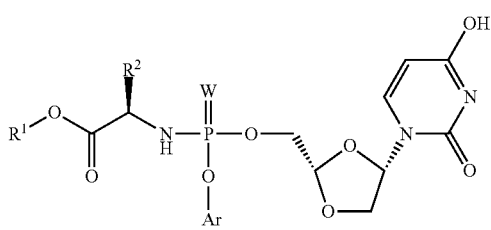
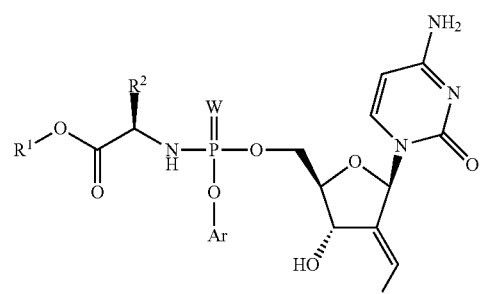
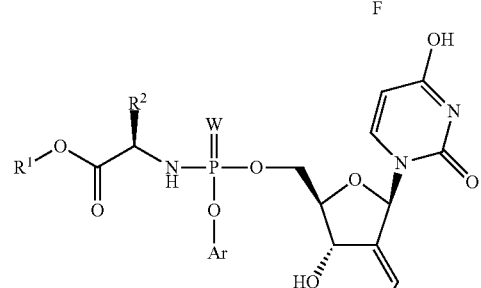
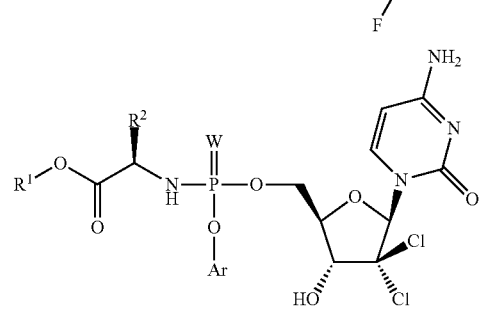
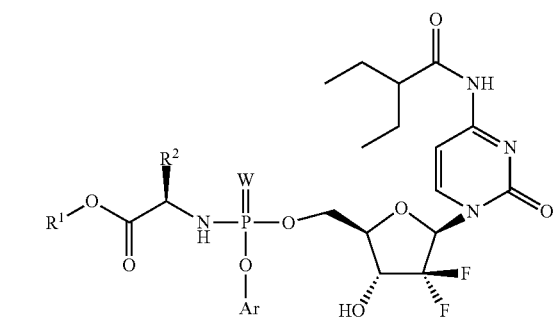
or a pharmaceutically acceptable salt, solvate, stereoisomeric form, tautomeric form or polymorphic form thereof, wherein W, Ar, $R^1$ and $R^2$ are as described in the context of Formula I.
In certain embodiments, provided herein are compounds according to any of the following formulae:
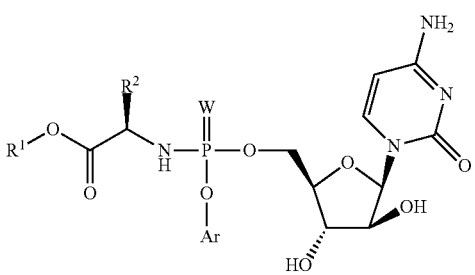
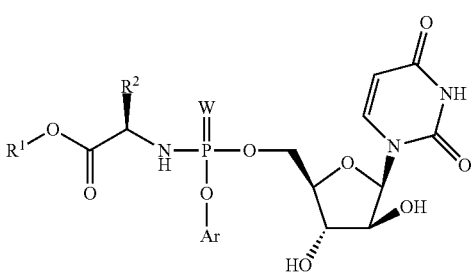
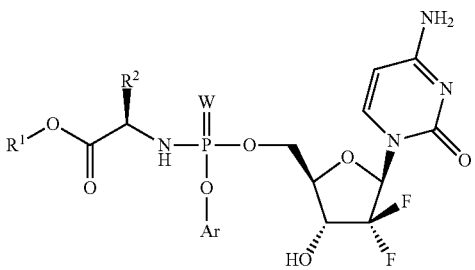
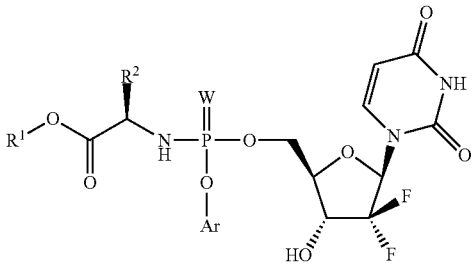

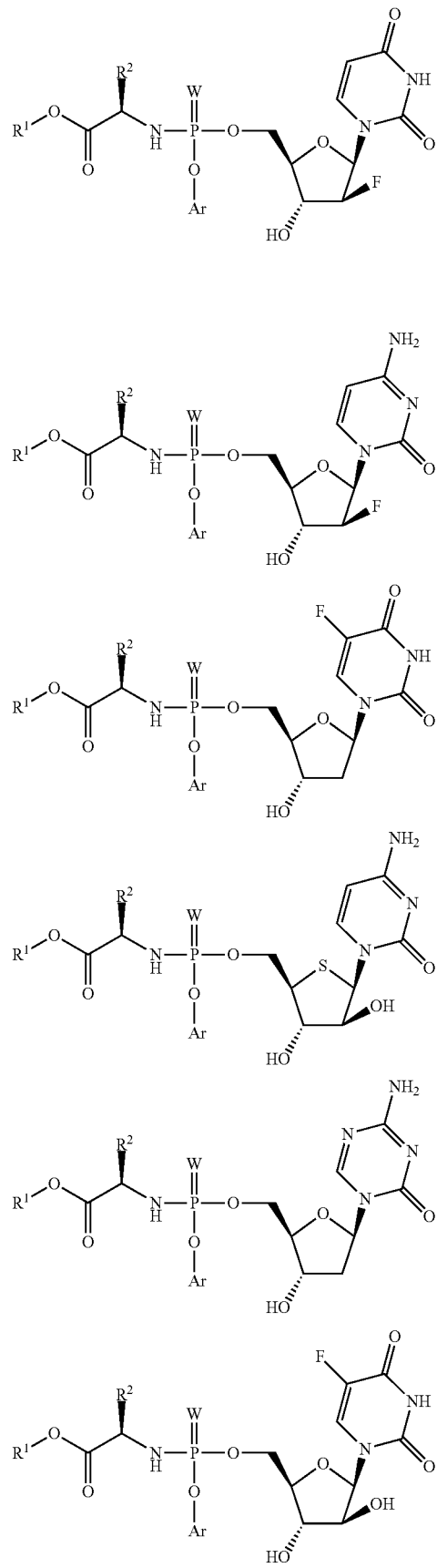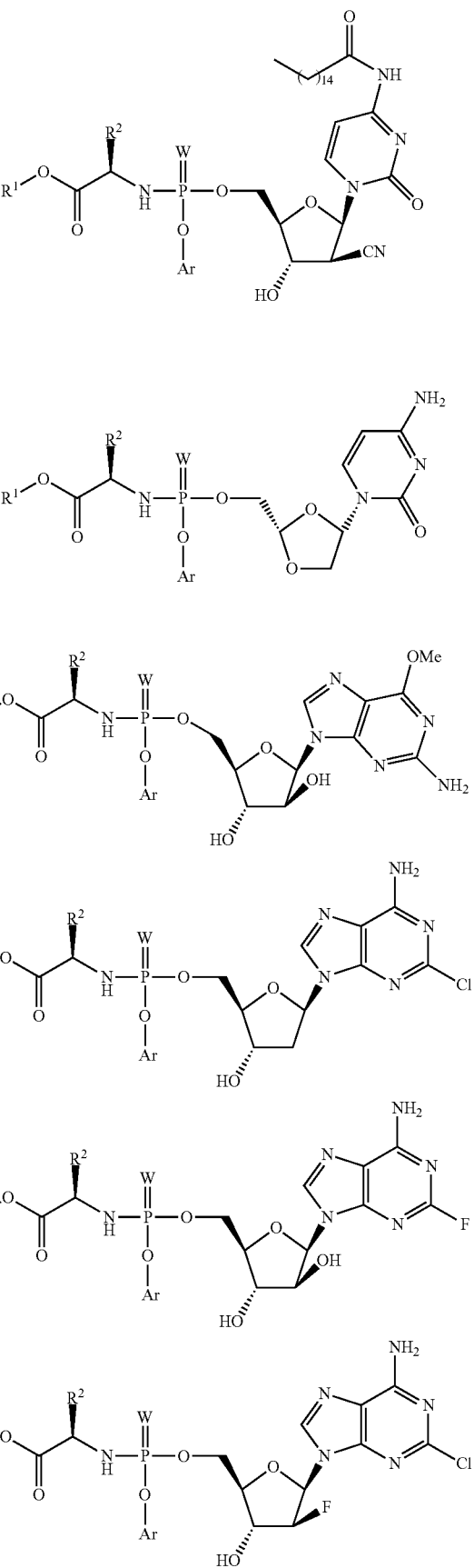

-continued

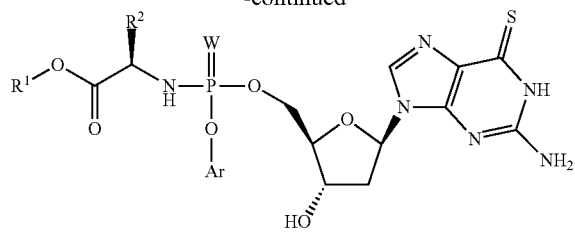
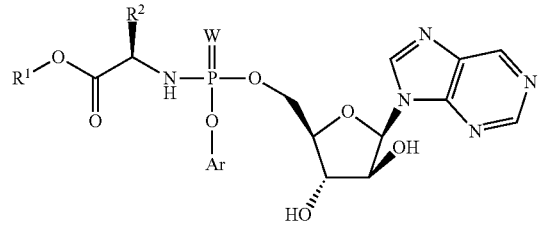
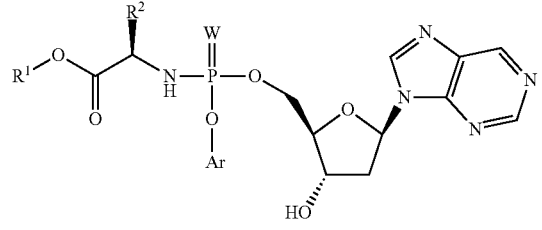
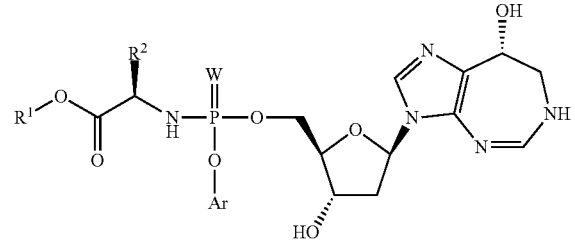
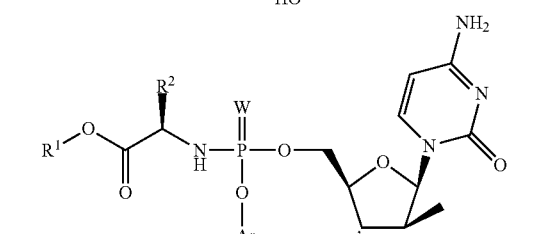
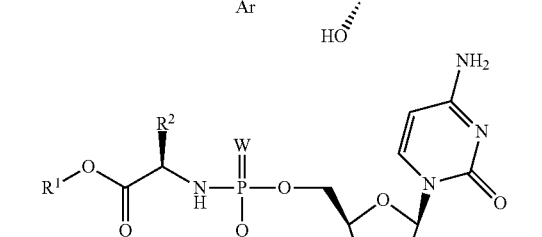
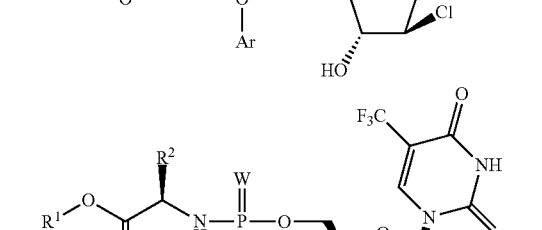
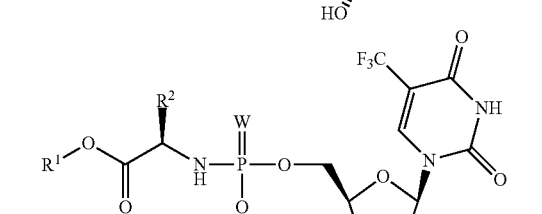

-continued

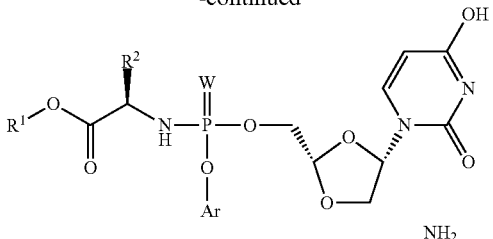
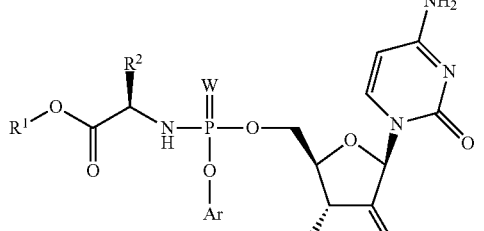
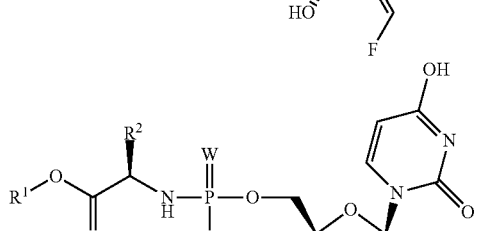
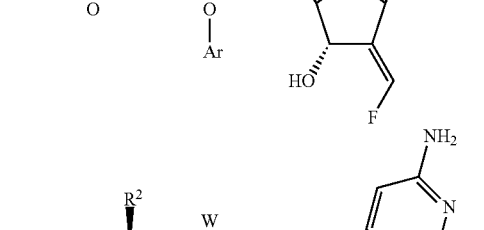
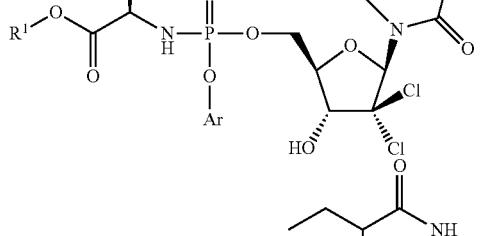
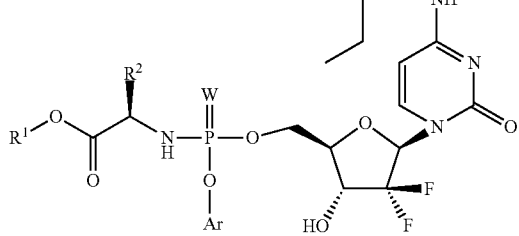
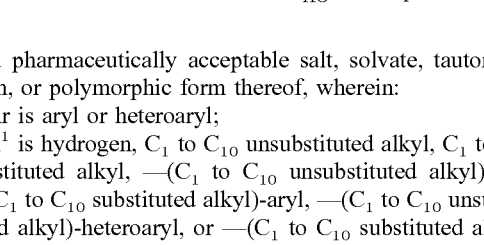

or a pharmaceutically acceptable salt, solvate, tautomeric form, or polymorphic form thereof, wherein:

Ar is aryl or heteroaryl;

$R^1$ is hydrogen, $C_1$ to $C_{10}$ unsubstituted alkyl, $C_1$ to $C_{10}$ substituted alkyl, —($C_1$ to $C_{10}$ unsubstituted alkyl)-aryl, —($C_1$ to $C_{10}$ substituted alkyl)-aryl, —($C_1$ to $C_{10}$ unsubstituted alkyl)-heteroaryl, or —($C_1$ to $C_{10}$ substituted alkyl)-heteroaryl;

$R^2$ is $C_1$ to $C_{10}$ unsubstituted alkyl, $C_1$ to $C_{10}$ substituted alkyl, —($C_1$ to $C_{10}$ unsubstituted alkyl)-aryl, —($C_1$ to $C_{10}$ substituted alkyl)-aryl, —($C_1$ to $C_{10}$ unsubstituted alkyl)-heterocyclo, —($C_1$ to $C_{10}$ substituted alkyl)-heterocyclo, —(C₁ to C₁₀ unsubstituted alkyl)-C(O)OH, —(C₁ to C₁₀ substituted alkyl)-C(O)OH, —(C₁ to C₁₀ unsubstituted alkyl)-heteroaryl, —(C₁ to C₁₀ substituted alkyl)-heteroaryl, —(C₁ to C₁₀ unsubstituted alkyl)-NR¹'R²', —(C₁ to C₁₀ substituted alkyl)-NR¹'R²', —(C₁ to C₁₀ unsubstituted alkyl)-OH, —(C₁ to C₁₀ substituted alkyl)-OH, —(C₁ to C₁₀ unsubstituted alkyl)-NR¹'—C(NH)—NR¹'R²', —(C₁ to C₁₀ substituted alkyl)-NR¹'—C(NH)—NR¹'R², —(C₁ to C₁₀ unsubstituted alkyl)-C(O)—NR¹'R²', —(C₁ to C₁₀ substituted alkyl)-C(O)—NR¹'R²', —(C₁ to C₁₀ unsubstituted alkyl)-SH, —(C₁ to C₁₀ substituted alkyl)-SH, —(C₁ to C₁₀ unsubstituted alkyl)-C(O)—NR¹'R²', —(C₁ to C₁₀ substituted alkyl)-C(O)—NR¹'R²', —(C₁ to C₁₀ unsubstituted alkyl)-S—(C₁ to C₁₀ unsubstituted alkyl), —(C₁ to C₁₀ unsubstituted alkyl)-S—(C₁ to C₁₀ substituted alkyl), —(C₁ to C₁₀ substituted alkyl)-S—(C₁ to C₁₀ unsubstituted alkyl), —(C₁ to C₁₀ substituted alkyl)-S—(C₁ to C₁₀ substituted alkyl), —(C₁ to C₁₀ unsubstituted alkyl)-aryl-OH, or —(C₁ to C₁₀ substituted alkyl)-aryl-OH;

$R^{1'}$ and $R^{2'}$ at each occurrence are independently hydrogen, $C_1$ to $C_{10}$ unsubstituted alkyl, $C_1$ to $C_{10}$ substituted alkyl, $C_2$-$C_{11}$ unsubstituted alkenyl, $C_2$-$C_{11}$ substituted alkenyl, $C_2$-$C_{11}$ unsubstituted alkynyl, $C_2$-$C_{11}$ substituted alkynyl, cycloalkyl, heterocyclo, aryl, or heteroaryl;

R' at each occurrence is independently $C_1$ to $C_{10}$ unsubstituted alkyl, $C_1$ to $C_{10}$ substituted alkyl, or cycloalkyl;

aryl at each occurrence is independently $C_6$-$C_{12}$ unsubstituted aryl; or $C_6$-$C_{12}$ aryl substituted with one or more fluoro, chloro, bromo, iodo, methyl, $CF_3$, $CCl_3$, $CFCl_2$, $CF_2Cl$, ethyl, $CH_2CF_3$, $CF_2CF_3$, propyl, isopropyl, butyl, isobutyl, secbutyl, t-butyl, pentyl, isopentyl, neopentyl, hexyl, isohexyl, 3-methylpentyl, 2,2-dimethylbutyl, 2,3-dimethylbutyl, hydroxyl, —NH₂, —NH—(C₁ to C₁₀ unsubstituted alkyl), —NH—(C₁ to C₁₀ substituted alkyl), —NH-aryl, —NH—(C₃-C₁₅ cycloalkyl), methoxy, ethoxy, n-propoxy, isopropoxy, n-butoxy, tert-butoxy, sec-butoxy, n-pentoxy, n-hexoxy, 1,2-dimethylbutoxy, oxo, epoxy, hydroxyl, nitro, cyano, sulfonic acid, sulfate, phosphonic acid, phosphate, or phosphonate;

cycloalkyl at each occurrence is independently $C_3$-$C_{15}$ unsubstituted cycloalkyl or $C_3$-$C_{14}$ cycloalkyl substituted with fluoro, chloro, bromo, iodo, oxo, epoxy, hydroxyl, carbonyl, sulfanyl, —NH₂, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate;

heterocyclo at each occurrence is independently a monovalent monocyclic or multicyclic non-aromatic that contains at least one non-aromatic ring containing one or more heteroatoms independently selected from O, S, and N in the ring, wherein heterocyclo is bonded through the non-aromatic ring, and wherein heterocyclo has from three to twenty ring atoms;

heteroaryl at each occurrence is independently a monovalent monocyclic or multicyclic aromatic that contains at least one aromatic ring containing one or more heteroatoms independently selected from O, S, and N in the ring, wherein heteroaryl is bonded through the aromatic ring, wherein the total number of heteroatoms in each ring is four or less and each ring contains at least one carbon atom, and wherein heteroaryl has from five to twenty ring atoms;

substituted alkenyl at each occurrence is independently a straight-chained or branched olefinically unsaturated hydrocarbon having at least one site of olefinic unsaturation substituted with fluoro, chloro, bromo, iodo, oxo, epoxy, hydroxyl, carbonyl, sulfanyl, —NH₂, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate;

substituted alkynyl at each occurrence is independently a straight-chained or branched acetylenically unsaturated hydrocarbon having at least one site of alkynyl unsaturation substituted with fluoro, chloro, bromo, iodo, oxo, epoxy, hydroxyl, carbonyl, sulfanyl, —NH₂, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate; and substituted alkyl at each occurrence is independently alkyl substituted with fluoro, chloro, bromo, iodo, oxo, epoxy, hydroxyl, carbonyl, sulfanyl, —NH₂, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate.

In certain embodiments, provided herein are compounds according to any of the following formulae:

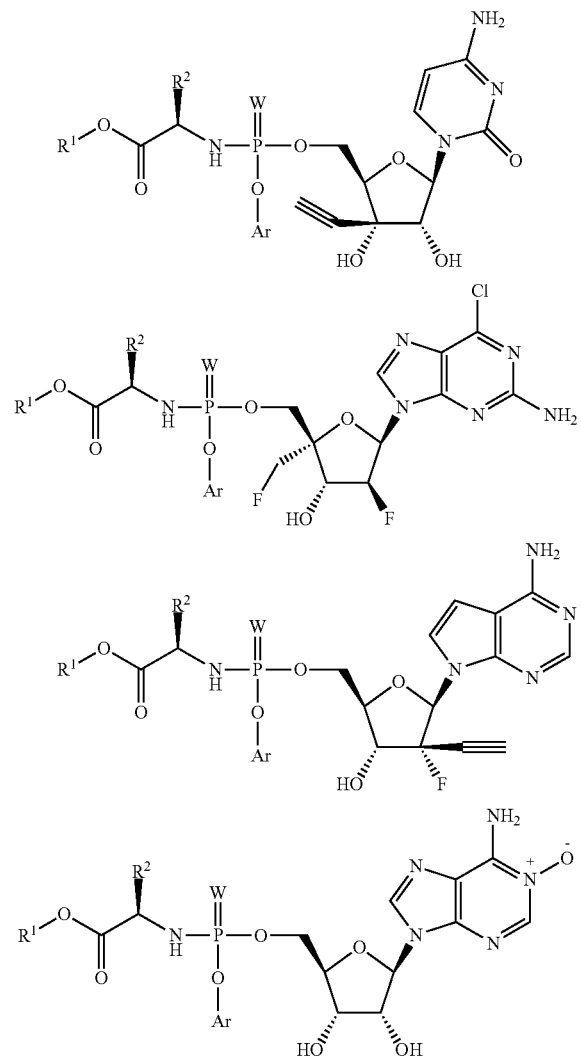

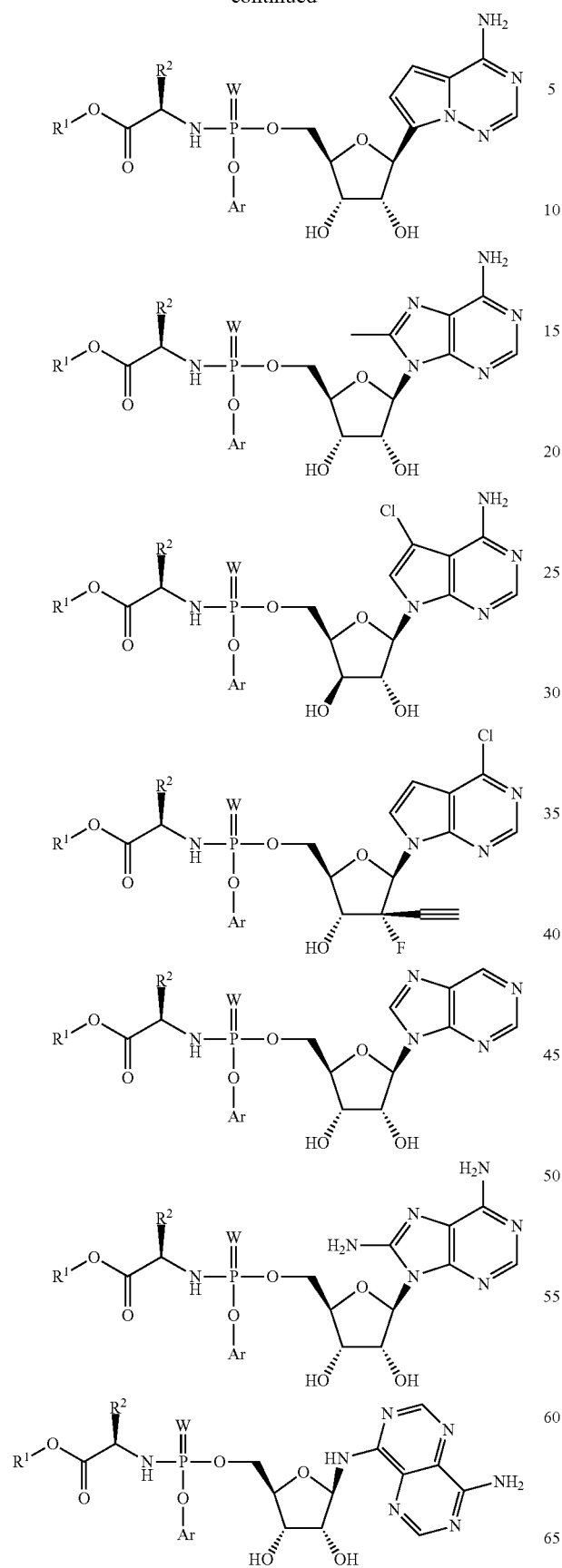
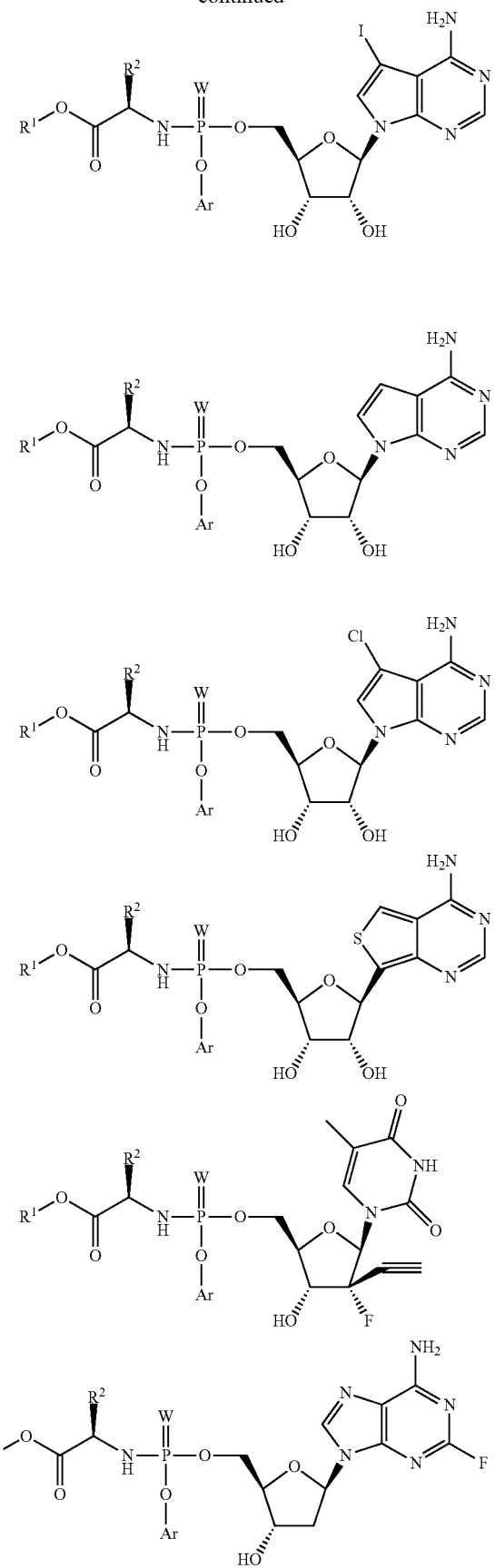

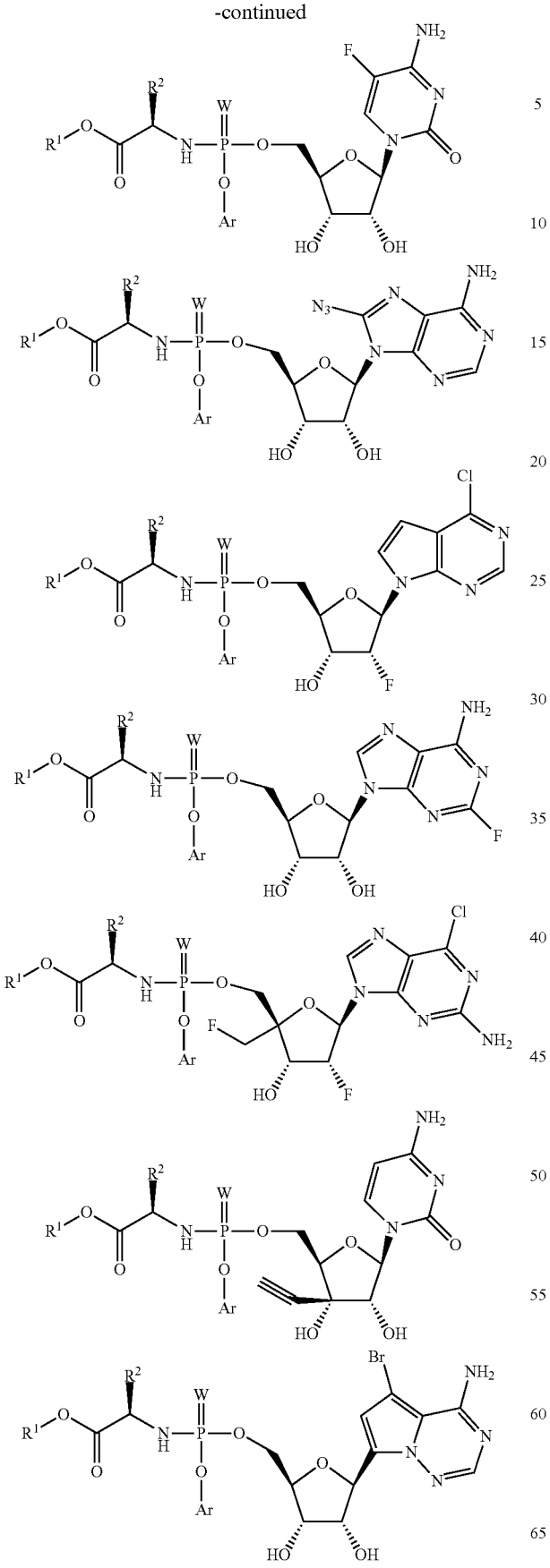
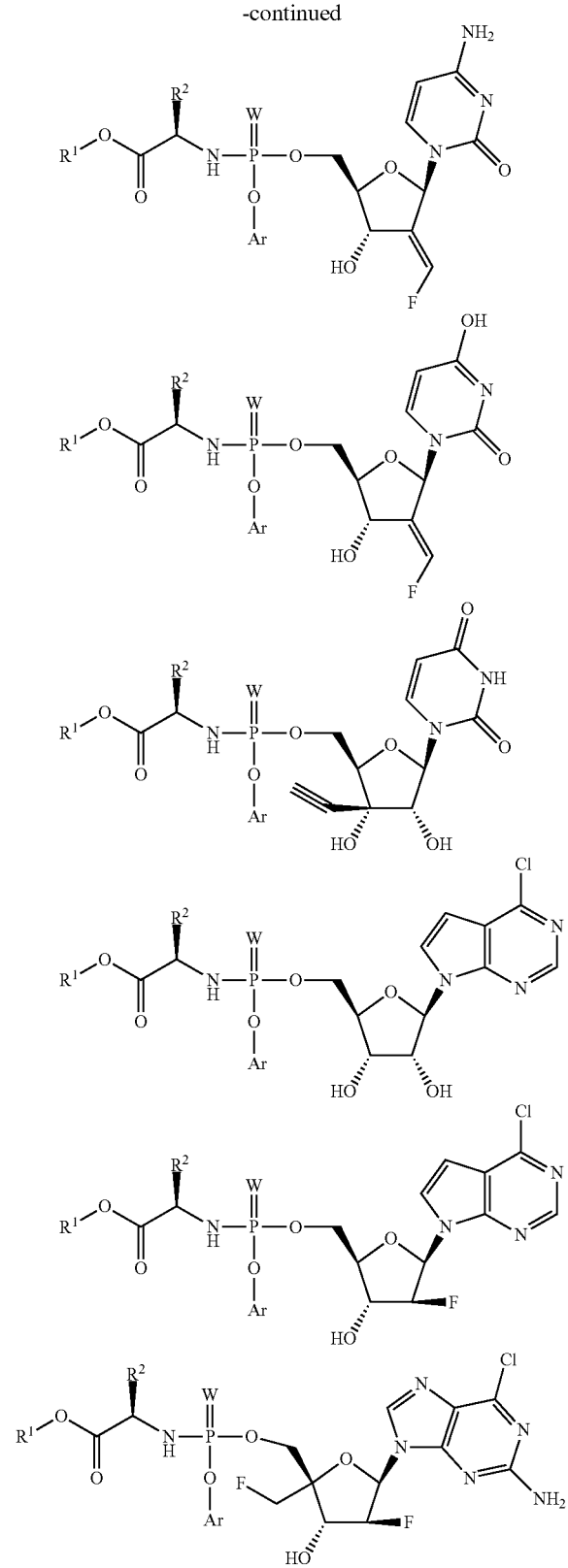
or a pharmaceutically acceptable salt, solvate, stereoisomeric form, tautomeric form or polymorphic form thereof, wherein W, Ar, $R^1$ and $R^2$ are as described in the context of Formula I.

In certain embodiments, provided herein are compounds according to any of the following formulae:
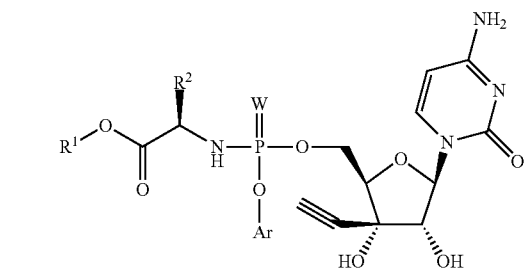
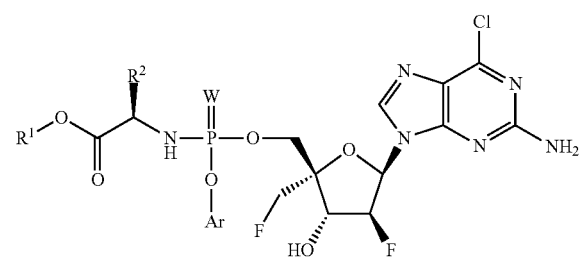
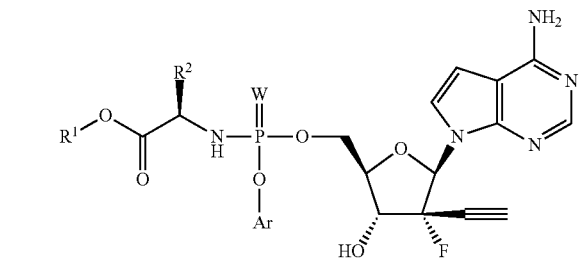
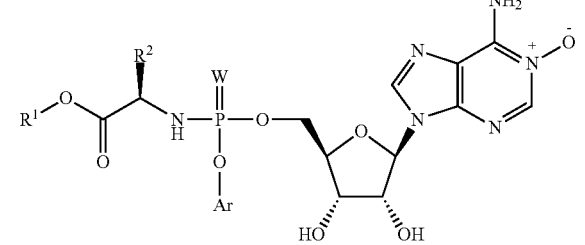
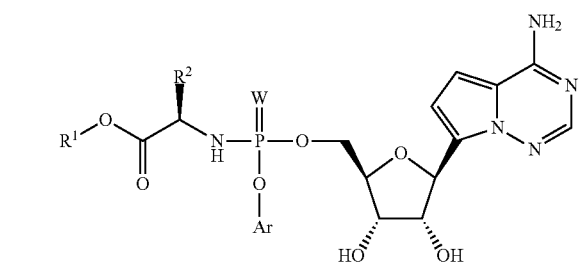
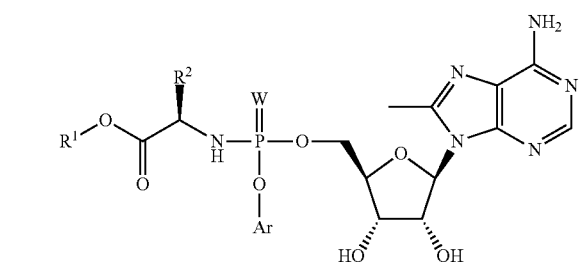
-continued
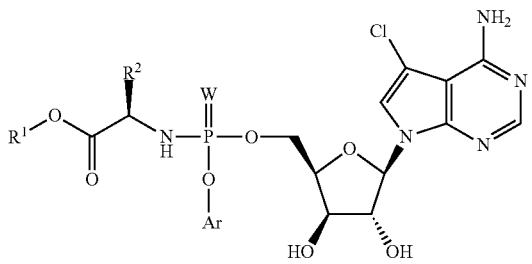
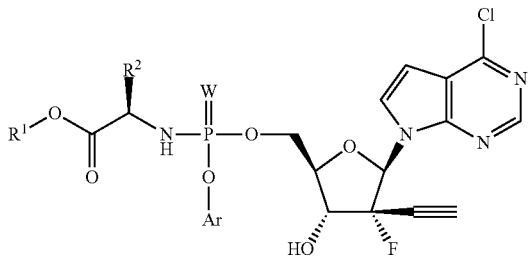
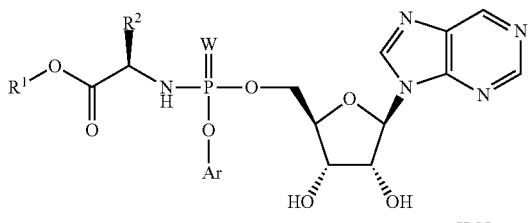
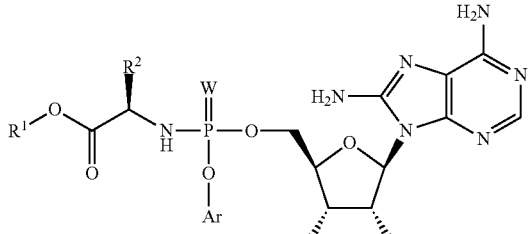
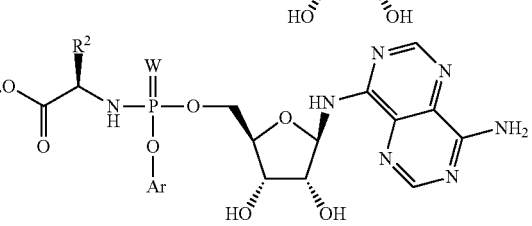
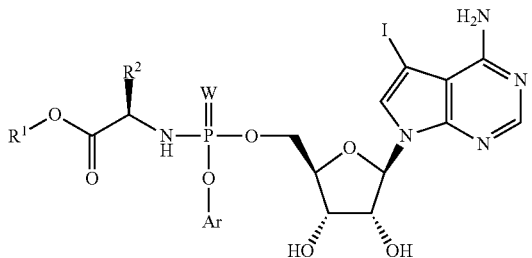
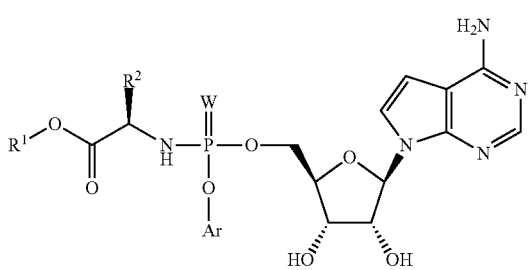

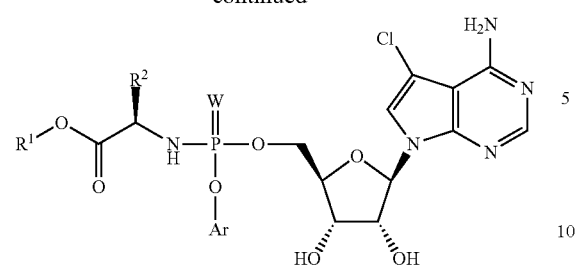
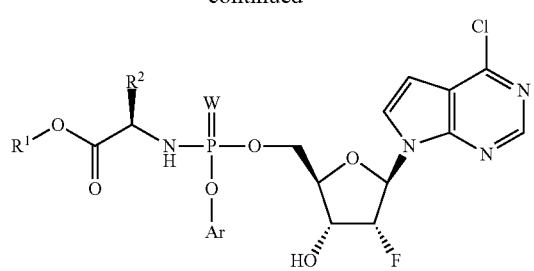
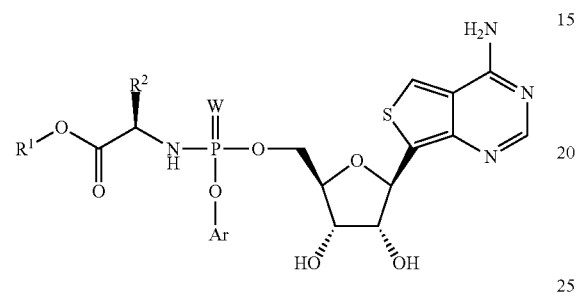
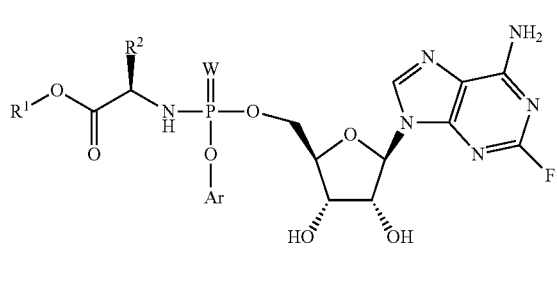
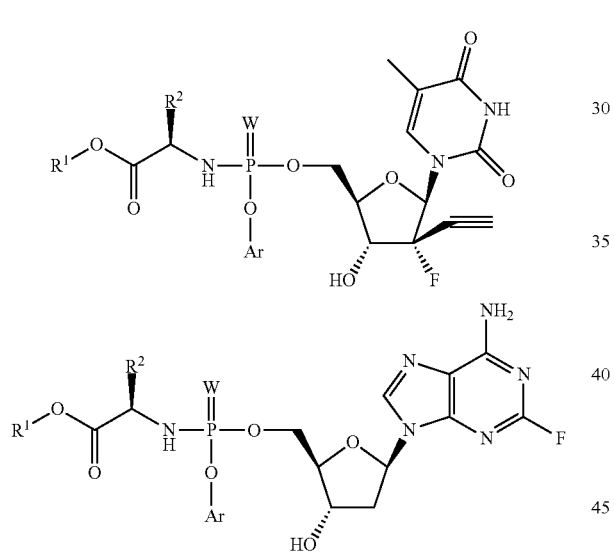
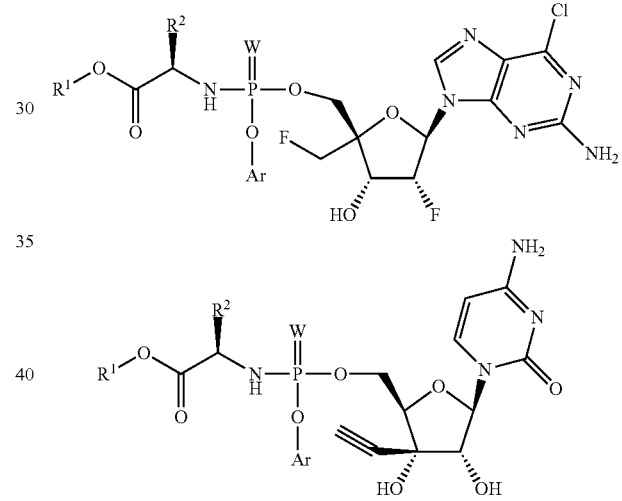
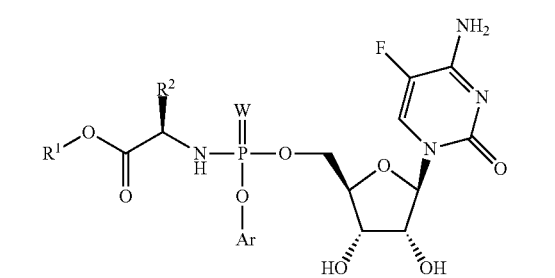
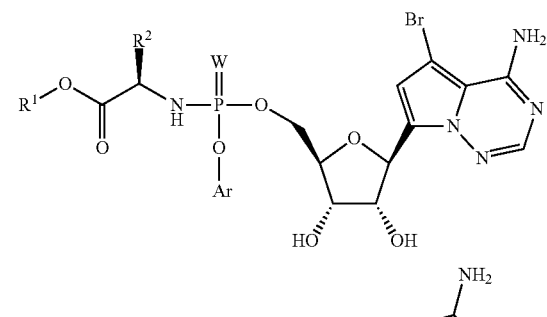
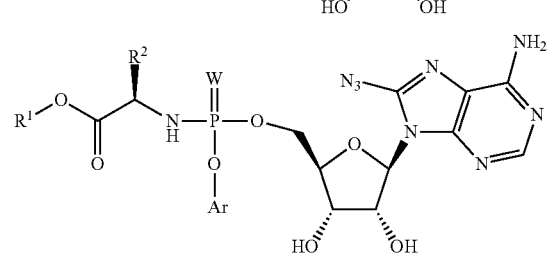
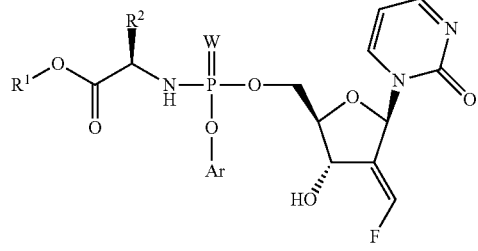

-continued

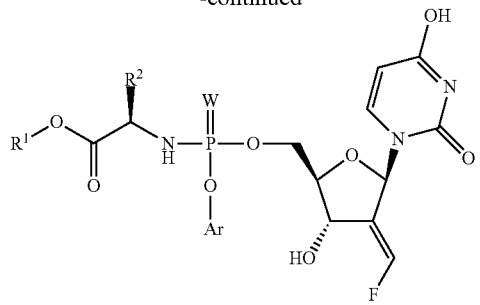

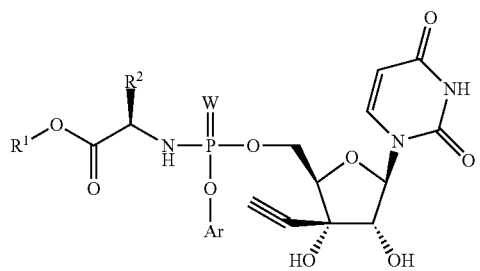

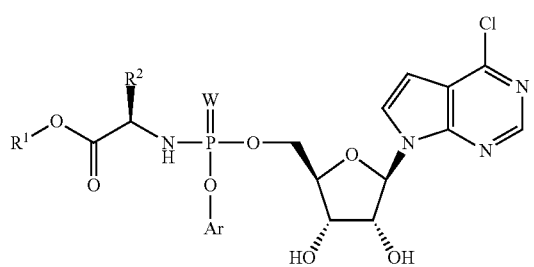

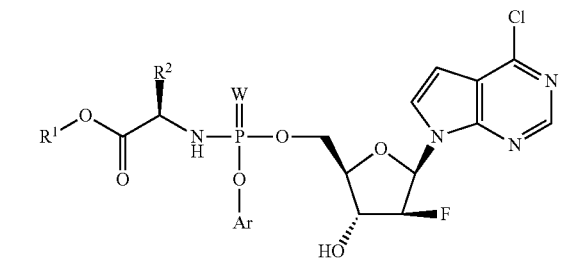

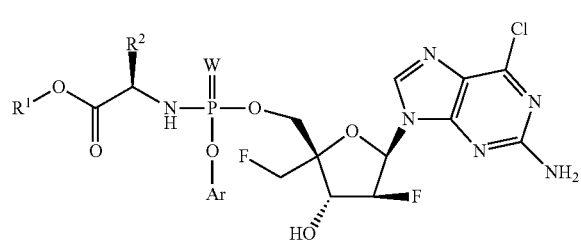

or a pharmaceutically acceptable salt, solvate, tautomeric form or polymorphic form thereof, wherein:

Ar is aryl or heteroaryl;

$R^1$ is hydrogen, $C_1$ to $C_{10}$ unsubstituted alkyl, $C_1$ to $C_{10}$ substituted alkyl, —($C_1$ to $C_{10}$ unsubstituted alkyl)-aryl, —($C_1$ to $C_{10}$ substituted alkyl)-aryl, —($C_1$ to $C_{10}$ unsubstituted alkyl)-heteroaryl, or —($C_1$ to $C_{10}$ substituted alkyl)-heteroaryl;

$R^2$ is $C_1$ to $C_{10}$ unsubstituted alkyl, $C_1$ to $C_{10}$ substituted alkyl, —($C_1$ to $C_{10}$ unsubstituted alkyl)-aryl, —($C_1$ to $C_{10}$ substituted alkyl)-aryl, —($C_1$ to $C_{10}$ unsubstituted alkyl)-heterocyclo, —($C_1$ to $C_{10}$ substituted alkyl)-heterocyclo, —($C_1$ to $C_{10}$ unsubstituted alkyl)-C(O)OH, —($C_1$ to $C_{10}$ substituted alkyl)-C(O)OH, —($C_1$ to $C_{10}$ unsubstituted alkyl)-heteroaryl, —($C_1$ to $C_{10}$ substituted alkyl)-heteroaryl, —($C_1$ to $C_{10}$ unsubstituted alkyl)-$NR^{1'}R^{2'}$, —($C_1$ to $C_{10}$ substituted alkyl)-$NR^{1'}R^{2'}$, —($C_1$ to $C_{10}$ unsubstituted alkyl)-OH, —($C_1$ to $C_{10}$ substituted alkyl)-OH, —($C_1$ to $C_{10}$ unsubstituted alkyl)-$NR^{1'}$—C(NH)—$NR^{1'}R^{2'}$, —($C_1$ to $C_{10}$ substituted alkyl)-$NR^{1'}$—C(NH)—$NR^{1'}R^2$, —($C_1$ to $C_{10}$ unsubstituted alkyl)-C(O)—$NR^{1'}R^{2'}$, —($C_1$ to $C_{10}$ substituted alkyl)-C(O)—$NR^{1'}R^{2'}$, —($C_1$ to $C_{10}$ unsubstituted alkyl)-SH, —($C_1$ to $C_{10}$ substituted alkyl)-SH, —($C_1$ to $C_{10}$ unsubstituted alkyl)-C(O)—$NR^{1'}R^{2'}$, —($C_1$ to $C_{10}$ substituted alkyl)-C(O)—$NR^{1'}R^{2'}$, —($C_1$ to $C_{10}$ unsubstituted alkyl)-S—($C_1$ to $C_{10}$ unsubstituted alkyl), —($C_1$ to $C_{10}$ unsubstituted alkyl)-S—($C_1$ to $C_{10}$ substituted alkyl), —($C_1$ to $C_{10}$ substituted alkyl)-S—($C_1$ to $C_{10}$ unsubstituted alkyl), —($C_1$ to $C_{10}$ substituted alkyl)-S—($C_1$ to $C_{10}$ substituted alkyl), —($C_1$ to $C_{10}$ unsubstituted alkyl)-aryl-OH, or —($C_1$ to $C_{10}$ substituted alkyl)-aryl-OH;

$R^{1'}$ and $R^{2'}$ at each occurrence are independently hydrogen, $C_1$ to $C_{10}$ unsubstituted alkyl, $C_1$ to $C_{10}$ substituted alkyl, $C_2$-$C_{11}$ unsubstituted alkenyl, $C_2$-$C_{11}$ substituted alkenyl, $C_2$-$C_{11}$ unsubstituted alkynyl, $C_2$-$C_{11}$ substituted alkynyl, cycloalkyl, heterocyclo, aryl, or heteroaryl;

R' at each occurrence is independently $C_1$ to $C_{10}$ unsubstituted alkyl, $C_1$ to $C_{10}$ substituted alkyl, or cycloalkyl;

aryl at each occurrence is independently $C_6$-$C_{12}$ unsubstituted aryl; or $C_6$-$C_{12}$ aryl substituted with one or more fluoro, chloro, bromo, iodo, methyl, $CF_3$, $CCl_3$, $CFCl_2$, $CF_2Cl$, ethyl, $CH_2CF_3$, $CF_2CF_3$, propyl, isopropyl, butyl, isobutyl, secbutyl, t-butyl, pentyl, isopentyl, neopentyl, hexyl, isohexyl, 3-methylpentyl, 2,2-dimethylbutyl, 2,3-dimethylbutyl, hydroxyl, —$NH_2$, —NH—($C_1$ to $C_{10}$ unsubstituted alkyl), —NH—($C_1$ to $C_{10}$ substituted alkyl), —NH-aryl, —NH—($C_3$-$C_{15}$ cycloalkyl), methoxy, ethoxy, n-propoxy, isopropoxy, n-butoxy, tert-butoxy, sec-butoxy, n-pentoxy, n-hexoxy, 1,2-dimethylbutoxy, oxo, epoxy, hydroxyl, nitro, cyano, sulfonic acid, sulfate, phosphonic acid, phosphate, or phosphonate;

cycloalkyl at each occurrence is independently $C_3$-$C_{15}$ unsubstituted cycloalkyl or $C_3$-$C_{15}$ cycloalkyl substituted with fluoro, chloro, bromo, iodo, oxo, epoxy, hydroxyl, carbonyl, sulfanyl, —$NH_2$, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate;

heterocyclo at each occurrence is independently a monovalent monocyclic or multicyclic non-aromatic that contains at least one non-aromatic ring containing one or more heteroatoms independently selected from O, S, and N in the ring, wherein heterocyclo is bonded through the non-aromatic ring, and wherein heterocyclo has from three to twenty ring atoms;

heteroaryl at each occurrence is independently a monovalent monocyclic or multicyclic aromatic that contains at least one aromatic ring containing one or more heteroatoms independently selected from O, S, and N in the ring, wherein heteroaryl is bonded through the aromatic ring, wherein the total number of heteroatoms in each ring is four or less and each ring contains at least one carbon atom, and wherein heteroaryl has from five to twenty ring atoms;

substituted alkenyl at each occurrence is independently a straight-chained or branched olefinically unsaturated hydrocarbon having at least one site of olefinic unsaturation substituted with fluoro, chloro, bromo, iodo, oxo, epoxy, hydroxyl, carbonyl, sulfanyl, —NH₂, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate;

substituted alkynyl at each occurrence is independently a straight-chained or branched acetylenically unsaturated hydrocarbon having at least one site of alkynyl unsaturation substituted with fluoro, chloro, bromo, iodo, oxo, epoxy, hydroxyl, carbonyl, sulfanyl, —NH₂, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate; and substituted alkyl at each occurrence is independently alkyl substituted with fluoro, chloro, bromo, iodo, oxo, epoxy, hydroxyl, carbonyl, sulfanyl, —NH₂, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate.

In certain embodiments, provided herein are compounds according to any of the following formulae:

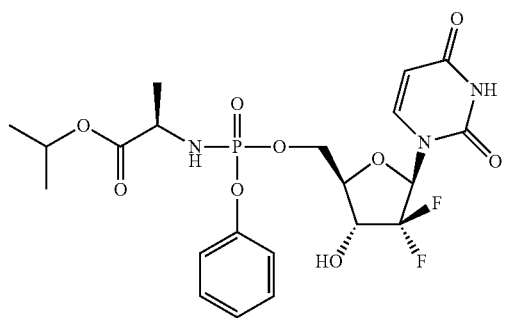

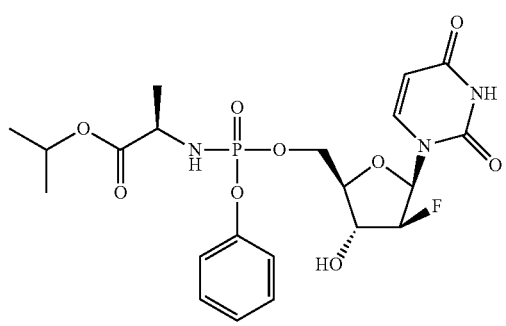

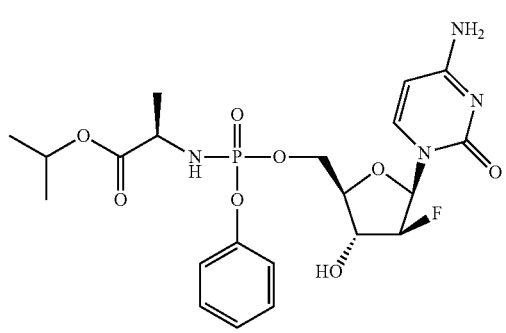

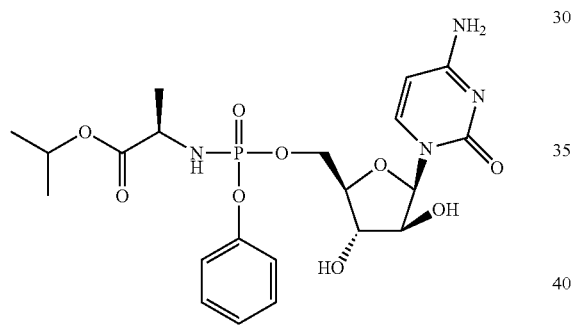

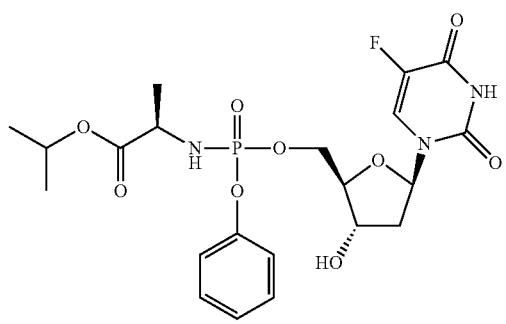

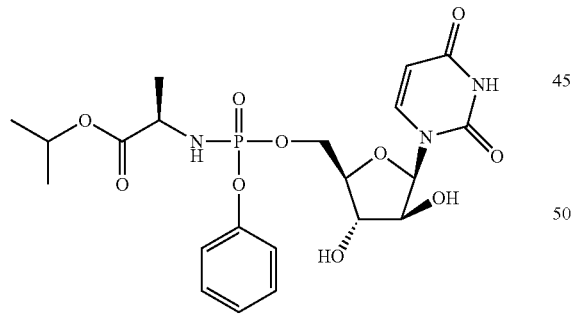

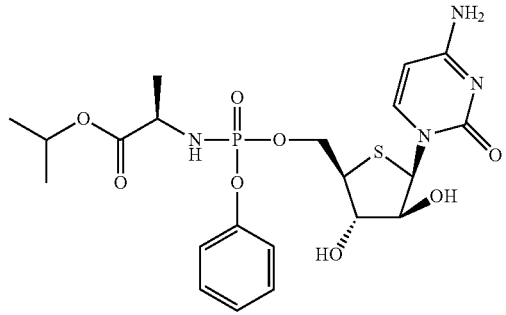

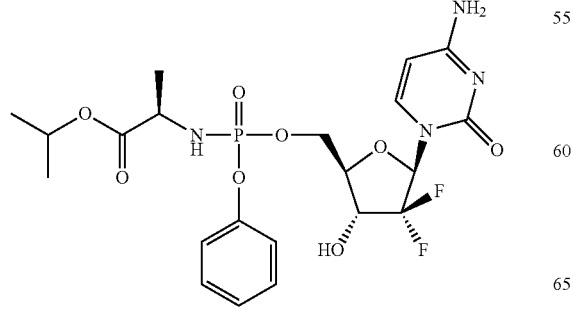

67
-continued
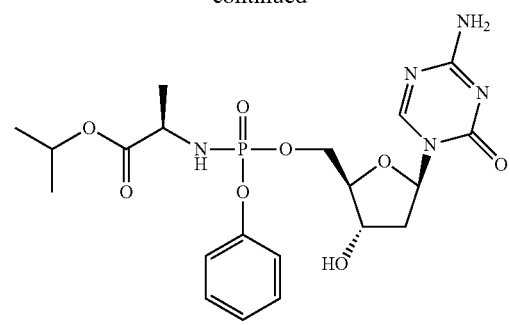
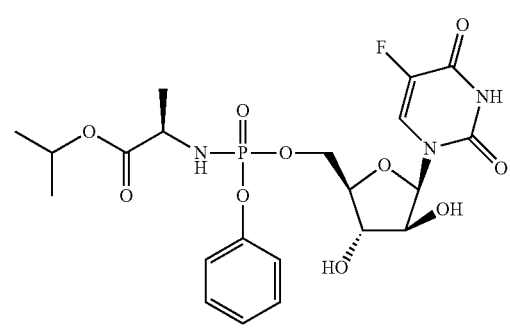
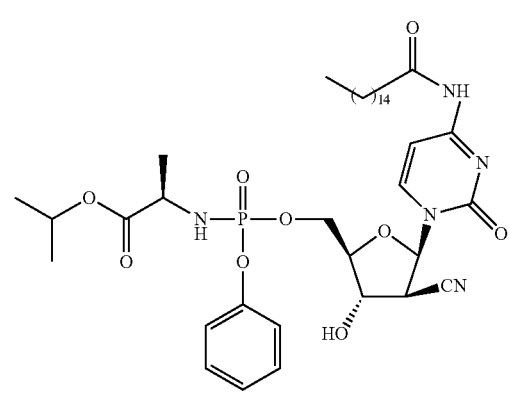
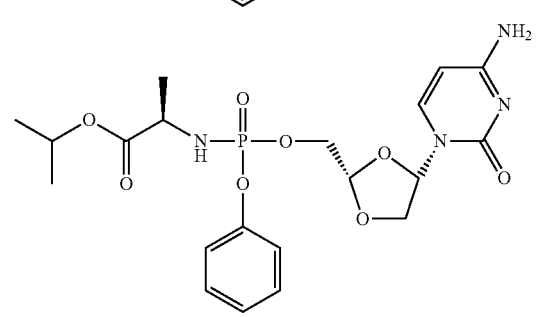
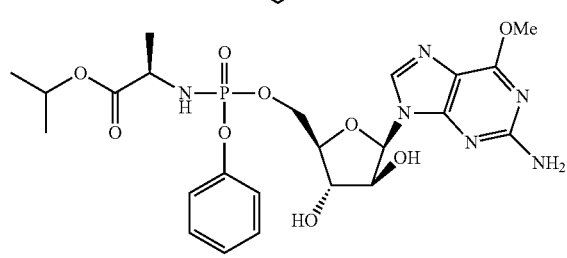
68
-continued
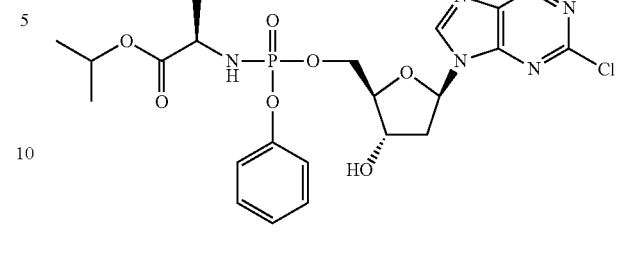
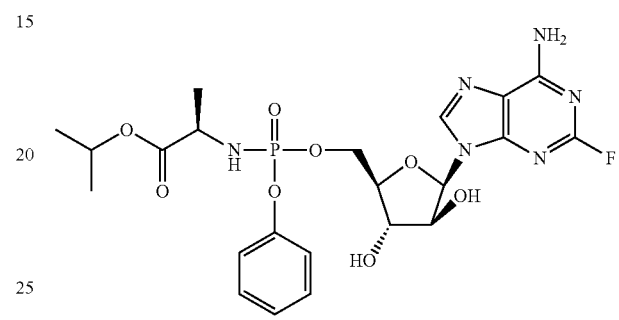
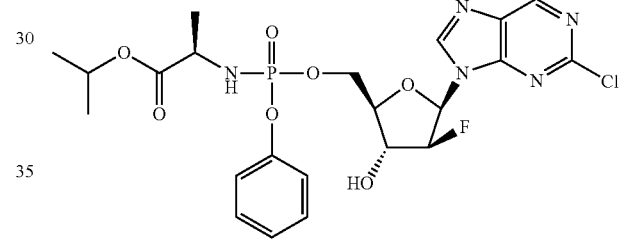
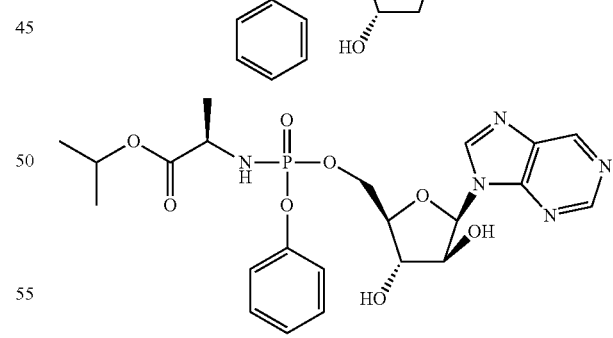
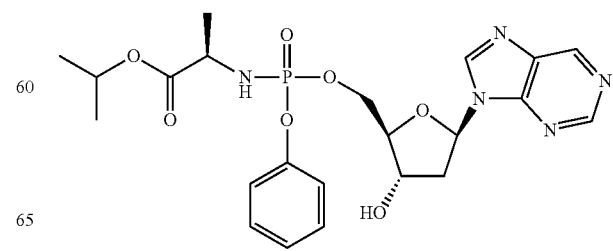

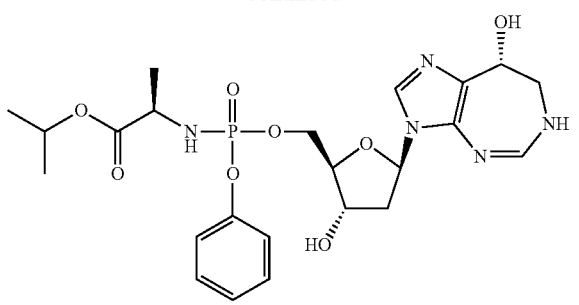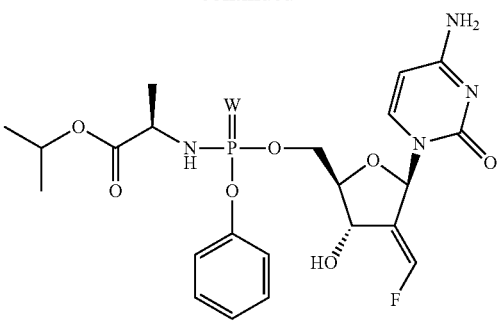
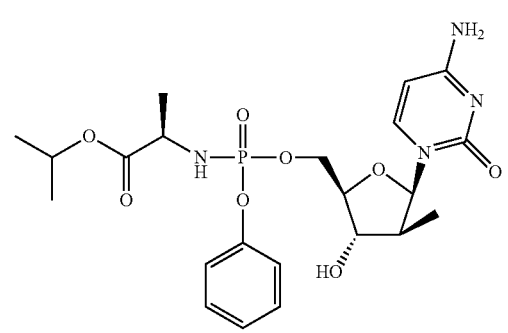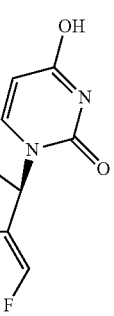
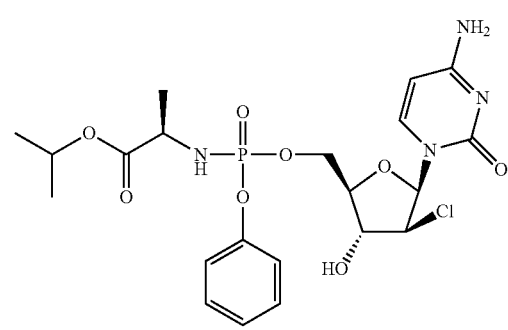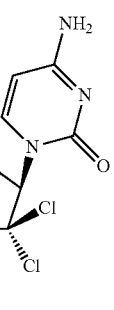
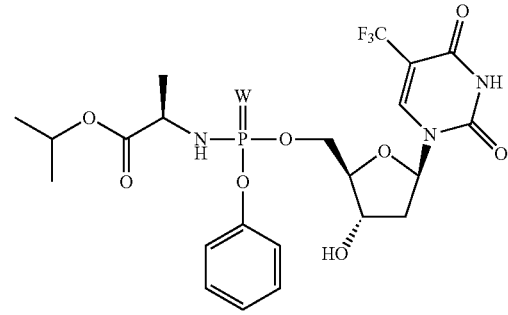
or a pharmaceutically acceptable salt, solvate, stereoisomeric form, tautomeric form or polymorphic form thereof.
In certain embodiments, provided herein are compounds according to any of the following formulae:
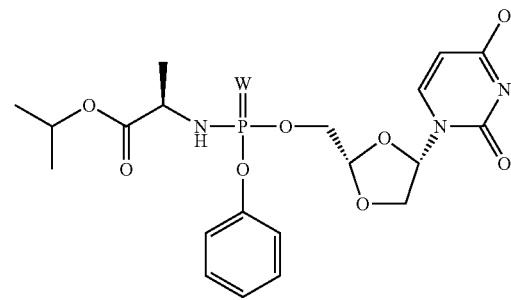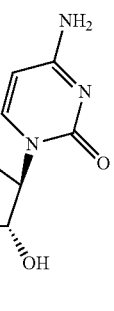

| 71 | 72 |
|---|---|
| -continued | -continued |
| 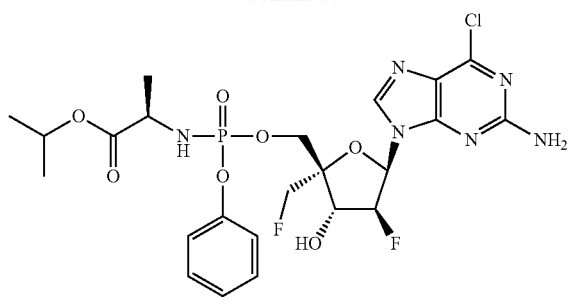 | 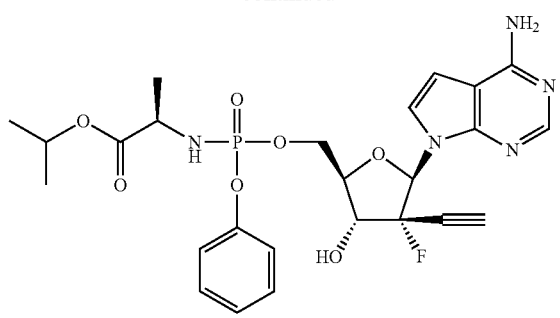 |
| 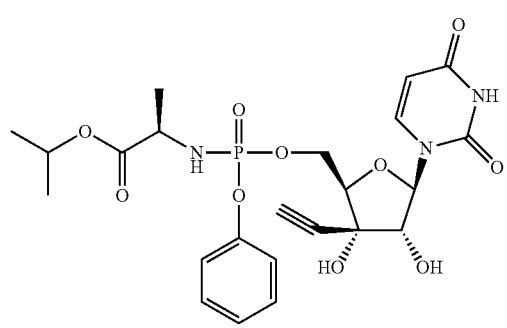 | 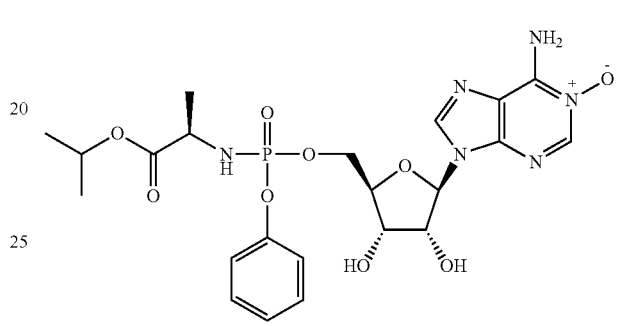 |
| 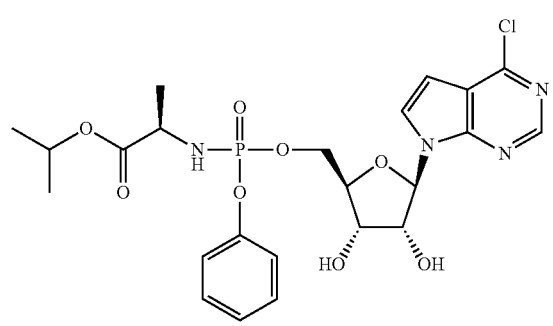 | 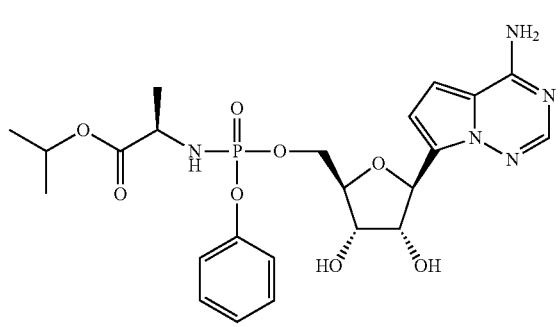 |
| 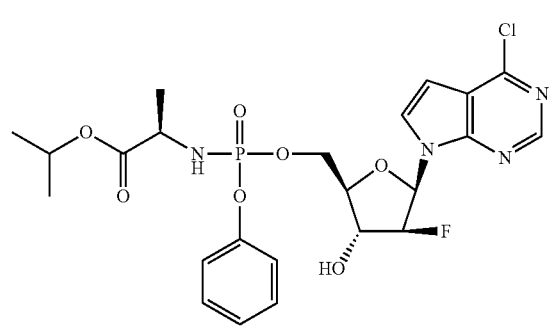 | 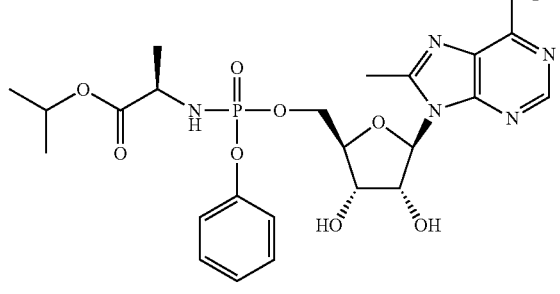 |
| 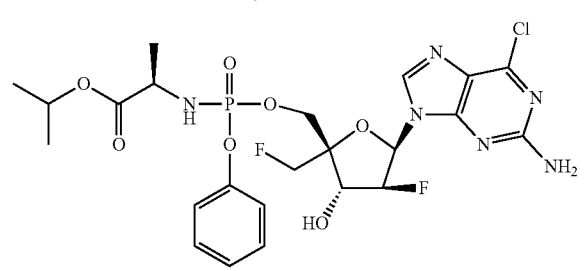 | 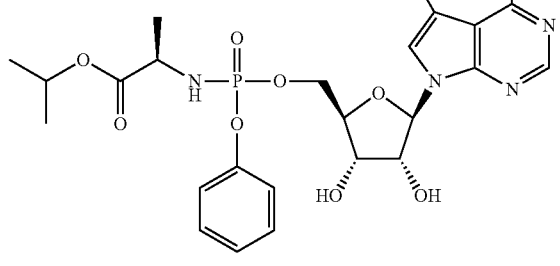 |

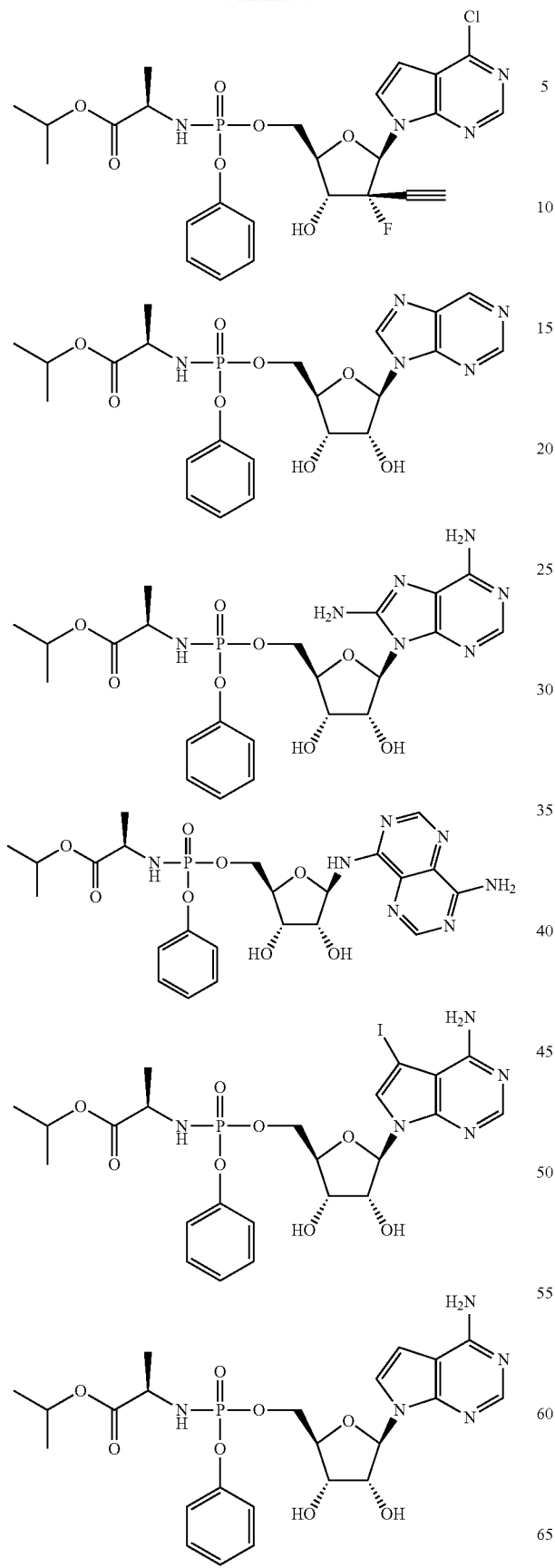
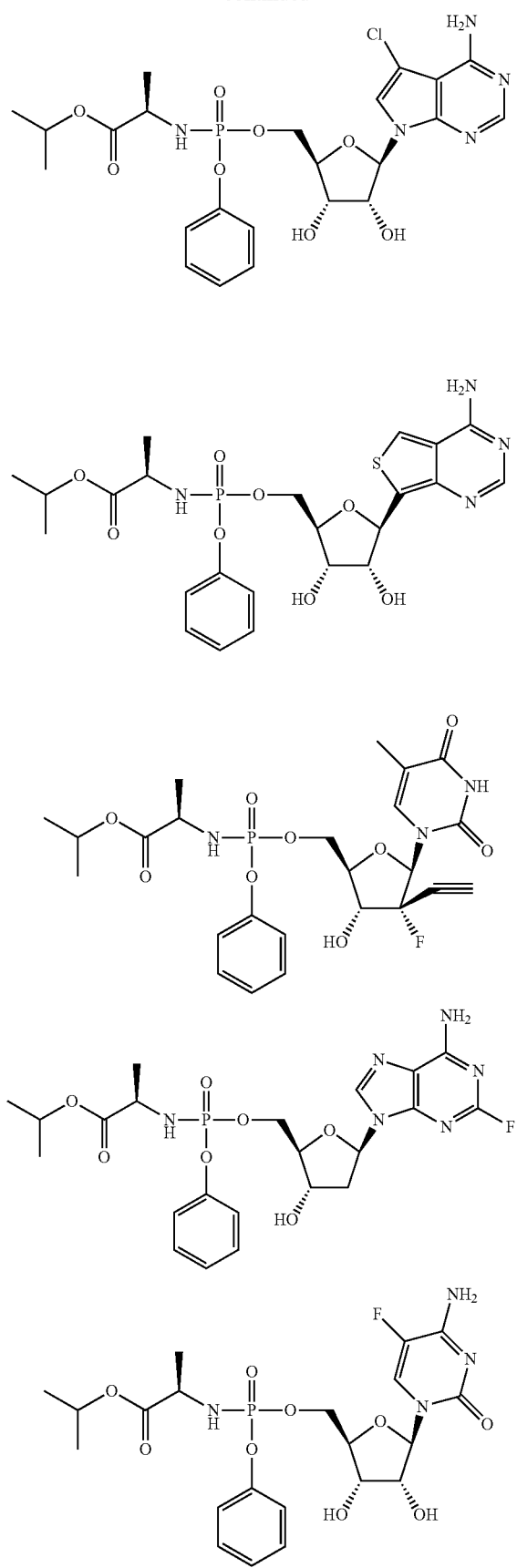

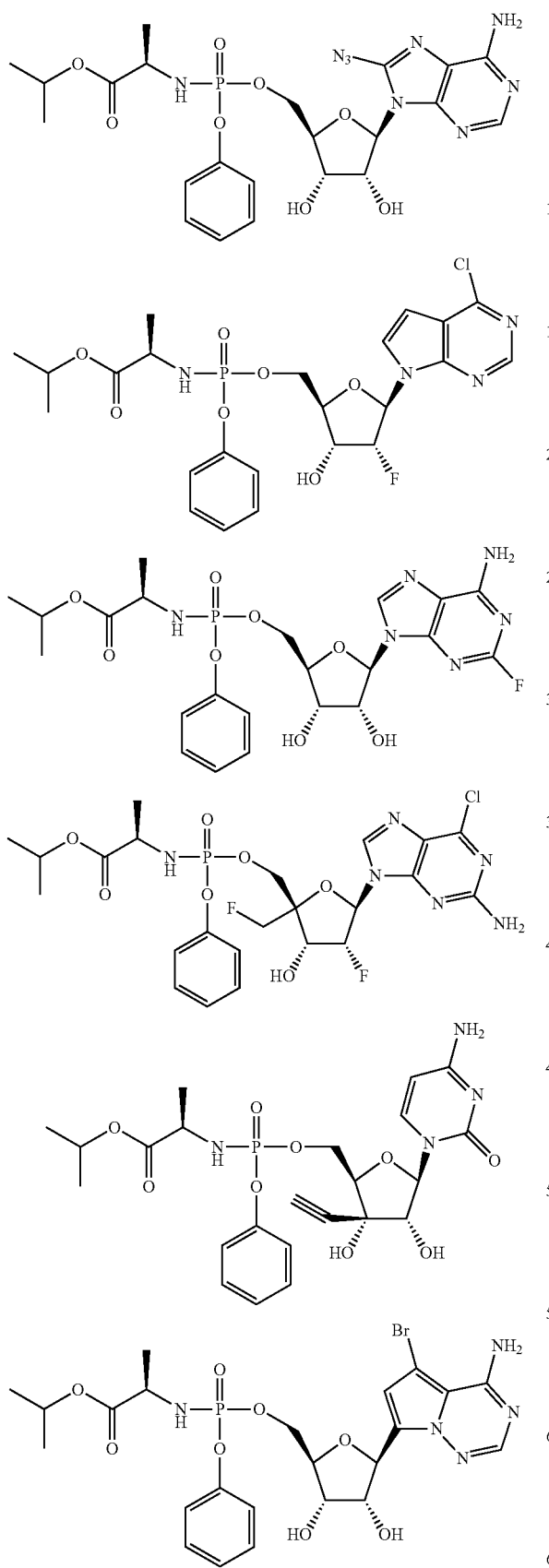

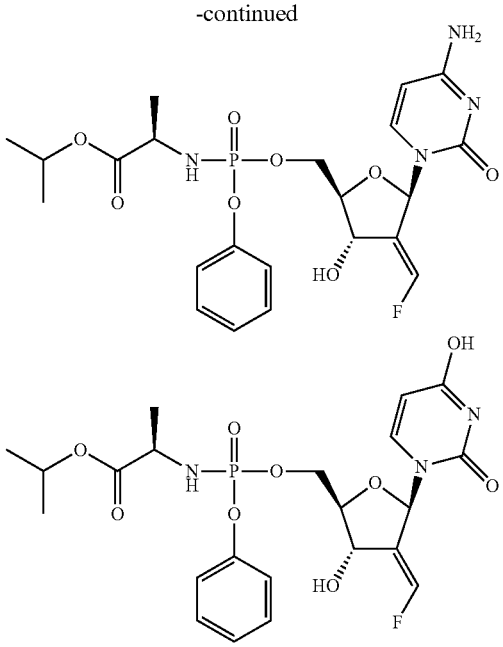

or a pharmaceutically acceptable salt, solvate, stereoisomeric form, tautomeric form or polymorphic form thereof.

In certain embodiments provided herein is a compound according to any of Formulas 1a-98c:

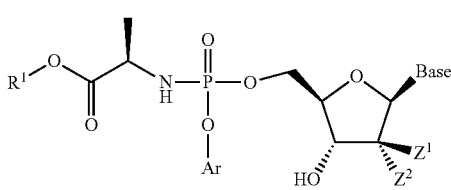

1a-98a

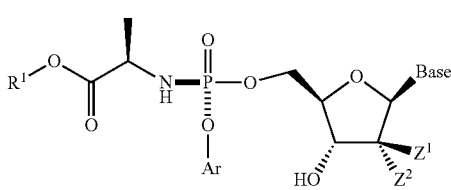

1b-98b

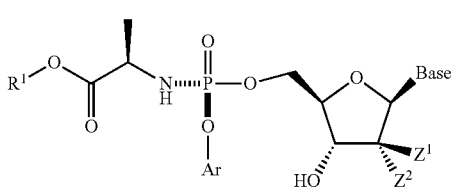

1c-98c

| # | R¹ | Ar | Z² | Z¹ | Base |
|---|---|---|---|---|---|
| 1a/b/c | —CH(CH₃)₂ | —C₆H₅ | —H | —OH | |
| 2a/b/c | —CH(CH₃)₂ | —C₆H₅ | —F | —OH | |
| 3a/b/c | —CH(CH₃)₂ | —C₆H₅ | —OH | —F | |
| 4a/b/c | —CH(CH₃)₂ | —C₆H₅ | —F | —F | cytosine |
| 5a/b/c | —CH(CH₃)₂ | —C₆H₅ | —H | —F | |
| 6a/b/c | —CH(CH₃)₂ | —C₆H₅ | —Cl | —F | |
| 7a/b/c | —CH(CH₃)₂ | —C₆H₅ | —Cl | —Cl | |
| 8a/b/c | —CH(CH₃)₂ | —C₆H₅ | —H | —Cl | |
| 9a/b/c | —CH(CH₃)₂ | —C₆H₅ | —F | —Cl | |

-continued

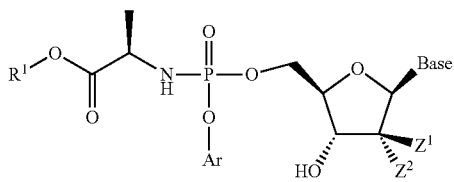
1a-98a

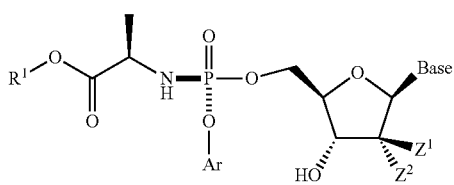
1b-98b

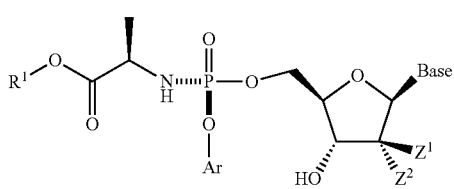
1c-98c

| # | R¹ | Ar | Z² | Z¹ | Base |
|---|---|---|---|---|---|
| 10a/b/c | —CH(CH₃)₂ | —C₆H₅ | —H | —OH | 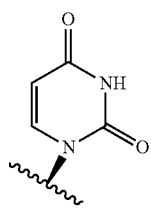 |
| 11a/b/c | —CH(CH₃)₂ | —C₆H₅ | —F | —OH | |
| 12a/b/c | —CH(CH₃)₂ | —C₆H₅ | —OH | —F | |
| 13a/b/c | —CH(CH₃)₂ | —C₆H₅ | —F | —F | |
| 14a/b/c | —CH(CH₃)₂ | —C₆H₅ | —H | —F | |
| 15a/b/c | —CH(CH₃)₂ | —C₆H₅ | —Cl | —F | |
| 16a/b/c | —CH(CH₃)₂ | —C₆H₅ | —Cl | —Cl | |
| 17a/b/c | —CH(CH₃)₂ | —C₆H₅ | —H | —Cl | |
| 18a/b/c | —CH(CH₃)₂ | —C₆H₅ | —F | —Cl | |
| 19a/b/c | —CH(CH₃)₂ | —C₆H₅ | —H | —OH | 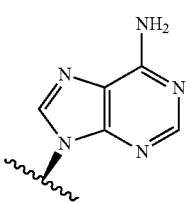 |
| 20a/b/c | —CH(CH₃)₂ | —C₆H₅ | —F | —OH | |
| 21a/b/c | —CH(CH₃)₂ | —C₆H₅ | —OH | —F | |
| 22a/b/c | —CH(CH₃)₂ | —C₆H₅ | —F | —F | |
| 23a/b/c | —CH(CH₃)₂ | —C₆H₅ | —H | —F | |
| 24a/b/c | —CH(CH₃)₂ | —C₆H₅ | —Cl | —F | |
| 25a/b/c | —CH(CH₃)₂ | —C₆H₅ | —Cl | —Cl | |
| 26a/b/c | —CH(CH₃)₂ | —C₆H₅ | —H | —Cl | |
| 27a/b/c | —CH(CH₃)₂ | —C₆H₅ | —F | —Cl | |
| 28a/b/c | —CH(CH₃)₂ | —C₆H₅ | —H | —OH | 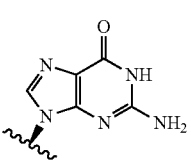 |
| 29a/b/c | —CH(CH₃)₂ | —C₆H₅ | —F | —OH | |
| 30a/b/c | —CH(CH₃)₂ | —C₆H₅ | —OH | —F | |
| 31a/b/c | —CH(CH₃)₂ | —C₆H₅ | —F | —F | |
| 32a/b/c | —CH(CH₃)₂ | —C₆H₅ | —H | —F | |
| 33a/b/c | —CH(CH₃)₂ | —C₆H₅ | —Cl | —F | |
| 34a/b/c | —CH(CH₃)₂ | —C₆H₅ | —Cl | —Cl | |
| 35a/b/c | —CH(CH₃)₂ | —C₆H₅ | —H | —Cl | |
| 36a/b/c | —CH(CH₃)₂ | —C₆H₅ | —F | —Cl | |

-continued

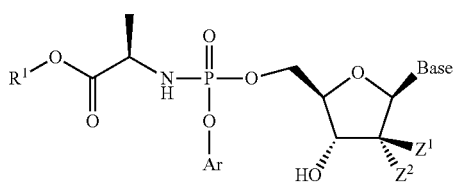
1a-98a

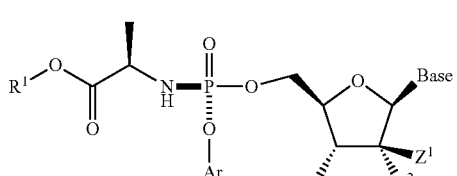
1b-98b

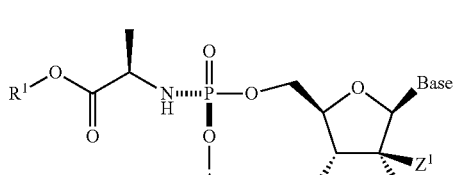
1c-98c

| # | R¹ | Ar | Z² | Z¹ | Base |
|---|---|---|---|---|---|
| 37a/b/c | —CH(CH₃)₂ | —C₆H₅ | —H | —OH | 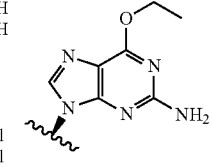 |
| 38a/b/c | —CH(CH₃)₂ | —C₆H₅ | —F | —OH | |
| 39a/b/c | —CH(CH₃)₂ | —C₆H₅ | —OH | —F | |
| 40a/b/c | —CH(CH₃)₂ | —C₆H₅ | —F | —F | |
| 41a/b/c | —CH(CH₃)₂ | —C₆H₅ | —H | —F | |
| 42a/b/c | —CH(CH₃)₂ | —C₆H₅ | —Cl | —F | |
| 43a/b/c | —CH(CH₃)₂ | —C₆H₅ | —Cl | —Cl | |
| 44a/b/c | —CH(CH₃)₂ | —C₆H₅ | —H | —Cl | |
| 45a/b/c | —CH(CH₃)₂ | —C₆H₅ | —F | —Cl | |
| 46a/b/c | —CH(CH₃)₂ | —C₆H₅ | —H | —OH | 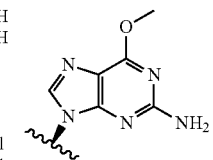 |
| 47a/b/c | —CH(CH₃)₂ | —C₆H₅ | —F | —OH | |
| 48a/b/c | —CH(CH₃)₂ | —C₆H₅ | —OH | —F | |
| 49a/b/c | —CH(CH₃)₂ | —C₆H₅ | —F | —F | |
| 50a/b/c | —CH(CH₃)₂ | —C₆H₅ | —H | —F | |
| 51a/b/c | —CH(CH₃)₂ | —C₆H₅ | —Cl | —F | |
| 52a/b/c | —CH(CH₃)₂ | —C₆H₅ | —Cl | —Cl | |
| 53a/b/c | —CH(CH₃)₂ | —C₆H₅ | —H | —Cl | |
| 54a/b/c | —CH(CH₃)₂ | —C₆H₅ | —F | —Cl | |
| 55a/b/c | —CH(CH₃)₂ | —C₆H₅ | —H | —OH | 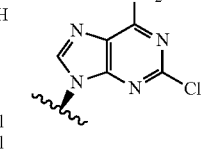 |
| 56a/b/c | —CH(CH₃)₂ | —C₆H₅ | —F | —OH | |
| 57a/b/c | —CH(CH₃)₂ | —C₆H₅ | —OH | —F | |
| 58a/b/c | —CH(CH₃)₂ | —C₆H₅ | —F | —F | |
| 59a/b/c | —CH(CH₃)₂ | —C₆H₅ | —H | —F | |
| 60a/b/c | —CH(CH₃)₂ | —C₆H₅ | —Cl | —F | |
| 61a/b/c | —CH(CH₃)₂ | —C₆H₅ | —Cl | —Cl | |
| 62a/b/c | —CH(CH₃)₂ | —C₆H₅ | —H | —Cl | |
| 63a/b/c | —CH(CH₃)₂ | —C₆H₅ | —H | —OH | 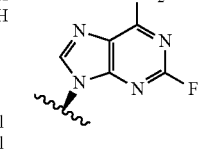 |
| 64a/b/c | —CH(CH₃)₂ | —C₆H₅ | —F | —OH | |
| 65a/b/c | —CH(CH₃)₂ | —C₆H₅ | —OH | —F | |
| 66a/b/c | —CH(CH₃)₂ | —C₆H₅ | —F | —F | |
| 67a/b/c | —CH(CH₃)₂ | —C₆H₅ | —H | —F | |
| 68a/b/c | —CH(CH₃)₂ | —C₆H₅ | —Cl | —F | |
| 69a/b/c | —CH(CH₃)₂ | —C₆H₅ | —Cl | —Cl | |
| 70a/b/c | —CH(CH₃)₂ | —C₆H₅ | —H | —Cl | |
| 71a/b/c | —CH(CH₃)₂ | —C₆H₅ | —F | —Cl | |

-continued

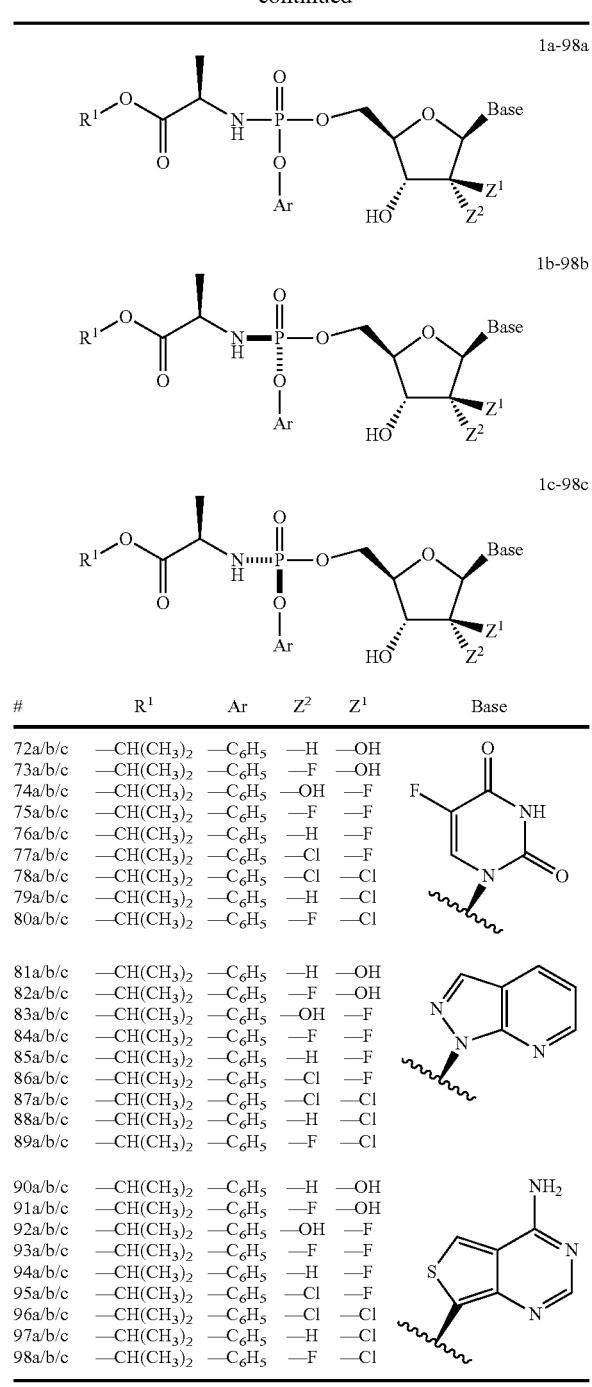

| # | R¹ | Ar | Z² | Z¹ | Base |
|---|---|---|---|---|---|
| 72a/b/c | —CH(CH₃)₂ | —C₆H₅ | —H | —OH | |
| 73a/b/c | —CH(CH₃)₂ | —C₆H₅ | —F | —OH | |
| 74a/b/c | —CH(CH₃)₂ | —C₆H₅ | —OH | —F | |
| 75a/b/c | —CH(CH₃)₂ | —C₆H₅ | —F | —F | |
| 76a/b/c | —CH(CH₃)₂ | —C₆H₅ | —H | —F | |
| 77a/b/c | —CH(CH₃)₂ | —C₆H₅ | —Cl | —F | |
| 78a/b/c | —CH(CH₃)₂ | —C₆H₅ | —Cl | —Cl | |
| 79a/b/c | —CH(CH₃)₂ | —C₆H₅ | —H | —Cl | |
| 80a/b/c | —CH(CH₃)₂ | —C₆H₅ | —F | —Cl | |
| 81a/b/c | —CH(CH₃)₂ | —C₆H₅ | —H | —OH | |
| 82a/b/c | —CH(CH₃)₂ | —C₆H₅ | —F | —OH | |
| 83a/b/c | —CH(CH₃)₂ | —C₆H₅ | —OH | —F | |
| 84a/b/c | —CH(CH₃)₂ | —C₆H₅ | —F | —F | |
| 85a/b/c | —CH(CH₃)₂ | —C₆H₅ | —H | —F | |
| 86a/b/c | —CH(CH₃)₂ | —C₆H₅ | —Cl | —F | |
| 87a/b/c | —CH(CH₃)₂ | —C₆H₅ | —Cl | —Cl | |
| 88a/b/c | —CH(CH₃)₂ | —C₆H₅ | —H | —Cl | |
| 89a/b/c | —CH(CH₃)₂ | —C₆H₅ | —F | —Cl | |
| 90a/b/c | —CH(CH₃)₂ | —C₆H₅ | —H | —OH | |
| 91a/b/c | —CH(CH₃)₂ | —C₆H₅ | —F | —OH | |
| 92a/b/c | —CH(CH₃)₂ | —C₆H₅ | —OH | —F | |
| 93a/b/c | —CH(CH₃)₂ | —C₆H₅ | —F | —F | |
| 94a/b/c | —CH(CH₃)₂ | —C₆H₅ | —H | —F | |
| 95a/b/c | —CH(CH₃)₂ | —C₆H₅ | —Cl | —F | |
| 96a/b/c | —CH(CH₃)₂ | —C₆H₅ | —Cl | —Cl | |
| 97a/b/c | —CH(CH₃)₂ | —C₆H₅ | —H | —Cl | |
| 98a/b/c | —CH(CH₃)₂ | —C₆H₅ | —F | —Cl | | or a pharmaceutically acceptable salt, solvate, stereoisomeric form, tautomeric form or polymorphic form thereof. In the table, each row provides three structures—one according to the left structure (1a-98a), one according to the middle left structure (1b-98b), and one according to the right structure (1c-90c). For instance, the first row provides compound 1a according to the top left structure, compound 1b according to the top middle structure, and compound 1c according to the top right structure, each with the indicated variables in the row.

In certain embodiments provided herein is a compound according to any of Formulas 101a-198c:

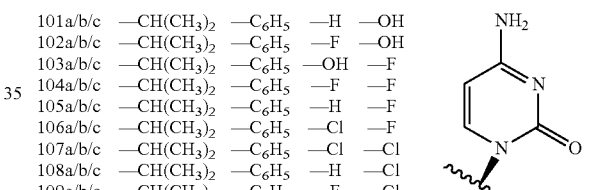

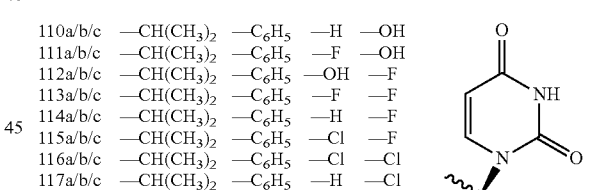

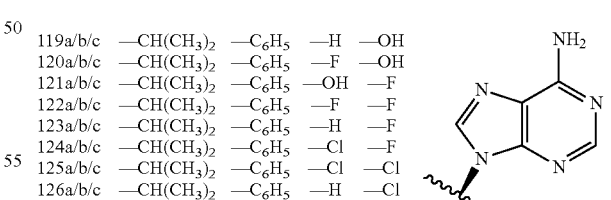

| # | R¹ | Ar | Z² | Z¹ | Base |
|---|---|---|---|---|---|
| 101a/b/c | —CH(CH₃)₂ | —C₆H₅ | —H | —OH | |
| 102a/b/c | —CH(CH₃)₂ | —C₆H₅ | —F | —OH | |
| 103a/b/c | —CH(CH₃)₂ | —C₆H₅ | —OH | —F | |
| 104a/b/c | —CH(CH₃)₂ | —C₆H₅ | —F | —F | |
| 105a/b/c | —CH(CH₃)₂ | —C₆H₅ | —H | —F | |
| 106a/b/c | —CH(CH₃)₂ | —C₆H₅ | —Cl | —F | |
| 107a/b/c | —CH(CH₃)₂ | —C₆H₅ | —Cl | —Cl | |
| 108a/b/c | —CH(CH₃)₂ | —C₆H₅ | —H | —Cl | |
| 109a/b/c | —CH(CH₃)₂ | —C₆H₅ | —F | —Cl | |
| 110a/b/c | —CH(CH₃)₂ | —C₆H₅ | —H | —OH | |
| 111a/b/c | —CH(CH₃)₂ | —C₆H₅ | —F | —OH | |
| 112a/b/c | —CH(CH₃)₂ | —C₆H₅ | —OH | —F | |
| 113a/b/c | —CH(CH₃)₂ | —C₆H₅ | —F | —F | |
| 114a/b/c | —CH(CH₃)₂ | —C₆H₅ | —H | —F | |
| 115a/b/c | —CH(CH₃)₂ | —C₆H₅ | —Cl | —F | |
| 116a/b/c | —CH(CH₃)₂ | —C₆H₅ | —Cl | —Cl | |
| 117a/b/c | —CH(CH₃)₂ | —C₆H₅ | —H | —Cl | |
| 118a/b/c | —CH(CH₃)₂ | —C₆H₅ | —F | —Cl | |
| 119a/b/c | —CH(CH₃)₂ | —C₆H₅ | —H | —OH | |
| 120a/b/c | —CH(CH₃)₂ | —C₆H₅ | —F | —OH | |
| 121a/b/c | —CH(CH₃)₂ | —C₆H₅ | —OH | —F | |
| 122a/b/c | —CH(CH₃)₂ | —C₆H₅ | —F | —F | |
| 123a/b/c | —CH(CH₃)₂ | —C₆H₅ | —H | —F | |
| 124a/b/c | —CH(CH₃)₂ | —C₆H₅ | —Cl | —F | |
| 125a/b/c | —CH(CH₃)₂ | —C₆H₅ | —Cl | —Cl | |
| 126a/b/c | —CH(CH₃)₂ | —C₆H₅ | —H | —Cl | |
| 127a/b/c | —CH(CH₃)₂ | —C₆H₅ | —F | —Cl | |
| 128a/b/c | —CH(CH₃)₂ | —C₆H₅ | —H | —OH | |
| 129a/b/c | —CH(CH₃)₂ | —C₆H₅ | —F | —OH | |
| 130a/b/c | —CH(CH₃)₂ | —C₆H₅ | —OH | —F | |
| 131a/b/c | —CH(CH₃)₂ | —C₆H₅ | —F | —F | |
| 132a/b/c | —CH(CH₃)₂ | —C₆H₅ | —H | —F | |
| 133a/b/c | —CH(CH₃)₂ | —C₆H₅ | —Cl | —F | |
| 134a/b/c | —CH(CH₃)₂ | —C₆H₅ | —Cl | —Cl | |
| 135a/b/c | —CH(CH₃)₂ | —C₆H₅ | —H | —Cl | |
| 136a/b/c | —CH(CH₃)₂ | —C₆H₅ | —F | —Cl | |

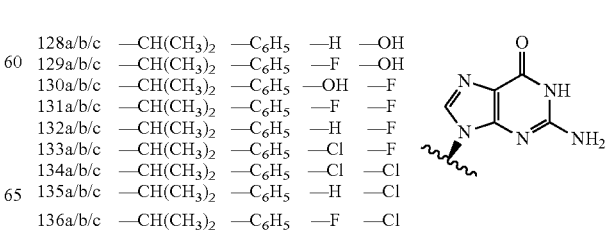

101a-198a

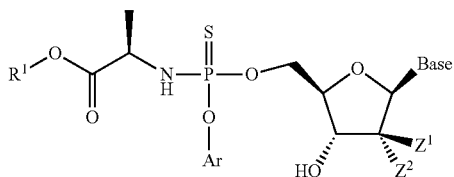

101b-198b

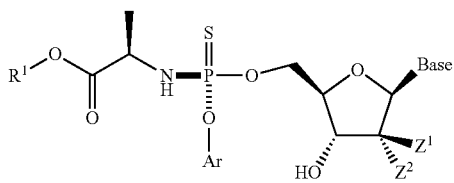

101c-198c

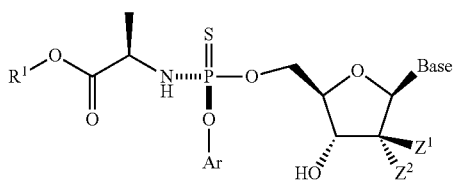

| # | $R^1$ | Ar | $Z^2$ | $Z^1$ | Base |
|---|---|---|---|---|---|
| 137a/b/c | —CH(CH$_3$)$_2$ | —C$_6$H$_5$ | —H | —OH | 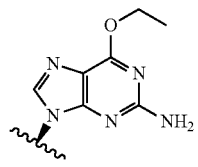 |
| 138a/b/c | —CH(CH$_3$)$_2$ | —C$_6$H$_5$ | —F | —OH | |
| 139a/b/c | —CH(CH$_3$)$_2$ | —C$_6$H$_5$ | —OH | —F | |
| 140a/b/c | —CH(CH$_3$)$_2$ | —C$_6$H$_5$ | —F | —F | |
| 141a/b/c | —CH(CH$_3$)$_2$ | —C$_6$H$_5$ | —H | —F | |
| 142a/b/c | —CH(CH$_3$)$_2$ | —C$_6$H$_5$ | —Cl | —F | |
| 143a/b/c | —CH(CH$_3$)$_2$ | —C$_6$H$_5$ | —Cl | —Cl | |
| 144a/b/c | —CH(CH$_3$)$_2$ | —C$_6$H$_5$ | —H | —Cl | |
| 145a/b/c | —CH(CH$_3$)$_2$ | —C$_6$H$_5$ | —F | —Cl | |
| 146a/b/c | —CH(CH$_3$)$_2$ | —C$_6$H$_5$ | —H | —OH | 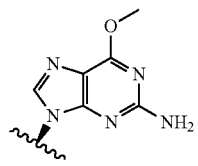 |
| 147a/b/c | —CH(CH$_3$)$_2$ | —C$_6$H$_5$ | —F | —OH | |
| 148a/b/c | —CH(CH$_3$)$_2$ | —C$_6$H$_5$ | —OH | —F | |
| 149a/b/c | —CH(CH$_3$)$_2$ | —C$_6$H$_5$ | —F | —F | |
| 150a/b/c | —CH(CH$_3$)$_2$ | —C$_6$H$_5$ | —H | —F | |
| 151a/b/c | —CH(CH$_3$)$_2$ | —C$_6$H$_5$ | —Cl | —F | |
| 152a/b/c | —CH(CH$_3$)$_2$ | —C$_6$H$_5$ | —Cl | —Cl | |
| 153a/b/c | —CH(CH$_3$)$_2$ | —C$_6$H$_5$ | —H | —Cl | |
| 154a/b/c | —CH(CH$_3$)$_2$ | —C$_6$H$_5$ | —F | —Cl | |
| 155a/b/c | —CH(CH$_3$)$_2$ | —C$_6$H$_5$ | —H | —OH | 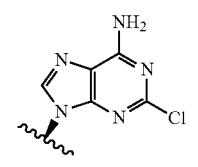 |
| 156a/b/c | —CH(CH$_3$)$_2$ | —C$_6$H$_5$ | —F | —OH | |
| 157a/b/c | —CH(CH$_3$)$_2$ | —C$_6$H$_5$ | —OH | —F | |
| 158a/b/c | —CH(CH$_3$)$_2$ | —C$_6$H$_5$ | —F | —F | |
| 159a/b/c | —CH(CH$_3$)$_2$ | —C$_6$H$_5$ | —H | —F | |
| 160a/b/c | —CH(CH$_3$)$_2$ | —C$_6$H$_5$ | —Cl | —F | |
| 161a/b/c | —CH(CH$_3$)$_2$ | —C$_6$H$_5$ | —Cl | —Cl | |
| 162a/b/c | —CH(CH$_3$)$_2$ | —C$_6$H$_5$ | —H | —Cl | |
| 163a/b/c | —CH(CH$_3$)$_2$ | —C$_6$H$_5$ | —H | —OH | 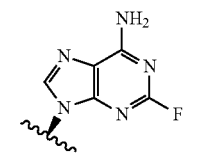 |
| 164a/b/c | —CH(CH$_3$)$_2$ | —C$_6$H$_5$ | —F | —OH | |
| 165a/b/c | —CH(CH$_3$)$_2$ | —C$_6$H$_5$ | —OH | —F | |
| 166a/b/c | —CH(CH$_3$)$_2$ | —C$_6$H$_5$ | —F | —F | |
| 167a/b/c | —CH(CH$_3$)$_2$ | —C$_6$H$_5$ | —H | —F | |
| 168a/b/c | —CH(CH$_3$)$_2$ | —C$_6$H$_5$ | —Cl | —F | |
| 169a/b/c | —CH(CH$_3$)$_2$ | —C$_6$H$_5$ | —Cl | —Cl | |
| 170a/b/c | —CH(CH$_3$)$_2$ | —C$_6$H$_5$ | —H | —Cl | |
| 171a/b/c | —CH(CH$_3$)$_2$ | —C$_6$H$_5$ | —F | —Cl | |

101a-198a

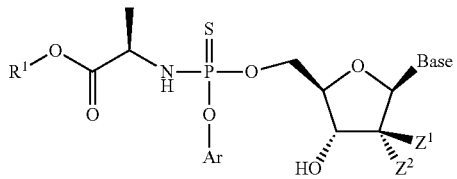

101b-198b

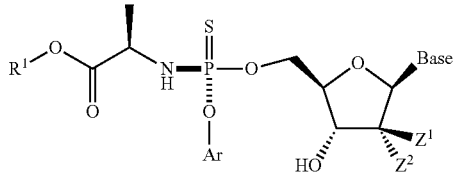

101c-198c

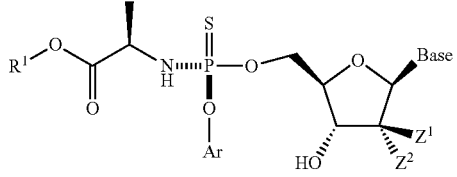

| # | $R^1$ | Ar | $Z^2$ | $Z^1$ | Base |
|---|---|---|---|---|---|
| 172a/b/c | —CH(CH$_3$)$_2$ | —C$_6$H$_5$ | —H | —OH | 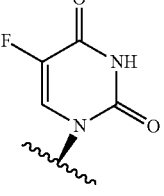 |
| 173a/b/c | —CH(CH$_3$)$_2$ | —C$_6$H$_5$ | —F | —OH | |
| 174a/b/c | —CH(CH$_3$)$_2$ | —C$_6$H$_5$ | —OH | —F | |
| 175a/b/c | —CH(CH$_3$)$_2$ | —C$_6$H$_5$ | —F | —F | |
| 176a/b/c | —CH(CH$_3$)$_2$ | —C$_6$H$_5$ | —H | —F | |
| 177a/b/c | —CH(CH$_3$)$_2$ | —C$_6$H$_5$ | —Cl | —F | |
| 178a/b/c | —CH(CH$_3$)$_2$ | —C$_6$H$_5$ | —Cl | —Cl | |
| 179a/b/c | —CH(CH$_3$)$_2$ | —C$_6$H$_5$ | —H | —Cl | |
| 180a/b/c | —CH(CH$_3$)$_2$ | —C$_6$H$_5$ | —F | —Cl | |
| 181a/b/c | —CH(CH$_3$)$_2$ | —C$_6$H$_5$ | —H | —OH | 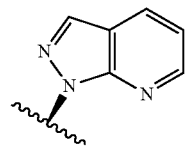 |
| 182a/b/c | —CH(CH$_3$)$_2$ | —C$_6$H$_5$ | —F | —OH | |
| 183a/b/c | —CH(CH$_3$)$_2$ | —C$_6$H$_5$ | —OH | —F | |
| 184a/b/c | —CH(CH$_3$)$_2$ | —C$_6$H$_5$ | —F | —F | |
| 185a/b/c | —CH(CH$_3$)$_2$ | —C$_6$H$_5$ | —H | —F | |
| 186a/b/c | —CH(CH$_3$)$_2$ | —C$_6$H$_5$ | —Cl | —F | |
| 187a/b/c | —CH(CH$_3$)$_2$ | —C$_6$H$_5$ | —Cl | —Cl | |
| 188a/b/c | —CH(CH$_3$)$_2$ | —C$_6$H$_5$ | —H | —Cl | |
| 189a/b/c | —CH(CH$_3$)$_2$ | —C$_6$H$_5$ | —F | —Cl | |
| 190a/b/c | —CH(CH$_3$)$_2$ | —C$_6$H$_5$ | —H | —OH | 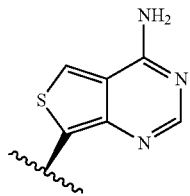 |
| 191a/b/c | —CH(CH$_3$)$_2$ | —C$_6$H$_5$ | —F | —OH | |
| 192a/b/c | —CH(CH$_3$)$_2$ | —C$_6$H$_5$ | —OH | —F | |
| 193a/b/c | —CH(CH$_3$)$_2$ | —C$_6$H$_5$ | —F | —F | |
| 194a/b/c | —CH(CH$_3$)$_2$ | —C$_6$H$_5$ | —H | —F | |
| 195a/b/c | —CH(CH$_3$)$_2$ | —C$_6$H$_5$ | —Cl | —F | |
| 196a/b/c | —CH(CH$_3$)$_2$ | —C$_6$H$_5$ | —Cl | —Cl | |
| 197a/b/c | —CH(CH$_3$)$_2$ | —C$_6$H$_5$ | —H | —Cl | |
| 198a/b/c | —CH(CH$_3$)$_2$ | —C$_6$H$_5$ | —F | —Cl | | or a pharmaceutically acceptable salt, solvate, stereoisomeric form, tautomeric form or polymorphic form thereof.

In certain embodiments provided herein is a compound according to any of Formulas 200a-200c:

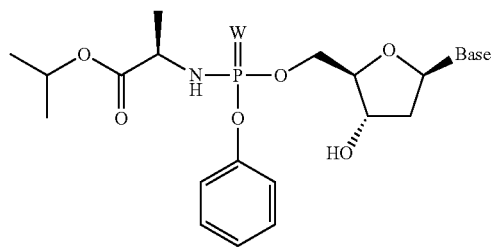

200a

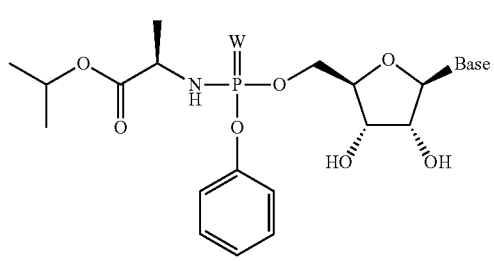

300a

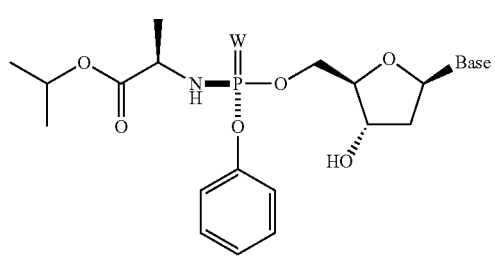

200b

300b

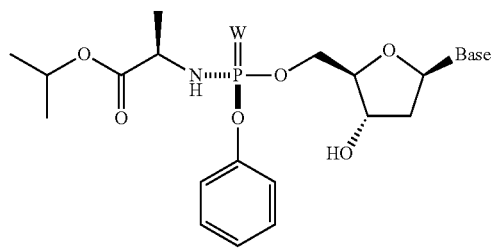

200c

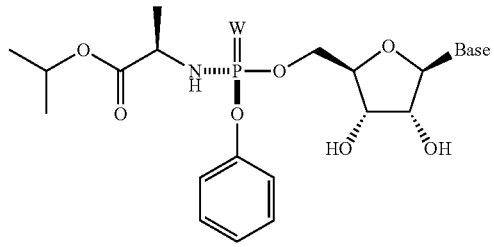

300c or a pharmaceutically acceptable salt, solvate, stereoisomeric form, tautomeric form or polymorphic form thereof, wherein W and Base are as described in formula I, above. In particular embodiments, Base is selected from the group consisting of:

or a pharmaceutically acceptable salt, solvate, stereoisomeric form, tautomeric form or polymorphic form thereof, wherein W and Base are as described in formula I, above. In particular embodiments, Base is selected from the group consisting of:

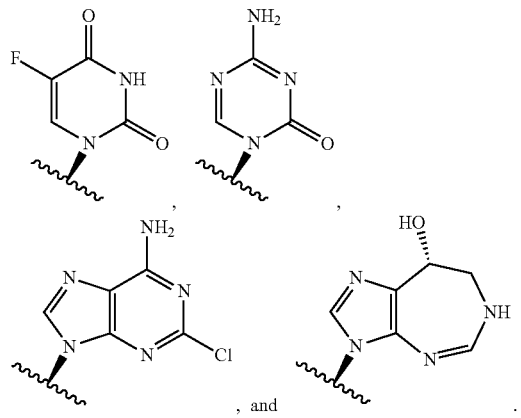

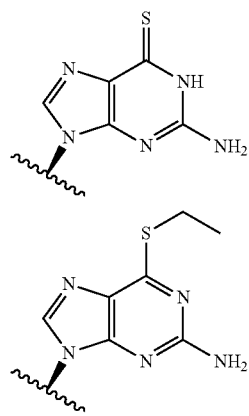

and

In particular embodiments, W is S. In certain embodiments, W is O.

In certain embodiments provided herein is a compound according to any of Formulas 300a-300c:

In particular embodiments, W is S. In certain embodiments, W is O.

In certain embodiments provided herein is a compound according to any of Formulas 400a-429c:

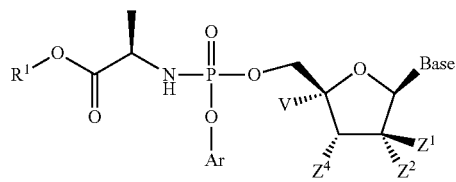

400a-429a

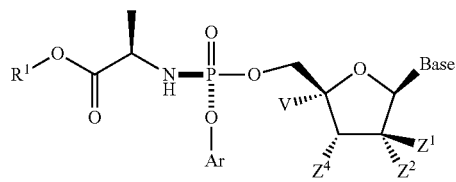

400b-429b

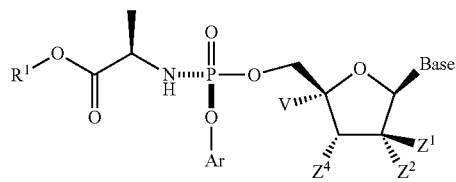

400c-429c

| # | R¹ | Ar | V | Z⁴ | Z² | Z¹ | Base |
|---|---|---|---|---|---|---|---|
| 400a/b/c | —CH(CH₃)₂ | —C₆H₅ | —H | —C≡CH | —H | —H | |
| 401a/b/c | —CH(CH₃)₂ | —C₆H₅ | —H | —F | —H | —H | |
| 402a/b/c | —CH(CH₃)₂ | —C₆H₅ | —H | —NH₂ | —H | —H | cytosine |
| 403a/b/c | —CH(CH₃)₂ | —C₆H₅ | —F | —OH | —F | —H | |
| 404a/b/c | —CH(CH₃)₂ | —C₆H₅ | —H | —OH | —H | —CN | |
| 405a/b/c | —CH(CH₃)₂ | —C₆H₅ | —NH₂ | —OH | —H | —CN | |
| 406a/b/c | —CH(CH₃)₂ | —C₆H₅ | —H | —C≡CH | —H | —H | |
| 407a/b/c | —CH(CH₃)₂ | —C₆H₅ | —H | —F | —H | —H | |
| 408a/b/c | —CH(CH₃)₂ | —C₆H₅ | —H | —NH₂ | —H | —H | uracil |
| 409a/b/c | —CH(CH₃)₂ | —C₆H₅ | —F | —OH | —F | —H | |
| 410a/b/c | —CH(CH₃)₂ | —C₆H₅ | —H | —OH | —H | —CN | |
| 411a/b/c | —CH(CH₃)₂ | —C₆H₅ | —NH₂ | —OH | —H | —CN | |
| 412a/b/c | —CH(CH₃)₂ | —C₆H₅ | —H | —C≡CH | —H | —H | |
| 413a/b/c | —CH(CH₃)₂ | —C₆H₅ | —H | —F | —H | —H | |
| 414a/b/c | —CH(CH₃)₂ | —C₆H₅ | —H | —NH₂ | —H | —H | adenine |
| 415a/b/c | —CH(CH₃)₂ | —C₆H₅ | —F | —OH | —F | —H | |
| 416a/b/c | —CH(CH₃)₂ | —C₆H₅ | —H | —OH | —H | —CN | |
| 417a/b/c | —CH(CH₃)₂ | —C₆H₅ | —NH₂ | —OH | —H | —CN | |

-continued

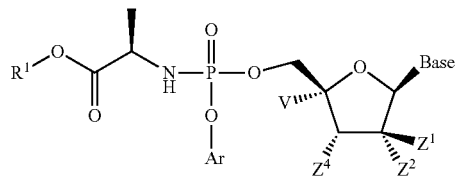

400a-429a

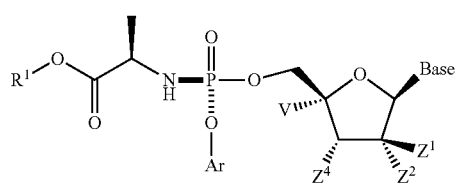

400b-429b

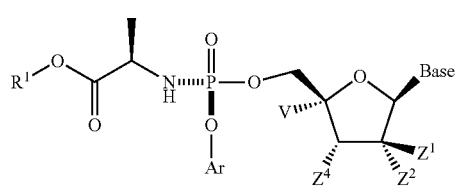

400c-429c

| # | R¹ | Ar | V | Z⁴ | Z² | Z¹ | Base |
|---|---|---|---|---|---|---|---|
| 418a/b/c | —CH(CH₃)₂ | —C₆H₅ | —H | —C≡CH | —H | —H | 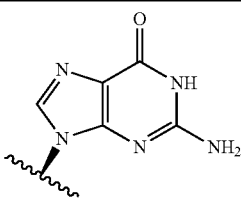 |
| 419a/b/c | —CH(CH₃)₂ | —C₆H₅ | —H | —F | —H | —H | |
| 420a/b/c | —CH(CH₃)₂ | —C₆H₅ | —H | —NH₂ | —H | —H | |
| 421a/b/c | —CH(CH₃)₂ | —C₆H₅ | —F | —OH | —F | —H | |
| 422a/b/c | —CH(CH₃)₂ | —C₆H₅ | —H | —OH | —H | —CN | |
| 423a/b/c | —CH(CH₃)₂ | —C₆H₅ | —NH₂ | —OH | —H | —CN | |
| 424a/b/c | —CH(CH₃)₂ | —C₆H₅ | —H | —C≡CH | —H | —H | 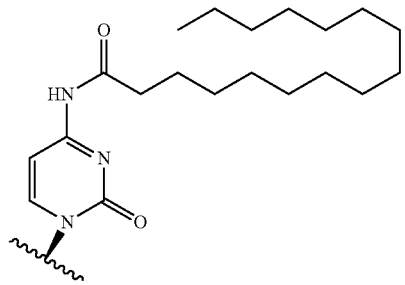 |
| 425a/b/c | —CH(CH₃)₂ | —C₆H₅ | —H | —F | —H | —H | |
| 426a/b/c | —CH(CH₃)₂ | —C₆H₅ | —H | —NH₂ | —H | —H | |
| 427a/b/c | —CH(CH₃)₂ | —C₆H₅ | —F | —OH | —F | —H | |
| 428a/b/c | —CH(CH₃)₂ | —C₆H₅ | —H | —OH | —H | —CN | |
| 429a/b/c | —CH(CH₃)₂ | —C₆H₅ | —NH₂ | —OH | H | —CN | | or a pharmaceutically acceptable salt, solvate, stereoisomeric form, tautomeric form or polymorphic form thereof.

In certain embodiments provided herein is a compound according to any of Formulas 430a-459c:

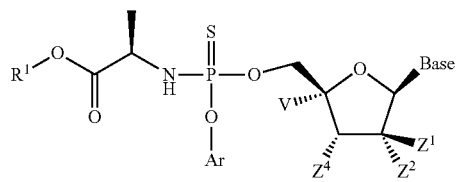

430a-459a

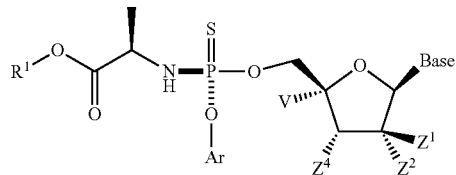

430b-459b

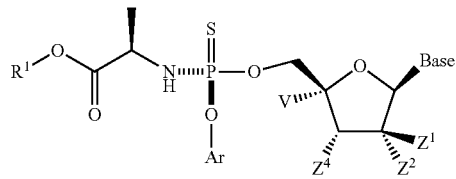

430c-459c

| # | R¹ | Ar | V | Z⁴ | Z² | Z¹ | Base |
|---|---|---|---|---|---|---|---|
| 430a/b/c | —CH(CH₃)₂ | —C₆H₅ | —H | —C≡CH | —H | —H | cytosine |
| 431a/b/c | —CH(CH₃)₂ | —C₆H₅ | —H | —F | —H | —H | |
| 432a/b/c | —CH(CH₃)₂ | —C₆H₅ | —H | —NH₂ | —H | —H | |
| 433a/b/c | —CH(CH₃)₂ | —C₆H₅ | —F | —OH | —F | —H | |
| 434a/b/c | —CH(CH₃)₂ | —C₆H₅ | —H | —OH | —H | —CN | |
| 435a/b/c | —CH(CH₃)₂ | —C₆H₅ | —NH₂ | —OH | —H | —CN | |
| 436a/b/c | —CH(CH₃)₂ | —C₆H₅ | —H | —C≡CH | —H | —H | uracil |
| 437a/b/c | —CH(CH₃)₂ | —C₆H₅ | —H | —F | —H | —H | |
| 438a/b/c | —CH(CH₃)₂ | —C₆H₅ | —H | —NH₂ | —H | —H | |
| 439a/b/c | —CH(CH₃)₂ | —C₆H₅ | —F | —OH | —F | —H | |
| 440a/b/c | —CH(CH₃)₂ | —C₆H₅ | —H | —OH | —H | —CN | |
| 441a/b/c | —CH(CH₃)₂ | —C₆H₅ | —NH₂ | —OH | —H | —CN | |
| 442a/b/c | —CH(CH₃)₂ | —C₆H₅ | —H | —C≡CH | —H | —H | adenine |
| 443a/b/c | —CH(CH₃)₂ | —C₆H₅ | —H | —F | —H | —H | |
| 444a/b/c | —CH(CH₃)₂ | —C₆H₅ | —H | —NH₂ | —H | —H | |
| 445a/b/c | —CH(CH₃)₂ | —C₆H₅ | —F | —OH | —F | —H | |
| 446a/b/c | —CH(CH₃)₂ | —C₆H₅ | —H | —OH | —H | —CN | |
| 447a/b/c | —CH(CH₃)₂ | —C₆H₅ | —NH₂ | —OH | —H | —CN | |

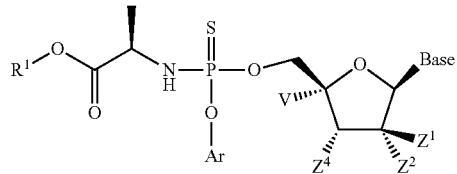

430a-459a

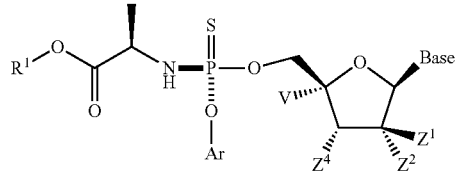

430b-459b

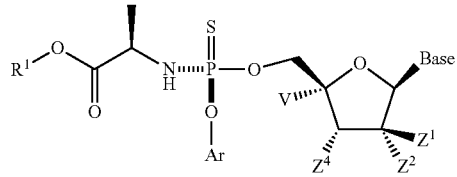

430c-459c

| # | R¹ | Ar | V | Z⁴ | Z² | Z¹ | Base |
|---|---|---|---|---|---|---|---|
| 448a/b/c | —CH(CH₃)₂ | —C₆H₅ | —H | —C≡CH | —H | —H | |
| 449a/b/c | —CH(CH₃)₂ | —C₆H₅ | —H | —F | —H | —H | |
| 450a/b/c | —CH(CH₃)₂ | —C₆H₅ | —H | —NH₂ | —H | —H | 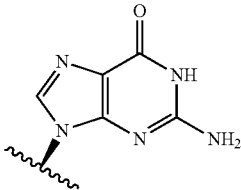 |
| 451a/b/c | —CH(CH₃)₂ | —C₆H₅ | —F | —OH | —F | —H | |
| 452a/b/c | —CH(CH₃)₂ | —C₆H₅ | —H | —OH | —H | —CN | |
| 453a/b/c | —CH(CH₃)₂ | —C₆H₅ | —NH₂ | —OH | —H | —CN | |
| 454a/b/c | —CH(CH₃)₂ | —C₆H₅ | —H | —C≡CH | —H | —H | |
| 455a/b/c | —CH(CH₃)₂ | —C₆H₅ | —H | —F | —H | —H | |
| 456a/b/c | —CH(CH₃)₂ | —C₆H₅ | —H | —NH₂ | —H | —H | 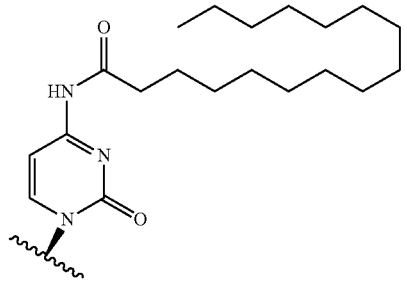 |
| 457a/b/c | —CH(CH₃)₂ | —C₆H₅ | —F | —OH | —F | —H | |
| 458a/b/c | —CH(CH₃)₂ | —C₆H₅ | —H | —OH | —H | —CN | |
| 459a/b/c | —CH(CH₃)₂ | —C₆H₅ | —NH₂ | —OH | —H | —CN | | or a pharmaceutically acceptable salt, solvate, stereoisomeric form, tautomeric form or polymorphic form thereof.

In certain embodiments provided herein is a compound according to any of Formulas 460a-468c:

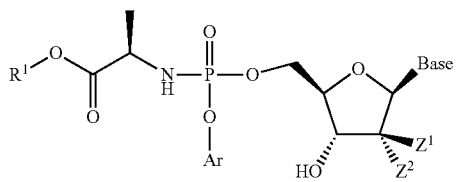
460a-468a

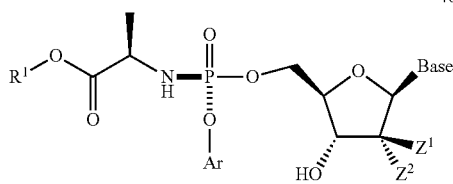
460b-468b

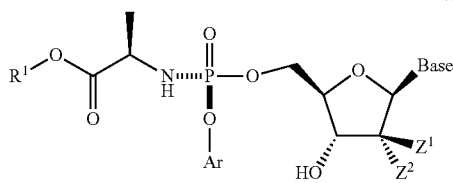
460c-468c

| # | R¹ | Ar | Z² | Z¹ | Base |
|---|---|---|---|---|---|
| 460a/b/c | —CH(CH$_3$)$_2$ | —C$_6$H$_5$ | —H | —OH | |
| 461a/b/c | —CH(CH$_3$)$_2$ | —C$_6$H$_5$ | —F | —OH | |
| 462a/b/c | —CH(CH$_3$)$_2$ | —C$_6$H$_5$ | —OH | —F | |
| 463a/b/c | —CH(CH$_3$)$_2$ | —C$_6$H$_5$ | —F | —F | |
| 464a/b/c | —CH(CH$_3$)$_2$ | —C$_6$H$_5$ | —H | —F | |
| 465a/b/c | —CH(CH$_3$)$_2$ | —C$_6$H$_5$ | —Cl | —F | |
| 466a/b/c | —CH(CH$_3$)$_2$ | —C$_6$H$_5$ | —Cl | —Cl | |
| 467a/b/c | —CH(CH$_3$)$_2$ | —C$_6$H$_5$ | —H | —Cl | |
| 468a/b/c | —CH(CH$_3$)$_2$ | —C$_6$H$_5$ | —F | —Cl | | or a pharmaceutically acceptable salt, solvate, stereoisomeric form, tautomeric form or polymorphic form thereof. In the table, each row provides three structures—one according to the left structure (460a-468a), one according to the middle left structure (460b-468b), and one according to the right structure (460c-460c). For instance, the first row provides compound 1a according to the top left structure, compound 1b according to the top middle structure, and compound 1c according to the top right structure, each with the indicated variables in the row.

In certain embodiments provided herein is a compound according to any of Formulas 469a-477c:

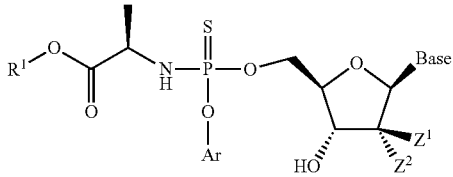
469a-477a

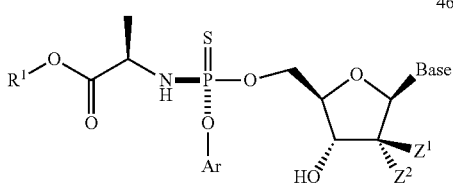
469b-477b

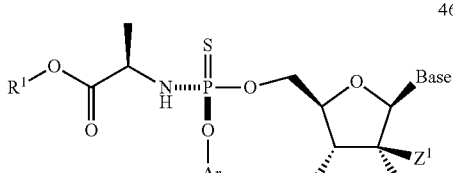
469c-477c

| # | R¹ | Ar | Z² | Z¹ | Base |
|---|---|---|---|---|---|
| 469a/b/c | —CH(CH$_3$)$_2$ | —C$_6$H$_5$ | —H | —OH | |
| 470a/b/c | —CH(CH$_3$)$_2$ | —C$_6$H$_5$ | —F | —OH | |
| 471a/b/c | —CH(CH$_3$)$_2$ | —C$_6$H$_5$ | —OH | —F | |
| 472a/b/c | —CH(CH$_3$)$_2$ | —C$_6$H$_5$ | —F | —F | |
| 473a/b/c | —CH(CH$_3$)$_2$ | —C$_6$H$_5$ | —H | —F | |
| 474a/b/c | —CH(CH$_3$)$_2$ | —C$_6$H$_5$ | —Cl | —F | |
| 475a/b/c | —CH(CH$_3$)$_2$ | —C$_6$H$_5$ | —Cl | —Cl | |
| 476a/b/c | —CH(CH$_3$)$_2$ | —C$_6$H$_5$ | —H | —Cl | |
| 477a/b/c | —CH(CH$_3$)$_2$ | —C$_6$H$_5$ | —F | —Cl | | or a pharmaceutically acceptable salt, solvate, stereoisomeric form, tautomeric form or polymorphic form thereof. In the table, each row provides three structures—one according to the left structure (469a-477a), one according to the middle left structure (469b-477b), and one according to the right structure (469c-477c). For instance, the first row provides compound 1a according to the top left structure, compound 1b according to the top middle structure, and compound 1c according to the top right structure, each with the indicated variables in the row.

In some embodiments, provided herein are:
(a) compounds as described herein, e.g., of Formulas I-XVIII and 1-477c, and pharmaceutically acceptable salts and compositions thereof;
(b) compounds as described herein, e.g., of Formulas I-XVIII and 1-477c, and pharmaceutically acceptable salts and compositions thereof for use in the treatment and/or prophylaxis of a liver cancer;
(c) processes for the preparation of compounds as described herein, e.g., of Formulas I-XVIII and 1-477c, as described in more detail elsewhere herein;
(d) pharmaceutical formulations comprising a compound as described herein, e.g., of Formulas I-XVIII and 1-477c, or a pharmaceutically acceptable salt thereof together with a pharmaceutically acceptable carrier or diluent;
(e) pharmaceutical formulations comprising a compound as described herein, e.g., of Formulas I-XVIII and 1-477c, or a pharmaceutically acceptable salt thereof together with one or more other effective anti-cancer agents, optionally in a pharmaceutically acceptable carrier or diluent;

(f) a method for the treatment and/or prophylaxis of a host with liver cancer that includes the administration of an effective amount of a compound as described herein, e.g., of Formulas I-XVIII and 1-477c, its pharmaceutically acceptable salt or composition; or (g) a method for the treatment and/or prophylaxis of a host with liver cancer that includes the administration of an effective amount of a compounds as described herein, e.g., of Formulas I-XVIII and 1-477c, its pharmaceutically acceptable salt or composition in combination and/or alternation with one or more effective anti-cancer agent.

Optically Active Compounds

It is appreciated that compounds provided herein have several chiral centers and may exist in and be isolated in optically active and racemic forms. Some compounds may exhibit polymorphism. It is to be understood that any racemic, optically-active, diastereomeric, polymorphic, or stereoisomeric form, or mixtures thereof, of a compound provided herein, which possess the useful properties described herein is within the scope of the invention. It being well known in the art how to prepare optically active forms (for example, by resolution of the racemic form by recrystallization techniques, by synthesis from optically-active starting materials, by chiral synthesis, or by chromatographic separation using a chiral stationary phase).

The compounds described herein, i.e. compounds of any of Formulas I-XVIII and 1-477c, may have one or more chiral (asymmetric) centers. The present disclosure encompasses all stereoisomeric forms of the compounds described herein. Centers of asymmetry that are present in the compounds described herein, can all independently of one another have (R) or (S) configuration. When bonds to a chiral atom, such as carbon or phosphorus, are depicted as straight lines in the structural formulas of the compounds described herein, or when a compound name is recited without an (R) or (S) chiral designation for a chiral atom, it is understood that both the (R) and (S) configurations of each such chiral atoms, and hence each enantiomer or diastereomer and mixtures thereof, are embraced within the structural formula or by the name. The production of specific stereoisomers or mixtures thereof may be identified in the Examples where such stereoisomers or mixtures were obtained, but this in no way limits the inclusion of all stereoisomers and mixtures thereof from being within the scope of the present disclosure.

Since the 1' and 4' carbons of a nucleoside are chiral, their non-hydrogen substituents (the base and the CHOR groups, respectively) can be either cis (on the same side) or trans (on opposite sides) with respect to the sugar ring system. The four optical isomers therefore are represented by the following configurations (when orienting the sugar moiety in a horizontal plane such that the oxygen atom is in the back): cis (with both groups "up", which corresponds to the configuration of naturally occurring β-D nucleosides), cis (with both groups "down", which is a non-naturally occurring β-L configuration), trans (with the C2' substituent "up" and the C4' substituent "down"), and trans (with the C2' substituent "down" and the C4' substituent "up"). The "D-nucleosides" are cis nucleosides in a natural configuration and the "L-nucleosides" are cis nucleosides in the non-naturally occurring configuration.

Likewise, most amino acids are chiral (designated as L or D, wherein the L enantiomer is the naturally occurring configuration) and can exist as separate enantiomers.

Examples of methods to obtain optically active materials are known in the art, and include at least the following.

i) physical separation of crystals—a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization—a technique whereby the individual enantiomers are separately crystallized from a solution of the racemate, possible only if the latter is a conglomerate in the solid state;

iii) enzymatic resolutions—a technique whereby partial or complete separation of a racemate by virtue of differing rates of reaction for the enantiomers with an enzyme;

iv) enzymatic asymmetric synthesis—a synthetic technique whereby at least one step of the synthesis uses an enzymatic reaction to obtain an enantiomerically pure or enriched synthetic precursor of the desired enantiomer;

v) chemical asymmetric synthesis—a synthetic technique whereby the desired enantiomer is synthesized from an achiral precursor under conditions that produce asymmetry (i.e., chirality) in the product, which may be achieved using chiral catalysts or chiral auxiliaries;

vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography—a technique whereby the enantiomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography—a technique whereby the racemate is volatilized and enantiomers are separated by virtue of their differing interactions in the gaseous mobile phase with a column containing a fixed non-racemic chiral adsorbent phase;

xii) extraction with chiral solvents—a technique whereby the enantiomers are separated by virtue of preferential dissolution of one enantiomer into a particular chiral solvent;

a) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

In some embodiments, provided is a composition of a 5'-D-amino acid phosphoramidate compound that comprises a substantially pure designated enantiomer of the 5'-D-amino acid phosphoramidate compound. In certain embodiments, in the methods and compounds of this invention, the compounds are substantially free of other enantiomers. In some embodiments, a composition includes a compound that is at least 85%, 90%, 95%, 98%, 99% or 100% by weight, of the compound, the remainder comprising other chemical species or enantiomers.

In an embodiment, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound described herein, e.g., a compound of any of Formulas I-XVIII and 1-477c, or it can be done on a final racemic product. Absolute stereochemistry may be determined by X-ray crystallography of crystalline products or crystalline intermediates which are derivatized, if necessary, with a reagent containing a stereogenic center of known configuration. Alternatively, absolute stereochemistry may be determined by Vibrational Circular Dichroism (VCD) spectroscopic analysis. The present invention includes all such isomers, as well as salts, solvates (which includes hydrates) and solvated salts of such racemates, enantiomers, diastereomers and tautomers and mixtures thereof.

Isotopically Enriched Compounds

Also provided herein are isotopically enriched compounds, including but not limited to isotopically enriched 5'-D-amino acid phosphoramidate compounds.

Isotopic enrichment (for example, deuteration) of pharmaceuticals to improve pharmacokinetics ("PK"), pharmacodynamics ("PD"), and toxicity profiles, has been demonstrated previously with some classes of drugs. See, for example, Lijinsky et. al., Food Cosmet. Toxicol., 20: 393 (1982); Lijinsky et. al., J. Nat. Cancer Inst., 69: 1127 (1982); Mangold et. al., Mutation Res. 308: 33 (1994); Gordon et. al., Drug Metab. Dispos., 15: 589 (1987); Zello et. al., Metabolism, 43: 487 (1994); Gately et. al., J. Nucl. Med., 27: 388 (1986); Wade D, Chem. Biol. Interact. 117: 191 (1999).

Isotopic enrichment of a drug can be used, for example, to (1) reduce or eliminate unwanted metabolites, (2) increase the half-life of the parent drug, (3) decrease the number of doses needed to achieve a desired effect, (4) decrease the amount of a dose necessary to achieve a desired effect, (5) increase the formation of active metabolites, if any are formed, and/or (6) decrees the production of deleterious metabolites in specific tissues and/or create a more effective drug and/or a safer drug for combination therapy, whether the combination therapy is intentional or not.

Replacement of an atom for one of its isotopes often will result in a change in the reaction rate of a chemical reaction. This phenomenon is known as the Kinetic Isotope Effect ("KIE"). For example, if a C—H bond is broken during a rate-determining step in a chemical reaction (i.e. the step with the highest transition state energy), substitution of a deuterium for that hydrogen will cause a decrease in the reaction rate and the process will slow down. This phenomenon is known as the Deuterium Kinetic Isotope Effect ("DKIE"). (See, e.g., Foster et al., Adv. Drug Res., vol. 14, pp. 1-36 (1985); Kushner et al., Can. J. Physiol. Pharmacol., vol. 77, pp. 79-88 (1999)).

The magnitude of the DKIE can be expressed as the ratio between the rates of a given reaction in which a C—H bond is broken, and the same reaction where deuterium is substituted for hydrogen. The DKIE can range from about 1 (no isotope effect) to very large numbers, such as 50 or more, meaning that the reaction can be fifty, or more, times slower when deuterium is substituted for hydrogen. High DKIE values may be due in part to a phenomenon known as tunneling, which is a consequence of the uncertainty principle. Tunneling is ascribed to the small mass of a hydrogen atom, and occurs because transition states involving a proton can sometimes form in the absence of the required activation energy. Because deuterium has more mass than hydrogen, it statistically has a much lower probability of undergoing this phenomenon.

Tritium ("T") is a radioactive isotope of hydrogen, used in research, fusion reactors, neutron generators and radiopharmaceuticals. Tritium is a hydrogen atom that has 2 neutrons in the nucleus and has an atomic weight close to 3. It occurs naturally in the environment in very low concentrations, most commonly found as $T_2O$. Tritium decays slowly (half-life=12.3 years) and emits a low energy beta particle that cannot penetrate the outer layer of human skin. Internal exposure is the main hazard associated with this isotope, yet it must be ingested in large amounts to pose a significant health risk. As compared with deuterium, a lesser amount of tritium must be consumed before it reaches a hazardous level. Substitution of tritium ("T") for hydrogen results in yet a stronger bond than deuterium and gives numerically larger isotope effects. Similarly, substitution of isotopes for other elements, including, but not limited to, $^{13}C$ or $^{14}C$ for carbon, $^{33}S$, $^{34}S$, or $^{36}S$ for sulfur, $^{15}N$ for nitrogen, and $^{17}O$ or $^{18}O$ for oxygen, may lead to a similar kinetic isotope effect.

For example, the DKIE was used to decrease the hepatotoxicity of halothane by presumably limiting the production of reactive species such as trifluoroacetyl chloride. However, this method may not be applicable to all drug classes. For example, deuterium incorporation can lead to metabolic switching. The concept of metabolic switching asserts that xenogens, when sequestered by Phase I enzymes, may bind transiently and re-bind in a variety of conformations prior to the chemical reaction (e.g., oxidation). This hypothesis is supported by the relatively vast size of binding pockets in many Phase I enzymes and the promiscuous nature of many metabolic reactions. Metabolic switching can potentially lead to different proportions of known metabolites as well as altogether new metabolites. This new metabolic profile may impart more or less toxicity.

The animal body expresses a variety of enzymes for the purpose of eliminating foreign substances, such as therapeutic agents, from its circulation system. Examples of such enzymes include the cytochrome P450 enzymes ("CYPs"), esterases, proteases, reductases, dehydrogenases, and monoamine oxidases, to react with and convert these foreign substances to more polar intermediates or metabolites for renal excretion. Some of the most common metabolic reactions of pharmaceutical compounds involve the oxidation of a carbon-hydrogen (C—H) bond to either a carbon-oxygen (C—O) or carbon-carbon (C—C) pi-bond. The resultant metabolites may be stable or unstable under physiological conditions, and can have substantially different pharmacokinetic, pharmacodynamic, and acute and long-term toxicity profiles relative to the parent compounds. For many drugs, such oxidations are rapid. These drugs therefore often require the administration of multiple or high daily doses.

Therefore, isotopic enrichment at certain positions of a compound provided herein will produce a detectable KIE that will affect the pharmacokinetic, pharmacologic, and/or toxicological profiles of a compound provided herein in comparison with a similar compound having a natural isotopic composition.

Preparation of Compounds

The compounds provided herein can be prepared, isolated or obtained by any method apparent to those of skill in the art. Compounds provided herein can be prepared according to the Exemplary Preparation Schemes provided below. Reaction conditions, steps and reactants not provided in the Exemplary Preparation Schemes would be apparent to, and known by, those skilled in the art.

Exemplary Preparation Schemes

Scheme 1

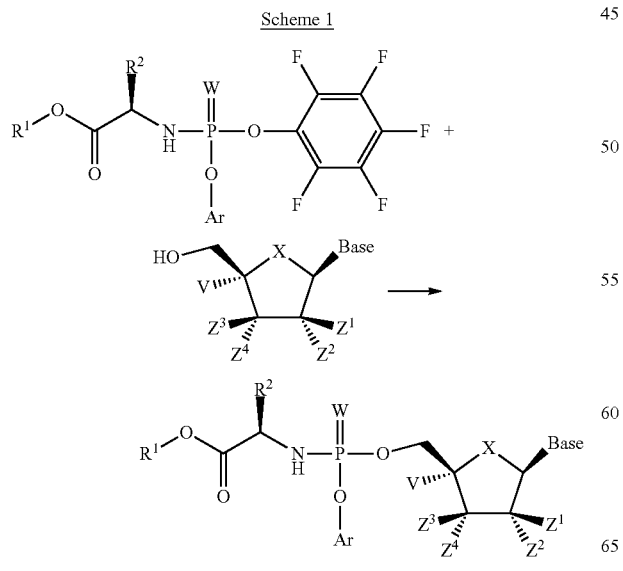

Scheme 2

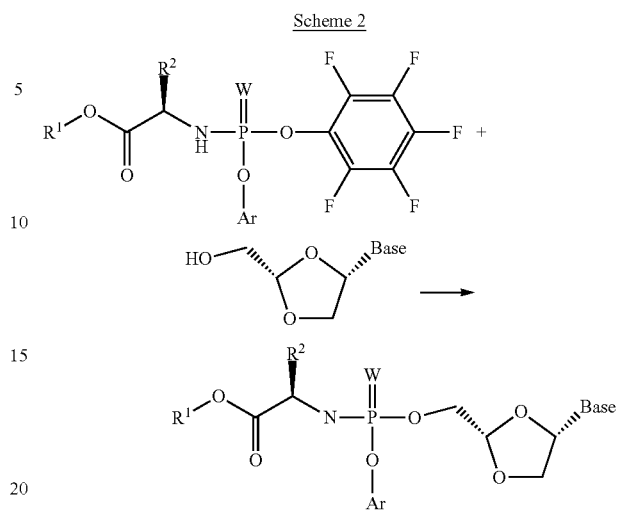

Scheme 3

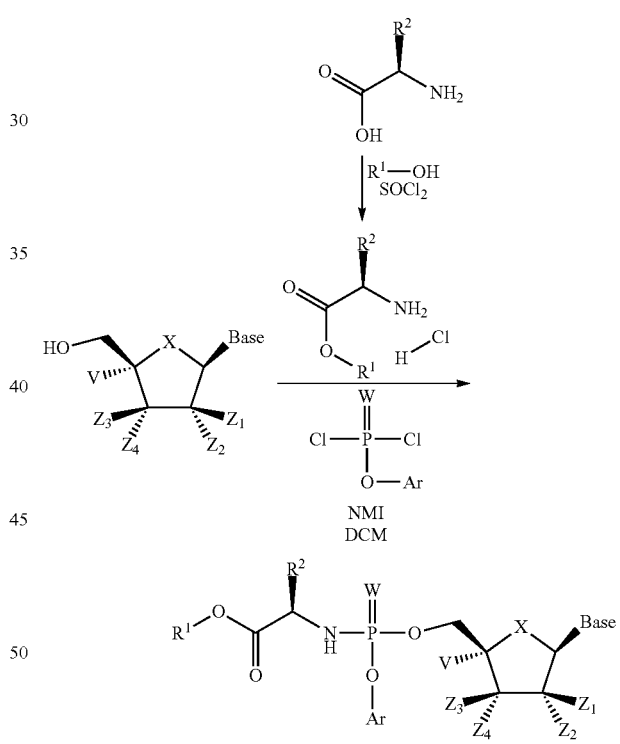

Scheme 4

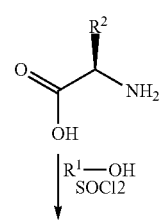

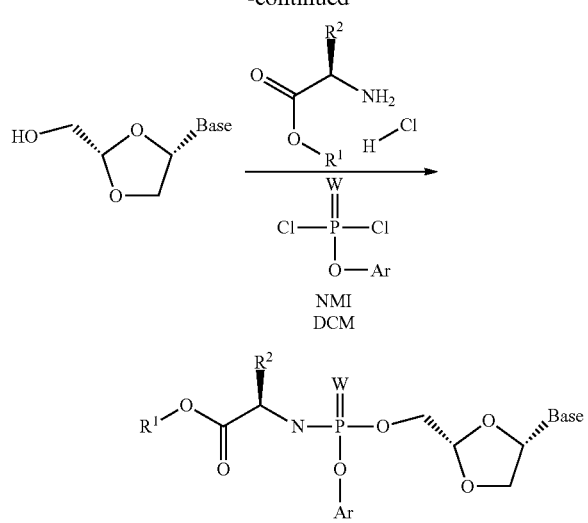

Scheme 5

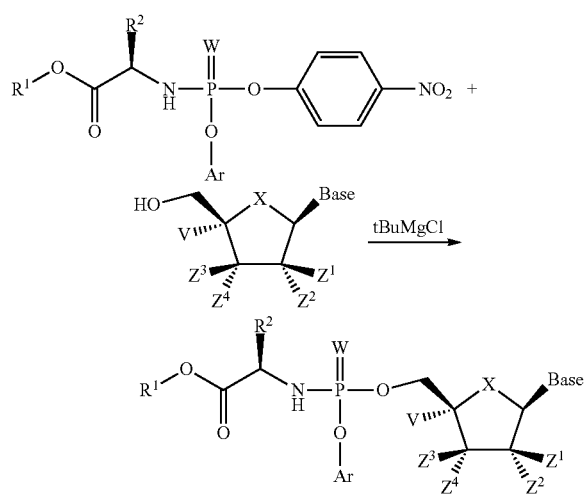

Scheme 6

In the Exemplary Preparation Schemes, the variables are as described in the context of Formula I or VI. Nucleosides can be prepared or obtained according to the knowledge in the art. Additional steps and reagents not provided in the Exemplary Preparation Schemes would be known to those of skill in the art. Exemplary methods of preparation are described in detail in the Examples herein.

Pharmaceutical Compositions and Methods of Administration

5'-D-amino acid phosphoramidate compounds can be formulated into pharmaceutical compositions using methods available in the art and those disclosed herein. Any of the compounds disclosed herein can be provided in the appropriate pharmaceutical composition and be administered by a suitable route of administration.

The methods provided herein encompass administering pharmaceutical compositions containing at least one compound as described herein, including a compound of general Formulas I-XVIII and 1-477c, if appropriate in the salt form, either used alone or in the form of a combination with one or more compatible and pharmaceutically acceptable carriers, such as diluents or adjuvants, or with another anticancer agent.

In certain embodiments, the second agent can be formulated or packaged with the compound provided herein. Of course, the second agent will only be formulated with the compound provided herein when, according to the judgment of those of skill in the art, such co-formulation should not interfere with the activity of either agent or the method of administration. In certain embodiments, the compound provided herein and the second agent are formulated separately. They can be packaged together, or packaged separately, for the convenience of the practitioner of skill in the art.

In clinical practice the active agents provided herein may be administered by any conventional route, in particular orally, parenterally, rectally or by inhalation (e.g. in the form of aerosols). In certain embodiments, the compound provided herein is administered orally.

Use may be made, as solid compositions for oral administration, of tablets, pills, hard gelatin capsules, powders or granules. In these compositions, the active product is mixed with one or more inert diluents or adjuvants, such as sucrose, lactose or starch.

These compositions can comprise substances other than diluents, for example a lubricant, such as magnesium stearate, or a coating intended for controlled release.

Use may be made, as liquid compositions for oral administration, of solutions which are pharmaceutically acceptable, suspensions, emulsions, syrups and elixirs containing inert diluents, such as water or liquid paraffin. These compositions can also comprise substances other than diluents, for example wetting, sweetening or flavoring products.

The compositions for parenteral administration can be emulsions or sterile solutions. Use may be made, as solvent or vehicle, of propylene glycol, a polyethylene glycol, vegetable oils, in particular olive oil, or injectable organic esters, for example ethyl oleate. These compositions can also contain adjuvants, in particular wetting, isotonizing, emulsifying, dispersing and stabilizing agents. Sterilization can be carried out in several ways, for example using a bacteriological filter, by radiation or by heating. They can also be prepared in the form of sterile solid compositions which can be dissolved at the time of use in sterile water or any other injectable sterile medium.

The compositions for rectal administration are suppositories or rectal capsules which contain, in addition to the active principle, excipients such as cocoa butter, semi-synthetic glycerides or polyethylene glycols.

The compositions can also be aerosols. For use in the form of liquid aerosols, the compositions can be stable sterile solutions or solid compositions dissolved at the time of use in apyrogenic sterile water, in saline or any other pharmaceutically acceptable vehicle. For use in the form of dry aerosols intended to be directly inhaled, the active principle is finely divided and combined with a water-soluble solid diluent or vehicle, for example dextran, mannitol or lactose.

In certain embodiments, a composition provided herein is a pharmaceutical composition or a single unit dosage form. Pharmaceutical compositions and single unit dosage forms provided herein comprise a prophylactically or therapeutically effective amount of one or more prophylactic or therapeutic agents (e.g., a compound provided herein, or other prophylactic or therapeutic agent), and a typically one or more pharmaceutically acceptable carriers or excipients. In a specific embodiment and in this context, the term "pharmaceutically acceptable" means approved by a regulatory agency of the Federal or a state government or listed in the U.S. Pharmacopeia or other generally recognized pharmacopeia for use in animals, and more particularly in humans. The term "carrier" includes a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water can be used as a carrier when the pharmaceutical composition is administered intravenously. Saline solutions and aqueous dextrose and glycerol solutions can also be employed as liquid carriers, particularly for injectable solutions. Examples of suitable pharmaceutical carriers are described in "Remington's Pharmaceutical Sciences" by E. W. Martin.

Typical pharmaceutical compositions and dosage forms comprise one or more excipients. Suitable excipients are well-known to those skilled in the art of pharmacy, and non-limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a subject and the specific active ingredients in the dosage form. The composition or single unit dosage form, if desired, can also contain minor amounts of wetting or emulsifying agents, or pH buffering agents.

Lactose free compositions provided herein can comprise excipients that are well known in the art and are listed, for example, in the U.S. Pharmocopia (USP) SP (XXI)/NF (XVI). In general, lactose free compositions comprise an active ingredient, a binder/filler, and a lubricant in pharmaceutically compatible and pharmaceutically acceptable amounts. Exemplary lactose free dosage forms comprise an active ingredient, microcrystalline cellulose, pre gelatinized starch, and magnesium stearate.

Further encompassed herein are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long term storage in order to determine characteristics such as shelf life or the stability of formulations over time. See, e.g., Jens T. Carstensen, Drug Stability: Principles & Practice, 2d. Ed., Marcel Dekker, New York, 1995, pp. 379 80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine can be anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions can be packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Further provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

The pharmaceutical compositions and single unit dosage forms can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Such compositions and dosage forms will contain a prophylactically or therapeutically effective amount of a prophylactic or therapeutic agent, in certain embodiments, in purified form, together with a suitable amount of carrier so as to provide the form for proper administration to the subject. The formulation should suit the mode of administration. In a certain embodiment, the pharmaceutical compositions or single unit dosage forms are sterile and in suitable form for administration to a subject, for example, an animal subject, such as a mammalian subject, for example, a human subject.

A pharmaceutical composition is formulated to be compatible with its intended route of administration. Examples of routes of administration include, but are not limited to, parenteral, e.g., intravenous, intradermal, subcutaneous, intramuscular, subcutaneous, oral, buccal, sublingual, inhalation, intranasal, transdermal, topical, transmucosal, intratumoral, intra-synovial and rectal administration. In a specific embodiment, the composition is formulated in accordance with routine procedures as a pharmaceutical composition adapted for intravenous, subcutaneous, intramuscular, oral, intranasal or topical administration to human beings. In an embodiment, a pharmaceutical composition is formulated in accordance with routine procedures for subcutaneous administration to human beings. Typically, compositions for intravenous administration are solutions in sterile isotonic aqueous buffer. Where necessary, the composition may also include a solubilizing agent and a local anesthetic such as lignocamne to ease pain at the site of the injection.

Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a subject, including suspensions (e.g., aqueous or non-aqueous liquid suspensions, oil in water emulsions, or a water in oil liquid emulsions), solutions, and elixirs; liquid dosage forms suitable for parenteral administration to a subject; and sterile solids (e.g., crystalline or amorphous solids) that can be reconstituted to provide liquid dosage forms suitable for parenteral administration to a subject.

The composition, shape, and type of dosage forms provided herein will typically vary depending on their use. For example, a dosage form used in the initial treatment of liver cancer may contain larger amounts of one or more of the active ingredients it comprises than a dosage form used in the maintenance treatment of the same cancer. Similarly, a parenteral dosage form may contain smaller amounts of one or more of the active ingredients it comprises than an oral dosage form used to treat the same disease or disorder. These and other ways in which specific dosage forms encompassed herein will vary from one another will be readily apparent to those skilled in the art. See, e.g., Remington's Pharmaceutical Sciences, 20th ed., Mack Publishing, Easton Pa. (2000).

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Typical dosage forms comprise a compound provided herein, or a pharmaceutically acceptable salt, solvate or hydrate thereof lie within the range of from about 0.1 mg to about 1000 mg per day, given as a single once-a-day dose in the morning or as divided doses throughout the day taken with food. Particular dosage forms can have about 0.1, 0.2, 0.3, 0.4, 0.5, 1.0, 2.0, 2.5, 5.0, 10.0, 15.0, 20.0, 25.0, 50.0, 100, 200, 250, 500 or 1000 mg of the active compound.

Oral Dosage Forms

Pharmaceutical compositions that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences, 20th ed., Mack Publishing, Easton Pa. (2000).

In certain embodiments, the oral dosage forms are solid and prepared under anhydrous conditions with anhydrous ingredients, as described in detail herein. However, the scope of the compositions provided herein extends beyond anhydrous, solid oral dosage forms. As such, further forms are described herein.

Typical oral dosage forms are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free flowing form such as powder or granules, optionally mixed with an excipient. Molded tablets can be made by molding in a suitable machine a mixture of the powdered compound moistened with an inert liquid diluent.

Examples of excipients that can be used in oral dosage forms include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre gelatinized starch, and mixtures thereof. The binder or filler in pharmaceutical compositions is typically present in from about 50 to about 99 weight percent of the pharmaceutical composition or dosage form.

Suitable forms of microcrystalline cellulose include, but are not limited to, the materials sold as AVICEL PH 101, AVICEL PH 103 AVICEL RC 581, AVICEL PH 105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC 581. Suitable anhydrous or low moisture excipients or additives include AVICEL PH 103™ and Starch 1500 LM.

Disintegrants are used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms include, but are not limited to, agar, alginic acid, calcium carbonate, microcrystalline cellulose, croscarmellose sodium, crospovidone, polacrilin potassium, sodium starch glycolate, potato or tapioca starch, pre gelatinized starch, other starches, clays, other algins, other celluloses, gums, and mixtures thereof.

Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB OSIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

Delayed Release Dosage Forms

Active ingredients such as the compounds provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500; each of which is incorporated herein by reference in its entirety. Such dosage forms can be used to provide slow or controlled release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled release formulations known to those of ordinary skill in the art, including those described herein, can be readily selected for use with the active ingredients provided herein. Thus encompassed herein are single unit dosage forms suitable for oral administration such as, but not limited to, tablets, capsules, gelcaps, and caplets that are adapted for controlled release.

All controlled release pharmaceutical products have a common goal of improving drug therapy over that achieved by their non-controlled counterparts. Ideally, the use of an optimally designed controlled release preparation in medical treatment is characterized by a minimum of drug substance being employed to cure or control the condition in a minimum amount of time. Advantages of controlled release formulations include extended activity of the drug, reduced dosage frequency, and increased subject compliance. In addition, controlled release formulations can be used to affect the time of onset of action or other characteristics, such as blood levels of the drug, and can thus affect the occurrence of side (e.g., adverse) effects.

Most controlled release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled release of an active ingredient can be stimulated by various conditions including, but not limited to, pH, temperature, enzymes, water, or other physiological conditions or compounds.

In certain embodiments, the drug may be administered using intravenous infusion, an implantable osmotic pump, a transdermal patch, liposomes, or other modes of administration. In certain embodiments, a pump may be used (see, Sefton, *CRC Crit. Ref. Biomed. Eng.* 14:201 (1987); Buchwald et al., *Surgery* 88:507 (1980); Saudek et al., *N. Engl. J. Med.* 321:574 (1989)). In another embodiment, polymeric materials can be used. In yet another embodiment, a controlled release system can be placed in a subject at an appropriate site determined by a practitioner of skill, i.e., thus requiring only a fraction of the systemic dose (see, e.g., Goodson, *Medical Applications of Controlled Release*, vol. 2, pp. 115-138 (1984)). Other controlled release systems are discussed in the review by Langer (*Science* 249:1527-1533 (1990)). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient in such parenteral compositions is highly dependent on the specific nature thereof, as well as the needs of the subject.

Parenteral Dosage Forms

In certain embodiments, provided are parenteral dosage forms. Parenteral dosage forms can be administered to subjects by various routes including, but not limited to, subcutaneous, intravenous (including bolus injection), intramuscular, and intraarterial. Because their administration typically bypasses subjects' natural defenses against contaminants, parenteral dosage forms are typically, sterile or capable of being sterilized prior to administration to a subject. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms.

Transdermal, Topical & Mucosal Dosage Forms

Also provided are transdermal, topical, and mucosal dosage forms. Transdermal, topical, and mucosal dosage forms include, but are not limited to, ophthalmic solutions, sprays, aerosols, creams, lotions, ointments, gels, solutions, emulsions, suspensions, or other forms known to one of skill in the art. See, e.g., Remington's Pharmaceutical Sciences, $16^{th}$, 18th and $20^{th}$ eds., Mack Publishing, Easton Pa. (1980, 1990 & 2000); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed herein are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane 1,3 diol, isopropyl myristate, isopropyl palmitate, mineral oil, and mixtures thereof to form lotions, tinctures, creams, emulsions, gels or ointments, which are nontoxic and pharmaceutically acceptable. Moisturizers or humectants can also be added to pharmaceutical compositions and dosage forms if desired. Examples of such additional ingredients are well known in the art. See, e.g., Remington's Pharmaceutical Sciences, $16^{th}$, 18th and $20^{th}$ eds., Mack Publishing, Easton Pa. (1980, 1990 & 2000).

Depending on the specific tissue to be treated, additional components may be used prior to, in conjunction with, or subsequent to treatment with active ingredients provided. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery enhancing or penetration enhancing agent. Different salts, hydrates or solvates of the active ingredients can be used to further adjust the properties of the resulting composition.

Dosage and Unit Dosage Forms

In human therapeutics, the doctor will determine the posology which he considers most appropriate according to a preventive or curative treatment and according to the age, weight, stage of the cancer and other factors specific to the subject to be treated. In certain embodiments, doses are from about 1 to about 1000 mg per day for an adult, or from about 5 to about 250 mg per day or from about 10 to 50 mg per day for an adult. In certain embodiments, doses are from about 5 to about 400 mg per day or 25 to 200 mg per day per adult. In certain embodiments, dose rates of from about 50 to about 500 mg per day are also contemplated.

In further aspects, provided are methods of treating or preventing a liver cancer in a subject by administering, to a subject in need thereof, an effective amount of a compound provided herein, or a pharmaceutically acceptable salt thereof. The amount of the compound or composition which will be effective in the prevention or treatment of a disorder or one or more symptoms thereof will vary with the nature and severity of the disease or condition, and the route by which the active ingredient is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject. Effective doses may be extrapolated from dose-response curves derived from in vitro or animal model test systems.

In certain embodiments, exemplary doses of a composition include milligram or microgram amounts of the active compound per kilogram of subject or sample weight (e.g., about 10 micrograms per kilogram to about 50 milligrams per kilogram, about 100 micrograms per kilogram to about 25 milligrams per kilogram, or about 100 microgram per kilogram to about 10 milligrams per kilogram). For compositions provided herein, in certain embodiments, the dosage administered to a subject is 0.140 mg/kg to 3 mg/kg of the subject's body weight, based on weight of the active compound. In certain embodiments, the dosage administered to a subject is between 0.20 mg/kg and 2.00 mg/kg, or between 0.30 mg/kg and 1.50 mg/kg of the subject's body weight.

In certain embodiments, the recommended daily dose range of a composition provided herein for the conditions described herein lie within the range of from about 0.1 mg to about 1000 mg per day, given as a single once-a-day dose or as divided doses throughout a day. In certain embodiments, the daily dose is administered twice daily in equally divided doses. In certain embodiments, a daily dose range should be from about 10 mg to about 200 mg per day, in other embodiments, between about 10 mg and about 150 mg per day, in further embodiments, between about 25 and about 100 mg per day. It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the composition provided herein are also encompassed by the herein described dosage amounts and dose frequency schedules. Further, when a subject is administered multiple dosages of a composition provided herein, not all of the dosages need be the same. For example, the dosage administered to the subject may be increased to improve the prophylactic or therapeutic effect of the composition or it may be decreased to reduce one or more side effects that a particular subject is experiencing.

In certain embodiment, the dosage of the composition provided herein, based on weight of the active compound, administered to prevent, treat, manage, or ameliorate a disorder, or one or more symptoms thereof in a subject is 0.1 mg/kg, 1 mg/kg, 2 mg/kg, 3 mg/kg, 4 mg/kg, 5 mg/kg, 6 mg/kg, 10 mg/kg, or 15 mg/kg or more of a subject's body weight. In another embodiment, the dosage of the composition or a composition provided herein administered to prevent, treat, manage, or ameliorate a disorder, or one or more symptoms thereof in a subject is a unit dose of 0.1 mg to 200 mg, 0.1 mg to 100 mg, 0.1 mg to 50 mg, 0.1 mg to 25 mg, 0.1 mg to 20 mg, 0.1 mg to 15 mg, 0.1 mg to 10 mg, 0.1 mg to 7.5 mg, 0.1 mg to 5 mg, 0.1 to 2.5 mg, 0.25 mg to 20 mg, 0.25 to 15 mg, 0.25 to 12 mg, 0.25 to 10 mg, 0.25 mg to 7.5 mg, 0.25 mg to 5 mg, 0.5 mg to 2.5 mg, 1 mg to 20 mg, 1 mg to 15 mg, 1 mg to 12 mg, 1 mg to 10 mg, 1 mg to 7.5 mg, 1 mg to 5 mg, or 1 mg to 2.5 mg.

In certain embodiments, treatment or prevention can be initiated with one or more loading doses of a compound or composition provided herein followed by one or more maintenance doses. In such embodiments, the loading dose can be, for instance, about 60 to about 400 mg per day, or about 100 to about 200 mg per day for one day to five weeks. The loading dose can be followed by one or more maintenance doses. In certain embodiments, each maintenance does is, independently, about from about 10 mg to about 200 mg per day, between about 25 mg and about 150 mg per day, or between about 25 and about 80 mg per day. Maintenance doses can be administered daily and can be administered as single doses, or as divided doses.

In certain embodiments, a dose of a compound or composition provided herein can be administered to achieve a steady-state concentration of the active ingredient in blood or serum of the subject. The steady-state concentration can be determined by measurement according to techniques available to those of skill or can be based on the physical characteristics of the subject such as height, weight and age. In certain embodiments, a sufficient amount of a compound or composition provided herein is administered to achieve a steady-state concentration in blood or serum of the subject of from about 300 to about 4000 ng/mL, from about 400 to about 1600 ng/mL, or from about 600 to about 1200 ng/mL. In some embodiments, loading doses can be administered to achieve steady-state blood or serum concentrations of about 1200 to about 8000 ng/mL, or about 2000 to about 4000 ng/mL for one to five days. In certain embodiments, maintenance doses can be administered to achieve a steady-state concentration in blood or serum of the subject of from about 300 to about 4000 ng/mL, from about 400 to about 1600 ng/mL, or from about 600 to about 1200 ng/mL.

In certain embodiments, administration of the same composition may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent may be repeated and the administration may be separated by at least at least 1 day, 2 days, 3 days, 5 days, 10 days, 15 days, 30 days, 45 days, 2 months, 75 days, 3 months, or 6 months.

In certain aspects, provided herein are unit dosages comprising a compound, or a pharmaceutically acceptable salt thereof, in a form suitable for administration. Such forms are described in detail herein. In certain embodiments, the unit dosage comprises 1 to 1000 mg, 5 to 250 mg or 10 to 50 mg active ingredient. In particular embodiments, the unit dosages comprise about 1, 5, 10, 25, 50, 100, 125, 250, 500 or 1000 mg active ingredient. Such unit dosages can be prepared according to techniques familiar to those of skill in the art.

The dosages of the second agents are to be used in the combination therapies provided herein. In certain embodiments, dosages lower than those which have been or are currently being used to prevent or treat liver cancer are used in the combination therapies provided herein. The recommended dosages of second agents can be obtained from the knowledge of those of skill. For those second agents that are approved for clinical use, recommended dosages are described in, for example, Hardman et al., eds., 1996, Goodman & Gilman's The Pharmacological Basis Of Basis Of Therapeutics $9^{th}$ Ed, Mc-Graw-Hill, New York; Physician's Desk Reference (PDR) $57^{th}$ Ed., 2003, Medical Economics Co., Inc., Montvale, N.J., which are incorporated herein by reference in its entirety.

In various embodiments, the therapies (e.g., a compound provided herein and the second agent) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours apart. In various embodiments, the therapies are administered no more than 24 hours apart or no more than 48 hours apart. In certain embodiments, two or more therapies are administered within the same patient visit. In other embodiments, the compound provided herein and the second agent are administered concurrently.

In other embodiments, the compound provided herein and the second agent are administered at about 2 to 4 days apart, at about 4 to 6 days apart, at about 1 week part, at about 1 to 2 weeks apart, or more than 2 weeks apart.

In certain embodiments, administration of the same agent may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same agent may be repeated and the administration may be separated by at least at least 1 day, 2 days, 3 days, 5 days, 10 days, 15 days, 30 days, 45 days, 2 months, 75 days, 3 months, or 6 months.

In certain embodiments, a compound provided herein and a second agent are administered to a patient, for example, a mammal, such as a human, in a sequence and within a time interval such that the compound provided herein can act together with the other agent to provide an increased benefit than if they were administered otherwise. For example, the second active agent can be administered at the same time or sequentially in any order at different points in time; however, if not administered at the same time, they should be administered sufficiently close in time so as to provide the desired therapeutic or prophylactic effect. In certain embodiments, the compound provided herein and the second active agent exert their effect at times which overlap. Each second active agent can be administered separately, in any appropriate form and by any suitable route. In other embodiments, the compound provided herein is administered before, concurrently or after administration of the second active agent.

In certain embodiments, the compound provided herein and the second agent are cyclically administered to a patient. Cycling therapy involves the administration of a first agent (e.g., a first prophylactic or therapeutic agents) for a period of time, followed by the administration of a second agent and/or third agent (e.g., a second and/or third prophylactic or therapeutic agents) for a period of time and repeating this sequential administration. Cycling therapy can reduce the development of resistance to one or more of the therapies, avoid or reduce the side effects of one of the therapies, and/or improve the efficacy of the treatment.

In certain embodiments, the compound provided herein and the second active agent are administered in a cycle of less than about 3 weeks, about once every two weeks, about once every 10 days or about once every week. One cycle can comprise the administration of a compound provided herein and the second agent by infusion over about 90 minutes every cycle, about 1 hour every cycle, about 45 minutes every cycle. Each cycle can comprise at least 1 week of rest, at least 2 weeks of rest, at least 3 weeks of rest. The number of cycles administered is from about 1 to about 12 cycles, more typically from about 2 to about 10 cycles, and more typically from about 2 to about 8 cycles.

In other embodiments, courses of treatment are administered concurrently to a patient, i.e., individual doses of the second agent are administered separately yet within a time interval such that the compound provided herein can work together with the second active agent. For example, one component can be administered once per week in combination with the other components that can be administered once every two weeks or once every three weeks. In other words, the dosing regimens are carried out concurrently even if the therapeutics are not administered simultaneously or during the same day.

The second agent can act additively or synergistically with the compound provided herein. In certain embodiments, the compound provided herein is administered concurrently with one or more second agents in the same pharmaceutical composition. In another embodiment, a compound provided herein is administered concurrently with one or more second agents in separate pharmaceutical compositions. In still another embodiment, a compound provided herein is administered prior to or subsequent to administration of a second agent. Also contemplated are administration of a compound provided herein and a second agent by the same or different routes of administration, e.g., oral and parenteral. In certain embodiments, when the compound provided herein is administered concurrently with a second agent that potentially produces adverse side effects including, but not limited to, toxicity, the second active agent can advantageously be administered at a dose that falls below the threshold that the adverse side effect is elicited.

Kits

Also provided are kits for use in methods of treatment of a liver cancer such as hepatocellular carcinoma, cholangiocarcinoma, or biliary tract cancer. The kits can include a compound or composition provided herein, a second agent or composition, and instructions providing information to a health care provider regarding usage for treating the disorder. Instructions may be provided in printed form or in the form of an electronic medium such as a floppy disc, CD, or DVD, or in the form of a website address where such instructions may be obtained. A unit dose of a compound or composition provided herein, or a second agent or composition, can include a dosage such that when administered to a subject, a therapeutically or prophylactically effective plasma level of the compound or composition can be maintained in the subject for at least 1 days. In some embodiments, a compound or composition can be included as a sterile aqueous pharmaceutical composition or dry powder (e.g., lyophilized) composition.

In some embodiments, suitable packaging is provided. As used herein, "packaging" includes a solid matrix or material customarily used in a system and capable of holding within fixed limits a compound provided herein and/or a second agent suitable for administration to a subject. Such materials include glass and plastic (e.g., polyethylene, polypropylene, and polycarbonate) bottles, vials, paper, plastic, and plastic-foil laminated envelopes and the like. If e-beam sterilization techniques are employed, the packaging should have sufficiently low density to permit sterilization of the contents.

Methods of Use

Provided herein is a method for treating liver cancer in a subject, which comprises contacting the subject with a therapeutically effective amount of a nucleotide analog disclosed herein, e.g., a 5'-D-amino acid phosphoramidate compound of Formulas I-XVIII and 1-477c, including a single enantiomer, a mixture of an enantiomeric pair, an individual diastereomer, a mixture of diastereomers, or a tautomeric form thereof; or a pharmaceutically acceptable salt, solvate, prodrug, phosphate, or active metabolite thereof. Liver cancers which can be treated include primary and secondary liver cancers. In particular embodiments, the liver cancer is hepatocellular carcinoma, cholangiocarcinoma, or biliary tract cancer. In particular embodiments, the liver cancer is a metastasis in the liver originated from other cancers (such as colon cancer, pancreatic cancer, etc.).

Provided herein is a method for inhibiting the growth of a liver cancer cell, which comprises contacting the cell with a therapeutically effective amount of a 5'-D-amino acid phosphoramidate compound disclosed herein, e.g., a 5'-D-amino acid phosphoramidate compound of Formulas I-XVIII and 1-477c, including a single enantiomer, a mixture of an enantiomeric pair, an individual diastereomer, a mixture of diastereomers, or a tautomeric form thereof; or a pharmaceutically acceptable salt, solvate, prodrug, phosphate, or active metabolite thereof. In certain embodiments, the liver cancer is hepatocellular carcinoma, cholangiocarcinoma, or biliary tract cancer. In particular embodiments, the cancer is hepatocellular carcinoma.

Provided herein is a method for inhibiting replication of a liver cancer cell, which comprises contacting the cell with a therapeutically effective amount of a 5'-D-amino acid phosphoramidate compound disclosed herein, e.g., a 5'-D- amino acid phosphoramidate compound of Formulas I-XVIII and 1-477c, including a single enantiomer, a mixture of an enantiomeric pair, an individual diastereomer, a mixture of diastereomers, or a tautomeric form thereof; or a pharmaceutically acceptable salt, solvate, prodrug, phosphate, or active metabolite thereof. In certain embodiments, the liver cancer is hepatocellular carcinoma, cholangiocarcinoma, or biliary tract cancer. In particular embodiments, the cancer is hepatocellular carcinoma.

Provided herein is a method for inhibiting the growth of a liver tumor, which comprises contacting the liver tumor with a 5'-D-amino acid phosphoramidate compound disclosed herein, e.g., a 5'-D-amino acid phosphoramidate compound of Formulas I-XVIII and 1-477c, including a single enantiomer, a mixture of an enantiomeric pair, an individual diastereomer, a mixture of diastereomers, or a tautomeric form thereof; or a pharmaceutically acceptable salt, solvate, prodrug, phosphate, or active metabolite thereof. In certain embodiments, the liver cancer is hepatocellular carcinoma, cholangiocarcinoma, or biliary tract cancer. In particular embodiments, the cancer is hepatocellular carcinoma.

In certain embodiments, provided herein are methods for the treatment and/or prophylaxis of a subject with liver cancer that includes the administration of an effective amount of a nucleoside compound disclosed herein, e.g., a nucleoside compound of Formulas I-XVIII and 1-477c, including a single enantiomer, a mixture of an enantiomeric pair, an individual diastereomer, a mixture of diastereomers, or a tautomeric form thereof or a pharmaceutically acceptable salt, solvate, prodrug, phosphate, or active metabolite thereof. In certain embodiments, the liver cancer is hepatocellular carcinoma, cholangiocarcinoma, or biliary tract cancer. In particular embodiments, the cancer is hepatocellular carcinoma.

In certain embodiments, provided herein are methods for treating a liver cancer in a subject. In certain embodiments, the methods encompass the step of administering to the subject in need thereof an amount of a compound effective for the treatment or prevention of a liver cancer in combination with a second agent effective for the treatment or prevention of the cancer. The compound can be any compound as described herein, and the second agent can be any second agent described in the art or herein. In certain embodiments, the compound is in the form of a pharmaceutical composition or dosage form, as described elsewhere herein. In certain embodiments, the liver cancer is hepatocellular carcinoma, cholangiocarcinoma, or biliary tract cancer. In particular embodiments, the cancer is hepatocellular carcinoma.

In certain embodiments, provided herein are methods for the treatment and/or prophylaxis of a subject with liver cancer that includes the administration of an effective amount of a compounds provided herein, or a pharmaceutically acceptable salt thereof. In certain embodiments, provided herein are methods for treating a liver cancer in a subject. In certain embodiments, the methods encompass the step of administering to the subject in need thereof an amount of a compound effective for the treatment or prevention of a liver cancer in combination with a second agent effective for the treatment or prevention of the liver cancer. The compound can be any compound as described herein, and the second agent can be any second agent described in the art or herein. In certain embodiments, the compound is in the form of a pharmaceutical composition or dosage form, as described elsewhere herein. In certain embodiments, the liver cancer is hepatocellular carcinoma, cholangiocarcinoma, or biliary tract cancer. In particular embodiments, the cancer is hepatocellular carcinoma.

Assay Methods

Compounds can be assayed for liver cancer activity according to any assay known to those of skill in the art.

Further, compounds can be assayed for accumulation in liver cells of a subject according to any assay known to those of skill in the art. In certain embodiments, a compound can be administered to the subject, and a liver cell of the subject can be assayed for the compound or a derivative thereof, e.g. a nucleoside, nucleoside phosphate or nucleoside triphosphate derivative thereof.

In certain embodiments, a nucleoside compound is administered to cells, such as liver cells, in vivo or in vitro, and the nucleoside triphosphate levels delivered intracellularly are measured, to indicate delivery of the compound and triphosphorylation in the cell. The levels of intracellular nucleoside triphosphate can be measured using analytical techniques known in the art. Methods of detecting ddATP are described herein below by way of example, but other nucleoside triphosphates can be readily detected using the appropriate controls, calibration samples and assay techniques.

In certain embodiments, ddATP concentrations are measured in a sample by comparison to calibration standards made from control samples. The ddATP concentrations in a sample can be measured using an analytical method such as HPLC LC MS. In certain embodiments, a test sample is compared to a calibration curve created with known concentrations of ddATP to thereby obtain the concentration of that sample.

In certain embodiments, the samples are manipulated to remove impurities such as salts ($Na^+$, $K^+$, etc.) before analysis. In certain embodiments, the lower limit of quantitation is about ~0.2 pmol/mL for hepatocyte cellular extracts particularly where reduced salt is present.

In certain embodiments, the method allows successfully measuring triphosphate nucleotides formed at levels of 1-10,000 pmol per million cells in e.g. cultured hepatocytes and HepG2 cells.

Second Therapeutic Agents

In certain embodiments, the compounds and compositions provided herein are useful in methods of treatment of a liver cancer, that comprise further administration of a second agent effective for the treatment of the liver cancer in a subject in need thereof. The second agent can be any agent known to those of skill in the art to be effective for the treatment of the liver cancer, including those currently approved by the FDA.

In certain embodiments, a compound provided herein is administered in combination with one second agent. In further embodiments, a compound provided herein is administered in combination with two second agents. In still further embodiments, a compound provided herein is administered in combination with two or more second agents.

As used herein, the term "in combination" includes the use of more than one therapy (e.g., one or more prophylactic and/or therapeutic agents). The use of the term "in combination" does not restrict the order in which therapies (e.g., prophylactic and/or therapeutic agents) are administered to a subject with a disorder. A first therapy (e.g., a prophylactic or therapeutic agent such as a compound provided herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to a subject with a disorder.

As used herein, the term "synergistic" includes a combination of a compound provided herein and another therapy (e.g., a prophylactic or therapeutic agent) which has been or is currently being used to prevent, manage or treat a disorder, which is more effective than the additive effects of the therapies. A synergistic effect of a combination of therapies (e.g., a combination of prophylactic or therapeutic agents) permits the use of lower dosages of one or more of the therapies and/or less frequent administration of said therapies to a subject with a disorder. The ability to utilize lower dosages of a therapy (e.g., a prophylactic or therapeutic agent) and/or to administer said therapy less frequently reduces the toxicity associated with the administration of said therapy to a subject without reducing the efficacy of said therapy in the prevention or treatment of a disorder). In addition, a synergistic effect can result in improved efficacy of agents in the prevention or treatment of a disorder. Finally, a synergistic effect of a combination of therapies (e.g., a combination of prophylactic or therapeutic agents) may avoid or reduce adverse or unwanted side effects associated with the use of either therapy alone.

The active compounds provided herein can be administered in combination or alternation with another therapeutic agent, in particular an anti-cancer agent. In combination therapy, effective dosages of two or more agents are administered together, whereas in alternation or sequential-step therapy, an effective dosage of each agent is administered serially or sequentially. The dosages given will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

In certain embodiments, the second agent is selected from the group consisting of sorafenib tosylate (Nexavar), radiation therapy, selective internal radiation therapy (e.g., SIR-Spheres and TheraSphere), ethiodized oil (Lipidol), pexastimogene devacirepvec (Pexa-Vec, JX-594, Jennarex), Quinacrine (Clevelane BioLabs), CC-223 (Celgene), CF102 (Can-Fite), SGI-110 (Astex), and G-202 (Genspera).

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: g (grams); mg (milligrams); mL (milliliters); µL (microliters); mM (millimolar); µM (micromolar); Hz (Hertz); MHz (megahertz); mmol (millimoles); hr or hrs (hours); min (minutes); MS (mass spectrometry); ESI (electrospray ionization); TLC (thin layer chromatography); HPLC (high pressure liquid chromatography); THF (tetrahydrofuran); CDCl$_3$ (deuterated chloroform); AcOH (acetic acid); DCM (dichloromethane); DMSO (dimethylsulfoxide); DMSO-d$_6$ (deuterated dimethylsulfoxide); EtOAc (ethyl acetate); MeOH (methanol); and BOC (t-butyloxycarbonyl).

For all of the following examples, standard work-up and purification methods known to those skilled in the art can be utilized. Unless otherwise indicated, all temperatures are expressed in ° C. (degrees Centigrade). All reactions are conducted at room temperature unless otherwise noted. Synthetic methodologies illustrated herein are intended to exemplify the applicable chemistry through the use of specific examples and are not indicative of the scope of the disclosure.

Example 1

Preparation of Nucleotides

Compound 4

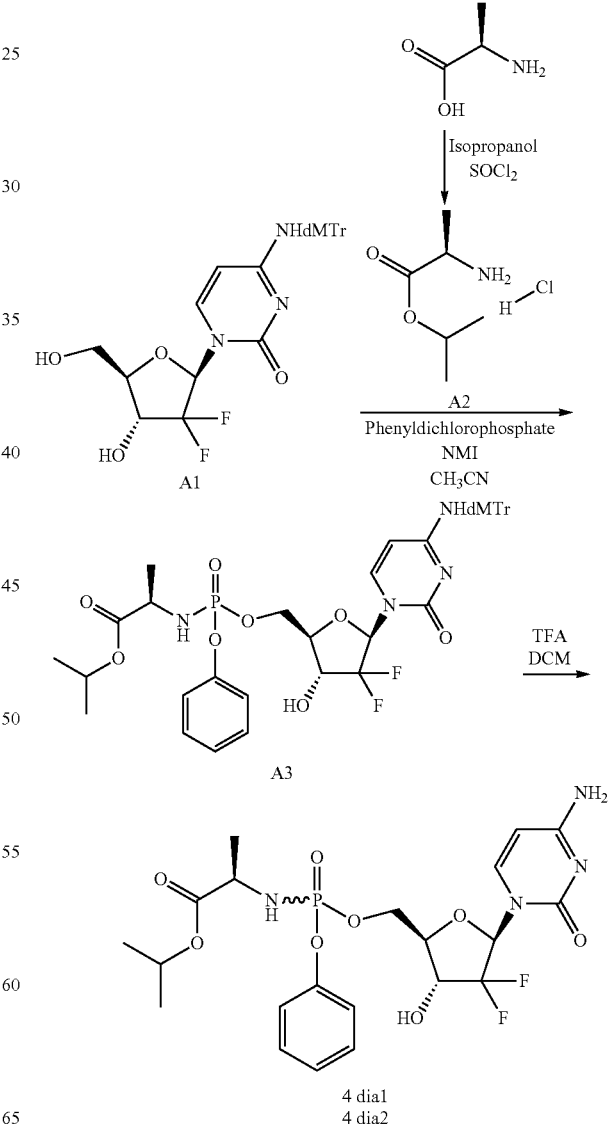

Compound A2

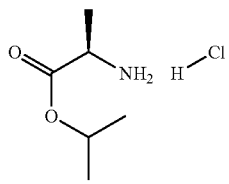

To a solution of D-Alanine (56.12 mmol) in isopropanol (2.3 mL/mmol) was added at room temperature, under nitrogen, thionyl chloride (280.61 mmol) dropwise. The reaction mixture was stirred at 85° C. for 4 hours. The reaction was monitored by TLC (eluent: DCM/MeOH: 10%, developing bath: ninhydrine). The reaction mixture was concentrated under reduced pressure and the crude compound was dried under vacuo overnight. The compound was triturated in diisopropylether, filtered, washed with pentane and diisopropylether, filtered and dried under vacuo at 40° C. for 4 hours to afford the pure compound as HCl salt in 98% yield. $^1$H NMR (DMSO-$d_6$, 400 MHz) δ (ppm) 1.22 (m, 6H), 1.40 (d, J=7.19 Hz, 3H), 3.95-4.01 (m, 1H), 4.98 (heptuplet, J=6.21 Hz, 1H), 8.53-8.58 (m, 3H).

Compound A3

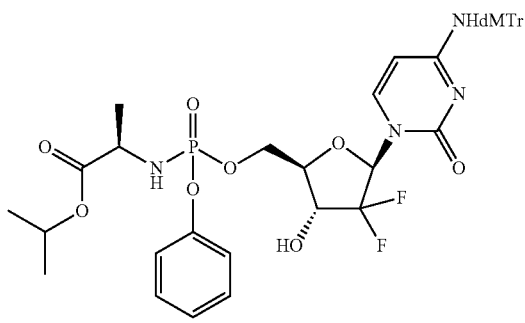

To a solution of A2 (5.20 mmol) in anhydrous dichloromethane (8 mL/mmol) was added under nitrogen at −30° C. phenyldichlorophosphate (5.20 mmol) followed by N-methylimidazole (20.0 mmol). The reaction mixture was stirred from −30° C. to room temperature for 1 hour. Compound A1 (4.00 mmol) was added to the reaction mixture under nitrogen at −30° C. The reaction mixture was stirred at room temperature for 4 days. The reaction was monitored by LC/MS. The mixture was concentrated under reduced pressure. The residue was dissolved with ethyl acetate then washed with a 1N HCl solution, water and brine. The organic layer was filtered and concentrated under reduced pressure. The crude residue was purified by flash chromatography on silica gel (eluent: DCM/ethanol: 0 to 10%) to afford the mixture of diastereoisomers as a colorless glue in 12% yield. MS (ESI) m/z=835.1 (MH$^+$).

Compound 4

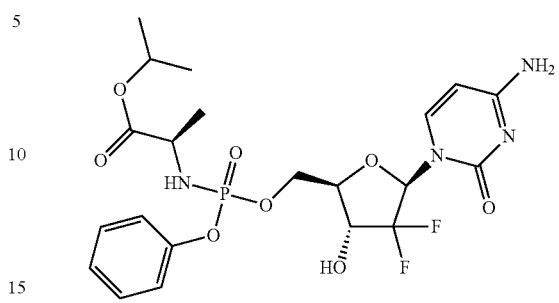

To a solution of A3 (0.063 mmol) in anhydrous dichloromethane (10 mL/mmol) was added under nitrogen trifluoroacetic acid (0.64 mmol). The reaction mixture was stirred at room temperature overnight and monitored by LC/MS. The mixture was concentrated under reduced pressure. The crude residue was purified by flash chromatography on silica gel (eluent: DCM/methanol: 0 to 20%) followed by preparative MS/HPLC and by chiral HPLC (Chiralpak IA 4.6×250 mm; 5 um) to afford the two diastereoisomers of 4.

Compound 4 (diastereoisomer 1): White solid; MS (ESI) m/z=533.2 (MH$^+$); $^1$H NMR (DMSO-$d_6$, 400 MHz) δ (ppm) 7.52-7.50 (m, 2H), 7.46 (brs, 1H), 7.40-7.36 (m, 2H), 7.21-7.18 (m, 3H), 6.43 (d, J=6.23 Hz, 1H), 6.18 (t, J=8.31 Hz, 1H), 6.09 (dd, J=12.80 Hz, 9.92 Hz, 1H), 5.75 (d, J=7.52 Hz, 1H), 4.85 (heptuplet, J=6.24 Hz, 1H), 4.37-4.16 (m, 3H), 4.05-4.02 (m, 1H), 3.83-3.73 (m, 1H), 1.21 (d, J=7.06 Hz, 3H), 1.15 (d, J=6.29 Hz, 3H), 1.145 (d, J=6.29 Hz, 3H); $^{31}$P NMR (DMSO-$d_6$, 162 MHz) δ (ppm) 3.93 (s, 1P); $^{19}$F NMR (DMSO-$d_6$, 376 MHz) δ (ppm) −115.32−(−116.51) (m, 2F).

Compound 4 (diastereoisomer 2): white solid; MS (ESI) m/z=533.2 (MH$^+$); $^1$H NMR (DMSO-$d_6$, 400 MHz) δ (ppm) 7.46-7.36 (m, 5H), 7.23-7.17 (m, 3H), 6.45 (d, J=6.35 Hz, 1H), 6.19-6.12 (m, 2H), 5.77 (d, J=7.57 Hz, 1H), 4.86 (heptuplet, J=6.26 Hz, 1H), 4.35-4.30 (m, 1H), 4.26-4.20 (m, 1H), 4.13 (brs, 1H), 4.01-3.99 (m, 1H), 3.84-3.74 (m, 1H), 1.23 (d, J=7.01 Hz, 3H), 1.15 (d, J=6.29 Hz, 3H), 1.145 (d, J=6.29 Hz, 3H); $^{31}$P NMR (DMSO-$d_6$, 162 MHz) δ (ppm) 3.47 (s, 1P); $^{19}$F NMR (DMSO-$d_6$, 376 MHz) δ (ppm) −115.35−(−116.32) (m, 2F).

Compound 7

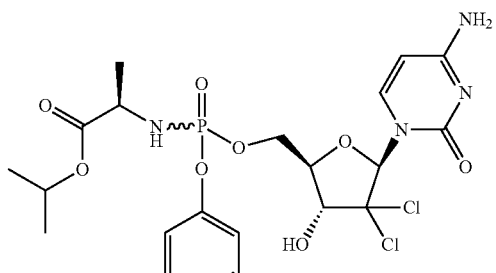

(Two Diastereomers)

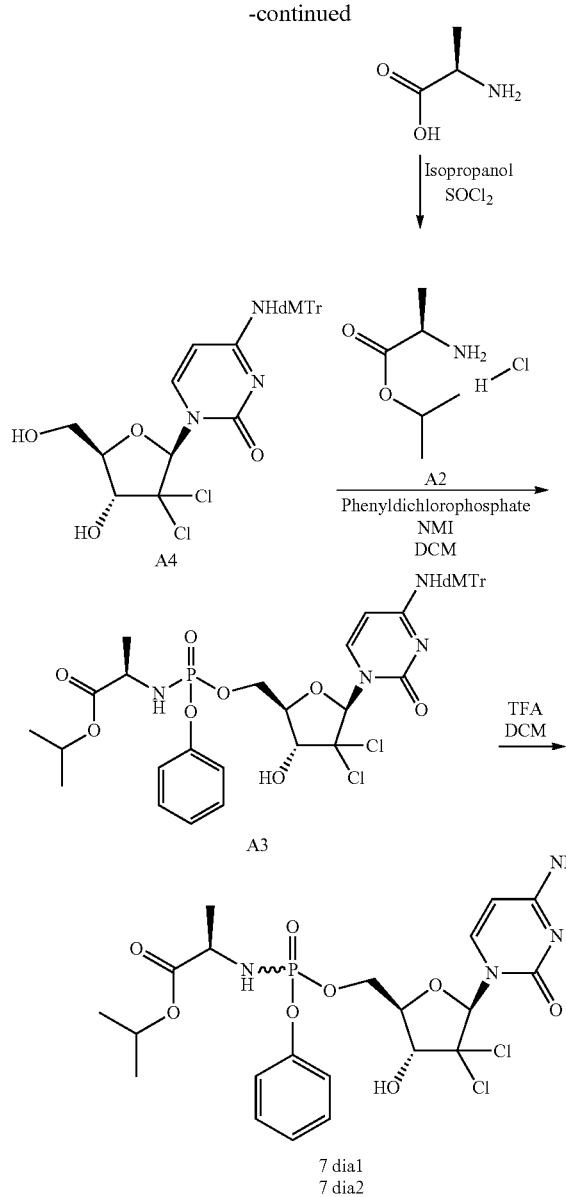

Compound A5

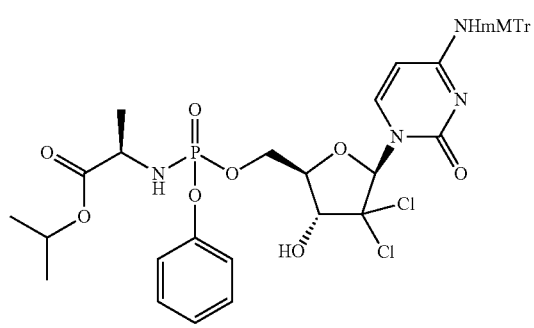

To a solution of A2 (2.14 mmol) in anhydrous dichloromethane (8 mL/mmol) was added under nitrogen at −41° C. phenyldichlorophosphate (2.14 mmol) followed by N-methylimidazole (7.52 mmol). The reaction mixture was stirred from −41° C. to room temperature for 3 hours. Compound A4 (0.75 mmol) was added to the reaction mixture under nitrogen. The reaction mixture was stirred at room temperature for 2 hours. The reaction was monitored by LC/MS. The mixture was concentrated under reduced pressure. The residue was dissolved with ethyl acetate (250 mL) then washed with a 1N HCl solution (2×200 mL), water (200 mL) and brine (200 mL). The organic layer was filtered and concentrated under reduced pressure. The crude residue was purified by flash chromatography on silica gel (eluent: DCM/ethanol: 0 to 3%) to afford the mixture of diastereoisomers A5 as a white solid in 26% yield. $^{31}$P NMR (DMSO-$d_6$, 162 MHz) δ (ppm) 3.45 (s, 0.42P), 3.80 (s, 0.58P); MS (ESI) m/z=837.2 (MH$^+$).

To a solution of A5 (0.063 mmol) in anhydrous dichloromethane (10 mL/mmol) was added under nitrogen trifluoroacetic acid (0.64 mmol). The reaction mixture was stirred at room temperature for 3-4 hours and monitored by LC/MS. The mixture was concentrated under reduced pressure. The crude residue was purified by flash chromatography on silica gel (eluent: DCM/ethanol: 0 to 20%) followed by RP-18 chromatography (eluent: H$_2$O/CH$_3$CN: 0 to 100%), and by preparative MS/HPLC to afford the two diastereoisomers of 7.

Compound 7

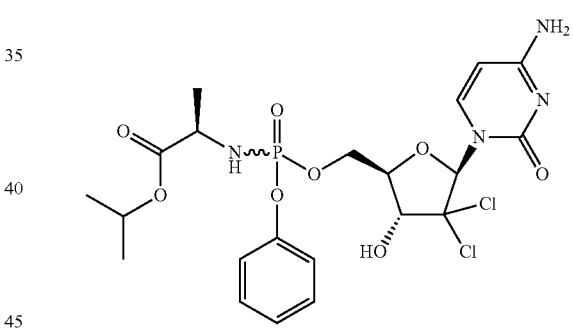

Compound 7 (diastereoisomer 1): white freeze-dried compound; 12% yield; $^1$H NMR (DMSO-$d_6$, 400 MHz) δ (ppm) 1.12 (t, J=6.90 Hz, 6H), 1.21 (d, J=7.12 Hz, 3H), 3.70-3.80 (m, 1H), 3.97-4.00 (m, 1H), 4.22-4.27 (m, 2H), 4.33-4.37 (m, 1H), 4.84 (heptuplet, J=6.29 Hz, 1H), 5.74 (d, J=7.26 Hz, 1H), 6.16 (dd, J=13.07 Hz and 10.14 Hz, 1H), 6.54 (s, 1H), 6.89 (d, J=5.03 Hz, 1H), 7.16-7.22 (m, 3H), 7.35-7.39 (m, 4H), 7.51 (d, J=7.55 Hz, 1H); $^{31}$P NMR (DMSO-$d_6$, 162 MHz) δ (ppm) 3.41 (s, 1P); MS (ESI) m/z=564.9 (MH$^+$).

Compound 7 (diastereoisomer 2): crystallized in CH$_3$CN: white solid; 93% purity (contaminated by 7% of dia 1); 13% yield; $^1$H NMR (DMSO-$d_6$, 400 MHz) δ (ppm) 1.13 (d, J=6.22 Hz, 6H), 1.19 (d, J=7.04 Hz, 3H), 3.71-3.81 (m, 1H), 3.99-4.02 (m, 1H), 4.26-4.32 (m, 2H), 4.34-4.38 (m, 1H), 4.84 (heptuplet, J=6.02 Hz, 1H), 5.71 (d, J=7.53 Hz, 1H), 6.07 (dd, J=12.29 Hz and 10.14 Hz, 1H), 6.54 (s, 1H), 6.86 (d, J=4.14 Hz, 1H), 7.17-7.19 (m, 3H), 7.35-7.39 (m, 4H), 7.56 (d, J=7.53 Hz, 1H); $^{31}$P NMR (DMSO-$d_6$, 162 MHz) δ (ppm) 3.86 (s, 1P); MS (ESI) m/z=565.0 (MH$^+$).

Compound 36a

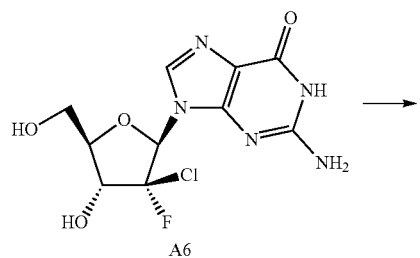

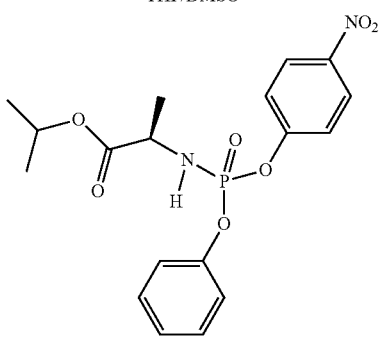

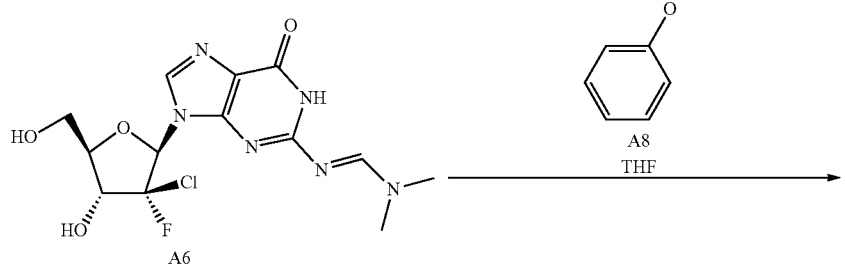

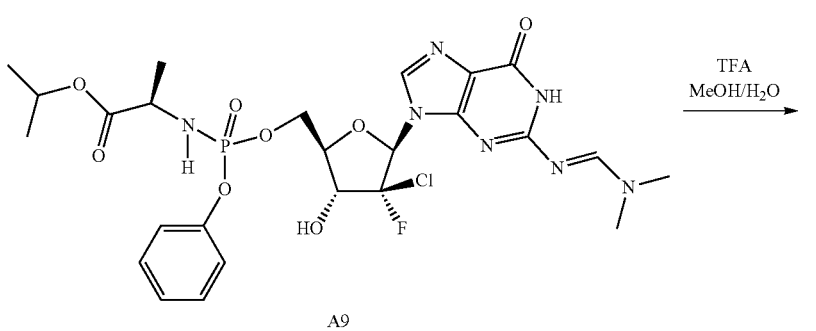

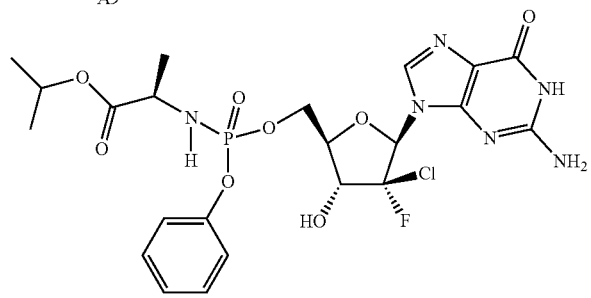

To a solution of compound A6 (0.74 mmol) in N,N-Dimethylformamide (4 mL/mmol) was added N,N-dimethylformamide dimethyl acetal (2.23 mmol). The reaction mixture was stirred at room temperature over a weekend and then concentrated under reduced pressure. The crude residue was purified by flash chromatography on silica (DCM/MeOH: 0 to 20%) to afford compound A7 in 71% yield. MS (ESI) m/z=375.0 (MH$^+$).

To a solution of compound A7 (0.53 mmol) in THF (20 mL/mmol) were added at 0° C., under nitrogen, tert-butylmagnesium chloride (1.0M in THF; 1.64 mmol) and DMSO (1 mL). The reaction mixture was stirred at room temperature for 2 days and then compound A8 (0.64 mmol) in THF (2 mL) was added. The reaction mixture was stirred for 3 days at room temperature and then filtered and concentrated under reduced pressure. The crude residue was purified by flash chromatography on silica (DCM/MeOH: 0 to 20%) to afford compound A9 (mixture of P-diastereoisomers) as an orange residue in 5% yield. MS (ESI) m/z=644.2 (MH+).

To a solution of compound A9 (0.024 mmol) in MeOH (20 mL/mmol) and water (10 mL/mmol) was added trifluoroacetic acid (0.26 mmol). The reaction mixture was stirred at room temperature overnight and then concentrated under reduced pressure. The crude residue was purified by RP-18 chromatography (eluent: $H_2O/CH_3CN$: 0 to 40%) to afford compound 36a (mixture of P-diastereoisomers) as a white solid in 52% yield. MS (ESI) m/z=589.2 (MH+); $^1H$ NMR (MeOD, 400 MHz) δ (ppm) 7.86-7.83 (m, 1H), 7.40-7.35 (m, 2H), 7.29-7.18 (m, 3H), 6.32-6.28 (m, 1H), 5.01-4.93 (m, 1H), 4.64-4.56 (m, 3H), 4.21-4.14 (m, 1H), 3.96-3.88 (m, 1H), 1.35-1.32 (m, 3H), 1.23-1.17 (m, 6H); $^{31}P$ NMR (MeOD, 162 MHz) δ (ppm) 4.13 (s, 0.66P), 3.56 (s, 0.34P); $^{19}F$ NMR (MeOD, 376.50 MHz) δ (ppm) −122.8 (s, 0.34F), −123.16 (s, 0.66F).

Example 2

In Vitro Inhibition of Hep G2 Hepatocytes

Materials
Cells were grown in RPMI-1640 supplemented with L-glutamine and 10% FBS: HepG2.
Method
96 well plates of HepG2 cell line were seeded with the optimized number of cells per well in a total volume of 50 μL per well. The plates were left overnight. Some wells were seeded with 100 μL of media for media control. The following day, cells were exposed to test compounds. At same time as drug exposure, a CTG assay was conducted on 1st plate for the 0 hr count.

2× stocks of each compound in media were prepared for dosing, as follows:

| | |
|---|---|
| 100,000 nM: | 40 μL 10 mM + 3.96 mL medium |
| 20,000 nM: | 1 mL 100,000 nM + 4 mL mix |
| 4,000 nM: | 1 mL 20,000 nM + 4 mL mix |
| 800 nM: | 1 mL 4,000 nM + 4 mL mix |
| 160 nM: | 1 mL 800 nM + 4 mL mix |
| 32 nM: | 1 mL 160 nM + 4 mL mix |
| 6.4 nM: | 1 mL 32 nM + 4 mL mix |
| 1.28 nM: | 1 mL 6.4 nM + 4 mL mix |

50 μL of above 2× stocks were added to cells and medium already on plate to give final concentrations. 50 μL media were added to cell control wells, and 50 μL of mix added to vehicle control wells. 10 μM Dox was added to appropriate wells. Cells exposed to test compounds were incubated at 37° C. for 72 hr followed by a CTG assay.
CellTiter-Glo
At the end of the 72 hr exposure period, plates were removed for a CellTiter-Glo (CTG) assay from a 37° C., 5% $CO_2$ incubator and placed on the bench at room temperature for 30 mins. 100 μL of CellTiter-Glo reagent was added and mixed for 2 mins, followed by a further 10 min incubation at room temperature. Luminescence was recorded using Synergy 4.0.

Results are provided in Table 1.

TABLE 1

In Vitro Inhibition of Hep G2 Hepatocytes

| Compound | $IC_{50}$ (nM) |
|---|---|
| Compound 4, Diastereomer 1 | + |
| Compound 4, Diastereomer 2 | + |
| (Diastereomer 2) | ++ |
| | +++++ |

$IC_{50}$ (nM) is provided as follows:
+++++ ≤ 10 < ++++ ≤ 100 < +++ ≤ 1,000 < ++ ≤ 10,000 < +

Example 3

Plasma and Liver Pharmacokinetics Following a Single Oral Dose in CD-1 Mice

A single oral dose of test compound in PEG 200 (dose volume 5 mL/kg) was administered to C57BL/6 male mice. Five untreated animals were used for the collection of control plasma and liver. Terminal plasma and liver samples were collected from three animals per time point at 1, 2, 4, 12, and 24 hours post dose. Liver specimens were collected from all animals immediately after the incision. Freezing forceps stored in liquid nitrogen were used to freeze the liver before excision.

Plasma samples were analyzed for analyte by LC-MS/MS. The internal standards (IS) were trazodone and D3-2'-MeG. For protein precipitation and extraction, each plasma sample (50 μL) was treated with 500 μL of 0.2% formic acid in acetonitrile and 20 μL of the internal standard working solution. After vortexing and centrifugation, 500 μL of the sample extracts were transferred to a new plate, dried under $N_2$ at ~28° C., and reconstituted with 75 μL of 0.2% FA in water. The extracts were chromatographed on an Aquasil C18 column using a gradient system of 0.2% formic acid in water and acetonitrile. The analytes were detected and quantified by tandem mass spectrometry in positive ion mode on an MDS Sciex API5000 equipped with a Turbo Ionspray® interface. The calibration range was 0.500 (LLOQ) to 500 ng/mL in mouse plasma. The corresponding range for molar units was 1.67 to 1672 pmol/mL.

Liver samples were analyzed for corresponding active triphosphate species by LC-MS/MS. Triphosphate levels were assayed by homogenizing (on ice) a known weight of mouse liver with 4× volume of 0.95 M trichloroacetic acid (TCA). Internal standard solution was added to the homogenate followed by neutralization with 20% ammonium hydroxide solution and addition of 500 µL 1% formic acid. The tissue samples were extracted by weak anion exchange solid phase extraction (SPE). Post extraction, the eluates were evaporated under nitrogen, followed by reconstitution before injection onto the LC-MS/MS system. The samples were chromatographed on a Luna NH2 column using a gradient system of ammonium acetate (1 mM to 20 mM and pH 8.0 to pH 10.0) in water and acetonitrile (70:30). The analyte was detected and quantified by tandem mass spectrometry in positive ion mode on an API4000 equipped with a Turbo Ionspray® interface. The calibration range was 10 to 10000 pmol/mL in mouse liver homogenate (50 to 50000 pmol/g of mouse liver).

Results are provided in Table 2.

TABLE 2

Mouse Liver Pharmacokinetics

| Compound | Dose (mg/kg) | Analyte | $T_{max}$ (hr) | $C_{max}$ (pmol/g) | $AUC_{last}$ (hr · pmol/g) | $T_{last}$ (hr) | $C_{last}$ (pmol/g) |
|---|---|---|---|---|---|---|---|
| (Diastereomer 2) | 200 | GemCTP | 4 | ++ | ++ | 24 | + |
|  |  | GemUTP | 4 | ++ | ++ | 24 | + |
| Compound 4, Diastereomer 2 | 182 | GemCTP | 2 | ++++ | +++ | 24 | + |
|  |  | GemUTP | 1 | + | + | 4 | + |
| (Diastereomer 1) | 200 | GemCTP | 2 | +++++ | ++++ | 24 | + |
|  |  | GemUTP | 4 | ++ | +++ | 4 | ++ |
| Compound 4, Diastereomer 1 | 182 | GemCTP | 4 | +++++ | +++++ | 24 | + |
|  |  | GemUTP | 4 | +++ | ++++ | 4 | +++ |
| Gemcitabine | 90 | GemCTP | 1 | ++ | + | 24 | + |
|  |  | GemUTP | 2 | ++ | + | 24 | + |

$AUC_{last}$ is provided as follows:
+ ≤ 10,000 < ++ ≤ 50,000 < +++ ≤ 150,000 < ++++ ≤ 500,000 < +++++

$C_{max}$ and $C_{last}$ are provided as follows:
+ ≤ 10,000 < ++ ≤ 5,000 < +++ ≤ 15,000 < ++++ ≤ 50,000 < +++++

The chemical structures of the analytes GemU TP and GemC TP are:

The chemical structure of gemcitabine is provided below.

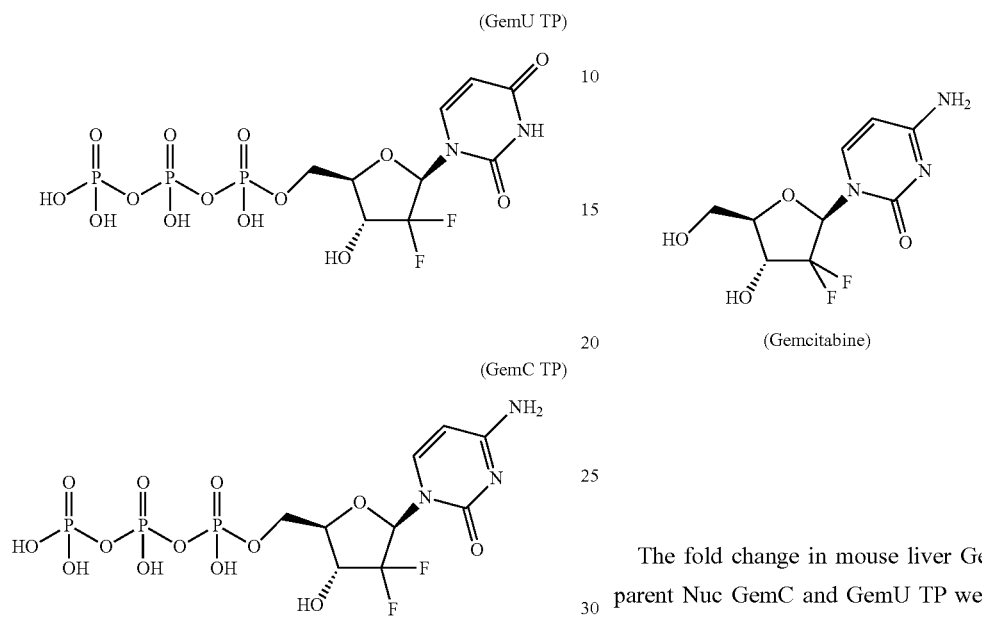

(GemU TP)

(GemC TP)

(Gemcitabine)

The fold change in mouse liver GemC TP compared to parent Nuc GemC and GemU TP were calculated and are provided in Table 3.

TABLE 3

| Fold Change in Mouse Liver | | |
| --- | --- | --- |
| | Fold change Mouse Liver GemC TP compared to Gemcitabine | Fold change Mouse Liver GemC TP produced compared to GemU TP |
| Gemcitabine | N/A | + |
| Compound 4, Diastereomer 1 | ++++++ | ++++ |
| Compound 4, Diastereomer 2 | ++ | +++ |
| | ++++ | +++ |

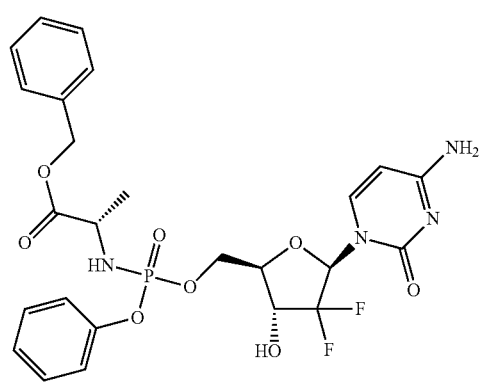 [SMILES: C[C@H](NP(=O)(OC[C@H]1O[C@@H](n2ccc(N)nc2=O)C(F)(F)[C@@H]1O)Oc1ccccc1)C(=O)OCc1ccccc1]

(Diastereomer 1)

TABLE 3-continued

Fold Change in Mouse Liver

| | Fold change Mouse Liver GemC TP compared to Gemcitabine | Fold change Mouse Liver GemC TP produced compared to GemU TP |
|---|---|---|
| (Diastereomer 2) | + | + |

Fold change is provided as follows:
+ ≤ 5 < ++ ≤ 10 < +++ ≤ 25 < ++++ ≤ 50 < +++++ ≤ 100 < ++++++

While the claimed subject matter has been described in terms of various embodiments, the skilled artisan will appreciate that various modifications, substitutions, omissions, and changes may be made without departing from the spirit thereof. Accordingly, it is intended that the scope of the claimed subject matter is limited solely by the scope of the following claims, including equivalents thereof.

What is claimed is:

1. A compound according to Formula I or VI:

(I)

(VI)

or a pharmaceutically acceptable salt thereof, wherein:
Base¹ is

-continued or a tautomeric form thereof;
Base² is

-continued

[Structure: purine with R⁴ at 6-position, R^{7A} at 2-position, attached at N9]

or a tautomeric form thereof;
- $R^4$ is sulfanyl, —$NR^{1'}R^{2'}$, —($C_1$ to $C_{10}$ unsubstituted alkyl)-$NR^{1'}R^{2'}$, or —($C_1$ to $C_{10}$ substituted alkyl)-$NR^{1'}R^{2'}$;
- $R^7$ is hydrogen, hydroxyl, chloro, bromo, fluoro, iodo, or —$NR^{1'}R^{2'}$;
- wherein $R^{1'}$ and $R^{2'}$ at each occurrence are independently hydrogen, $C_1$ to $C_{10}$ unsubstituted alkyl, $C_1$ to $C_{10}$ substituted alkyl, $C_2$-$C_{11}$ unsubstituted alkenyl, $C_2$-$C_{11}$ substituted alkenyl, $C_2$-$C_{11}$ unsubstituted alkynyl, $C_2$-$C_{11}$ substituted alkynyl, cycloalkyl, heterocyclo, aryl, or heteroaryl;
- $R^{7A}$ is hydroxyl, chloro, bromo, fluoro, iodo, or —$NR^{1A}R^{2A}$;
- wherein $R^{1A}$ and $R^{2A}$ at each occurrence are independently $C_1$ to $C_{10}$ unsubstituted alkyl, $C_1$ to $C_{10}$ substituted alkyl, $C_2$-$C_{11}$ unsubstituted alkenyl, $C_2$-$C_{11}$ substituted alkenyl, $C_2$-$C_{11}$ unsubstituted alkynyl, $C_2$-$C_{11}$ substituted alkynyl, cycloalkyl, heterocyclo, aryl, or heteroaryl;
- X is O or S;
- W is O or S;
- Ar is aryl or heteroaryl;
- $R^1$ is hydrogen, alkyl, arylalkyl, or heteroarylalkyl;
- $R^2$ is alkyl, arylalkyl, heterocycloalkyl, carboxylalkyl, heteroarylalkyl, aminoalkyl, hydroxylalkyl, aminoiminoaminoalkyl, aminocarbonylalkyl, sulfanylalkyl, carbamoylalkyl, alkylsulfanylalkyl, or hydroxylarylalkyl;
- $Z^1$ is hydrogen, hydroxyl, halogen, or cyano;
- $Z^2$ is hydrogen, hydroxyl, or halogen;
- $Z^3$ is hydrogen;
- $Z^4$ is hydroxyl, halogen, amino, or alkynyl;
- V is hydrogen, halogen, or amino;
- subject to the proviso that when, in Formula I: $Z^1$ is hydrogen, then: either V is halogen; or $Z^4$ is halogen, amino, or alkynyl.

2. The compound of claim 1 according to Formula Ia or Ib:

(Ia) [Structure]

(Ib) [Structure]

or a pharmaceutically acceptable salt thereof.

3. The compound of claim 1, or a pharmaceutically acceptable salt thereof, wherein:
Base¹ is

[Structure: purine with R⁴ at 6-position, R⁷ at 2-position]

or a tautomeric form thereof;
Base² is

[Structure: purine with R⁴ at 6-position, R^{7A} at 2-position]

or a tautomeric form thereof;
- Ar is aryl or heteroaryl;
- $R^1$ is hydrogen, $C_1$ to $C_{10}$ unsubstituted alkyl, $C_1$ to $C_{10}$ substituted alkyl, —($C_1$ to $C_{10}$ unsubstituted alkyl)-aryl, —($C_1$ to $C_{10}$ substituted alkyl)-aryl, —($C_1$ to $C_{10}$ unsubstituted alkyl)-heteroaryl, or —($C_1$ to $C_{10}$ substituted alkyl)-heteroaryl;
- $R^2$ is $C_1$ to $C_{10}$ unsubstituted alkyl, $C_1$ to $C_{10}$ substituted alkyl, —($C_1$ to $C_{10}$ unsubstituted alkyl)-aryl, —($C_1$ to $C_{10}$ substituted alkyl)-aryl, —($C_1$ to $C_{10}$ unsubstituted alkyl)-heterocyclo, —($C_1$ to $C_{10}$ substituted alkyl)-heterocyclo, —($C_1$ to $C_{10}$ unsubstituted alkyl)-C(O)OH, —($C_1$ to $C_{10}$ substituted alkyl)-C(O)OH, —($C_1$ to $C_{10}$ unsubstituted alkyl)-heteroaryl, —($C_1$ to $C_{10}$ substituted alkyl)-heteroaryl, —($C_1$ to $C_{10}$ unsubstituted alkyl)-$NR^{1'}R^{2'}$, —($C_1$ to $C_{10}$ substituted alkyl)-$NR^{1'}R^{2'}$, —($C_1$ to $C_{10}$ unsubstituted alkyl)-OH, —($C_1$ to $C_{10}$ substituted alkyl)-OH, —($C_1$ to $C_{10}$ unsubstituted alkyl)-$NR^{1'}$—C(NH)—$NR^{1'}R^{2'}$, —($C_1$ to $C_{10}$ substituted alkyl)-$NR^{1'}$—C(NH)—$NR^{1'}R^{2'}$, —($C_1$ to $C_{10}$ unsubstituted alkyl)-C(O)—$NR^{1'}R^{2'}$, —($C_1$ to $C_{10}$ substituted alkyl)-C(O)—$NR^{1'}R^{2'}$, —($C_1$ to $C_{10}$ unsubstituted alkyl)-SH, —($C_1$ to $C_{10}$ substituted alkyl)-SH, —($C_1$ to $C_{10}$ unsubstituted alkyl)-C(O)—$NR^{1'}R^{2'}$, —($C_1$ to $C_{10}$ substituted alkyl)-C(O)—$NR^{1'}R^{2'}$, —($C_1$ to $C_{10}$ unsubstituted alkyl)-S—($C_1$ to $C_{10}$ unsubstituted alkyl), —($C_1$ to $C_{10}$ unsubstituted alkyl)-S—($C_1$ to $C_{10}$ substituted alkyl), —($C_1$ to $C_{10}$ substituted alkyl)-S—($C_1$ to $C_{10}$ unsubstituted alkyl), —($C_1$ to $C_{10}$ substituted alkyl)-S—($C_1$ to $C_{10}$ substituted alkyl), —($C_1$ to $C_{10}$ unsubstituted alkyl)-aryl-OH, or —($C_1$ to $C_{10}$ substituted alkyl)-aryl-OH;
- $Z^1$ is hydrogen, hydroxyl, chloro, bromo, fluoro, iodo, or cyano;
- $Z^2$ is hydrogen, hydroxyl, chloro, bromo, fluoro, or iodo;
- $Z^4$ is hydroxyl, chloro, bromo, fluoro, iodo, —$NR^{1'}R^{2'}$, $C_2$-$C_{11}$ unsubstituted alkynyl, or $C_2$-$C_{11}$ substituted alkynyl;
- V is hydrogen, chloro, bromo, fluoro, iodo, or —$NR^{1'}R^{2'}$;

R$^{1'}$ and R$^{2'}$ at each occurrence are independently hydrogen, C$_1$ to C$_{10}$ unsubstituted alkyl, C$_1$ to C$_{10}$ substituted alkyl, C$_2$-C$_{11}$ unsubstituted alkenyl, C$_2$-C$_{11}$ substituted alkenyl, C$_2$-C$_{11}$ unsubstituted alkynyl, C$_2$-C$_{11}$ substituted alkynyl, cycloalkyl, heterocyclo, aryl, or heteroaryl;

aryl at each occurrence is independently C$_6$-C$_{12}$ unsubstituted aryl; or C$_6$-C$_{12}$ aryl substituted with one or more fluoro, chloro, bromo, iodo, methyl, CF$_3$, CCl$_3$, CFCl$_2$, CF$_2$Cl, ethyl, CH$_2$CF$_3$, CF$_2$CF$_3$, propyl, isopropyl, butyl, isobutyl, secbutyl, t-butyl, pentyl, isopentyl, neopentyl, hexyl, isohexyl, 3-methylpentyl, 2,2-dimethylbutyl, 2,3-dimethylbutyl, hydroxyl, —NH$_2$, —NH—(C$_1$ to C$_{10}$ unsubstituted alkyl), —NH—(C$_1$ to C$_{10}$ substituted alkyl), —NH-aryl, —NH—(C$_3$-C$_{15}$ cycloalkyl), methoxy, ethoxy, n-propoxy, isopropoxy, n-butoxy, tert-butoxy, sec-butoxy, n-pentoxy, n-hexoxy, 1,2-dimethylbutoxy, oxo, epoxy, hydroxyl, nitro, cyano, sulfonic acid, sulfate, phosphonic acid, phosphate, or phosphonate;

cycloalkyl at each occurrence is independently C$_3$-C$_{15}$ unsubstituted cycloalkyl or C$_3$-C$_{15}$ cycloalkyl substituted with fluoro, chloro, bromo, iodo, oxo, epoxy, hydroxyl, carbonyl, sulfanyl, —NH$_2$, methoxy, ethoxy, n-propoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate;

heterocyclo at each occurrence is independently a monovalent monocyclic or multicyclic non-aromatic that contains at least one non-aromatic ring containing one or more heteroatoms independently selected from O, S, and N in the ring, wherein heterocyclo is bonded through the non-aromatic ring, and wherein heterocyclo has from three to twenty ring atoms;

heteroaryl at each occurrence is independently a monovalent monocyclic or multicyclic aromatic that contains at least one aromatic ring containing one or more heteroatoms independently selected from O, S, and N in the ring, wherein heteroaryl is bonded through the aromatic ring, wherein the total number of heteroatoms in each ring is four or less and each ring contains at least one carbon atom, and wherein heteroaryl has from five to twenty ring atoms;

substituted alkenyl at each occurrence is independently a straight-chained or branched olefinically unsaturated hydrocarbon having at least one site of olefinic unsaturation substituted with fluoro, chloro, bromo, iodo, oxo, epoxy, hydroxyl, carbonyl, sulfanyl, —NH$_2$, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate;

substituted alkynyl at each occurrence is independently a straight-chained or branched acetylenically unsaturated hydrocarbon having at least one site of alkynyl unsaturation substituted with fluoro, chloro, bromo, iodo, oxo, epoxy, hydroxyl, carbonyl, sulfanyl, —NH$_2$, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate;

substituted alkyl at each occurrence is independently alkyl substituted with fluoro, chloro, bromo, iodo, oxo, epoxy, hydroxyl, carbonyl, sulfanyl, —NH$_2$, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate; and subject to the proviso that when, in Formula I: Z$^1$ is hydrogen, then: either V is chloro, bromo, fluoro, iodo; or Z$^4$ is chloro, bromo, fluoro, iodo, —NR$^{1'}$R$^{2'}$, C$_2$-C$_{11}$ unsubstituted alkynyl, or C$_2$-C$_{11}$ substituted alkynyl.

4. The compound of claim 1 according to Formula II, IIa or IIb:

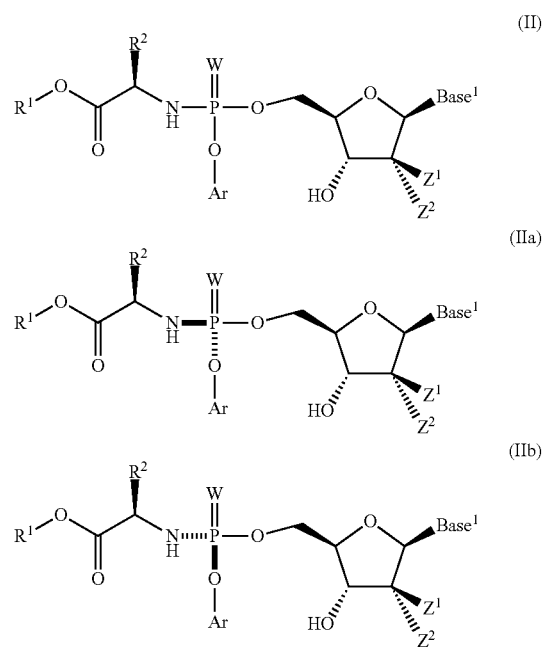

or a pharmaceutically acceptable salt thereof, wherein Z$^1$ is hydrogen, hydroxyl, halogen, or cyano.

5. The compound of claim 4, or a pharmaceutically acceptable salt thereof, wherein:

Base$^1$ is

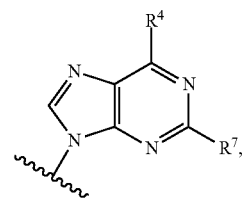

or a tautomeric form thereof;

Ar is aryl or heteroaryl;

R$^1$ is hydrogen, C$_1$ to C$_{10}$ unsubstituted alkyl, C$_1$ to C$_{10}$ substituted alkyl, —(C$_1$ to C$_{10}$ unsubstituted alkyl)-aryl, —(C$_1$ to C$_{10}$ substituted alkyl)-aryl, —(C$_1$ to C$_{10}$ unsubstituted alkyl)-heteroaryl, or —(C$_1$ to C$_{10}$ substituted alkyl)-heteroaryl;

R$^2$ is C$_1$ to C$_{10}$ unsubstituted alkyl, C$_1$ to C$_{10}$ substituted alkyl, —(C$_1$ to C$_{10}$ unsubstituted alkyl)-aryl, —(C$_1$ to C$_{10}$ substituted alkyl)-aryl, —(C$_1$ to C$_{10}$ unsubstituted alkyl)-heterocyclo, —(C$_1$ to C$_{10}$ substituted alkyl)-heterocyclo, —(C$_1$ to C$_{10}$ unsubstituted alkyl)-C(O)OH, —(C$_1$ to C$_{10}$ substituted alkyl)-C(O)OH, —(C$_1$ to C$_{10}$ unsubstituted alkyl)-heteroaryl, —(C$_1$ to C$_{10}$ substituted alkyl)-heteroaryl, —(C$_1$ to C$_{10}$ unsubstituted alkyl)-NR$^{1'}$R$^{2'}$, —(C$_1$ to C$_{10}$ substituted alkyl)-NR$^{1'}$R$^{2'}$, —(C$_1$ to C$_{10}$ unsubstituted alkyl)-OH, —(C$_1$ to C$_{10}$ substituted alkyl)-OH, —(C$_1$ to C$_{10}$ unsubstituted alkyl)-NR$^{1'}$—C(NH)—NR$^{1'}$R$^{2'}$, —(C$_1$ to C$_{10}$ substituted alkyl)-NR$^{1'}$—C(NH)—NR$^1$R$^2$, —(C$_1$ to C$_{10}$ unsubstituted alkyl)-C(O)—NR$^{1'}$R$^{2'}$, —(C$_1$ to C$_{10}$ substituted alkyl)-C(O)—NR$^{1'}$R$^{2'}$, —(C$_1$ to C$_{10}$ unsubstituted alkyl)-SH, —(C$_1$ to C$_{10}$ substituted alkyl)-SH, —(C$_1$ to C$_{10}$ unsubstituted alkyl)-C(O)—NR$^{1'}$R$^{2'}$, —(C$_1$ to C$_{10}$ substituted alkyl)-C(O)—NR$^{1'}$R$^{2'}$, —(C$_1$ to C$_{10}$ unsubstituted alkyl)-S—(C$_1$ to C$_{10}$ unsubstituted alkyl), —(C$_1$ to C$_{10}$ unsubstituted alkyl)-S—(C$_1$ to C$_{10}$ substituted alkyl), —(C$_1$ to C$_{10}$ substituted alkyl)-S—(C$_1$ to C$_{10}$ unsubstituted alkyl), —(C$_1$ to C$_{10}$ substituted alkyl)-S—(C$_1$ to C$_{10}$ substituted alkyl), —(C$_1$ to C$_{10}$ unsubstituted alkyl)-aryl-OH, or —(C$_1$ to C$_{10}$ substituted alkyl)-aryl-OH;

$Z^1$ is hydrogen, hydroxyl, chloro, bromo, fluoro, iodo, or cyano;

$Z^2$ is hydrogen, hydroxyl, chloro, bromo, fluoro, or iodo;

$R^4$ is sulfanyl, —NR$^{1'}$R$^{2'}$, —(C$_1$ to C$_{10}$ unsubstituted alkyl)-NR$^{1'}$R$^{2'}$, or —(C$_1$ to C$_{10}$ substituted alkyl)-NR$^{1'}$R$^{2'}$;

$R^7$ is hydrogen, hydroxyl, chloro, bromo, fluoro, iodo, or —NR$^{1'}$R$^{2'}$;

$R^{1'}$ and $R^{2'}$ at each occurrence are independently hydrogen, C$_1$ to C$_{10}$ unsubstituted alkyl, C$_1$ to C$_{10}$ substituted alkyl, C$_2$-C$_{11}$ unsubstituted alkenyl, C$_2$-C$_{11}$ substituted alkenyl, C$_2$-C$_{11}$ unsubstituted alkynyl, C$_2$-C$_{11}$ substituted alkynyl, cycloalkyl, heterocyclo, aryl, or heteroaryl;

aryl at each occurrence is independently C$_6$-C$_{12}$ unsubstituted aryl; or C$_6$-C$_{12}$ aryl substituted with one or more fluoro, chloro, bromo, iodo, methyl, CF$_3$, CCl$_3$, CFCl$_2$, CF$_2$Cl, ethyl, CH$_2$CF$_3$, CF$_2$CF$_3$, propyl, isopropyl, butyl, isobutyl, secbutyl, t-butyl, pentyl, isopentyl, neopentyl, hexyl, isohexyl, 3-methylpentyl, 2,2-dimethylbutyl, 2,3-dimethylbutyl, hydroxyl, —NH$_2$, —NH—(C$_1$ to C$_{10}$ unsubstituted alkyl), —NH—(C$_1$ to C$_{10}$ substituted alkyl), —NH-aryl, —NH—(C$_3$-C$_{15}$ cycloalkyl), methoxy, ethoxy, n-propoxy, isopropoxy, n-butoxy, tert-butoxy, sec-butoxy, n-pentoxy, n-hexoxy, 1,2-dimethylbutoxy, oxo, epoxy, hydroxyl, nitro, cyano, sulfonic acid, sulfate, phosphonic acid, phosphate, or phosphonate;

cycloalkyl at each occurrence is independently C$_3$-C$_{15}$ unsubstituted cycloalkyl or C$_3$-C$_{15}$ cycloalkyl substituted with fluoro, chloro, bromo, iodo, oxo, epoxy, hydroxyl, carbonyl, sulfanyl, —NH$_2$, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate;

heterocyclo at each occurrence is independently a monovalent monocyclic or multicyclic non-aromatic that contains at least one non-aromatic ring containing one or more heteroatoms independently selected from O, S, and N in the ring, wherein heterocyclo is bonded through the non-aromatic ring, and wherein heterocyclo has from three to twenty ring atoms;

heteroaryl at each occurrence is independently a monovalent monocyclic or multicyclic aromatic that contains at least one aromatic ring containing one or more heteroatoms independently selected from O, S, and N in the ring, wherein heteroaryl is bonded through the aromatic ring, wherein the total number of heteroatoms in each ring is four or less and each ring contains at least one carbon atom, and wherein heteroaryl has from five to twenty ring atoms;

substituted alkenyl at each occurrence is independently a straight-chained or branched olefinically unsaturated hydrocarbon having at least one site of olefinic unsaturation substituted with fluoro, chloro, bromo, iodo, oxo, epoxy, hydroxyl, carbonyl, sulfanyl, —NH$_2$, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate;

substituted alkynyl at each occurrence is independently a straight-chained or branched acetylenically unsaturated hydrocarbon having at least one site of alkynyl unsaturation substituted with fluoro, chloro, bromo, iodo, oxo, epoxy, hydroxyl, carbonyl, sulfanyl, —NH$_2$, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate;

substituted alkyl at each occurrence is independently alkyl substituted with fluoro, chloro, bromo, iodo, oxo, epoxy, hydroxyl, carbonyl, sulfanyl, —NH$_2$, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate; and subject to the proviso that when, in Formula II: $Z^1$ is hydrogen, then: either $Z^4$ is chloro, bromo, fluoro, iodo, —NR$^{1'}$R$^{2'}$, C$_2$-C$_{11}$ unsubstituted alkynyl, or C$_2$-C$_{11}$ substituted alkynyl.

6. The compound of claim 1 according to Formula III, IIIa or IIIb:

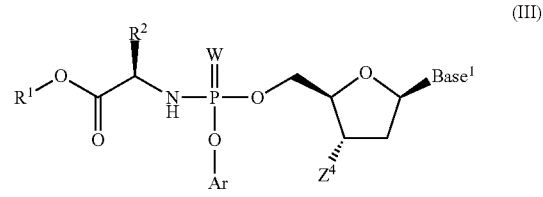
(III)

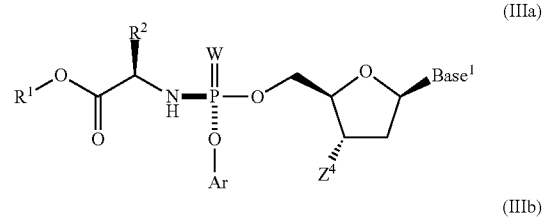
(IIIa)

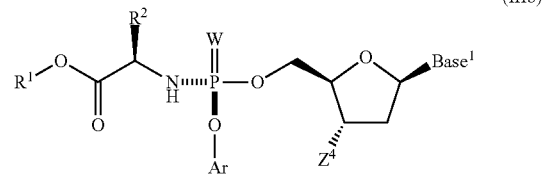
(IIIb)

or a pharmaceutically acceptable salt thereof, wherein $Z^4$ is fluoro, amino, or alkynyl.

7. The compound of claim 6, or a pharmaceutically acceptable salt thereof, wherein:

Base¹ is

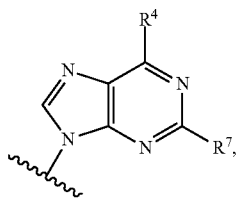

or a tautomeric form thereof;
Ar is aryl or heteroaryl;
R¹ is hydrogen, $C_1$ to $C_{10}$ unsubstituted alkyl, $C_1$ to $C_{10}$ substituted alkyl, —($C_1$ to $C_{10}$ unsubstituted alkyl)-aryl, —($C_1$ to $C_{10}$ substituted alkyl)-aryl, —($C_1$ to $C_{10}$ unsubstituted alkyl)-heteroaryl, or —($C_1$ to $C_{10}$ substituted alkyl)-heteroaryl;
R² is $C_1$ to $C_{10}$ unsubstituted alkyl, $C_1$ to $C_{10}$ substituted alkyl, —($C_1$ to $C_{10}$ unsubstituted alkyl)-aryl, —($C_1$ to $C_{10}$ substituted alkyl)-aryl, —($C_1$ to $C_{10}$ unsubstituted alkyl)-heterocyclo, —($C_1$ to $C_{10}$ substituted alkyl)-heterocyclo, —($C_1$ to $C_{10}$ unsubstituted alkyl)-C(O)OH, —($C_1$ to $C_{10}$ substituted alkyl)-C(O)OH, —($C_1$ to $C_{10}$ unsubstituted alkyl)-heteroaryl, —($C_1$ to $C_{10}$ substituted alkyl)-heteroaryl, —($C_1$ to $C_{10}$ unsubstituted alkyl)-NR¹'R²', —($C_1$ to $C_{10}$ substituted alkyl)-NR¹'R²', —($C_1$ to $C_{10}$ unsubstituted alkyl)-OH, —($C_1$ to $C_{10}$ substituted alkyl)-OH, —($C_1$ to $C_{10}$ unsubstituted alkyl)-NR¹'—C(NH)—NR¹'R²', —($C_1$ to $C_{10}$ substituted alkyl)-NR¹'—C(NH)—NR¹'R²', —($C_1$ to $C_{10}$ unsubstituted alkyl)-C(O)—NR¹'R²', —($C_1$ to $C_{10}$ substituted alkyl)-C(O)—NR¹'R²', —($C_1$ to $C_{10}$ unsubstituted alkyl)-SH, —($C_1$ to $C_{10}$ substituted alkyl)-SH, —($C_1$ to $C_{10}$ unsubstituted alkyl)-C(O)—NR¹'R²', —($C_1$ to $C_{10}$ substituted alkyl)-C(O)—NR¹'R²', —($C_1$ to $C_{10}$ unsubstituted alkyl)-S—($C_1$ to $C_{10}$ unsubstituted alkyl), —($C_1$ to $C_{10}$ unsubstituted alkyl)-S—($C_1$ to $C_{10}$ substituted alkyl), —($C_1$ to $C_{10}$ substituted alkyl)-S—($C_1$ to $C_{10}$ unsubstituted alkyl), —($C_1$ to $C_{10}$ substituted alkyl)-S—($C_1$ to $C_{10}$ substituted alkyl), —($C_1$ to $C_{10}$ unsubstituted alkyl)-aryl-OH, or —($C_1$ to $C_{10}$ substituted alkyl)-aryl-OH;
$Z^4$ is fluoro, —NR¹'R²', $C_2$-$C_{11}$ unsubstituted alkynyl, or $C_2$-$C_{11}$ substituted alkynyl;
R⁴ is sulfanyl, —NR¹'R²', —($C_1$ to $C_{10}$ unsubstituted alkyl)-NR¹'R²', or —($C_1$ to $C_{10}$ substituted alkyl)-NR¹'R²';
R⁷ is hydrogen, hydroxyl, chloro, bromo, fluoro, iodo, or —NR¹'R²';
R¹' and R²' at each occurrence are independently hydrogen, $C_1$ to $C_{10}$ unsubstituted alkyl, $C_1$ to $C_{10}$ substituted alkyl, $C_2$-$C_{11}$ unsubstituted alkenyl, $C_2$-$C_{11}$ substituted alkenyl, $C_2$-$C_{11}$ unsubstituted alkynyl, $C_2$-$C_{11}$ substituted alkynyl, cycloalkyl, heterocyclo, aryl, or heteroaryl;
aryl at each occurrence is independently $C_6$-$C_{12}$ unsubstituted aryl; or $C_6$-$C_{12}$ aryl substituted with one or more fluoro, chloro, bromo, iodo, methyl, $CF_3$, $CCl_3$, $CFCl_2$, $CF_2Cl$, ethyl, $CH_2CF_3$, $CF_2CF_3$, propyl, isopropyl, butyl, isobutyl, secbutyl, t-butyl, pentyl, isopentyl, neopentyl, hexyl, isohexyl, 3-methylpentyl, 2,2-dimethylbutyl, 2,3-dimethylbutyl, hydroxyl, —$NH_2$, —NH—($C_1$ to $C_{10}$ unsubstituted alkyl), —NH—($C_1$ to $C_{10}$ substituted alkyl), —NH-aryl, —NH—($C_3$-$C_{15}$ cycloalkyl), methoxy, ethoxy, n-propoxy, isopropoxy, n-butoxy, tert-butoxy, sec-butoxy, n-pentoxy, n-hexoxy, 1,2-dimethylbutoxy, oxo, epoxy, hydroxyl, nitro, cyano, sulfonic acid, sulfate, phosphonic acid, phosphate, or phosphonate;
cycloalkyl at each occurrence is independently $C_3$-$C_{15}$ unsubstituted cycloalkyl or $C_3$-$C_{15}$ cycloalkyl substituted with fluoro, chloro, bromo, iodo, oxo, epoxy, hydroxyl, carbonyl, sulfanyl, —$NH_2$, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate;
heterocyclo at each occurrence is independently a monovalent monocyclic or multicyclic non-aromatic that contains at least one non-aromatic ring containing one or more heteroatoms independently selected from O, S, and N in the ring, wherein heterocyclo is bonded through the non-aromatic ring, and wherein heterocyclo has from three to twenty ring atoms;
heteroaryl at each occurrence is independently a monovalent monocyclic or multicyclic aromatic that contains at least one aromatic ring containing one or more heteroatoms independently selected from O, S, and N in the ring, wherein heteroaryl is bonded through the aromatic ring, wherein the total number of heteroatoms in each ring is four or less and each ring contains at least one carbon atom, and wherein heteroaryl has from five to twenty ring atoms;
substituted alkenyl at each occurrence is independently a straight-chained or branched olefinically unsaturated hydrocarbon having at least one site of olefinic unsaturation substituted with fluoro, chloro, bromo, iodo, oxo, epoxy, hydroxyl, carbonyl, sulfanyl, —$NH_2$, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate;
substituted alkynyl at each occurrence is independently a straight-chained or branched acetylenically unsaturated hydrocarbon having at least one site of alkynyl unsaturation substituted with fluoro, chloro, bromo, iodo, oxo, epoxy, hydroxyl, carbonyl, sulfanyl, —$NH_2$, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate;
substituted alkyl at each occurrence is independently alkyl substituted with fluoro, chloro, bromo, iodo, oxo, epoxy, hydroxyl, carbonyl, sulfanyl, —$NH_2$, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate.

8. The compound of claim 1 according to Formula IV, IVa or IVb:

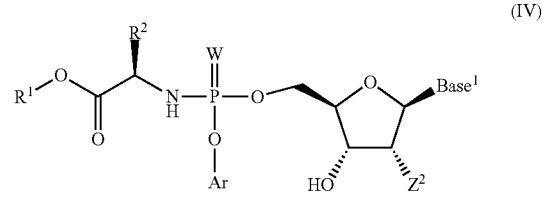

-continued

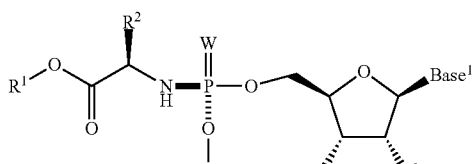
(IVa)

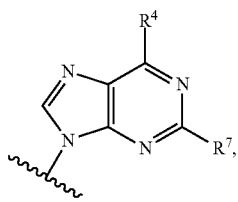
(IVb)

or a pharmaceutically acceptable salt thereof, wherein $Z^2$ is hydrogen or hydroxyl.

9. The compound of claim 8, or a pharmaceutically acceptable salt thereof, wherein:
Base$^1$ is

[structure with $R^4$ and $R^7$ substituents on purine]

or a tautomeric form thereof;
Ar is aryl or heteroaryl;
$R^1$ is hydrogen, $C_1$ to $C_{10}$ unsubstituted alkyl, $C_1$ to $C_{10}$ substituted alkyl, —($C_1$ to $C_{10}$ unsubstituted alkyl)-aryl, —($C_1$ to $C_{10}$ substituted alkyl)-aryl, —($C_1$ to $C_{10}$ unsubstituted alkyl)-heteroaryl, or —($C_1$ to $C_{10}$ substituted alkyl)-heteroaryl;
$R^2$ is $C_1$ to $C_{10}$ unsubstituted alkyl, $C_1$ to $C_{10}$ substituted alkyl, —($C_1$ to $C_{10}$ unsubstituted alkyl)-aryl, —($C_1$ to $C_{10}$ substituted alkyl)-aryl, —($C_1$ to $C_{10}$ unsubstituted alkyl)-heterocyclo, —($C_1$ to $C_{10}$ substituted alkyl)-heterocyclo, —($C_1$ to $C_{10}$ unsubstituted alkyl)-C(O)OH, —($C_1$ to $C_{10}$ substituted alkyl)-C(O)OH, —($C_1$ to $C_{10}$ unsubstituted alkyl)-heteroaryl, —($C_1$ to $C_{10}$ substituted alkyl)-heteroaryl, —($C_1$ to $C_{10}$ unsubstituted alkyl)-NR$^{1'}$R$^{2'}$, —($C_1$ to $C_{10}$ substituted alkyl)-NR$^{1'}$R$^{2'}$, —($C_1$ to $C_{10}$ unsubstituted alkyl)-OH, —($C_1$ to $C_{10}$ substituted alkyl)-OH, —($C_1$ to $C_{10}$ unsubstituted alkyl)-NR$^{1'}$—C(NH)—NR$^{1'}$R$^{2'}$, —($C_1$ to $C_{10}$ substituted alkyl)-NR$^{1'}$—C(NH)—NR$^{1'}$R$^{2'}$, —($C_1$ to $C_{10}$ unsubstituted alkyl)-C(O)—NR$^{1'}$R$^{2'}$, —($C_1$ to $C_{10}$ substituted alkyl)-C(O)—NR$^{1'}$R$^{2'}$, —($C_1$ to $C_{10}$ unsubstituted alkyl)-SH, —($C_1$ to $C_{10}$ substituted alkyl)-SH, —($C_1$ to $C_{10}$ unsubstituted alkyl)-C(O)—NR$^{1'}$R$^{2'}$, —($C_1$ to $C_{10}$ substituted alkyl)-C(O)—NR$^{1'}$R$^{2'}$, —($C_1$ to $C_{10}$ unsubstituted alkyl)-S—($C_1$ to $C_{10}$ unsubstituted alkyl), —($C_1$ to $C_{10}$ unsubstituted alkyl)-S—($C_1$ to $C_{10}$ substituted alkyl), —($C_1$ to $C_{10}$ substituted alkyl)-S—($C_1$ to $C_{10}$ unsubstituted alkyl), —($C_1$ to $C_{10}$ substituted alkyl)-S—($C_1$ to $C_{10}$ substituted alkyl), —($C_1$ to $C_{10}$ unsubstituted alkyl)-aryl-OH, or —($C_1$ to $C_{10}$ substituted alkyl)-aryl-OH;
$R^4$ is sulfanyl, —NR$^{1'}$R$^{2'}$, —($C_1$ to $C_{10}$ unsubstituted alkyl)-NR$^{1'}$R$^{2'}$, or —($C_1$ to $C_{10}$ substituted alkyl)-NR$^{1'}$R$^{2'}$;
$R^7$ is hydrogen, hydroxyl, chloro, bromo, fluoro, iodo, or —NR$^{1'}$R$^{2'}$;
$R^{1'}$ and $R^{2'}$ at each occurrence are independently hydrogen, $C_1$ to $C_{10}$ unsubstituted alkyl, $C_1$ to $C_{10}$ substituted alkyl, $C_2$-$C_{11}$ unsubstituted alkenyl, $C_2$-$C_{11}$ substituted alkenyl, $C_2$-$C_{11}$ unsubstituted alkynyl, $C_2$-$C_{11}$ substituted alkynyl, cycloalkyl, heterocyclo, aryl, or heteroaryl;
aryl at each occurrence is independently $C_6$-$C_{12}$ unsubstituted aryl; or $C_6$-$C_{12}$ aryl substituted with one or more fluoro, chloro, bromo, iodo, methyl, $CF_3$, $CCl_3$, $CFCl_2$, $CF_2Cl$, ethyl, $CH_2CF_3$, $CF_2CF_3$, propyl, isopropyl, butyl, isobutyl, secbutyl, t-butyl, pentyl, isopentyl, neopentyl, hexyl, isohexyl, 3-methylpentyl, 2,2-dimethylbutyl, 2,3-dimethylbutyl, hydroxyl, —NH$_2$, —NH—($C_1$ to $C_{10}$ unsubstituted alkyl), —NH—($C_1$ to $C_{10}$ substituted alkyl), —NH-aryl, —NH—($C_3$-$C_{15}$ cycloalkyl), methoxy, ethoxy, n-propoxy, isopropoxy, n-butoxy, tert-butoxy, sec-butoxy, n-pentoxy, n-hexoxy, 1,2-dimethylbutoxy, oxo, epoxy, hydroxyl, nitro, cyano, sulfonic acid, sulfate, phosphonic acid, phosphate, or phosphonate;
cycloalkyl at each occurrence is independently $C_3$-$C_{15}$ unsubstituted cycloalkyl or $C_3$-$C_{15}$ cycloalkyl substituted with fluoro, chloro, bromo, iodo, oxo, epoxy, hydroxyl, carbonyl, sulfanyl, —NH$_2$, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate;
heterocyclo at each occurrence is independently a monovalent monocyclic or multicyclic non-aromatic that contains at least one non-aromatic ring containing one or more heteroatoms independently selected from O, S, and N in the ring, wherein heterocyclo is bonded through the non-aromatic ring, and wherein heterocyclo has from three to twenty ring atoms;
heteroaryl at each occurrence is independently a monovalent monocyclic or multicyclic aromatic that contains at least one aromatic ring containing one or more heteroatoms independently selected from O, S, and N in the ring, wherein heteroaryl is bonded through the aromatic ring, wherein the total number of heteroatoms in each ring is four or less and each ring contains at least one carbon atom, and wherein heteroaryl has from five to twenty ring atoms;
substituted alkenyl at each occurrence is independently a straight-chained or branched olefinically unsaturated hydrocarbon having at least one site of olefinic unsaturation substituted with fluoro, chloro, bromo, iodo, oxo, epoxy, hydroxyl, carbonyl, sulfanyl, —NH$_2$, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate;
substituted alkynyl at each occurrence is independently a straight-chained or branched acetylenically unsaturated hydrocarbon having at least one site of alkynyl unsaturation substituted with fluoro, chloro, bromo, iodo, oxo, epoxy, hydroxyl, carbonyl, sulfanyl, —NH$_2$, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate; and
substituted alkyl at each occurrence is independently alkyl substituted with fluoro, chloro, bromo, iodo, oxo, epoxy, hydroxyl, carbonyl, sulfanyl, —NH$_2$, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate.

10. The compound of claim 1 according to Formula V, Va or Vb:

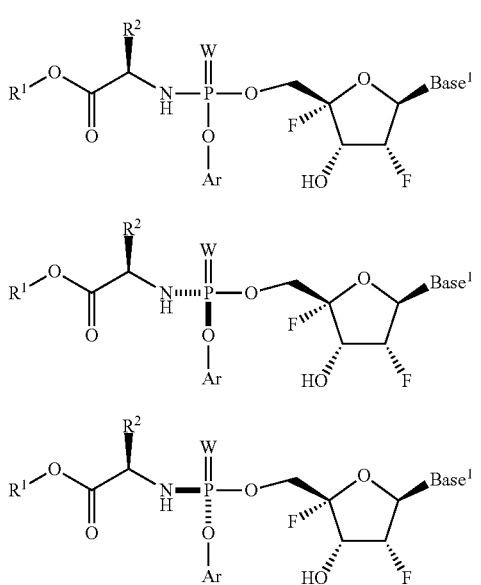

or a pharmaceutically acceptable salt thereof.

11. The compound of claim 10, or a pharmaceutically acceptable salt thereof, wherein:
Base$^1$ is

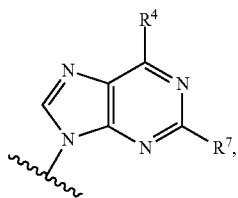

or a tautomeric form thereof;
Ar is aryl or heteroaryl;
$R^1$ is hydrogen, $C_1$ to $C_{10}$ unsubstituted alkyl, $C_1$ to $C_{10}$ substituted alkyl, —($C_1$ to $C_{10}$ unsubstituted alkyl)-aryl, —($C_1$ to $C_{10}$ substituted alkyl)-aryl, —($C_1$ to $C_{10}$ unsubstituted alkyl)-heteroaryl, or —($C_1$ to $C_{10}$ substituted alkyl)-heteroaryl;
$R^2$ is $C_1$ to $C_{10}$ unsubstituted alkyl, $C_1$ to $C_{10}$ substituted alkyl, —($C_1$ to $C_{10}$ unsubstituted alkyl)-aryl, —($C_1$ to $C_{10}$ substituted alkyl)-aryl, —($C_1$ to $C_{10}$ unsubstituted alkyl)-heterocyclo, —($C_1$ to $C_{10}$ substituted alkyl)-heterocyclo, —($C_1$ to $C_{10}$ unsubstituted alkyl)-C(O)OH, —($C_1$ to $C_{10}$ substituted alkyl)-C(O)OH, —($C_1$ to $C_{10}$ unsubstituted alkyl)-heteroaryl, —($C_1$ to $C_{10}$ substituted alkyl)-heteroaryl, —($C_1$ to $C_{10}$ unsubstituted alkyl)-NR$^{1'}$R$^{2'}$, —($C_1$ to $C_{10}$ substituted alkyl)-NR$^{1'}$R$^{2'}$, —($C_1$ to $C_{10}$ unsubstituted alkyl)-OH, —($C_1$ to $C_{10}$ substituted alkyl)-OH, —($C_1$ to $C_{10}$ unsubstituted alkyl)-NR$^{1'}$—C(NH)—NR$^{1'}$R$^{2'}$, —($C_1$ to $C_{10}$ substituted alkyl)-NR$^{1'}$—C(NH)—NR$^{1'}$R$^{2'}$, —($C_1$ to $C_{10}$ unsubstituted alkyl)-C(O)—NR$^{1'}$R$^{2'}$, —($C_1$ to $C_{10}$ substituted alkyl)-C(O)—NR$^{1'}$R$^{2'}$, —($C_1$ to $C_{10}$ unsubstituted alkyl)-SH, —($C_1$ to $C_{10}$ substituted alkyl)-SH, —($C_1$ to $C_{10}$ unsubstituted alkyl)-C(O)—NR$^{1'}$R$^{2'}$, —($C_1$ to $C_{10}$ substituted alkyl)-C(O)—NR$^{1'}$R$^{2'}$, —($C_1$ to $C_{10}$ unsubstituted alkyl)-S—($C_1$ to $C_{10}$ unsubstituted alkyl), —($C_1$ to $C_{10}$ unsubstituted alkyl)-S—($C_1$ to $C_{10}$ substituted alkyl), —($C_1$ to $C_{10}$ substituted alkyl)-S—($C_1$ to $C_{10}$ unsubstituted alkyl), —($C_1$ to $C_{10}$ substituted alkyl)-S—($C_1$ to $C_{10}$ substituted alkyl), —($C_1$ to $C_{10}$ unsubstituted alkyl)-aryl-OH, or —($C_1$ to $C_{10}$ substituted alkyl)-aryl-OH;
$R^4$ is sulfanyl, —NR$^{1'}$R$^{2'}$, —($C_1$ to $C_{10}$ unsubstituted alkyl)-NR$^{1'}$R$^{2'}$, or —($C_1$ to $C_{10}$ substituted alkyl)-NR$^{1'}$R$^{2'}$;
$R^7$ is hydrogen, hydroxyl, chloro, bromo, fluoro, iodo, or —NR$^{1'}$R$^{2'}$;
$R^{1'}$ and $R^{2'}$ at each occurrence are independently hydrogen, $C_1$ to $C_{10}$ unsubstituted alkyl, $C_1$ to $C_{10}$ substituted alkyl, $C_2$-$C_{11}$ unsubstituted alkenyl, $C_2$-$C_{11}$ substituted alkenyl, $C_2$-$C_{11}$ unsubstituted alkynyl, $C_2$-$C_{11}$ substituted alkynyl, cycloalkyl, heterocyclo, aryl, or heteroaryl;
aryl at each occurrence is independently $C_6$-$C_{12}$ unsubstituted aryl; or $C_6$-$C_{12}$ aryl substituted with one or more fluoro, chloro, bromo, iodo, methyl, CF$_3$, CCl$_3$, CFCl$_2$, CF$_2$Cl, ethyl, CH$_2$CF$_3$, CF$_2$CF$_3$, propyl, isopropyl, butyl, isobutyl, secbutyl, t-butyl, pentyl, isopentyl, neopentyl, hexyl, isohexyl, 3-methylpentyl, 2,2-dimethylbutyl, 2,3-dimethylbutyl, hydroxyl, —NH$_2$, —NH—($C_1$ to $C_{10}$ unsubstituted alkyl), —NH—($C_1$ to $C_{10}$ substituted alkyl), —NH-aryl, —NH—($C_3$-$C_{15}$ cycloalkyl), methoxy, ethoxy, n-propoxy, isopropoxy, n-butoxy, tert-butoxy, sec-butoxy, n-pentoxy, n-hexoxy, 1,2-dimethylbutoxy, oxo, epoxy, hydroxyl, nitro, cyano, sulfonic acid, sulfate, phosphonic acid, phosphate, or phosphonate;
cycloalkyl at each occurrence is independently $C_3$-$C_{15}$ unsubstituted cycloalkyl or $C_3$-$C_{15}$ cycloalkyl substituted with fluoro, chloro, bromo, iodo, oxo, epoxy, hydroxyl, carbonyl, sulfanyl, —NH$_2$, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate;
heterocyclo at each occurrence is independently a monovalent monocyclic or multicyclic non-aromatic that contains at least one non-aromatic ring containing one or more heteroatoms independently selected from O, S, and N in the ring, wherein heterocyclo is bonded through the non-aromatic ring, and wherein heterocyclo has from three to twenty ring atoms;
heteroaryl at each occurrence is independently a monovalent monocyclic or multicyclic aromatic that contains at least one aromatic ring containing one or more heteroatoms independently selected from O, S, and N in the ring, wherein heteroaryl is bonded through the aromatic ring, wherein the total number of heteroatoms in each ring is four or less and each ring contains at least one carbon atom, and wherein heteroaryl has from five to twenty ring atoms;
substituted alkenyl at each occurrence is independently a straight-chained or branched olefinically unsaturated hydrocarbon having at least one site of olefinic unsaturation substituted with fluoro, chloro, bromo, iodo, oxo, epoxy, hydroxyl, carbonyl, sulfanyl, —NH$_2$, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate;

substituted alkynyl at each occurrence is independently a straight-chained or branched acetylenically unsaturated hydrocarbon having at least one site of alkynyl unsaturation substituted with fluoro, chloro, bromo, iodo, oxo, epoxy, hydroxyl, carbonyl, sulfanyl, —NH$_2$, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate; and substituted alkyl at each occurrence is independently alkyl substituted with fluoro, chloro, bromo, iodo, oxo, epoxy, hydroxyl, carbonyl, sulfanyl, —NH$_2$, methoxy, ethoxy, n-propoxy, isopropoxy, n-butoxy, tert-butoxy, sec-butoxy, n-pentoxy, n-hexoxy, 1,2-dimethylbutoxy, nitro, cyano, sulfonic acid, sulfate, phosphonic acid, phosphate, or phosphonate.

12. The compound of claim 1, wherein $Z^1$ is —OH; $Z^2$ is —H; $Z^3$ is —H; $Z^4$ is —OH; and V is —H.
13. The compound of claim 1, wherein $Z^1$ is —OH; $Z^2$ is —F; $Z^3$ is —H; $Z^4$ is —OH; and V is —H.
14. The compound of any of claim 1, wherein $Z^1$ is —F; $Z^2$ is —OH; $Z^3$ is —H; $Z^4$ is —H; and V is —H.
15. The compound of any of claim 1, wherein $Z^1$ is —F; $Z^2$ is —F; $Z^3$ is —H; $Z^4$ is —OH; and V is —H.
16. The compound of any of claim 1, wherein $Z^1$ is —F; $Z^2$ is —H; $Z^3$ is —H; $Z^4$ is —OH; and V is —H.
17. The compound of any of claim 1, wherein $Z^1$ is —F; $Z^2$ is —Cl; $Z^3$ is —H; $Z^4$ is —OH; and V is —H.
18. The compound of any of claim 1, wherein $Z^1$ is —Cl; $Z^2$ is —Cl; $Z^3$ is —H; $Z^4$ is —OH; and V is —H.
19. The compound of any of claim 1, wherein $Z^1$ is —Cl; $Z^2$ is —H; $Z^3$ is —H; $Z^4$ is —OH; and V is —H.
20. The compound of any of claim 1, wherein $Z^1$ is —Cl; $Z^2$ is —F; $Z^3$ is —H; $Z^4$ is —OH; and V is —H.
21. The compound of any of claim 1, wherein $Z^1$ is —F; $Z^2$ is —F; $Z^3$ is —H; $Z^4$ is —OH; and V is —H.
22. The compound of any of claim 1, wherein $Z^1$ is —CN; $Z^2$ is —H; $Z^3$ is —H; $Z^4$ is —OH; and V is —H.
23. The compound of any of claim 1, wherein $Z^1$ is —H; $Z^2$ is —H; $Z^3$ is —H; $Z^4$ is —C≡CH; and V is —H.
24. The compound of any of claim 1, wherein $Z^1$ is —H; $Z^2$ is —H; $Z^3$ is —H; $Z^4$ is —F; and V is —H.
25. The compound of any of claim 1, wherein $Z^1$ is —H; $Z^2$ is —H; $Z^3$ is —H; $Z^4$ is —NH$_2$; and V is —H.
26. The compound of any of claim 1, wherein $Z^1$ is —H; $Z^2$ is —F; $Z^3$ is —H; $Z^4$ is —OH; and V is —F.
27. The compound of any of claim 1, wherein $Z^1$ is —CN; $Z^2$ is —H; $Z^3$ is —H; $Z^4$ is —OH; and V is —H.
28. The compound of any of claim 1, wherein $Z^1$ is —CN; $Z^2$ is —H; $Z^3$ is —H; $Z^4$ is —OH; and V is —NH$_2$.
29. The compound of claim 1, wherein $Z^1$ is —H; $Z^2$ is —H; $Z^3$ is —H; $Z^4$ is —OH; and Base$^1$ is selected from

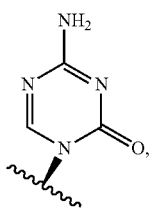

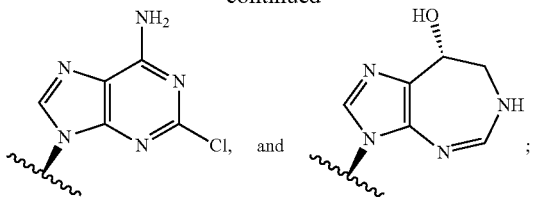

and Base$^2$ is selected from

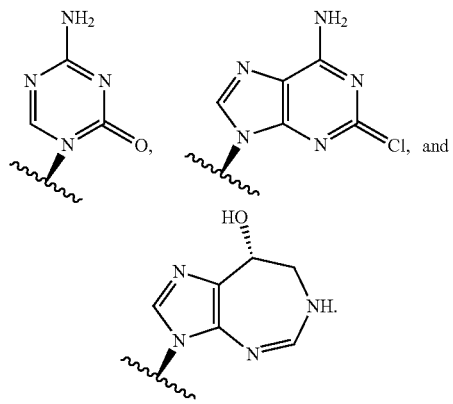

30. The compound of claim 1, wherein $Z^1$ is —H; $Z^2$ is —OH; $Z^3$ is —H; $Z^4$ is —OH; and Base$^1$ and Base$^2$ are selected from

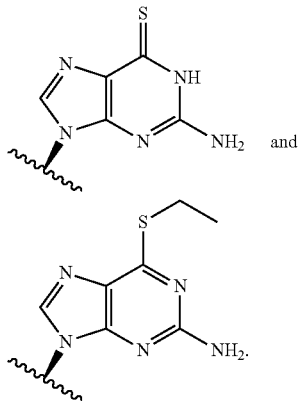

31. The compound of any of claim 1, wherein $R^2$ is methyl.
32. The compound of any of claim 1, wherein Ar is phenyl.
33. The compound of any of claim 1, wherein $R^1$ is isopropyl.
34. The compound of claim 1, wherein:
Base$^1$ is

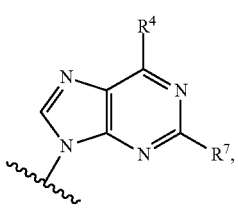

or a tautomeric form thereof;

Base² is

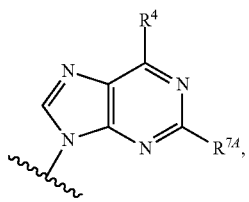

or a tautomeric form thereof;

R⁴ is sulfanyl, amino, or aminoalkyl;

R⁷ is hydrogen, hydroxyl, halogen, or amino; and

R⁷ᴬ is hydroxyl or halogen.

35. The compound of any of claim 1, wherein the group N-linked to the phosphorus atom is a D-amino acid residue, or a derivative thereof.

36. The compound of any of claim 1, with $R_P$ stereochemistry.

37. The compound of any of claim 1, with $S_P$ stereochemistry.

38. The compound of any of claim 1, that is isolated.

39. A pharmaceutical composition comprising the compound of claim 1 and a pharmaceutically acceptable excipient, carrier or diluent.

40. The pharmaceutical composition of claim 39, wherein the composition is an oral formulation.

41. A method for the treatment of a subject with liver cancer in a host in need thereof, comprising the administration of an effective amount of a compound of claim 1.

42. The method of claim 41, wherein the host is a human.

43. The method of claim 41 wherein the liver cancer is hepatocellular carcinoma, cholangiocarcinoma, or biliary tract cancer.

44. The method of claim 41, wherein the administration directs a substantial amount of the compound, or pharmaceutically acceptable salt thereof, to a liver of the subject.

45. A compound, or a pharmaceutically acceptable salt thereof, said compound selected from:

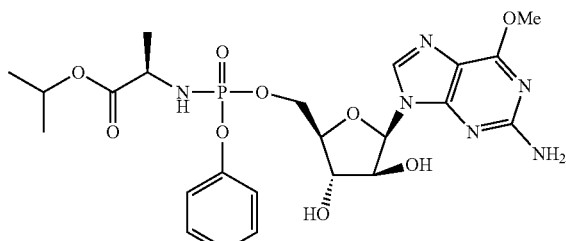

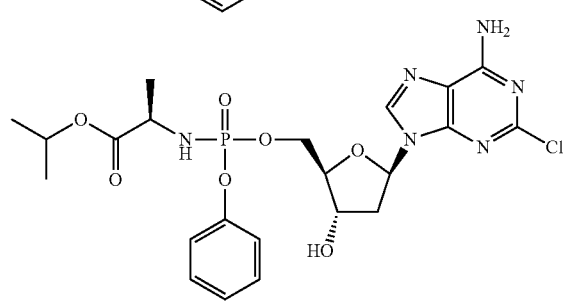

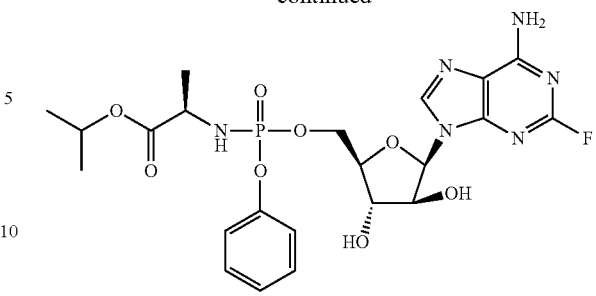

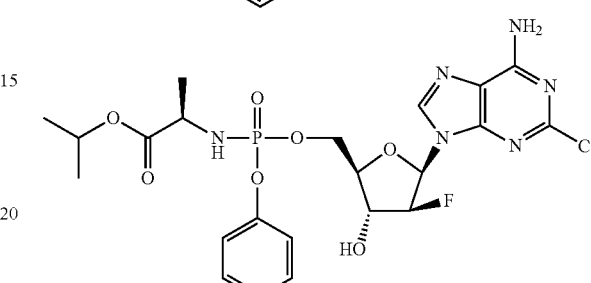

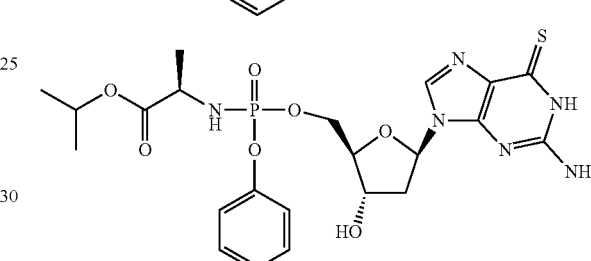

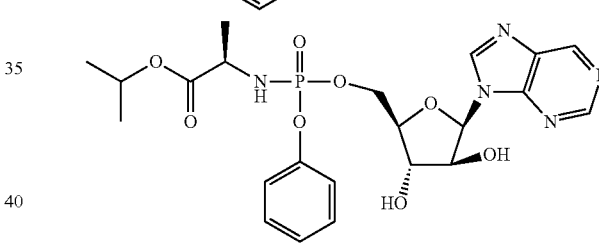

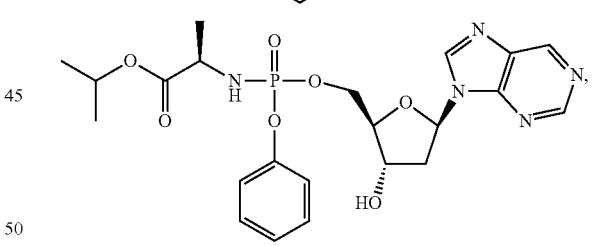

and

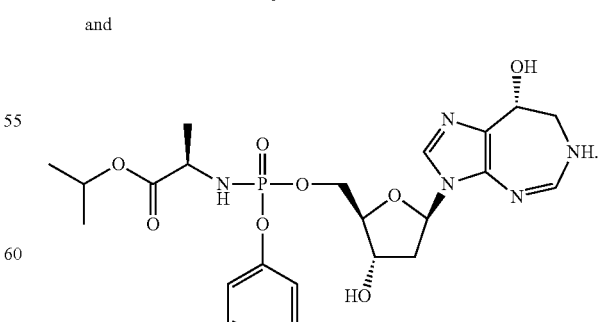

46. A compound, or a pharmaceutically acceptable salt thereof, said compound selected from:

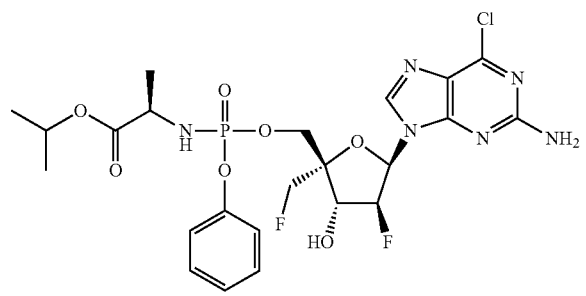
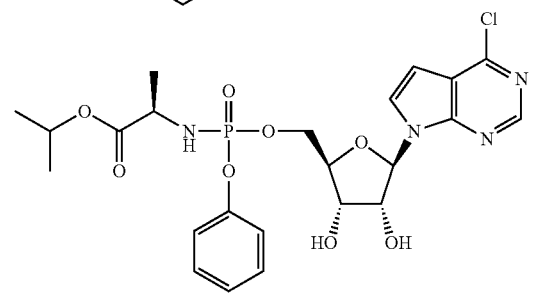
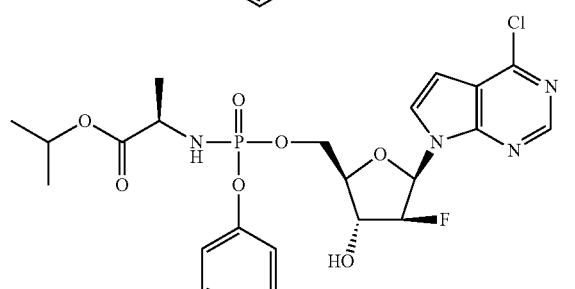
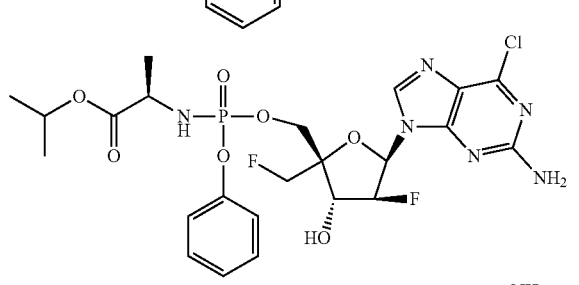
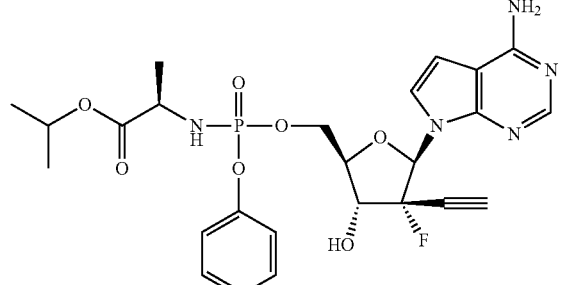
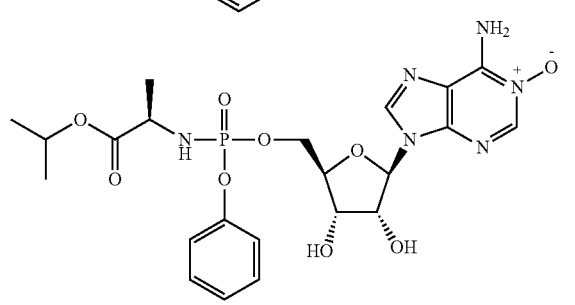
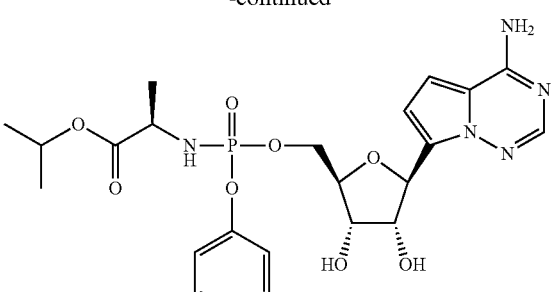
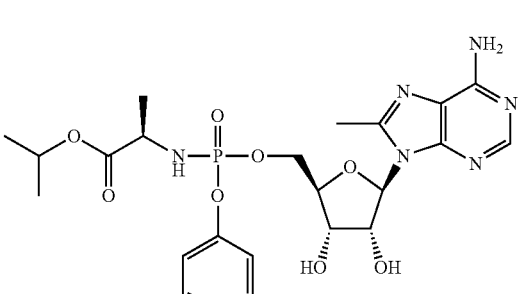
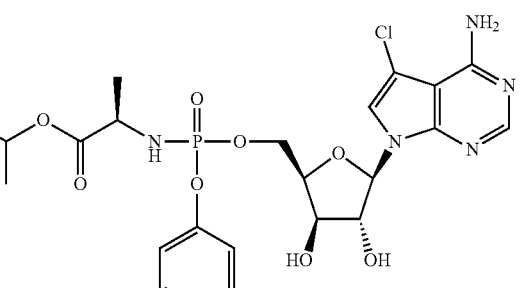
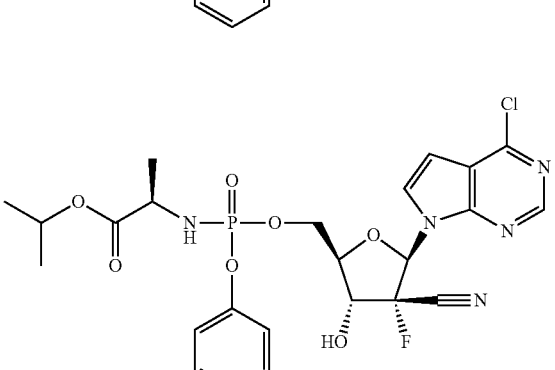
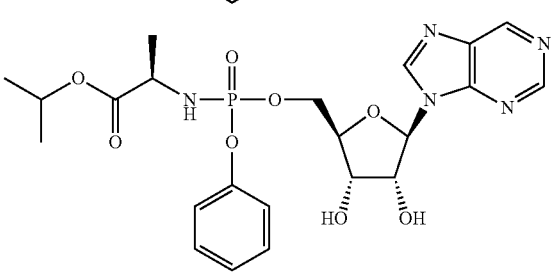

151
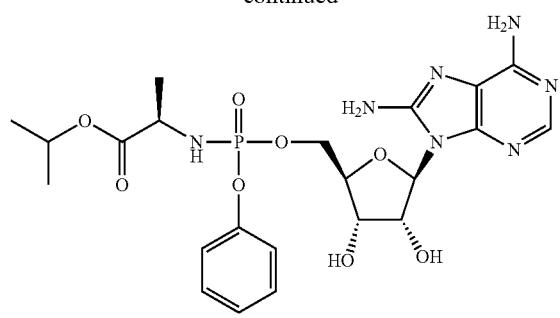
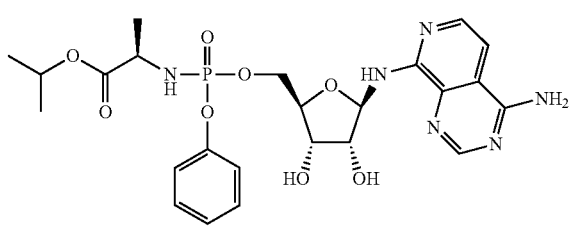
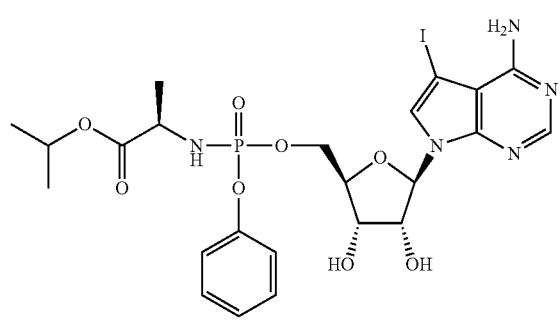
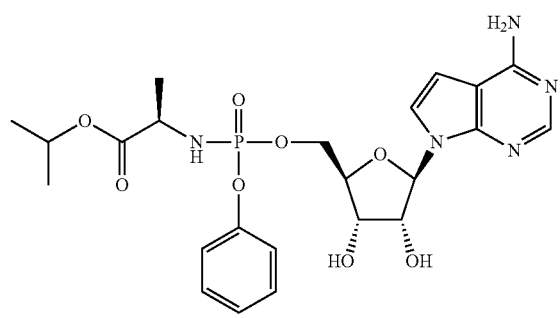
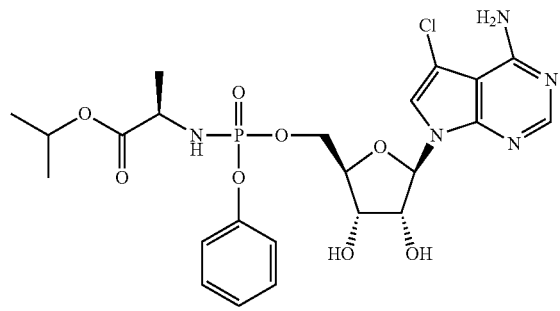
152
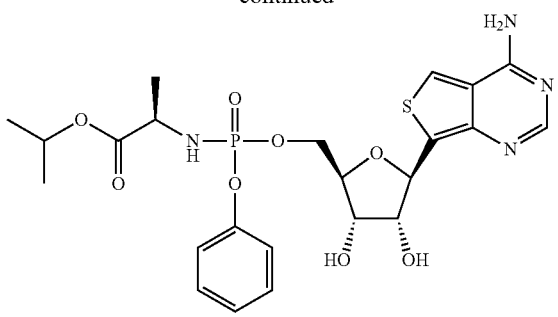
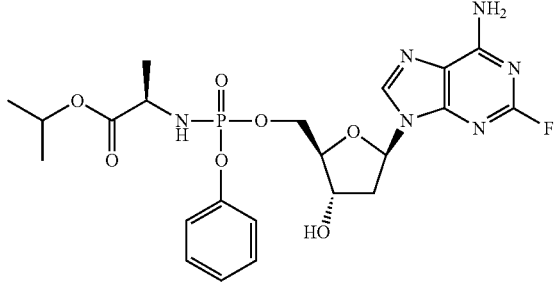
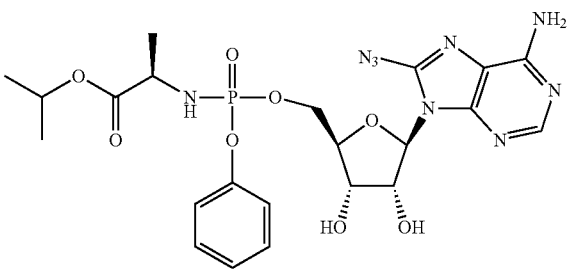
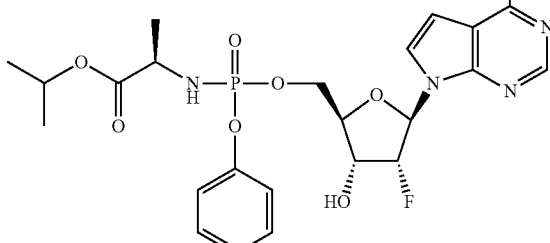
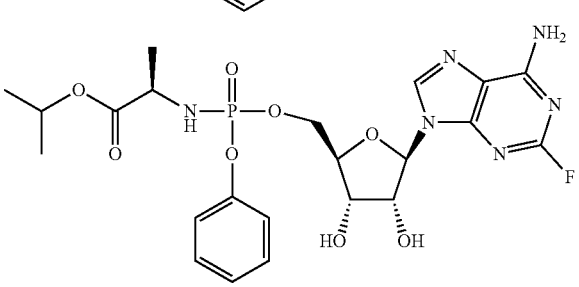
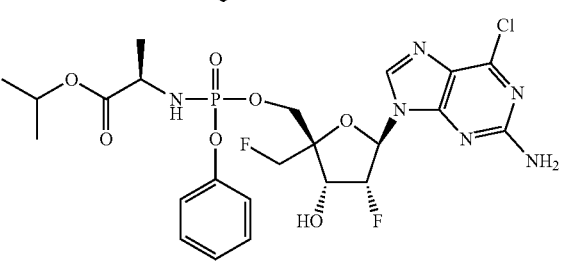

-continued
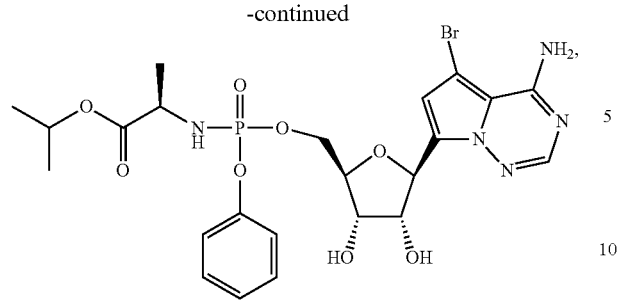
and
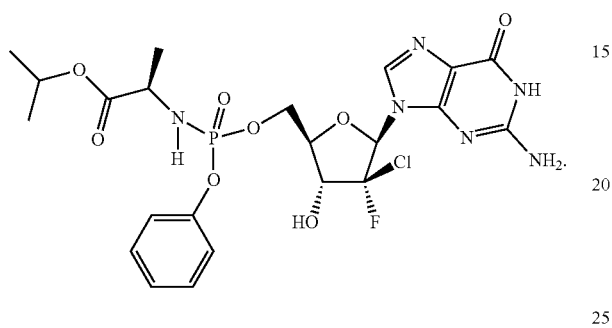
* * * * *